(12) United States Patent
Liu et al.

(10) Patent No.: US 8,710,071 B2
(45) Date of Patent: Apr. 29, 2014

(54) COMPOUNDS, COMPOSITIONS AND METHODS FOR REDUCING LIPID LEVELS

(75) Inventors: Haiyan Liu, Mountain View, CA (US); Gaoping Li, Mountain View, CA (US); Junbo Wang, Shanghai (CN); Jingwen Liu, Mountain View, CA (US)

(73) Assignee: CVI Pharmaceuticals Limited, George Town, Grand Cayman (KY)

( * ) Notice: Subject to any disclaimer, the term of this patent is extended or adjusted under 35 U.S.C. 154(b) by 264 days.

(21) Appl. No.: 13/141,310

(22) PCT Filed: Dec. 22, 2009

(86) PCT No.: PCT/US2009/069331
§ 371 (c)(1),
(2), (4) Date: Sep. 6, 2011

(87) PCT Pub. No.: WO2010/075469
PCT Pub. Date: Jul. 1, 2010

(65) Prior Publication Data
US 2012/0004223 A1    Jan. 5, 2012

Related U.S. Application Data

(60) Provisional application No. 61/140,551, filed on Dec. 23, 2008.

(51) Int. Cl.
*A61K 31/4745* (2006.01)
*C07D 471/06* (2006.01)

(52) U.S. Cl.
USPC ................ 514/284; 546/71; 546/48; 514/280

(58) Field of Classification Search
USPC ............................... 514/284, 280; 546/71, 48
See application file for complete search history.

(56) References Cited

U.S. PATENT DOCUMENTS

| | | | |
|---|---|---|---|
| 3,932,384 | A | 1/1976 | Sawa et al. |
| 4,645,772 | A | 2/1987 | Stambach et al. |
| 6,255,317 | B1 | 7/2001 | Kim et al. |
| 8,003,795 | B2 * | 8/2011 | Liu et al. .................. 546/48 |
| 2008/0124404 | A1 | 5/2008 | Liu et al. |

FOREIGN PATENT DOCUMENTS

| | | |
|---|---|---|
| CN | 1330650 | 1/2002 |
| JP | 08-059469 | 3/1996 |
| JP | 2000-191662 | 7/2000 |
| JP | 2008-513382 | 5/2008 |
| WO | WO 2008/040192 | 4/2008 |
| WO | WO-2009/002873 | 12/2008 |

OTHER PUBLICATIONS

First Office Action Issued in Chinese Application No. 200980151491.7 issued Nov. 30, 2012.

Blanchard, Wesley A.; "Synthesis of the necines related to the Senecio alkaloids";(Jan. 1, 1959); Database CA [Online] Chemical Abstracts Service of Columbus, Ohio, US; Retrieved from STN Database accession No. 1959:89579; and Blanchard, Wesley A.: "Synthesis of the necines related to the Senecio alkaloids" 66 PP; Avail.: Univ. Microfilms (Ann Arbor, Mich.) From: Dissertation Abstr. 19, 2461-2, 1959. (1 pg.).
Chinnasamy, Pennamuthiriar, et al.; "3,10-Dimethoxyprotoberberines"; Arch. Pharm. (1987); 320, pp. 790-798.
International Preliminary Report on Patentability (Chaper II of the Patent Cooperation Treaty); in re PCT International Application No. PCT/US2009/069331; filed: Dec. 22, 2009; Applicant: CVI Pharmaceuticals Limited; mailed: Sep. 14, 2010. (15 pgs.).
International Search Report and Written Opinion of the International Searching Authority; in re PCT International Application No. PCT/US2009/069331; filed: Dec. 22, 2009; Applicant: CVI Pharmaceuticals Limited; mailed: Mar. 16, 2010. (19 pgs.).
Memetzidis, G., et al.;Structure-affinity relationships of berbines or 5,6,13,13a-tetrahydro-8$H$-dibenzo(a,g) quinolizines at α-adrenoceptors; Eur. J. Med Chem. (1991); 26, pp. 605-611.
Memetzidis, Georges, et al.; "Synthesis of Aromatic Chloroberbines"; Heterocycles, (1990); vol. 31, No. 2, pp. 341-351.
Nagata, Wataru, et al.; "Synthetic Studies on Isoquinoline Alkaloids. II. *.1) Selective Conversion of 3,9,10-Substituted Tetrahydroprotoberberines into 3,9,10-Substituted 14-Deoxoprotopines. Total Synthesis of 3,9,10-Substituted 5,6,7,8,13,14-Hexhydrodibenz(c,g)azecines2)"; Pharmaceutical Society of Japan (1975); vol. 23, pp. 2878-2890.
Stambach, J.F., et al.; "Phosgenation of Benzyltetrahydroisoquinolines: A New Method of Berbines and Berbin-8 Ones Synthesis"; Teirahedron (1985); vol. 41, No. 1, pp. 169-172.
Stambach, Jean-Francois, et al.; "Selective Acetylation of Berbin-8-One Synthesis of 2-Methoxyberbine"; Heterocycles (1993); vol. 36, No. 4, pp. 819-824.

(Continued)

*Primary Examiner* — Charanjit Aulakh
(74) *Attorney, Agent, or Firm* — Foley & Lardner LLP

(57) ABSTRACT

The present technology relates to compounds of Formulas (V) and methods of making and using such compounds. Methods of use include prevention and treatment of hyperlipidemia, hypercholesterolemia, hypertriglyceridemia, hepatic steatosis, and metabolic syndrome. Compounds disclosed herein also lower total cholesterol, LDL-cholesterol, and triglycerides and increase hepatic LDL receptor expression, inhibit PCSK9 expression, and activate AMP-activated protein kinase.

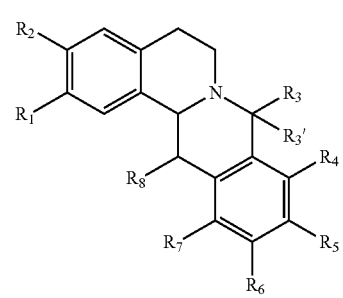

40 Claims, 14 Drawing Sheets

(56) References Cited

OTHER PUBLICATIONS

Takemoto, Tsnematsu, et al.; "Reactions of protoberberine-type alkaloids. I. Reaction of Dihdroberberine with alkyl halides" Database CA [Online] Chemical Abstracts Service, Columbus Ohio, US; retrieved from STN Database accession No. 1963: 403686; and Takemoto, Tsunematsu, et al.; "Reactions of protoberberine-type alkaloids. I. Reaction of Dihdroberberine with alkyl halides"; (1962) 82, 1408-13 ISSN: 0031-6903, (1pg.).

Second Office Action received for Chinese Appln. No. 200980151491.7 issued May 6, 2013. (English Translation Provided).

Third Office Action in CN application No. 200980151491.7 dtd Nov. 6, 2013 (English translation—4 pages).

Notice of Reasons for Rejection in Japanese Appln. No. 2011-542588 mailed Jan. 24, 2014 (includes English translation—5 pages).

* cited by examiner

COMPOUNDS, COMPOSITIONS AND METHODS FOR REDUCING LIPID LEVELS

RELATED APPLICATIONS

The present application is a U.S. national stage application of International Application No. PCT/US2009/069331, filed on Dec. 22, 2009, which claims the benefit of U.S. Provisional Patent Application No. 61/140,551, filed Dec. 23, 2008, the entire contents of each of which are hereby incorporated by reference for all purposes.

FIELD

The present technology is related to methods, compounds and compositions to treat hyperlipidemia, including hypertriglyceridemia and hypercholesterolemia, as well as hepatic steatosis and metabolic syndrome.

SUMMARY

In accordance with one aspect, the present technology provides methods of reducing plasma and/or hepatic lipid levels of a subject in need thereof, which comprises administering to the said subject a lipid-lowering effective amount of a compound, composition or extract described herein. The lipid level to be reduced can be one or more of total cholesterol, LDL-cholesterol, triglycerides, and unesterified long chain fatty acids. In another aspect, the present technology provides methods for treating a disease or condition selected from the group consisting of hyperlipidemia, hypercholesterolemia, hypertriglyceridemia, hepatic steatosis and metabolic syndrome, comprising administering to a subject in need thereof a therapeutically effective amount of a compound, composition or extract described herein.

In one aspect, the present technology provides lipid lowering agents, including hypocholesterolemic and/or hypotriglyceridemic compounds, and derivatives of such compounds, from a variety of plants including *Corydalis, Leontice, Mahonia, Fumaria, Legnephora, Stephania. Chelidonium, Hunnemannia, Coptis, Guatteria, Pachypodanthium; Chasmanthera, Fibraurea; Cheilanthes, Dicranostigma; Glaucium*; and *Chelidonium*. In some embodiments, the compounds are obtained from the plant species selected from the group consisting of *Corydalis (ambigua, bulbosa, cava, chaerophylla, pallida, solida, thalictrifolia, tuberosa, turtschaminowii Besser), Leontice (leontopetalum), Mahonia (aquifolium), Fumaria Legnephora (moorii), Stephania (glabra, tetranda), Chelidonium (majus), Hunnemannia (fumariaefolia), Coptis (groenlandica), Guatteria (discolor). Pachypodanthium (staudtii); Chasmanthera (dependens), Fibraurea (chloroleuea); Cheilanthes Dicranostigma. (lepiopodum); Glaucium (vitellinum); Corydalis* yan hu suo; and *Corydalis* Xiar Ri Wu.

In certain embodiments the lipid lowering agent is isoquinolinyl-containing alkaloid from, e.g., a *Corydalis* extract or a derivative of a *Corydalis* compound, such as a compound of Formulae I, II, III, or IV as shown herein. Exemplary lipid lowering agents include substantially pure corlumidin (CLMD), (+)-corlumidin, (+)-CLMD, corypalmine (CRPM), 14R-(+)-corypalmine (14R-(+)-CRPM), tetrahydropalmatine (THP), 14R-(+)-tetrahydropalmatine (14R-(+)-THP), corydaline (CRDL), 14R,13S-(+)-corydaline (14R,13S-(+)-CRDL), bicuculline (BCCL), d-(+)-bicuculline (d-(+)-BCCL), and Egenine (EGN), (+)-egenine ((+)-EGN).

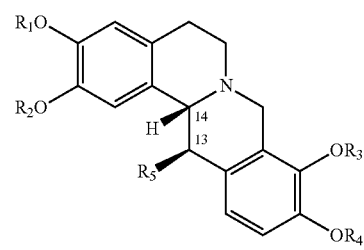

Formula I

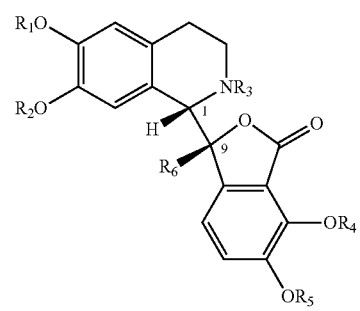

Formula II

For compounds of either Formula I or Formula II, $R_1$, $R_2$, $R_3$, $R_4$, $R_5$, and $R_6$ are selected (independently, collectively, or in any combination) from H, halogen, hydroxy, $C_1$-$C_6$ alkyl, alkoxy, nitro, amino, aminoalkyl, trifluoromethyl, trifluoromethoxy, cycloalkyl, alkanoyl, alkanoyloxy, nitrile, dialkylamino, alkenyl, hydroxyalkyl, alkylaminoalkyl, aminoalkyl, dialkylaminoalkyl, haloalkyl, carboxyalkyl, alkoxyalkyl, carboxy, alkanoylamino, carbonylamino, carbamoyl, alkylsulfonylamino, and heterocyclyl groups. Preferably, $R_1$, $R_2$, $R_3$, $R_4$, $R_5$, and $R_6$ are not halogen when halogen would be covalently bonded to oxygen. In one aspect, the compounds of the present technology can also comprise one or more halogens as substituents at any position of Formula I or Formula II. In some embodiments, compounds of Formula I have the 14R-(+) stereochemical configuration. In some embodiments, compounds of Formula I have the 14S-(−) stereochemical configuration.

In some embodiments, the lipid lowering agents that may be used in methods described herein include compounds of Formula III and Formula IV:

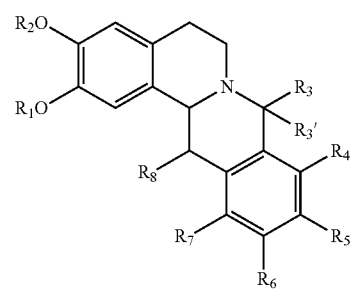

Formula III

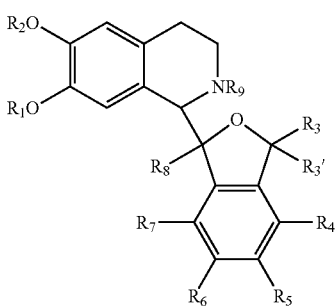

Formula IV or stereoisomers thereof, tautomers thereof, solvates thereof, and pharmaceutically acceptable salts thereof; wherein $R_1$ and $R_2$ are independently —H, —(CH$_2$)$_{0-6}$COOR', —C(O)R", or a substituted or unsubstituted alkyl, cycloalkyl, cycloalkylalkyl, alkenyl, aryl, aralkyl, heteroaryl, heteroarylalkyl, heterocyclyl, or heterocyclylalkyl group; or $R_1$ and $R_2$ together are a methylene group;

$R_3$ and $R_8$ are independently —H, —OH, —Cl, —Br, —F, —I, —CN, —NH$_2$, —C(O)NH$_2$, —COOH, or a substituted or unsubstituted alkyl, alkoxy, alkenyl, or aralkyl group;

$R_3'$ is H, or $R_3$ and $R_3'$ together are an oxo group;

$R_4$ is —H, halogen, —OR', —OSO$_2$R", —OC(O)R", —OC(O)OR", —OC(O)NR'R", —O-alkylene-NR'R', —O-alkylene-OSO$_2$R", —O-alkylene-S(O)$_{0-2}$R", —O-alkylene-NR'SO$_2$R", —O-alkylene-N(R')C(O)R', or a substituted or unsubstituted alkyl group;

$R_5$ and $R_6$ are independently —H, halogen, —OH, or a substituted or unsubstituted alkoxy group; or $R_4$ and $R_5$ together are a methylenedioxy group, or $R_5$ and $R_6$ together are a methylenedioxy group;

$R_7$ is H, halogen, OH, or a substituted or unsubstituted alkyl or alkoxy group;

$R_9$ is H or a substituted or unsubstituted alkyl group;

each R' is independently a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

each R" is independently a substituted or unsubstituted alkyl, alkenyl, cycloalkyl, cycloalkylalkyl, aryl, aralkyl, heteroaryl, heteroarylalkyl, heterocyclyl, or heterocyclylalkyl group.

In other embodiments, there are provided a second group of compounds of Formula III:

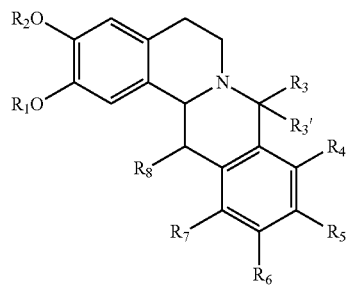

III stereoisomers thereof, tautomers thereof, solvates thereof, and pharmaceutically acceptable salts thereof; wherein $R_1$ and $R_2$ are independently —H, —(CH$_2$)$_{0-6}$COOR', —C(O)R", or a substituted or unsubstituted alkyl, cycloalkyl, cycloalkylalkyl, alkenyl, aryl, aralkyl, heteroaryl, heteroarylalkyl, heterocyclyl, or heterocyclylalkyl group; or $R_1$ and $R_2$ together are a methylene group;

$R_3$ and $R_8$ are independently —H, —OH, —Cl, —Br, —F, —I, —CN, —NH$_2$, —C(O)NH$_2$, —COOH, or a substituted or unsubstituted alkyl, alkenyl, alkoxy or aralkyl group;

$R_3'$ is —H, or $R_3$ and $R_3'$ together are an oxo group;

$R_4$ is —H, halogen, —OR', —OSO$_2$R", —OC(O)R", —OC(O)OR", —OC(O)NR'R", —O-alkylene-NR'R', —O-alkylene-OSO$_2$R", —O-alkylene-S(O)$_{0-2}$R", —O-alkylene-NR'SO$_2$R", —O-alkylene-N(R)C(O)R', or a substituted or unsubstituted alkyl group;

$R_5$ and $R_6$ are independently —H, halogen, —OH, or a substituted or unsubstituted alkoxy group; or $R_4$ and $R_5$ together are a methylenedioxy group, or $R_5$ and $R_6$ together are a methylenedioxy group;

$R_7$ is —H, halogen, —OH, or a substituted or unsubstituted alkyl or alkoxy group;

each R' is independently a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

each R" is independently a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

with the proviso that when $R_4$ is —H, —OH or a $C_{1-4}$ alkoxy group, then $R_5$ is not —H, —OH or a $C_{1-4}$ alkoxy group; and when $R_1$ and $R_2$ are both —CH; or when $R_1$ and $R_2$ together are a methylene group, then $R_5$ is not OH or a $C_{1-2}$ alkoxy group, and $R_4$ and $R_5$ together are not a methylenedioxy group; and when $R_4$ is OC(O)R", then $R_5$ is not OC(O)R" or methoxy.

In still other embodiments, there are provided compounds of Formula V and Formula VI:

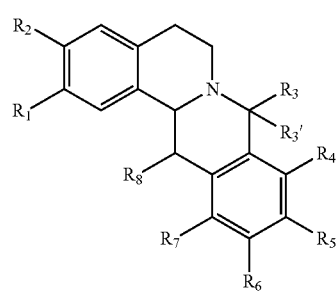

V

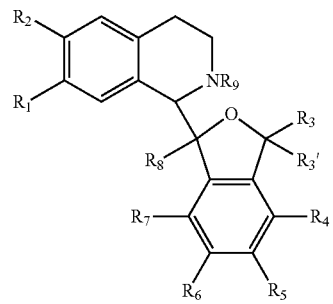

VI

In compounds of Formulas V and VI, $R_1$ and $R_2$ are independently —H, —(CH$_2$)$_{0-6}$COOR', —C(O)R", —OR', —NR$_{10}$R$_{11}$, —C(O)NR$_{10}$R$_{11}$, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group; or $R_1$ and $R_2$ together are a 1,2-dioxyethylene group; provided that $R_1$ and $R_2$ are not both —OR;

$R_3$ and $R_8$ are independently —H, —OH, —Cl, —Br, —F, —I, —CN, —NH$_2$, —C(O)NH$_2$, —COOH, or a substituted or unsubstituted alkyl, alkenyl, alkoxy or aralkyl group;

$R_3'$ is —H, or $R_3$ and $R_3'$ together are an oxo group;

$R_4$ is —H, halogen, —OR', —OSO$_2$R", —OC(O)R", —OC(O)OR", —OC(O)NR'R", —O-alkylene-NR'R', —O-alkylene-OSO$_2$R", —O-alkylene-S(O)$_{0-2}$R", —O-alkylene-NR'SO$_2$R", —O-alkylene-N(R')C(O)R', or a substituted or unsubstituted alkyl group;

$R_5$ and $R_6$ are independently —H, halogen, —OH, or a substituted or unsubstituted alkoxy group; or $R_4$ and $R_5$ together are a methylenedioxy group, or $R_5$ and $R_5'$ together are a methylenedioxy group;

$R_7$ is —H, halogen, —OH, or a substituted or unsubstituted alkyl or alkoxy group;

$R_{10}$ and $R_{11}$ are independently H, —C(O)OR", or a substituted or unsubstituted alkyl group;

each R' is independently a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

each R" is independently a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

with the proviso that when $R_1$ and $R_2$ are both H, then $R_4$ is halogen, —OSO$_2$R", —OC(O)R", —OC(O)OR", —OC(O)NR'R", —O-alkylene-NR'R', —O-alkylene-OSO$_2$R", —O-alkylene-S(O)$_{0-2}$R", —O-alkylene-NR'SO$_2$R", —O-alkylene-N(R')C(O)R, or a substituted or unsubstituted alkyl group.

In another aspect, a lipid lowering agent of the present technology is part of a pharmaceutical composition containing one or more excipients, carriers, or fillers. In one embodiment, the pharmaceutical composition is packaged in unit dosage form. The unit dosage form is effective in lowering lipid levels (e.g., at least one of total cholesterol, LDL-cholesterol, triglyceride, and unesterified long chain fatty acids) in the bloodstream and/or in the liver when administered to a subject in need thereof.

Still another aspect of the present technology is a pharmaceutical pack or kit containing a lipid lowering agent according to the present technology and a second agent. The second agent can be a cholesterol uptake inhibitor, a cholesterol synthesis inhibitor, a cholesterol absorption inhibitor, a bile acid sequestrant, a vitamin, an antihypertensive agent, or a platelet aggregation inhibitor. The second agent alternatively can be an HMG-CoA reductase inhibitor, an HMG-CoA synthase inhibitor, a squalene epoxidase inhibitor, an acyl-CoA cholesterol acyltransferase (ACAT) inhibitor, a microsomal triglyceride transfer protein (MTP) inhibitor, a peroxisome proliferator-activated receptor (PPAR) agonist, or an AMP-activated protein kinase (AMPK) activator. The second agent can also be an agent that increases low density lipoprotein receptor (LDLR) expression. The second agent can be a berberine compound, such as tetrahydroberberine.

Yet another aspect of the present technology is a method of synthesizing 14R-tetrahydropalmatine. The method includes treating berberine with boron trichloride in methylene chloride, methylating the product with methyl iodide and potassium carbonate in dry acetone, and hydrogenating the product using an asymmetric hydrogenation catalyst to yield 14R-tetrahydropalmatine.

DETAILED DESCRIPTION

Figure 1:
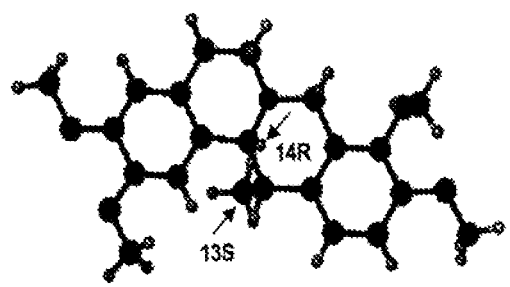
FIG. 1 shows the determination of the stereochemical configuration of CRDL by x-ray diffraction.

In various aspects, the present technology provides novel compounds, methods for reducing plasma and/or hepatic lipid levels, and methods for treating hyperlipidemia, hypercholesterolemia, hypertriglyceridemia, hepatic steatosis and metabolic syndrome. The compounds provided herein can be formulated into pharmaceutical compositions and medicaments that are useful in the disclosed methods. Also provided are the use of the compounds in preparing pharmaceutical formulations and medicaments, the use of the compounds in reducing plasma and/or hepatic lipid levels, and the use of the compounds in treating hyperlipidemia, hypercholesterolemia, hypertriglyceridemia, hepatic steatosis and metabolic syndrome.

The following terms are used throughout as defined below.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1]hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms.

In some embodiments, the alkenyl group has one, two, or three carbon-carbon double bonds. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, among others. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, butadienyl, pentadienyl, and hexadienyl.

Cycloalkenylalkyl groups are alkyl groups as defined above in which a hydrogen or carbon bond of the alkyl group is replaced with a bond to a cycloalkenyl group as defined above. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CCH$_3$, —CH$_2$C≡CCH$_3$, —C≡CCH$_2$CH(CH$_2$CH$_3$)$_2$, among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1.3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, triazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Although the phrase "heteroaryl groups" includes fused ring compounds, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —COOH group.

The term "ester" as used herein refers to —COOR$^{30}$ groups. R$^{30}$ is a substituted or unsubstituted alkyl, cycloalkyl, alkenyl, alkynyl, aryl, aralkyl, heterocyclylalkyl or heterocyclyl group as defined herein.

The term "amide" (or "amido") includes C- and N-amide groups, i.e., —C(O)NR$^{31}$R$^{32}$, and —NR$^{31}$C(O)R$^{32}$ groups, respectively. R$^{31}$ and R$^{32}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{31}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{33}$C(O)OR$^{34}$ and —OC(O)NR$^{33}$R$^{34}$ groups, respectively. R$^{33}$ and R$^{34}$ are independently a substituted or unsubstituted alkyl, alkenyl, alkynyl, cycloalkyl, aryl, aralkyl, heterocyclylalkyl, or heterocyclyl group as defined herein. R$^{33}$ may also be H.

The term "amine" (or "amino") as used herein refers to —NR$^{35}$R$^{36}$ groups, wherein R$^{35}$ and R$^{36}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{38}$R$^{39}$ and —NR$^{38}$SO$_2$R$^{39}$ groups, respectively. R$^{38}$ and R$^{39}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while sulfides include —SR$^{40}$ groups, sulfoxides include —S(O)R$^{41}$ groups, sulfones include —SO$_2$R$^{42}$ groups, and sulfonyls include —SO$_2$OR$^{43}$. R$^{40}$, R$^{41}$, R$^{42}$, and R$^{43}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR$^{44}$—C(O)—NR$^{45}$R$^{46}$ groups. R$^{44}$, R$^{45}$, and R$^{46}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{47}$)NR$^{48}$R$^{49}$ and —NR$^{47}$C(NR$^{48}$)R$^{49}$, wherein R$^{47}$, R$^{48}$, and R$^{49}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{50}$C(NR$^{51}$)NR$^{52}$R$^{53}$, wherein R$^{50}$, R$^{51}$, R$^{52}$ and R$^{53}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{54}$)=C(R$^{55}$)NR$^{56}$R$^{57}$ and —NR$^{54}$C(R$^{55}$)=C(R$^{56}$)R$^{57}$, wherein R$^{54}$, R$^{55}$, R$^{56}$ and R$^{57}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxy" as used herein can refer to —OH or its ionized form, —O$^-$.

The term "imide" refers to —C(O)NR$^{58}$C(O)R$^{59}$, wherein R$^{58}$ and R$^{59}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{60}$(NR$^{61}$) and —N(CR$^{60}$R$^{61}$) groups, wherein R$^{60}$ and R$^{61}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{60}$ and R$^{61}$ are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. Na$^+$, Li$^+$, K$^+$, Ca$^{2+}$, Mg$^{2+}$, Zn$^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, imidazoles may exhibit the following isomeric forms, which are referred to as tautomers of each other:

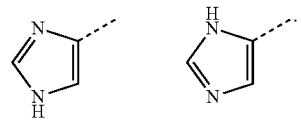

As readily understood by one skilled in the art, a wide variety of functional groups and other structures may exhibit tautomerism, and all tautomers of compounds as described herein are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Lipids include synthetic or naturally-occurring fat-soluble compounds, and include both neutral and amphipathic molecules. Amphipathic lipids typically comprise a hydrophilic component and a hydrophobic component. Exemplary lipids include fatty acids, triglycerides, neutral fats, phosphatides, glycolipids, aliphatic alcohols, waxes, terpenes, steroids such as cholesterol, and surfactants.

A "lipid lowering agent" as used herein refers to compounds that have one or more of the following effects when administered to a subject: increasing the hepatic expression of LDLR; increasing the half-life of LDLR mRNA in hepatocytes; increasing hepatic uptake of plasma LDL, cholesterol, or triglycerides; enhancing hepatic fatty acid oxidation, reducing hepatic triglyceride synthesis and secretion, and reducing the plasma and/or hepatic levels of total cholesterol, LDL-cholesterol, VLDL-cholesterol, or triglycerides. Lipid lowering agents as disclosed herein include compounds of Formulas I, II, III, IV, V and VI.

A "compound" or "derivative" as used herein refers to a chemical compound, either in partially purified or substantially pure form, which either has been obtained from a plant extract, such as a *Corydalis* extract, by one or more purification steps or which has been produced by chemical synthesis from any desired starting materials. A compound or derivative according to the present technology can be used either as a racemic mixture or as a pure stereoisomer. Preferred are pure stereoisomers which have activity as a lipid lowering agent.

A "partially purified" compound or derivative as used herein refers to a *Corydalis* compound or derivative thereof which is present in a chemical mixture that has been subjected to at least one separation or purification step resulting in the removal of at least one other chemical substance originally present in the initial extract or synthetic mixture containing the compound or derivative. A "substantially pure" compound or derivative is one which has been separated or purified to render the compound or derivative as the major chemical component of the substantially pure compound or derivative, i.e., comprising at least 50%, or in some embodiments at least 70%, at least 90%, or at least 95% or 99% on a molar basis.

In one aspect, the present technology provides methods of reducing plasma and/or hepatic lipid levels in a subject in need thereof, which comprises administering to said subject a lipid-lowering effective amount of a compound or composition as described herein. The lipid level to be reduced can be one or more of total cholesterol, LDL-cholesterol (LDL-c), triglycerides (TG), and unesterified long chain fatty acids.

The compounds and compositions described herein may be used in the treatment or prophylaxis of diseases that include, for example, hyperlipidemia, hypercholesterolemia, hypertriglyceridemia, fatty liver (hepatic steatosis), and metabolic syndrome. Methods of treatment include administering to a subject in need thereof a therapeutically effective amount of a compound or composition described herein. The compounds of the present technology can also be used in the treatment or prophylaxis of a disease state or malady characterized by or associated with elevated plasma or hepatic cholesterol or triglycerides. Generally, prophylactic or prophylaxis relates to a reduction in the likelihood of the patient developing a disorder such as hyperlipidemia, hypercholesterolemia, hypertriglyceridemia, fatty liver, or metabolic syndrome or proceeding to a diagnosis state for the disorder. For example, the compounds of the present technology can be used prophylacticly as a measure designed to preserve health and prevent the spread or maturation of disease in a patient. It is also appreciated that the various modes of treatment or prevention of a disease such as hyperlipidemia, hypercholesterolemia, hypertriglyceridemia, fatty liver, or metabolic syndrome can mean "substantial" treatment or prevention, which includes total but also less than total treatment or prevention, and in which some biologically or medically relevant result is achieved. Furthermore, treatment or treating as well as alleviating can refer to therapeutic treatment and prophylactic or preventative measures in which the object is to prevent, slow down (lessen) a disease state, condition or malady. For example, a subject can be successfully treated for hypercholesterolemia if after receiving through administration an effective or therapeutic amount of one or more compounds described herein, the subject shows observable and/or measurable reduction in or absence of one or more signs and symptoms of the particular disease such as, but not limited to reduced plasma total cholesterol, reduced plasma LDL-cholesterol, increased hepatic expression of LDL receptor (LDLR), reduced plasma triglycerides, reduced morbidity and mortality, or improvement in quality of life issues. The present technology also provides for methods of administering one or more compounds of the present technology to a patient in an effective amount for the treatment or prophylaxis of a disease such as, for example, hyperlipidemia, hypercholesterolemia, hypertriglyceridemia, fatty liver, or metabolic syndrome.

While not wishing to be bound by theory, it is believed that the compounds and compositions disclosed herein reduce lipid levels by increasing the hepatic expression of LDLR by increasing the stability of LDLR mRNA, by increasing LDLR gene transcription, by inhibiting the degradation of LDLR protein mediated through the proprotein convertase subtilisin/kexin type 9 (PCSK9), or all of the above potential cellular mechanisms. Increasing LDLR levels in the liver increases the uptake and processing of plasma LDL-c, resulting in reduced plasma levels of cholesterol, LDL-c, and triglycerides. In addition, the compounds may increase phosphorylation of acetyl CoA carboxylase (ACC) via the activation of AMP-activated protein likase (AMPK). Increased phosphorylation of ACC enhances fatty acid oxidation in the liver, leading to reduced hepatic TG accumulation and secretion of TG in the form of VLDL, which also contributes to the decreased plasma levels of TG. LDL-c, total cholesterol, and unesterified long chain fatty acids, resulting in the prevention or treatment of diseases related to hyperlipidemia.

Hence, in another aspect, the present technology provides methods of increasing LDLR expression, comprising administering to a subject in need thereof a therapeutically effective amount of a compound or composition as described herein, whereby LDLR expression in said subject is increased. In another aspect of the present technology, there are provided methods of decreasing plasma LDL-cholesterol and/or plasma triglycerides, comprising administering to a subject in need thereof a therapeutically effective amount of a compound or composition as described herein, whereby plasma LDL-cholesterol in said subject is decreased.

"Effective amount" refers to the amount of a compound or composition required to produce a desired effect. One example of an effective amount includes amounts or dosages that yield acceptable toxicity and bioavailability levels for therapeutic (pharmaceutical) use including, but not limited to, the treatment or prophylaxis of hyperlipidemia, hypercholesterolemia, hypertriglyceridemia, fatty liver, or metabolic syndrome. Another example of an effective amount includes amounts or dosages that are capable of preventing elevated plasma or hepatic cholesterol or triglycerides.

As used herein, a "subject" or "patient" is a mammal, such as a cat, dog, rodent or primate. Typically the subject is a human, and, preferably, a human suspected of having a disease associated with elevated plasma or hepatic cholesterol or triglycerides such as hyperlipidemia, hypercholesterolemia, hypertriglyceridemia, fatty liver, or metabolic syndrome. Subjects may further include mammals with elevated LDL levels, elevated VLDL levels, or diseases aggravated or triggered by hyperlipidemia such as cardiovascular diseases, including, atherosclerosis, coronary artery disease, angina pectoris, carotid artery disease, strokes, cerebral arteriosclerosis, myocardial infarction, cerebral infarction, restenosis following balloon angioplasty, intermittent claudication, high blood pressure, dyslipidemia post-prandial lipidemia and xanthoma. The term "subject" and "patient" can be used interchangeably.

In another aspect, the present technology provides lipid lowering agents, including compounds and compositions thereof. The compounds and compositions may be used in the lipid lowering methods and treatments described herein. In one embodiment, the present technology provides a compound of Formula I, a compound of Formula II, stereoisomers thereof, tautomers thereof, solvates thereof, and/or pharmaceutically acceptable salt thereof,

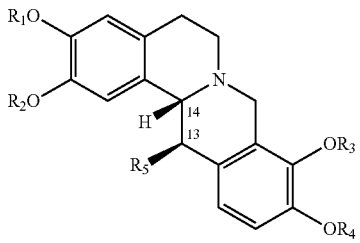

Formula I

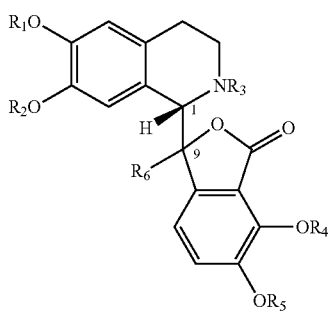

Formula II

For compounds of either Formula I or Formula II, $R_1$, $R_2$, $R_3$, $R_4$, $R_5$, and $R_6$ are selected (independently, collectively, or in any combination) from H, halogen, hydroxy, $C_1$-$C_6$ alkyl, alkoxy, nitro, amino, aminoalkyl, trifluoromethyl, trifluoromethoxy, cycloalkyl, alkanoyl, alkanoyloxy, nitrile, dialkylamino, alkenyl, hydroxyalkyl, alkylaminoalkyl, aminoalkyl, dialkylaminoalkyl, haloalkyl, carboxyalkyl, alkoxyalkyl, carboxy, alkanoylamino, carbonylamino, carbamoyl, alkylsulfonylamino, and heterocyclo groups. Preferably, $R_1$, $R_2$, $R_3$, $R_4$, $R_5$, and $R_6$ are not halogen when halogen would be covalently bonded to oxygen. In one aspect, the compounds of the present technology can also comprise one or more halogens as substituents at any position of Formula I or Formula II. In some embodiments, compounds of Formula I have the 14R-(+) stereochemical configuration and compounds of Formula II have the 1R-(+) stereochemical configuration.

In another embodiment, there are provided a first group of compounds of Formula III and compounds of Formula IV, as well as stereoisomers thereof, tautomers thereof, solvates thereof, and pharmaceutically acceptable salt thereof.

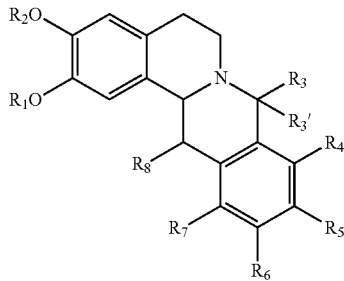

Formula III

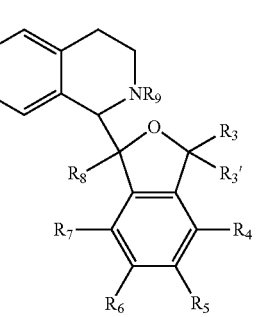

Formula IV

In compounds of Formulas III and IV, $R_1$ and $R_2$ are independently —H, —($CH_2$)$_{0-6}$COOR', —C(O)R", or a substituted or unsubstituted alkyl, cycloalkyl, cycloalkylalkyl, alkenyl, aryl, aralkyl, heteroaryl, heteroarylalkyl, heterocyclyl, or heterocyclylalkyl group; or $R_1$ and $R_2$ together are a methylene group;

$R_3$ and $R_8$ are independently —H, —OH, —Cl, —Br, —F, —I, —CN, —$NH_2$, —C(O)$NH_2$, —COOH, or a substituted or unsubstituted alkyl, alkoxy, alkenyl, or aralkyl group;

$R_3'$ is —H, or $R_3$ and $R_3'$ together are an oxo group;

$R_4$ is —H, halogen, —OR', —OSO$_2$R", —OC(O)R", —OC(O)OR", —OC(O)NR'R", —O-alkylene-NR'R', —O-alkylene-OSO$_2$R", —O-alkylene-S(O)$_{0-2}$R", —O-alkylene-NR'SO$_2$R", —O-alkylene-N(R')C(O)R', or a substituted or unsubstituted alkyl group;

$R_5$ and $R_6$ are independently —H, halogen, —OH, or a substituted or unsubstituted alkoxy group; or $R_4$ and $R_5$ together are a methylenedioxy group, or $R_5$ and $R_6$ together are a methylenedioxy group;

$R_7$ is —H, halogen, —OH, or a substituted or unsubstituted alkyl or alkoxy group;

$R_9$ is —H or a substituted or unsubstituted alkyl group;

each R' is independently a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

each R" is independently a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

In some embodiments of the first group of compounds of Formula III and compounds of Formula IV, $R_1$ and $R_2$ are independently —H, —$(CH_2)_{0-6}$COOR', —C(O)R", or a substituted or unsubstituted alkyl, cycloalkyl, cycloalkylalkyl, alkenyl, aryl, aralkyl, heteroaryl, heteroarylalkyl, heterocyclyl, or heterocyclylalkyl group; or $R_1$ and $R_2$ together are a methylene group;

$R_3$ and $R_8$ are independently —H, —OH, —Cl, —Br, —F, —I, —CN, —$NH_2$, —C(O)$NH_2$, —COON, or a substituted or unsubstituted alkyl, alkenyl, alkoxy, or aralkyl group;

$R_3$' is —H, or $R_3$ and $R_3$' together are an oxo group;

$R_4$ is —H, —OR', $OSO_2R"$, —OC(O)R", —OC(O)OR", —OC(O)NR'R", —O-alkylene-NR'R', —O-alkylene-$OSO_2R"$, —O-alkylene-$S(O)_{0-2}R"$, —O-alkylene-NR'$SO_2R"$, —O-alkylene-N(R')C(O)R', or a substituted or unsubstituted alkyl group;

$R_5$ and $R_6$ are independently —H, halogen, —OH, or a substituted or unsubstituted alkoxy group; or $R_4$ and $R_5$ together are a methylenedioxy group, or $R_5$ and $R_6$ together are a methylenedioxy group;

$R^7$ is —H, —Br, —Cl, or —F;

each R' is independently a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

each R" is independently a substituted or unsubstituted alkyl, alkenyl, cycloalkyl, cycloalkylalkyl, aryl, aralkyl, heteroaryl, heteroarylalkyl, heterocyclyl, or heterocyclylalkyl group.

In other embodiments of the first group of compounds of Formula III and compounds of Formula IV, $R_1$ and $R_2$ are independently —H, —$(CH_2)_{0-2}$COOR', —C(O)$(CH_2)_{0-2}$R", or a unsubstituted $C_{1-6}$ alkyl group; or $R_1$ and $R_2$ together are a methylene group;

$R_3$ and $R_3$' are each —H, or $R_3$ and $R_3$' together are an oxo group;

$R_4$ is —H, —OH, or a substituted or unsubstituted $C_{1-6}$ alkoxy, $C_{7-14}$ aralkoxy, —OC(O)—($C_{1-6}$ alkyl), —OC(O)-(aryl), —OC(O)-(aryl), —OC(O)—NH-(aryl), alkylene)-NH—($C_{2-6}$ alkyl), —O—($C_{2-6}$ alkylene)-NH-(tetrahydropyran), —O—($C_{2-6}$ alkylene)-NH-(thiomorpholine dioxide), —O—($C_{2-6}$ alkylene)-NH-(piperidinyl), —O—($C_{2-6}$ alkylene)-NH-(piperazinyl), alkylene)-NH-(morpholinyl), —O—($C_{2-6}$ alkylene)-NH-(aralkyl), —O—($C_{2-6}$ alkylene)-NH-(cyclopropyl), —$OSO_2$—($C_{3-6}$ cycloalkyl), —$OSO_2$-(aryl), alkylene)-$OSO_2$-(aryl), —$OSO_2$-(aralkyl), —O—($C_{2-6}$ alkylene)-$OSO_2$-(heteroaryl), —$OSO_2$—($C_{1-6}$ alkyl), —$OSO_2$-(pyridyl), —$OSO_2$-(thiazolyl), —O—($C_{2-6}$ alkylene)-$NHSO_2$-(aryl), —O—($C_{2-6}$ alkylene)-$NHSO_2$-(heteroaryl), —O—($C_2$ alkylene)-NHC(O)-(aryl), —O—($C_{2-6}$ alkylene)-NHC(O)-(heteroaryl), —O—($C_{0-4}$ alkyl)pyridyl, —O—($C_{0-4}$ alkyl)pyrimidinyl, —O—($C_{0-4}$ alkyl)morpholinyl, —O—($C_{0-4}$ alkyl)thiomorpholinyl, —O—($C_{0-4}$ alkyl) imidazolyl, —O—($C_{0-4}$ alkyl)thienyl. —O—($C_{0-4}$ alkyl)tetrahydropyranyl, —O—($C_{0-4}$ alkyl)tetrahydrofuranyl, —O—($C_{0-4}$ alkyl)pyrrolidinyl, —O—($C_{0-4}$ alkyl)piperidinyl, or —O—($C_{0-4}$ alkyl)piperazinyl group;

$R_5$ and $R_6$ are independently —H, —OH, or an unsubstituted $C_{1-6}$ alkoxy group; or $R_4$ and $R_5$ together are a methylenedioxy group, or $R_5$ and $R_6$ together are a methylenedioxy group; and $R_8$ is —H, —OH, —COON, or an unsubstituted alkyl or —$(CH_2)_{1-6}$-phenyl group.

In another embodiment, the present technology provides a second group of compounds of Formula III,

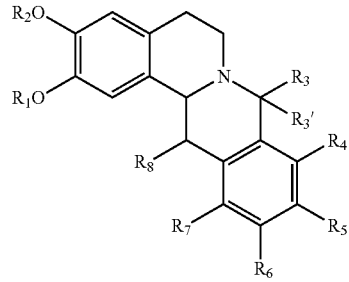

stereoisomers thereof, tautomers thereof, solvates thereof, and pharmaceutically acceptable salts thereof; wherein $R_1$ and $R_2$ are independently —H, —$(CH_2)_{0-6}$COOR', —C(O)R", or a substituted or unsubstituted alkyl, cycloalkyl, cycloalkylalkyl, alkenyl, aryl, aralkyl, heteroaryl, heteroarylalkyl, heterocyclyl, or heterocyclylalkyl group; or $R_1$ and $R_2$ together are a methylene group;

$R_3$ and $R_8$ are independently —H, —OH, —Cl, —Br, —F, —Cl, —CN, —$NH_2$, —C(O)$NH_2$, —COOH, or a substituted or unsubstituted alkyl, alkenyl, alkoxy or aralkyl group;

$R_3$' is —H, or $R_3$ and $R_3$' together are an oxo group;

$R_4$ is —H, halogen, —OR', —$OSO_2R"$, —OC(O)R", —OC(O)OR", —OC(O)NR'R", —O-alkylene-NR'R', —O-alkylene-$OSO_2R"$, —O-alkylene-$S(O)_{0-2}R"$, —O-alkylene-NR'$SO_2R"$, —O-alkylene-N(R')C(O)R', or a substituted or unsubstituted alkyl group;

$R_5$ and $R_6$ are independently —H, halogen, —OH, or a substituted or unsubstituted alkoxy group; or $R_4$ and $R_5$ together are a methylenedioxy group, or $R_5$ and $R_6$ together are a methylenedioxy group;

$R_7$ is —H, halogen, —OH, or a substituted or unsubstituted alkyl or alkoxy group;

each R' is independently a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

each R" is independently a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

with the proviso that when $R_4$ is —H, —OH or a $C_{1-4}$ alkoxy group, then $R_5$ is not —H, —OH or a $C_{1-4}$ alkoxy group; and when $R_1$ and $R_2$ are both —$CH_3$ or when $R_1$ and $R_2$ together are a methylene group, then $R_5$ is not OH or a $C_{1-2}$ alkoxy group, and $R_4$ and $R_5$ together are not a methylenedioxy group; and when $R_4$ is OC(O)R", then $R_5$ is not OC(O)R" or methoxy.

In some embodiments of the first and second groups of compounds of Formula III (collectively, "compounds of Formula III) and the compounds of Formula IV, $R_1$ and $R_2$ are independently —H, —$(CH_2)_{0-2}$COOR', —C(O)$(CH_2)_{0-2}$R", or a unsubstituted $C_{1-6}$ alkyl group; or $R_1$ and $R_2$ together are a methylene group. In other embodiments, $R_1$ and $R_2$ together are a methylene group.

In some embodiments of the compounds of Formula III and the compounds of Formula IV, $R_3$ and $R_3$' are each —H, or $R_3$ and $R_3$' together are an oxo group.

In some embodiments of compounds of Formula III and the compounds of Formula IV, $R_4$ is —H, —OR', —$OSO_2R"$, —OC(O)OR", —OC(O)NR'R", —O-alkylene-$OSO_2R"$, or —O-alkylene-NR'R'. In other embodiments, $R_4$ is —H, —OH, or a substituted or unsubstituted $C_{1-6}$ alkoxy, $C_{7-14}$ aralkoxy, —OC(O)—($C_{1-6}$ alkyl), —OC(O)-(aryl), —OC(O)

O-(aryl), —OC(O)—NH-(aryl), —O—($C_{2-6}$ alkylene)-NH—($C_{2-6}$ alkyl), —O—($C_{2-6}$ alkylene)-NH-(tetrahydropyran), —O—($C_{2-6}$ alkylene)-NH-(thiomorpholine dioxide), —O—($C_{2-6}$ alkylene)-NH-(piperidinyl), —O—($C_{2-6}$ alkylene)-NH-(piperazinyl), —O—($C_{2-6}$ alkylene)-NH-(morpholinyl), —O—($C_{2-6}$ alkylene)-NH-(aralkyl), alkylene)-NH-(cyclopropyl), —OSO$_2$—($C_{3-6}$ cycloalkyl), —OSO$_2$-(aryl), alkylene)-OSO$_2$-(aryl), —OSO$_2$-(aralkyl), —O—($C_{2-6}$ alkylene)-OSO$_2$-(heteroaryl), —OSO$_2$—($C_{1-6}$ alkyl), —OSO$_2$-(pyridyl), —OSO$_2$-(thiazolyl), —O—($C_{2-6}$ alkylene)-NHSO$_2$-(aryl), —O—($C_{2-6}$ alkylene)-NHSO$_2$-(heteroaryl), —O—($C_{2-6}$ alkylene)-NHC(O)-(aryl), —O—($C_{2-6}$ alkylene)-NHC(O)-(heteroaryl), —O—($C_{0-4}$ alkyl)pyridyl, —O—($C_{0-4}$ alkyl)pyrimidinyl, —O—($C_{0-4}$ alkyl)morpholinyl, alkyl)thiomorpholinyl, —O—($C_{0-4}$ alkyl)imidazolyl, —O—($C_{0-4}$ alkyl)thienyl, —O—($C_{0-4}$ alkyl)tetrahydropyranyl, —O—($C_{0-4}$ alkyl)tetrahydrofuranyl, alkyl)pyrrolidinyl, —O—($C_{0-4}$ alkyl)piperidinyl, or —O—($C_{0-4}$ alkyl)piperazinyl group.

In other embodiments of compounds of Formula III and compounds of Formula IV, $R_5$ is OH or unsubstituted alkoxy and $R_6$ is H.

In some embodiments of compounds of Formula III and compounds of Formula IV, $R_8$ is —H, —OH, —COOH, or an unsubstituted alkyl or —(CH$_2$)$_{1-6}$-phenyl group.

In certain embodiments of compounds of Formula III and compounds of Formula IV, $R_1$ and $R_2$ are independently —H, —(CH$_2$)$_{0-2}$COOR', —C(O)(CH$_2$)$_{0-2}$R", or a unsubstituted $C_{1-6}$ alkyl group; or $R_1$ and $R_2$ together are a methylene group;

$R_3$ and $R_3'$ are each —H, or $R_3$ and $R_3'$ together are an oxo group;

$R_4$ is —H, —OH, or a substituted or unsubstituted $C_{1-6}$ alkoxy, $C_{7-14}$ aralkoxy, —OC(O)—($C_{1-6}$ alkyl), —OC(O)-(aryl), —OC(O)O-(aryl), —OC(O)—NH-(aryl), —O—($C_{2-6}$ alkylene)-NH—($C_{2-6}$ alkyl), —O—($C_{2-6}$ alkylene)-NH-(tetrahydropyran), —O—($C_{2-6}$ alkylene)-NH-(thiomorpholine dioxide), —O—($C_{2-6}$ alkylene)-NH-(piperidinyl), —O—($C_{2-6}$ alkylene)-NH-(piperazinyl), —O—($C_{2-6}$ alkylene)-NH-(morpholinyl), —O—($C_{2-6}$ alkylene)-NH-(aralkyl), —O—($C_{2-6}$ alkylene)-NH-(cyclopropyl), —OSO$_2$—($C_{3-6}$ cycloalkyl), —OSO$_2$-(aryl), —O—($C_{2-6}$ alkylene)-OSO$_2$-(aryl), —OSO$_2$-(aralkyl), —O—($C_{2-6}$ alkylene)-OSO$_2$-(heteroaryl), —OSO$_2$—($C_{1-6}$ alkyl), —OSO$_2$-(pyridyl), —OSO$_2$-(thiazolyl), —O—($C_{2-6}$ alkylene)-NHSO$_2$-(aryl), —O—($C_{2-6}$ alkylene)-NHSO$_2$-(heteroaryl), —O—($C_{2-6}$ alkylene)-NHC(O)-(aryl), —O—($C_{2-6}$ alkylene)-NHC(O)-(heteroaryl), —O—($C_{0-4}$ alkyl)pyridyl, —O—($C_{0-4}$ alkyl)pyrimidinyl, —O—($C_{0-4}$ alkyl)morpholinyl, —O—($C_{0-4}$ alkyl)thiomorpholinyl, —O—($C_{0-4}$ alkyl) imidazolyl, —O—($C_{0-4}$ alkyl)thienyl, —O—($C_{0-4}$ alkyl)tetrahydropyranyl, —O—($C_{0-4}$ alkyl)tetrahydrofuranyl, —O—($C_{0-4}$ alkyl)pyrrolidinyl, —O—($C_{0-4}$ alkyl)piperidinyl, or —O—($C_{0-4}$ alkyl)piperazinyl group;

$R_5$ and $R_6$ are independently —H, —OH, or an unsubstituted $C_{1-6}$ alkoxy group; or $R_4$ and $R_5$ together are a methylenedioxy group, or $R_5$ and $R_6$ together are a methylenedioxy group; and $R_8$ is —H, —OH, —COOH, or an unsubstituted alkyl or —(CH$_2$)$_{1-6}$-phenyl group.

In other embodiments of the compounds of Formula III and compounds of Formula IV, $R_1$ and $R_2$ are independently —H, —CH$_3$, —CH$_2$COOH, —CH$_2$C(O)OCH$_2$CH$_3$, allyl, or $R_1$ and $R_2$ together are a methylene group;

$R_3$ and $R_3'$ are each —H, or $R_3$ and $R_3'$ together are an oxo group;

$R_4$ is —H, —OH, OCH$_3$, —OCH$_2$CH$_3$, —O(CH$_2$)$_2$OH, —OCH$_2$COOH, —OCH$_2$COOCH$_2$CH$_3$, —O(CH$_2$)$_2$COOH, —O(CH$_2$)$_2$CH$_2$Br, —O-acetyl, —O-benzoyl, —O—(CH$_2$)$_2$—NH—(CH$_2$)$_2$—N(CH$_3$)$_2$, —O—(CH$_2$)$_2$—NH—(CH$_2$)$_2$—OCH$_3$, —O—(CH$_2$)$_2$—NH—(CH$_2$)$_2$—SCH$_3$, —O—(CH$_2$)$_2$—NH-morpholinyl, —O—(CH$_2$)$_2$—NH—(CH$_2$)$_3$—N(CH$_3$)$_2$, —O—(CH$_2$)$_2$—NH-benzyl, —O—(CH$_2$)$_2$—NH—(CH$_2$)$_3$-(thiomorpholine dioxide), —O—(CH$_2$)$_2$—NH—(CH$_2$)$_3$-morpholinyl, —O—(CH$_2$)$_2$—NH—(CH$_2$)$_3$-tetrahydropyranyl, —O-pyridyl optionally substituted with one or two substituents selected from the group consisting of $C_{1-4}$ alkyl, —NO$_2$, and NH$_2$, —O—(CH$_2$)$_2$—S-phenyl, —OSO$_2$-naphthyl optionally substituted with di($C_{1-4}$ alkyl), —OSO$_2$—CF$_3$, —OSO$_2$-thiaolyl optionally substituted with acetamido, —O—(CH$_2$)$_{0-2}$SO$_2$-phenyl wherein the phenyl group is optionally substituted with one or two substituents selected from the group consisting of methyl, methoxy, fluoro, chloro, trifluoromethyl, and nitro, —OSO$_2$-cyclopentyl, —OSO$_2$-thienyl, —OSO$_2$-benzyl, —(CH$_2$)$_2$-cyclopropyl, —(CH$_2$)$_2$-morpholinyl, —(CH$_2$)$_2$-imidazolyl, —(CH$_2$)$_2$-pyrrolidinyl, or —(CH$_2$)$_2$-piperazinyl group, wherein the piperazinyl group is optionally substituted with methyl, isopropyl, or methoxyethyl;

$R_5$ and $R_6$ are independently —H, —OH, or —OCH$_3$; and $R_8$ is —H, methyl, ethyl, —COON, or benzyl.

While compounds of Formula III with either stereochemical configuration at position 14 exhibit lipid-lowering activity, the R-(+) stereochemical configuration may be preferred. In other embodiments, the S-(−) stereochemical configuration may be preferred. Thus, compounds of Formula III can be racemic at position 14 or can be a mixture of enantiomers having from 1% to 99% enantiomeric excess (e.e.) with respect to the to either stereochemical configuration. For example, the compound of Formula III may have at least 1%, at least 5%, at least 10%, at least 20%, at least 30%, at least 40%, at least 50%, at least 60%, at least 70%, at least 80%, at least 90%, at least 95%, at least 96%, at least 97%, at least 98%, or at least 99% e.e. Production and/or separation of either optical isomer of compounds of Formula III is within the skill in the art in view of the guidance provided herein.

Likewise, certain compounds of Formula IV having the R-(+) or the S-(−) stereochemical configuration at position 1 may exhibit improved lipid-lowering activity compared to the opposite configuration at this position. In certain embodiments, the compound of Formula IV is an equimolar mixture of stereoisomers at position 1. As the compound of Formula IV also has a stereocenter at position 9, two diastereomers having the R-(+) stereochemical configuration at position 1 are possible, as well as two diastereomers having the S-(−) stereochemical configuration are possible. In some embodiments, the compound of Formula IV has the (1R,9S) configuration and in others, the (1S,9S). In other embodiments, the compound of Formula IV can be a mixture of diastereomers having from 1% to 99% diastereomeric excess (d.e.) with respect to either stereochemical configuration at position 1. For example, the compound of Formula IV may have at least 1%, at least 5%, at least 10%, at least 20%, at least 30%, at least 40%, at least 50%, at least 60%, at least 70%, at least 80%, at least 90%, at least 95%, at least 96%, at least 97%, at least 98%, or at least 99% d.e. with respect to position 1.

In another aspect, the present technology provides compounds of Formula V and compounds of Formula VI, as well as stereoisomers thereof, tautomers thereof, solvates thereof, and pharmaceutically acceptable salt thereof.

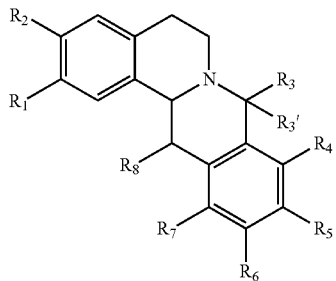

V

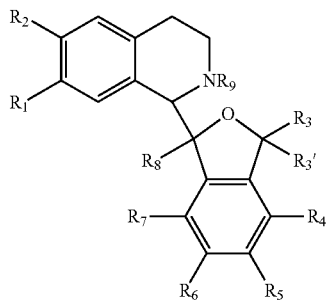

VI

In compounds of Formulas V and VI, $R_1$ and $R_2$ are independently —H, —$(CH_2)_{0-6}$COOR', —C(O)R", —OR', —$NR_{10}R_{11}$, —C(O)$NR_{10}R_{11}$, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group; or $R_1$ and $R_2$ together are a 1,2-dioxyethylene group; provided that $R_1$ and $R_2$ are not both —OR':

$R_3$ and $R_8$ are independently —H, —OH, —Cl, —Br, —F, —I, —CN, —$NH_2$, —C(O)$NH_2$, —COOH, or a substituted or unsubstituted alkyl, alkenyl, alkoxy or aralkyl group;

$R_3'$ is —H, or $R_3$ and $R_3'$ together are an oxo group;

$R_4$ is —H, halogen, —OR', —$OSO_2R"$, —OC(O)R", —OC(O)OR", —OC(O)NR'R", —O-alkylene-NR'R', —O-alkylene-$OSO_2R"$, —O-alkylene-$S(O)_{0-2}R"$, —O-alkylene-NR'$SO_2R"$, —O-alkylene-N(R')C(O)R', or a substituted or unsubstituted alkyl group;

$R_5$ and $R_6$ are independently —H, halogen, —OH, or a substituted or unsubstituted alkoxy group; or $R_4$ and $R_5$ together are a methylenedioxy group, or $R_5$ and $R_6$ together are a methylenedioxy group;

$R_7$ is —H, halogen, —OH, or a substituted or unsubstituted alkyl or alkoxy group;

$R_{10}$ and $R_{11}$ are independently H, —C(O)OR", or a substituted or unsubstituted alkyl group;

each R' is independently a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

each R" is independently a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

with the proviso that when $R_1$ and $R_2$ are both H, then $R_4$ is halogen, —$OSO_2R"$, —OC(O)R", —OC(O)OR", —OC(O)NR'R", —O-alkylene-NR'R', —O-alkylene-$OSO_2R"$, —O-alkylene-$S(O)_{0-2}R"$, —O-alkylene-NR'$SO_2R"$, —O-alkylene-N(R')C(O)R', or a substituted or unsubstituted alkyl group.

In some embodiments of the compounds of Formulas V and VI, $R_1$ and $R_2$ are independently —H, —$(CH_2)_{0-6}$COOR', —C(O)$NR_{10}R_{11}$, or a substituted or unsubstituted alkyl group; or $R_1$ and $R_2$ together are a 1,2-dioxyethylene group. In other embodiments, one of $R_1$ and $R_2$ is —OR' and the other is —H, —$(CH_2)_{0-6}$COOR', —C(O)$NR_{10}R_{11}$, or a substituted or unsubstituted alkyl group; or $R_1$ and $R_2$ together are a 1,2-dioxyethylene group. In some embodiments, $R_1$ and $R_2$ together are a 1,2-dioxyethylene group. In some embodiments, one of $R_1$ and $R_2$ is —OR' and the other is —H. In other embodiments, $R_2$ is —OR' and $R_1$ is —H. In some embodiments, R' is substituted or unsubstituted alkyl such as substituted or unsubstituted $C_{1-6}$ alkyl or $C_{1-4}$ alkyl. In some embodiments, $R_2$ is methoxy, ethoxy, or propoxy (e.g., n-propoxy or isopropoxy).

In some embodiments of the compounds of Formulas V and VI, $R_{10}$ and $R_{11}$ are independently H, $C_{1-6}$ alkyl optionally substituted with a hydroxy group.

In some embodiments of the compounds of Formulas V and VI, $R_3$ and $R_3'$ are each —H, or $R_3$ and $R_3'$ together are an oxo group.

In some embodiments of the compounds of Formulas V and VI, $R_4$ is —H, —OR', —$OSO_2R"$, —OC(O)R", —OC(O)OR", —OC(O)NR'R", —O-alkylene-$OSO_2R"$, or —O-alkylene-NR'R'. In other embodiments, $R_4$ is —H, —OR', —$OSO_2R"$, or —OC(O)R". In some embodiments, $R_4$ is —H, —OH, or a substituted or unsubstituted $C_{1-6}$ alkoxy, $C_{7-14}$ aralkoxy, —OC(O)—($C_{1-6}$ alkyl), —OC(O)-(aryl), —OC(O)O-(aryl), —OC(O)—NH-(aryl), —O—($C_{2-6}$ alkylene)-NH—($C_{2-6}$ alkyl), —O—($C_{2-6}$ alkylene)-NH-(tetrahydropyran), —O—($C_{2-6}$ alkylene)-NH-(thiomorpholine dioxide), —O—($C_{2-6}$ alkylene)-NH-(piperidinyl), —O—($C_{2-6}$ alkylene)-NH-(piperazinyl), —O—($C_{2-6}$ alkylene)-NH-(morpholinyl), —O—($C_{2-6}$ alkylene)-NH-(aralkyl), —O—($C_{2-6}$ alkylene)-NH-(cyclopropyl), —$OSO_2$—($C_{3-6}$ cycloalkyl), —$OSO_2$-(aryl), O—($C_{2-6}$ alkylene)-$OSO_2$-(aryl), —$OSO_2$-(aralkyl), —O—($C_{2-6}$ alkylene)-$OSO_2$-(heteroaryl), —$OSO_2$—($C_{1-6}$ alkyl), —$OSO_2$-(pyridyl), —$OSO_2$-(thiazolyl), —O—($C_{2-6}$ alkylene)-$NHSO_2$-(aryl), —O—($C_{2-6}$ alkylene)-$NHSO_2$-(heteroaryl), —O—($C_{2-6}$ alkylene)-NHC(O)-(aryl), —O—($C_{2-6}$ alkylene)-NHC(O)-(heteroaryl), —O—($C_{0-4}$ alkyl)pyridyl, —O—($C_{0-4}$ alkyl)pyrimidinyl, —O—($C_{0-4}$ alkyl)morpholinyl, —O—($C_{0-4}$ alkyl)thiomorpholinyl, —O—($C_{0-4}$ alkyl)imidazolyl, —O—($C_{0-4}$ alkyl)thienyl, —O—($C_{0-4}$ alkyl)tetrahydropyranyl, —O—($C_{0-4}$ alkyl)tetrahydrofuranyl, —O—($C_{0-4}$ alkyl)pyrrolidinyl, —O—($C_{0-4}$ alkyl)piperidinyl, or —O—($C_{0-4}$ alkyl)piperazinyl group. In some embodiments, $R_4$ is —H, —OH, or a substituted or unsubstituted $C_{1-6}$ alkoxy, —OC(O)—($C_{1-6}$ alkyl)-biotin, —$OSO_2$-(aryl), —O—($C_{2-6}$ alkylene)-$OSO_2$-(aryl), or —$OSO_2$-(aralkyl).

In some embodiments of the compounds of Formulas V and VI, the 14-position in Formula V or the 1-position in Formula VI is the R-(+) stereochemical configuration. In other embodiments, the 14-position in Formula V or the 1-position in Formula VI is the S-(–) stereochemical configuration. Thus, compounds of Formula V can be racemic at position 14 or can be a mixture of enantiomers having from 1% to 99% enantiomeric excess (e.e.) with respect to the to either stereochemical configuration. For example, the compound of Formula V may have at least 1%, at least 5%, at least 10%, at least 20%, at least 30%, at least 40%, at least 50%, at least 60%, at least 70%, at least 80%, at least 90%, at least 95%, at least 96%, at least 97%, at least 98%, or at least 99% e.e. Production and/or separation of either optical isomer of compounds of Formula V is within the skill in the art in view of the guidance provided herein.

Likewise, certain compounds of Formula VI having the R-(+) or the S-(–) stereochemical configuration at position 1 may exhibit improved lipid-lowering activity compared to the opposite configuration at this position. In certain embodiments, the compound of Formula VI is an equimolar mixture of stereoisomers at position 1. As the compound of Formula VI also has a stereocenter at position 9, two diastereomers having the R-(+) stereochemical configuration at position 1 are possible, as well as two diastereomers having the S-(−) stereochemical configuration are possible. In some embodiments, the compound of Formula VI has the (1R,9S) configuration and in others, the (1S,9S). In other embodiments, the compound of Formula VI can be a mixture of diastereomers having from 1% to 99% diastereomeric excess (d.e.) with respect to either stereochemical configuration at position 1. For example, the compound of Formula VI may have at least 1%, at least 5%, at least 10%, at least 20%, at least 30%, at least 40%, at least 50%, at least 60%, at least 70%, at least 80%, at least 90%, at least 95%, at least 96%, at least 97%, at least 98%, or at least 99% d.e. with respect to position 1.

In some embodiments of the compounds of Formulas V and VI, $R_5$ is OH or unsubstituted alkoxy and $R_5$ is H. In other embodiments, $R_6$ is H, and $R_7$ is H.

In some embodiments of the compounds of Formulas V and VI, $R_8$ is —H, —OH, —COOH, or an unsubstituted alkyl or —$(CH_2)_{1-6}$-phenyl group. In some embodiments, $R_8$ is —H or an unsubstituted $C_{1-4}$ alkyl group, such as methyl or ethyl.

In some embodiments of the compounds of Formulas V and VI, $R_1$ and $R_2$ are independently —H, —$(CH_2)_{0-6}COOR'$, —$NR_{10}R_{11}$, —$C(O)NR_{10}R_{11}$, or a substituted or unsubstituted alkyl group; or $R_1$ and $R_2$ together are a 1,2-dioxyethylene group;

$R_3$ and $R_3'$ are each —H, or $R_3$ and $R_3'$ together are an oxo group;

$R_4$ is —H, —OH, or a substituted or unsubstituted $C_{1-6}$ alkoxy, $C_{7-14}$ aralkoxy, —OC(O)—$(C_{1-6}$ alkyl), —OC(O)-(aryl), —OC(O)O-(aryl), —OC(O)—NH-(aryl), —O—$(C_{2-6}$ alkylene)-NH—$(C_{2-6}$ alkyl), —O—$(C_{2-6}$ alkylene)-NH-(tetrahydropyran), —O—$(C_{2-6}$ alkylene)-NH-(thiomorpholine dioxide), —O—$(C_{2-6}$ alkylene)-NH-(piperidinyl), —O—$(C_{2-6}$ alkylene)-NH-(piperazinyl), —O—$(C_{2-6}$ alkylene)-NH-(morpholinyl), —O—$(C_{2-6}$ alkylene)-NH-(aralkyl), —O—$(C_{2-6}$ alkylene)-NH-(cyclopropyl), —$OSO_2$—$(C_{3-6}$ cycloalkyl), —$OSO_2$-(aryl), —O—$(C_{2-6}$ alkylene)-$OSO_2$-(aryl), —$OSO_2$-(aralkyl), —O—$(C_{2-6}$ alkylene)-$OSO_2$-(heteroaryl), —$OSO_2$—$(C_{1-6}$ alkyl), —$OSO_2$-(pyridyl), —$OSO_2$-(thiazolyl), —O—$(C_{2-6}$ alkylene)-$NHSO_2$-(aryl), —O—$(C_{2-6}$ alkylene)-$NHSO_2$-(heteroaryl), —O—$(C_{2-6}$ alkylene)-NHC(O)-(aryl), —O—$(C_{2-6}$ alkylene)-NHC(O)-(heteroaryl), —O—$(C_{0-4}$ alkyl)pyridyl, —O—$(C_{0-4}$ alkyl)pyrimidinyl, —O—$(C_{0-4}$ alkyl)morpholinyl, —O—$(C_{0-4}$ alkyl)thiomorpholinyl, —O—$(C_{0-4}$ alkyl)imidazolyl, —O—$(C_{0-4}$ alkyl)thienyl, —O—$(C_{0-4}$ alkyl)tetrahydropyranyl, —O—$(C_{0-4}$ alkyl)tetrahydrofuranyl, —O—$(C_{0-4}$ alkyl)pyrrolidinyl, alkyl)piperidinyl, or —O—$(C_{0-4}$ alkyl)piperazinyl group;

$R_5$ and $R_6$ are independently —H, —OH, or an unsubstituted $C_{1-6}$ alkoxy group; or $R_4$ and $R_5$ together are a methylenedioxy group, or $R_5$ and $R_6$ together are a methylenedioxy group; and $R_8$ is —H, —OH, —COOH, or an unsubstituted alkyl or —$(CH_2)_{1-6}$-phenyl group.

In some embodiments of the compounds of Formulas V and VI, $R_1$ and $R_2$ are independently —H, —$CH_3$, —$CH_2OH$, —OH, —$OCH_3$, —$OCH_2CH_3$, —$OCH_2CH_2OH$, —COOH, —$C(O)N(CH_3)_2$, —$C(O)NH(CH_2CH_2OH)$, —$C(O)OCH_3$, —$NHCH_3$, —$N(CH_3)_2$, —$NC(O)OCH_2CH_3$, benzyloxy, or $R_1$ and $R_2$ together are a 1,2-dioxyethylene group;

$R_3$ and $R_3'$ are each —H, or $R_3$ and $R_3'$ together are an oxo group;

$R_4$ is —H, —OH, $OCH_3$, —$OCH_2CH_3$, —$O(CH_2)_2OH$, —$OCH_2COOH$, —$OCH_2COOCH_2CH_3$, —$O(CH_2)_2COOH$, —$O(CH_2)_2CH_2Br$, —O-acetyl, —O-benzoyl, —O—$(CH_2)_2$—NH—$(CH_2)_2$—$N(CH_3)_2$, —O—$(CH_2)_2$—NH—$(CH_2)_2$—$OCH_3$, —O—$(CH_2)_2$—NH—$(CH_2)_2$—$SCH_3$, —O—$(CH_2)_2$—NH-morpholinyl, —O—$(CH_2)_2$—NH—$(CH_2)_3$—$N(CH_3)_2$, —O—$(CH_2)_2$—NH-benzyl, —O—$(CH_2)_2$—NH—$(CH_2)_3$-(thiomorpholine dioxide), —O—$(CH_2)_2$—NH—$(CH_2)_3$-morpholinyl, —O—$(CH_2)_2$—NH—$(CH_2)_3$-tetrahydropyranyl, —O-pyridyl optionally substituted with one or two substituents selected from the group consisting of $C_{1-4}$ alkyl, —$NO_2$, and $NH_2$, —O—$(CH_2)_2$—S-phenyl, —$OSO_2$-naphthyl optionally substituted with di($C_{1-4}$ alkyl), —$OSO_2$—$CF_3$, —$OSO_2$-thiazolyl optionally substituted with acetamido, —O—$(CH_2)_{0-2}SO_2$-phenyl wherein the phenyl group is optionally substituted with one or two substituents selected from the group consisting of methyl, methoxy, fluoro, chloro, trifluoromethyl, and nitro, —$OSO_2$-cyclopentyl, —$OSO_2$-thienyl, —$OSO_2$-benzyl, —$(CH_2)_2$-cyclopropyl, —$(CH_2)_2$-morpholinyl, —$(CH_2)_2$-imidazolyl, —$(CH_2)_2$-pyrrolidinyl, or —$(CH_2)_2$-piperazinyl group, wherein the piperazinyl group is optionally substituted with methyl, isopropyl, or methoxyethyl;

$R_5$ and $R_6$ are independently —H, —OH, or —$OCH_3$; and $R_8$ is —H, methyl, ethyl, —COOH, or benzyl.

In some embodiments of compounds of Formulas V and VI. $R_4$ is —O—$(CH_2)_{0-2}$—$SO_2$-phenyl, wherein the phenyl group is optionally substituted with one or two substituents selected from the group consisting of methyl, methoxy, fluoro, chloro, trifluoromethyl, and nitro.

In some embodiments of compounds of Formulas V and VI, stereoisomers thereof, tautomers thereof, solvates thereof, and pharmaceutically acceptable salts thereof;

$R_1$ is selected from —$(CH_2)_{0-6}COOR'$, —$C(O)R''$, —$OR'$, —$NR_{10}R_{11}$, —$C(O)NR_{10}R_{11}$, or a substituted or unsubstituted alkyl, group;

$R_2$ is selected from —H, —$(CH_2)_{0-6}COOR'$, —$C(O)R''$, —$O(CH_2)_{1-4}$—$CO_2R'$, —$NR_{10}R_{11}$, —$C(O)NR_{10}R_{11}$, or a substituted or unsubstituted alkyl group; or $R_1$ and $R_2$ together are a 1,2-dioxyethylene group;

$R_8$ is —H, or an unsubstituted $C_{1-4}$ alkyl group;

$R_3$ and $R_3'$ are both —H;

$R_4$ is —OH, —$OSO_2R''$, —OC(O)—$(C_{1-6}$ alkyl)-biotin, or —O-alkylene-$S(O)_{0-2}R''$;

$R_5$ is —H, halogen, —OH, or a substituted or unsubstituted alkoxy group; or $R_4$ and $R_5$ together are a methylenedioxy group, or $R_5$ and $R_6$ together are a methylenedioxy group;

$R_6$ and $R_7$ are independently selected from —H or halogen;

$R_{10}$ and $R_{11}$ are independently H, —$C(O)OR''$, or a substituted or unsubstituted alkyl group;

each R' is independently a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group; and each R'' is independently a substituted or unsubstituted alkyl, alkenyl, cycloalkyl, cycloalkylalkyl, aryl, aralkyl, heteroaryl, heteroarylalkyl, heterocyclyl, or heterocyclylalkyl group.

In some embodiments of any of the compounds disclosed herein, R'' is a substituted or unsubstituted aryl group. In other embodiments, R'' is phenyl, optionally substituted with one or two halogen, e.g., one or two fluorine and/or chlorine. In some embodiments, R" is phenyl, optionally substituted with a fluorine.

In some embodiments of any of the compounds disclosed herein, $R_4$ is —$OSO_2R"$ or —O-alkylene-$S(O)_{0-2}R"$. In some embodiments, $R_4$ is —$OSO_2$-phenyl wherein the phenyl is optionally substituted with a fluorine.

Certain compounds of Formulas I, II, III, IV, V and VI may be isolated from plants. Compounds of Formulas I, II, III, IV, V and VI may also be prepared using the synthetic schemes described herein. Many such compounds may be made starting from natural products such as berberine. For example, Scheme 1 shows that berberine may be heated (e.g., 150-250° C.), preferably in a dry oven under reduced pressure, to selectively remove the position 19 (berberine numbering) methyl group and provide berberrubine.

clylalkyl. X may be halides such as Cl, Br, or I, or X may be other leaving groups such as mesylate, trifluoromethanesulfunate, p-toluenesulfonate and the like. The alkylation may be carried out in a suitable solvent such as DMF, dichloromethane, chloroform or acetone by stirring or refluxing at a suitable temperature (e.g., ambient or with heating) until the desired product is formed. Optionally, a base is used in the alkylation such as inorganic base (alkali metal carbonates) or an organic base (pyridine, triethylamine).

In the third step, compound A may be reduced using any suitable reducing agent to give tetrahydroberberine compound B. Typically, borohydrides may be used as the reducing agent, such as sodium borohydride, sodium cyanoborohydride, or sodium triacetoxyborohydride. The reaction may be carried out in any suitable solvent or mixture of solvents (e.g., alcohols such as methanol, ethanol, aqueous solutions

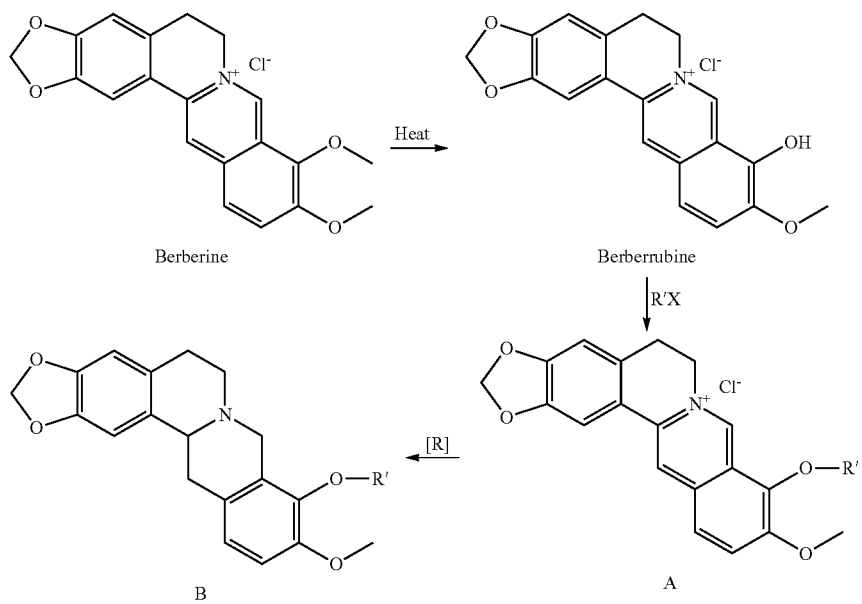

Scheme 1

The resulting hydroxyl group may be alkylated to provide product A. The alkylation may be carried out with a wide variety of alkylating agents R'X to provide various —OR' wherein R' is other than H such as alkyl, alkenyl, aralkyl, cycloalkyl, cycloalkylalkyl, heteroarylalkyl, and heterocythereof, and solutions of AcOH) at a suitable temperature. It is within the skill in the art to select a suitable temperature and reaction time for the reduction. Alternatively, the reduction may be carried out prior to the alkylation reaction (scheme not shown) so long as alkylation of the ring nitrogen is avoided.

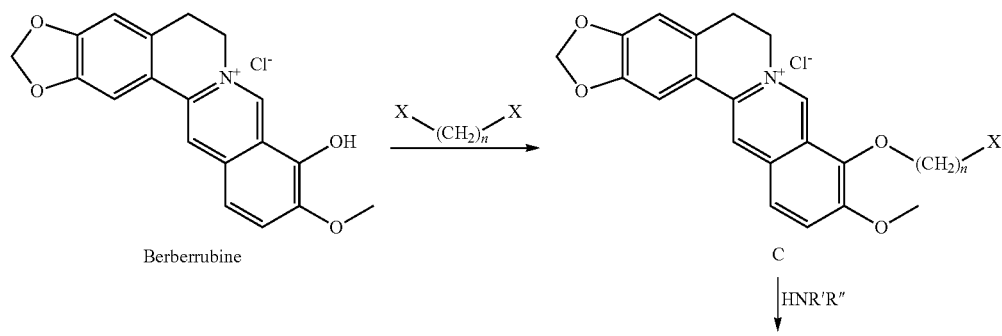

Scheme 2

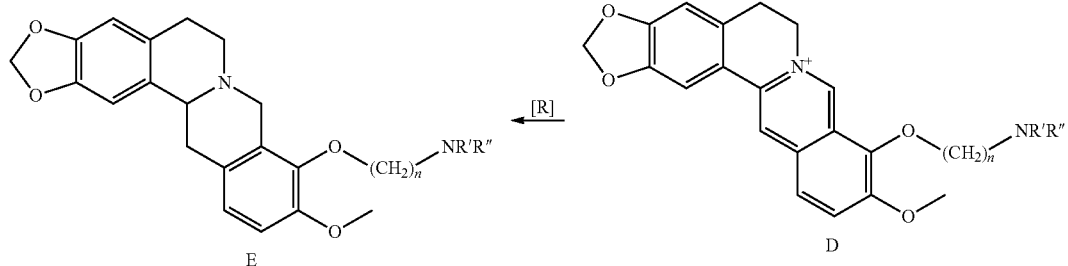

In a similar fashion, as shown in Scheme 2, berberrubine may be alkylated with a terminal dihaloalkane X—(CH$_2$)$_n$—X, (n=1-10) to allow for subsequent functionalization with an amine such as HNR'R". The alkylation reaction to give compound C may be carried out in a suitable solvent such as DMF, dichloromethane, chloroform or acetone by stirring or refluxing at a suitable temperature until the reaction is complete. Amination of compound C with HNR'R" (where R' and R" are as defined herein) to give compound D is optionally carried out in the presence of an inorganic base (alkali metal carbonates) or an organic base (pyridine, triethylamine) in a suitable solvent (e.g., DMF, dichloromethane or chloroform), and at a suitable temperature. Compound D is then reduced as described above to give compound E.

Scheme 3

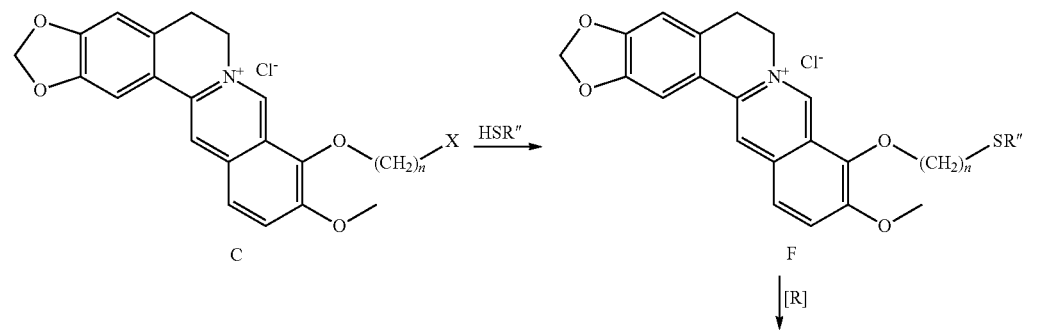

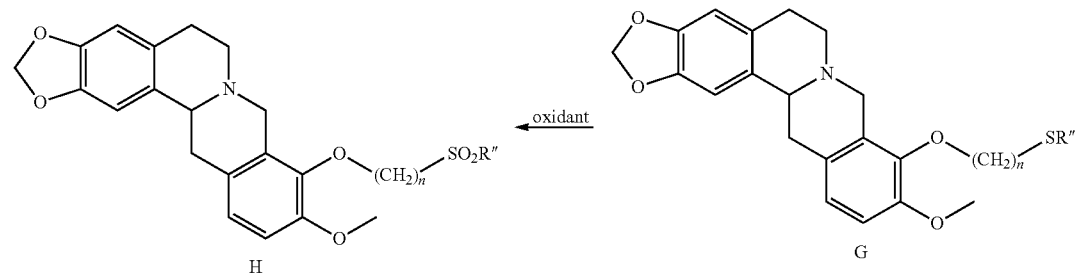

Similarly, as shown in Scheme 3, compound C in a suitable solvent may be reacted with various thiols (HSR") to give compound F. As described for the amination of C above, the reaction is optionally carried out in the presence of an inorganic or organic base. Reduction as described herein provides the tetrahydroberberine derivative, compound G. The sulfone H may be prepared by exposing compound G to a mild oxidant such as peroxybenzoic acids (e.g., meta-chloroperoxybenzoic acid).

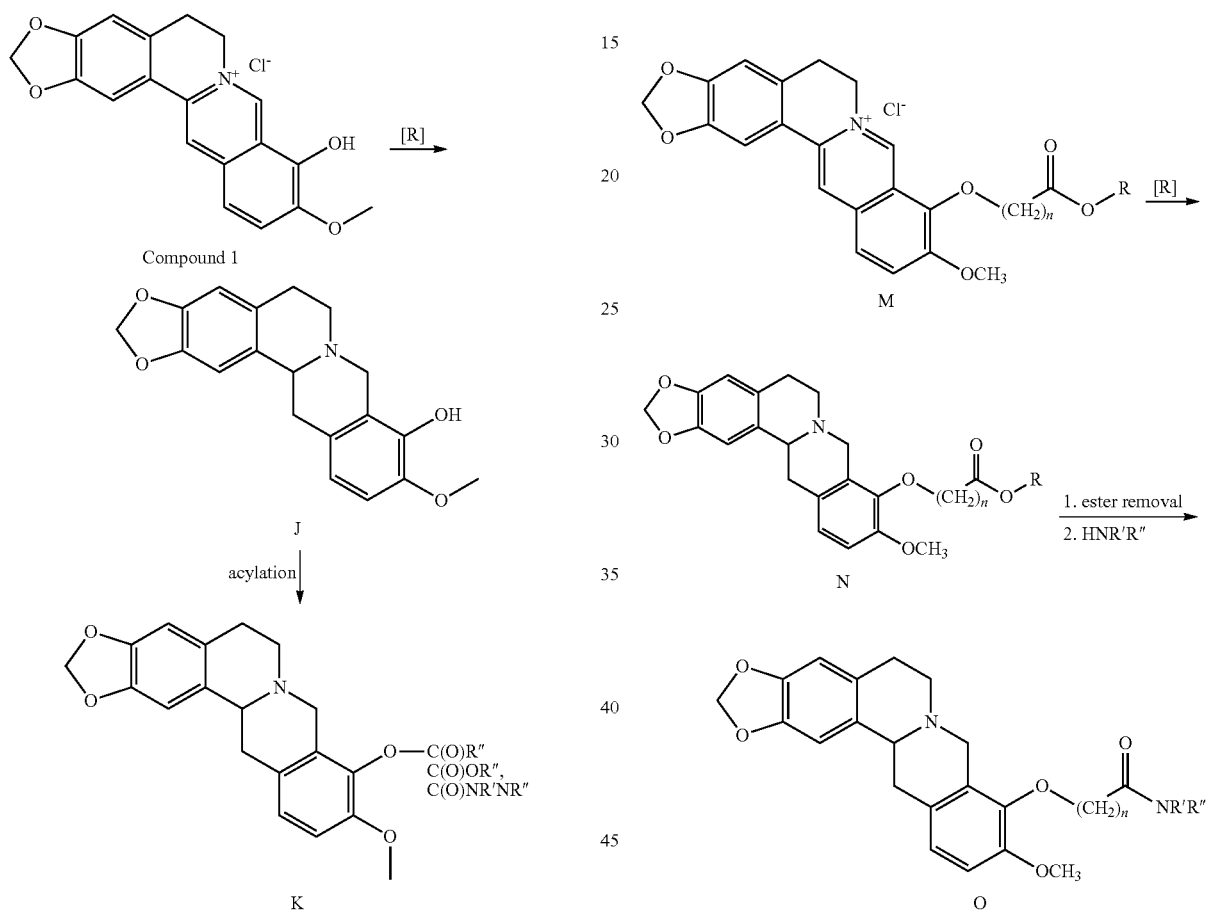

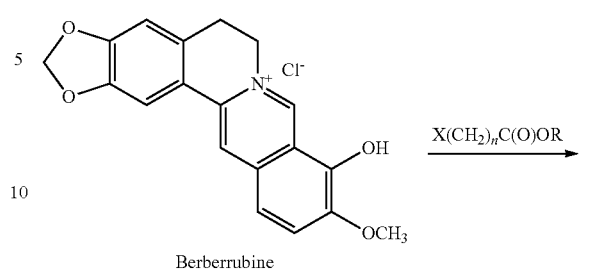

Scheme 4 shows a method for preparing acylated derivatives of berberrubine. Compound 1 may be reduced as described herein to give a tetrahydroberberine compound J. In the second step, compound J may be acylated with an acyl halide (e.g., R"C(O)X, where R" is as defined herein and X is a halide such as Cl or Br), a haloformate (e.g., R"OC(O)X), or an isocyanates (e.g., NC(O)R") to provide, respectively, the corresponding amide, urethane or carbonate. The acylation is typically carried out in a suitable solvent in the presence of an inorganic base (alkali metal carbonates) or an organic base (pyridine, triethylamine). Upon completion of the reaction, the reaction mixture is cooled, and the product is optionally subjected to further separation and purification steps to give the target compound K. Likewise, 12.4 sulfonyl groups may be installed by reaction of compound J with a sulfonyl halide, R"SO$_2$X, in the presence of an inorganic or organic base in a suitable solvent.

In another example of R$_4$ substituents, as shown in Scheme 5, berberrubine may be alkylated with a haloester (e.g., X(CH2)nCOOR, where X is a halo or other leaving group and R is a substituted or unsubstituted alkyl or aralkyl group) in a suitable solvent such as acetone, methanol, ethanol or mixtures thereof to give compound M. The latter compound may be reduced as described herein to give the tetrahydroberberine derivative N. The ester group may then be removed by standard methods known in the art such alkaline or acid hydrolysis or, in the case of suitable aralkyl esters, by hydrogenolysis with a suitable catalyst (e.g. Pd/C, Pt/C, etc.). The compound O amide may be formed from the resulting acid by standard techniques such as reacting HNR'R" in the presence of amide coupling reagents such as carbodiimides (e.g., DCC, EDC) in the presence of additives (HOBt, HOAt, DMAP), BOP, or by the formation of the corresponding acyl halide or mixed anhydride.

Scheme 6

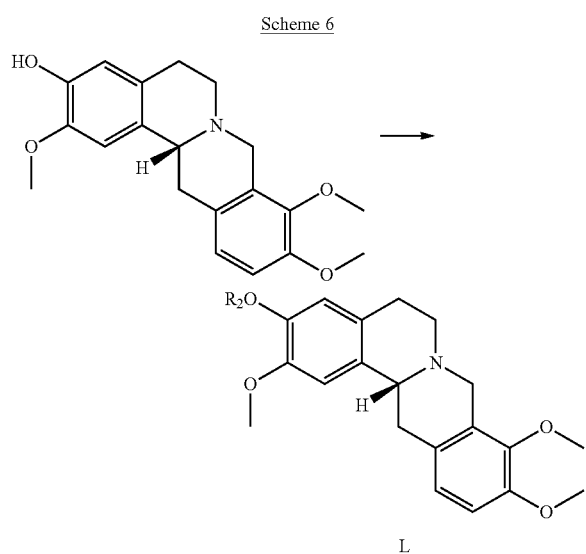

Compounds of Formulas I and III having various substituents at $R_2$ may be prepared by procedures analogous to those in schemes 1-4. Thus, for example, as shown in Scheme 6, corypalmine may be alkylated with $R_2X$, wherein $R_2$ is as defined herein and X can be a halo, sulfonyl or other leaving group under conditions described above. Similarly, the free hydroxyl in corypalmine may be acylated with an acyl halide in the presence of a base or a carboxylic acid in presence of, for example, a coupling agent such as EDC.HCl/DMAP to give the target compound L.

Scheme 7

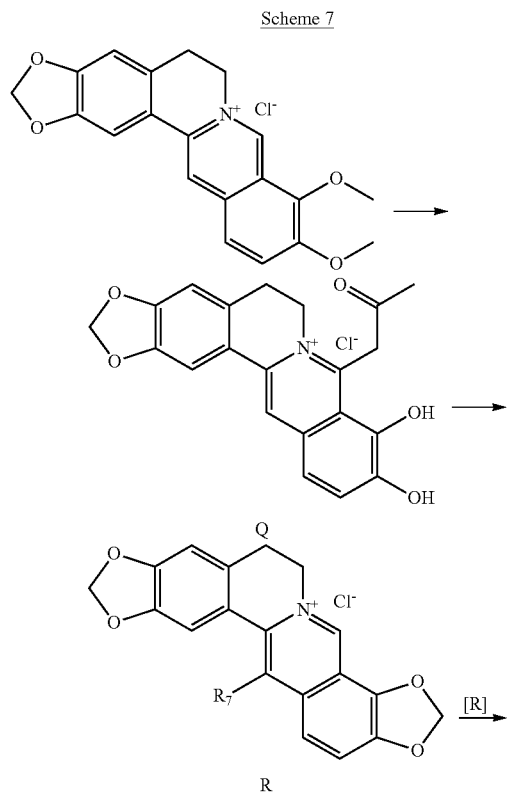

-continued

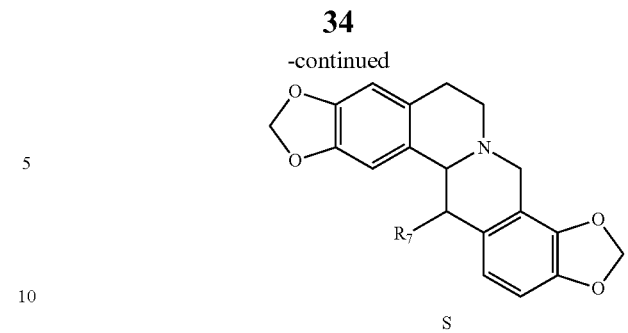

$R_8$ substituents may be installed at the 13-position of compounds of Formulas I and III as shown in Scheme 7. For example, an aqueous solution of berberine chloride may be reacted with acetone in presence of a suitable base such as alkali metal hydroxide to give the compound Q. The protected compound Q can subsequently be reacted with $R_7X$, wherein $R_7$ is as described herein and X is a halide, sulfonyl group or other leaving group. The reaction is conducted in a suitable solvent at a suitable temperature optionally in presence of an alkali metal halide such as potassium iodide to give compound R. Compound R is hydrogenated as described herein or with hydrogen using a suitable catalyst such as Pt/C to give the tetrahydroberberine compound S.

Scheme 8

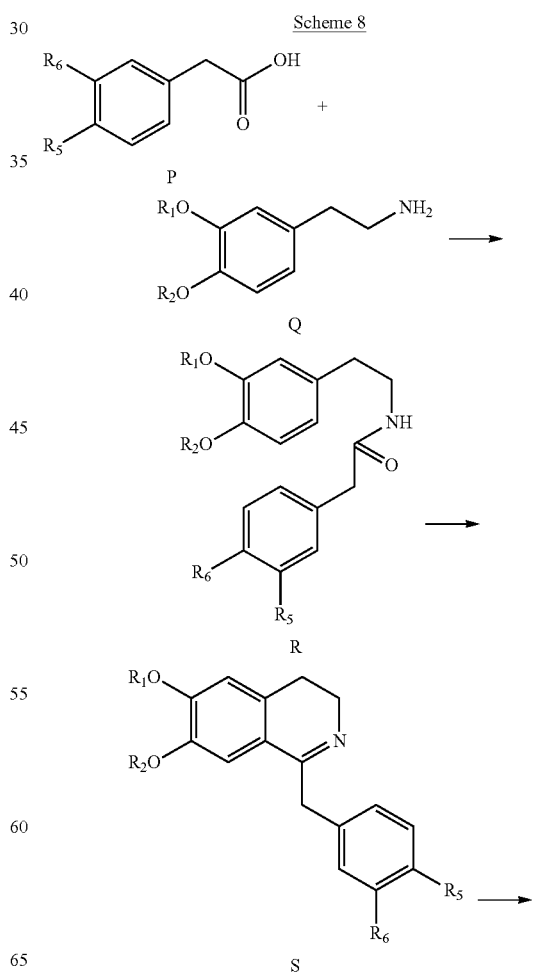

-continued

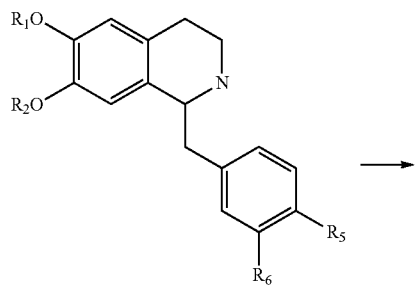
T

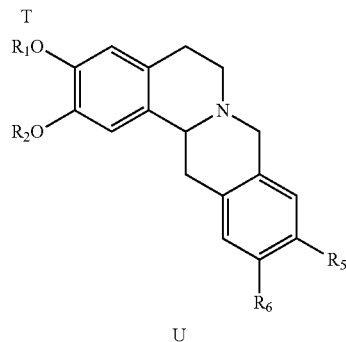
U

Compounds of Formulas I and III may be made by total synthesis as shown in Scheme 8. The phenylacetic acid P may be coupled to the phenethylamine Q using standard techniques for the formation of amide bonds such as the use of coupling reagents (e.g., EDC/HOBt, carbonyl diimidazole, etc.), via formation of the acyl halide or mixed anhydride of P. The resulting N-acyl β-arylethyl amine compound R may be subjected to a Bischler-Napieralski reaction in a suitable solvent such as benzene, toluene or xylene and in presence of a dehydrating agent such as POCl$_3$ to give the corresponding dihydroisoquinoline compound S. The latter compound may be reduced by any suitable method such as with sodium borohydride, sodium cyanoborohydride or the like to give compound T. Ring closure of compound T may be effected by reacting it with formaldehyde in a suitable solvent such as acetic acid to give the compound U, which is a compound of Formula I and III.

Scheme 8.1

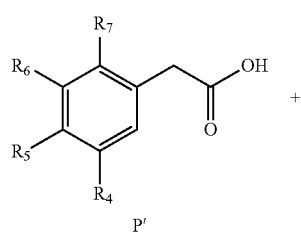
P'

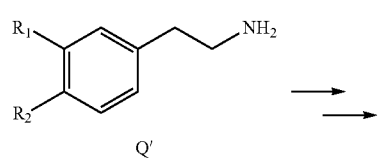
Q'

-continued

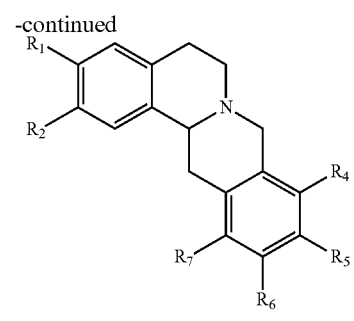
U'

Similarly, compounds of Formula V may also be prepared according to Scheme 8, using appropriately substituted phenethylamines (Q') and phenyl acetic acid derivatives (P'), (shown in Scheme 8.1).

Scheme 9

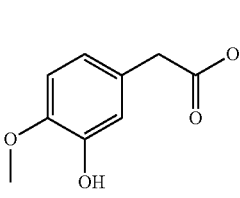
V 1. a) phenylboronic acid
   b) paraformaldehyde
2. H$_2$O

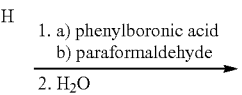

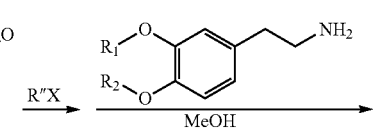

R"X
―――→
MeOH

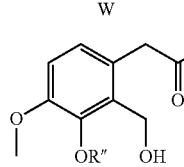

1. POCl$_3$
2. NaBH$_4$

X

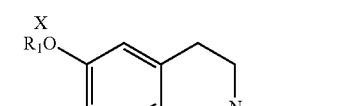
Y

Alternatively, Scheme 9 shows another general synthetic route to compounds of Formulas I and III. Phenyl acetic acid derivative V may be exposed consecutively to phenylboronic acid, followed by paraformaldehyde. Both stages of the reaction are typically heated, and the reaction with paraformaldehyde may be carried out under pressure in, e.g., a stainless steel bomb. Suitable solvents for this reaction include aromatic solvents such as toluene. The resulting boronate is hydrolyzed with water to give compound W. The latter compound may be alkylated with a wide variety of electrophiles, R'X, as described herein (e.g., for A in Scheme 1). Subsequently the amide may be formed with a phenethylamine compound as shown to give compound X. Ring closure using POCl$_3$ in a suitable solvent, such as toluene, followed by reduction as described herein, gives compound Y, an exemplary compound of formulas I or III. Compounds of Formula V may also be prepared according to Scheme 9, using appropriate starting materials (e.g., phenethylamine Q' and/or phenyl acetic acid derivatives P' as in Scheme 8.1).

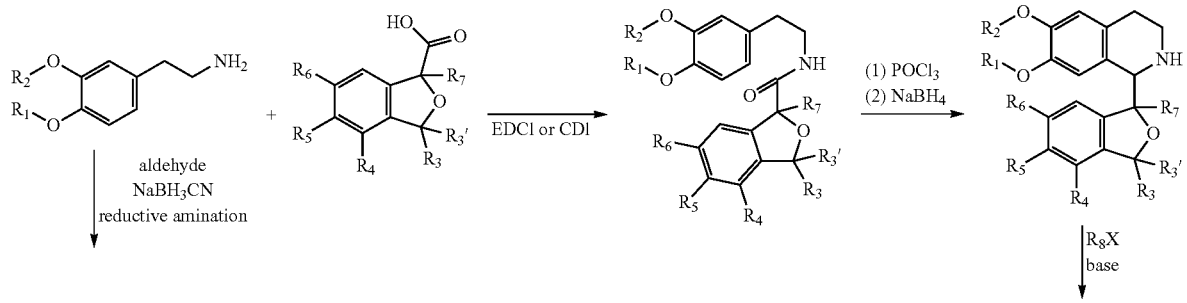

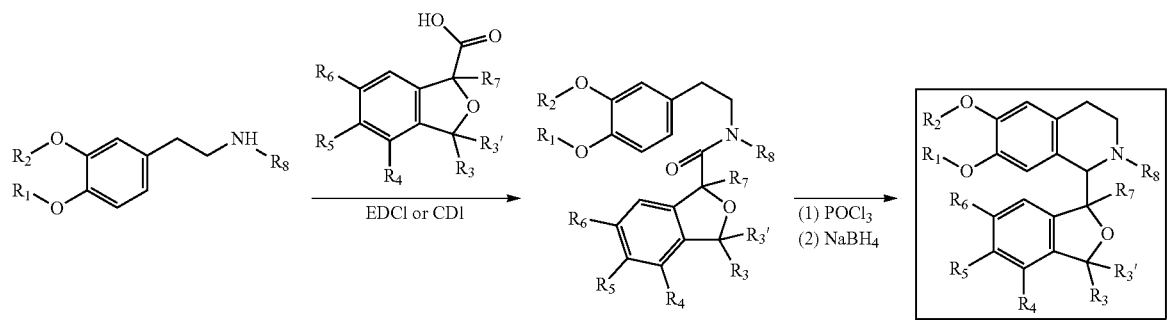

Compounds of Formulas II and IV may be prepared according to Scheme 10. Thus, the starting phenethylamine with $R_1$ and $R_2$ already in place may be made using standard techniques in the art. $R_8$ may be installed on the phenethylamine by reductive amination with an appropriate aldehyde (commercially available or prepared from the corresponding alcohol according to standard oxidation protocols). The starting carboxytetrahydroisobenzofuran may also be readily prepared using standard techniques. The phenethylamine and the arboxytetrahydroisobenzofuran may be coupled using amide coupling reagents or other standard techniques. Thus, for example, coupling may be effected in the presence of EDC/HOBt or carbonyl diimidazole among other coupling reagents. Compounds of Formula VI, may be made by a similar route, using the appropriate starting materials, such as, e.g., phenethylamine Q' shown in Scheme 8.1.

Another general synthetic route to compounds of Formulas II and IV is shown in Scheme 11. Compound A can be prepared through Bischler-Napieralsky cyclization of the corresponding phenethylamine, and can subsequently be reacted with lactone in the presence of a strong base, such as LDA, to afford the precursor B. The latter compound may be converted to various compounds of Formulas II and IV by reduction of the lactone carbonyl or reaction with, e.g., Grignard reagents to install $R_3$ and $R_3$'. Again, compounds of Formula VI, may be made by a similar route, using the appropriate starting materials, e.g. the same phenethyl amine Q' as in Scheme 8.1.

Scheme 11

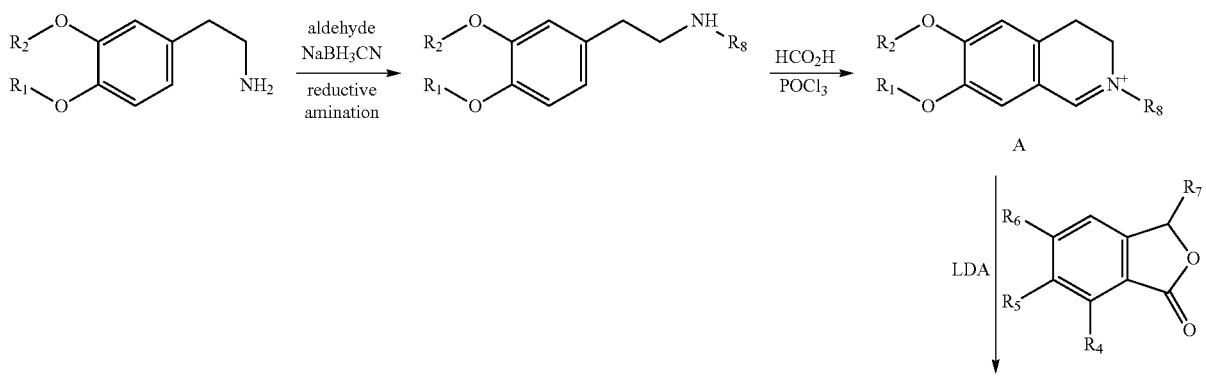

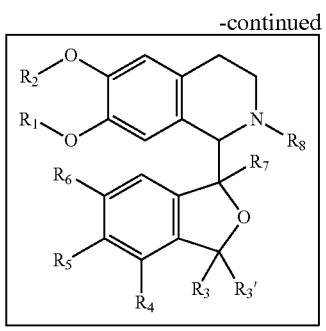
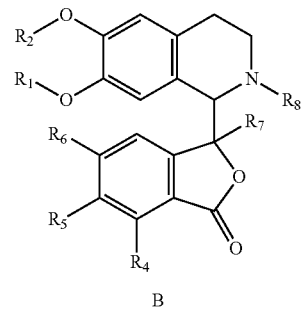

Still other methods of preparing compounds of Formulas II and IV may be adapted from literature procedures as outlined in Scheme 12 and described in the following references: Jerome L. Moniot and Maurice Shamma, "Conversion of berberine into phthalideisoquinolines" *J. Org. Chem.,* 1979, 44 (24), 4337-4342; Jerome L. Moniot, David M. Hindenlang, and Maurice Shamma, "Chemistry of 8,13-dioxoberbines" *J. Org. Chem.,* 1979, 44(24), 4343-4346; Tatsuya Shono, Hiroshi Hamaguchi, Manji Sasaki, Shumei Fujita, and Kimihiko Nagami, "Novel zinc-promoted alkylation of iminium salts. New synthesis of benzylisoquinoline, phthalidylisoquinoline, and protoberberine alkaloids and related compounds" *J. Org. Chem.,* 1983, 48(10), 1621-1628; R H Prager, J M Tippett and A D Ward, "Central nervous system active compounds. VIII. New syntheses of phthalide isoquinolines" *Aust. J. Chem.,* 1981, 34(5), 1085-1093; SI Clarke, B Kasum, R H Prager and A D Ward, "Central nervous system active compounds. XIII. The use of aminomethylene phthalides in the synthesis of phthalideisoquinoline alkaloids" *Aust. J. Chem.,* 1983, 36(12), 2493-2498; Nurani S, Narasimhan, Ravindra R. Joshi and (Mrs) Radhika S. Kusurkar, "An efficient synthesis of phthalideisoquinoline alkaloids" *J. Chem. Soc., Chem. Comm.,* 1985, 3, 177-178; Yoshikazu Kondo, Jiro Imai and Shigeo Nozoe, Reaction of protoberberine-type alkaloids. Part 13. Biogenetic conversion of protoberberine alkaloids into phthalideisoquinoline alkaloids" *J. Chem. Soc., Perkin. Trans.* 1, 1980, 919-926; Tetsuji Kametani, Toshio Honda, Hitoshi Inoue, and Keiichiro Fukumoto, "A One Step Synthesis of the Phthalideisoquinoline Alkaloid Cordrastine" *Heterocycl.* 1975, 3(12), 1091-1098; K. W. Bentley and A. W. Murray, "Ketolaudanosine" *J. Chem. Soc.,* 1963, 2487-2491.

Scheme 12

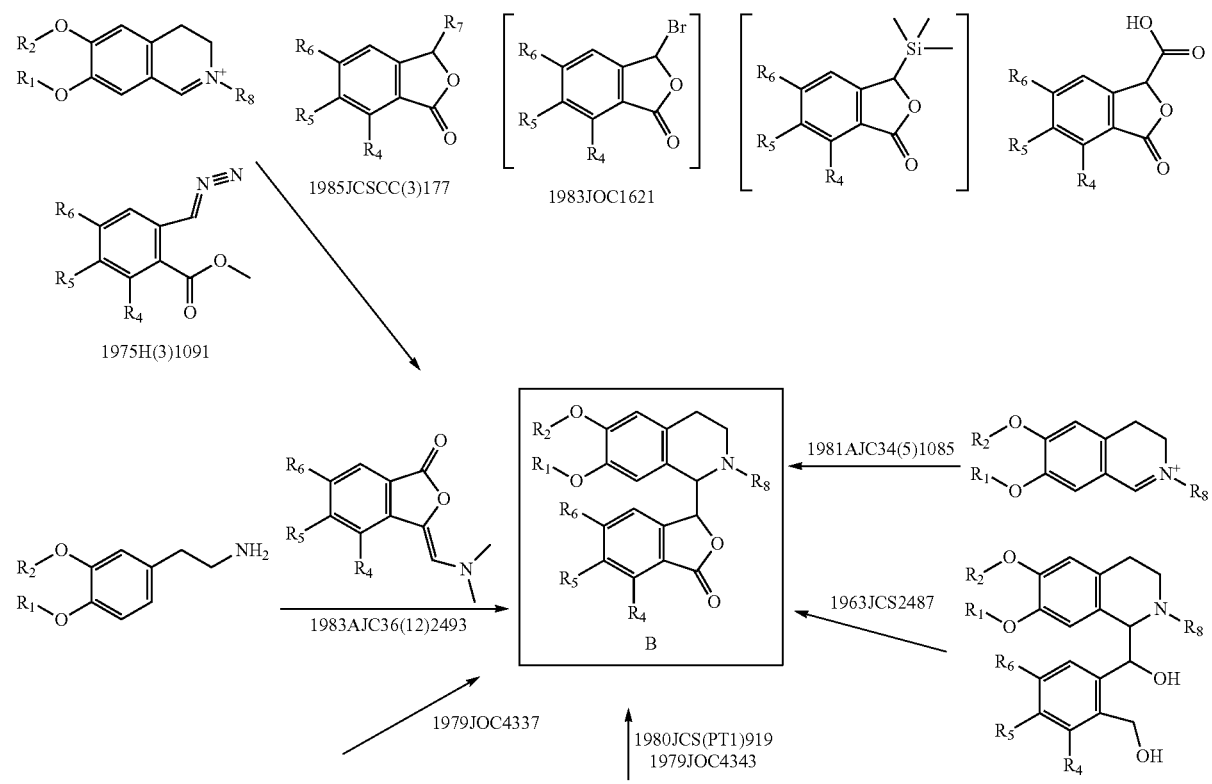

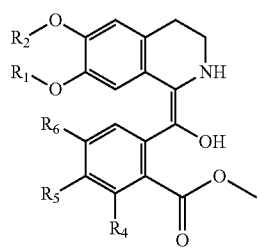 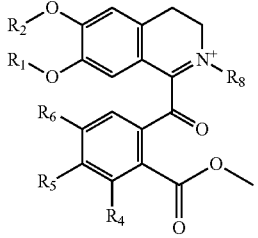

For example, Scheme 13 shows how compound B may be prepared as reported in *Aust. J. Chem.* 1983, 36(12), 2493. Compound D, prepared from 3H-isobenzofuran-1-one (A) in two steps, can react with various alkylating and acylating agents in the presence of base to afford the intermediate B.

Scheme 13

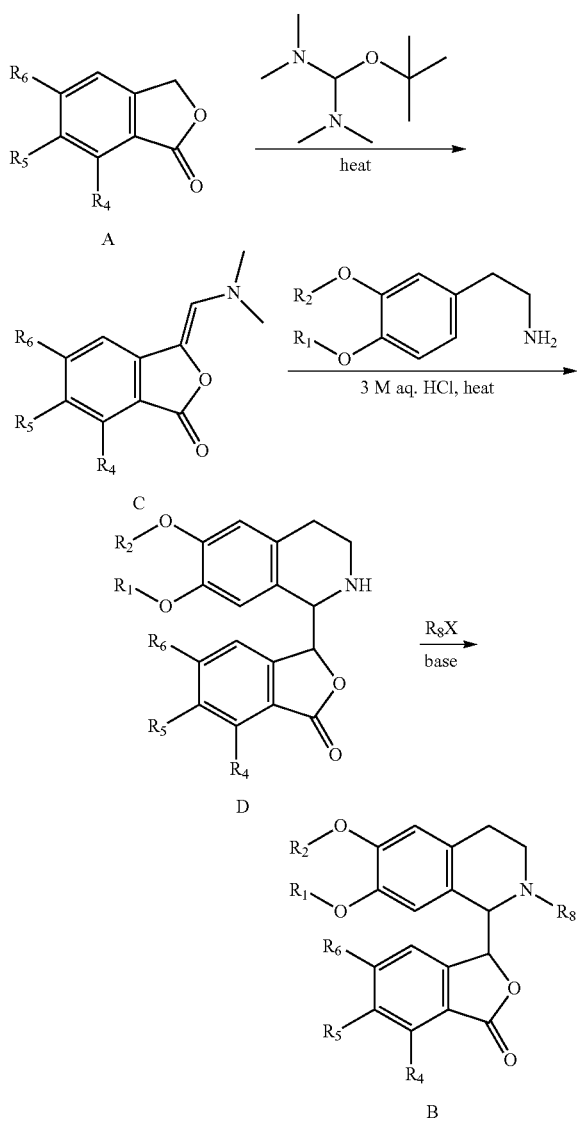

In another aspect, the instant present technology provides pharmaceutical compositions and medicaments comprising any of the compounds disclosed herein (e.g., compounds of Formulas I, II, III, IV, V, or VI) and a pharmaceutically acceptable carrier or one or more excipients or fillers. In some embodiments, there are provided pharmaceutical compositions for treating a condition selected from the group consisting of hyperlipidemia, hypercholesterolemia, hypertriglyceridemia, hepatic steatosis, and metabolic syndrome. Such compositions include a lipid-lowering effective amount of any compound as described herein, including but not limited to a compound of Formula III, Formula IV, Formula V, or Formula VI. In one embodiment, the pharmaceutical composition is packaged in unit dosage form. The unit dosage form is effective in lowering lipid levels (e.g., at least one of total cholesterol, LDL-cholesterol, triglyceride, and unesterified long chain fatty acids) in the bloodstream and/or in the liver when administered to a subject in need thereof.

The pharmaceutical compositions may be prepared by mixing one or more compounds of the present technology, pharmaceutically acceptable salts thereof, stereoisomers thereof, tautomers thereof, or solvates thereof, with pharmaceutically acceptable carriers, excipients, binders, diluents or the like to prevent and treat disorders associated with the effects of increased plasma and/or hepatic lipid levels. The compounds and compositions described herein may be used to prepare formulations and medicaments that prevent or treat a variety of disorders associated with increased plasma and/or hepatic lipid levels, e.g., hyperlipidemia, hypercholesterolemia, hepatic steatosis, and metabolic syndrome. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is nonvolatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of inventive compounds by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the inventive compound across the skin. The rate of such flux can be controlled by either providing a rate controlling membrane (e.g, as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co. New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount by simply administering a compound of the present technology to a patient in increasing amounts until the elevated plasma or hepatic cholesterol or triglycerides or progression of the disease state is decreased or stopped. The progression of the disease state can be assessed using in vivo imaging, as described, or by taking a tissue sample from a patient and observing the target of interest therein. The compounds of the present technology can be administered to a patient at dosage levels in the range of about 0.1 to about 1,000 mg per day. For a normal human adult having a body weight of about 70 kg, a dosage in the range of about 0.01 to about 100 mg per kg of body weight per day is sufficient. The specific dosage used, however, can vary or may be adjusted as considered appropriate by those of ordinary skill in the art. For example, the dosage can depend on a number of factors including the requirements of the patient, the severity of the condition being treated and the pharmacological activity of the compound being used. The determination of optimum dosages for a particular patient is well known to those skilled in the art.

Various assays and model systems can be readily employed to determine the therapeutic effectiveness of antihyperlipidemia treatment according to the present technology. For example, blood tests to measure total cholesterol as well as triglycerides, LDL and HDL levels are routinely given. Individuals with a total cholesterol level of greater than 200 mg/dL are considered borderline high risk for cardiovascular disease. Those with a total cholesterol level greater than 239 mg/dL are considered to be at high risk. An LDL level of less than 100 mg/dL is considered optimal. LDL levels between 130 to 159 mg/dL are borderline high risk. LDL levels between 160 to 189 mg/dL are at high risk for cardiovascular disease and those individuals with an LDL greater than 190 mg/dL are considered to be at very high risk for cardiovascular disease. Triglyceride levels of less than 150 mg/dL is considered normal. Levels between 150-199 mg/dL are borderline high and levels above 200 mg/dL are considered to put the individual at high risk for cardiovascular disease. Lipid levels can be determined by standard blood lipid profile tests. Effective amounts of the compositions of the present technology will lower elevated lipid levels by at least 10%, 20%, 30%, 50% or greater reduction, up to a 75-90%, or 95% or greater. Effective amounts will also move the lipid profile of an individual towards the optimal category for each lipid, i.e., decrease LDL levels from 190 mg/dL to within 130 to 159 mg/dL or even further to below 100 mg/dL. Effective amounts may further decrease LDL or triglyceride levels by about 10 to about 70 mg/dL, by about 20 to about 50 mg/dL, by about 20 to about 30 mg/dL, or by about 10 to about 20 mg/dL.

A variety of hyperlipidemia classification systems are known to persons of skill in the art. One such classification system is the Frederickson classification, which is summarized in Table 1 below.

TABLE 1

| Pheno-type | Elevated Lipoproteins | Elevated Lipid Levels | Plasma TC | Plasma TG | Relative Frequency (%)* |
|---|---|---|---|---|---|
| I | Chylomicrons | TG | N to ↑ | ↑↑↑↑ | <1 |
| IIa | LDL | TC | ↑↑ | N | 10 |
| IIb | LDL & VLDL | TC, TG | ↑↑ | ↑↑↑ | 40 |
| III | IDL | TC, TG | ↑↑ | ↑↑ | <1 |
| IV | VLDL | TG, TC | N to ↑ | ↑↑ | 45 |
| V | VLDL & chylomicron | TG, TC | ↑ to ↑↑ | ↑↑↑↑ | 5 |

IDL, intermediate-density lipoprotein; LDL, low-density lipoprotein; N, normal; TC, total cholesterol; TG, triglyceride; VLDL, very-low-density lipoprotein
*Approximate % of patients in the United States with hyperlipidemia.

Individuals may also be evaluated using a hs-CRP (high-sensitivity C-reactive protein) blood test. Those with a hs-CRP result of less than 1.0 mg/L are at low risk for cardiovascular disease. Individuals with a hs-CRP result between about 1.0 to 3.0 mg/L are at average risk for cardiovascular disease. Those with a hs-CRP result greater than 3.0 mg/L are at high risk of cardiovascular disease. Effective amounts of the compositions of the present technology will lower hs-CRP results below 3.0 mg/L. Effective amounts of the compositions of the present technology can lower hs-CRP results by about 0.5 to about 3.0 mg/L, and further by about 0.5 to about 2.0 mg/L.

Effectiveness of the compositions and methods of the present technology may also be demonstrated by a decrease in the symptoms of cardiovascular disease, edema, diabetes insipidus, hypertension, myocardial ischemia, congestive heart failure, arrhythmia, and hyperlipoproteinemia, the symptoms including shortness of breath, chest pain, leg pain, tiredness, confusion, vision changes, blood in urine, nosebleeds, irregular heartbeat, loss of balance or coordination, weakness, or vertigo.

For each of the indicated conditions described herein, test subjects will exhibit a 10%, 20%, 30%, 50% or greater reduction, up to a 75-90%, or 95% or greater, reduction, in one or more symptom(s) caused by, or associated with, hyperlipidemia, elevated cholesterol, elevated triglyceride, and/or a targeted cardiovascular disease or condition in the subject, compared to placebo-treated or other suitable control subjects.

The compounds of the present technology can also be administered to a patient along with other conventional therapeutic agents that may be useful in the treatment or prophylaxis of hyperlipidemic diseases. In one aspect, a method is provided for administering an effective amount of one or more compounds of the present technology to a patient suffering from or believed to be at risk of suffering from a disease characterized by elevated plasma or hepatic cholesterol or triglycerides. Moreover, the present technology relates to treating a hyperlipidemic disease by administering an effective amount of one or more compounds to a patient in need thereof. The methods of the present technology can also comprise administering, either sequentially or in combination with one or more compounds of the present technology, a conventional therapeutic agent in an amount that can potentially or synergistically be effective for the treatment or prophylaxis of a hyperlipidemic disease. Exemplary therapeutic agents for use in combination therapies with one or more compounds of the present technology include, but are not limited to, anti-inflammatory drugs, therapeutic antibodies and cholesterol lowering drugs such as, for example, statins.

In one aspect, a compound of the present technology is administered to a patient in an amount or dosage suitable for therapeutic use. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from $1\times10$ g/kg to 1 g/kg, preferably, $1\times10^{-3}$ g/kg to 1.0 g/kg. Dosage of a compound of the present technology can also vary from 0.01 mg/kg to 100 mg/kg or, preferably, from 0.1 mg/kg to 10 mg/kg.

Useful adjunctive therapeutic agents in combinatorial formulations and coordinate treatment methods include, for example, antihyperlipidemic agents; antidyslipidemic agents; antidiabetic agents, including, but not limited to metformin, rosiglitazone, plasma HDL-raising agents, including, but not limited to, nicotinic acid, fibrates; antihypercholesterolemic agents, including, but not limited to, cholesterol-uptake inhibitors; cholesterol biosynthesis inhibitors, e.g., HMG-CoA reductase inhibitors (also referred to as statins, such as lovastatin, simvastatin, pravastatin, fluvastatin, rosuvastatin, pitavastatin, and atorvastatin); HMG-CoA synthase inhibitors; squalene epoxidase inhibitors or squalene synthetase inhibitors (also known as squalene synthase inhibitors); microsomal triglyceride transfer protein (MTP) inhibitor; acyl-coenzyme A cholesterol acyltransferase (ACAT) inhibitors, including, but not limited to, melinamide; probucol; nicotinic acid and the salts thereof; niacinamide; cholesterol absorption inhibitors, including, but not limited to, beta-sitosterol or ezetimibe; bile acid sequestrant anion exchange resins, including, but not limited to cholestyramine, colestipol, colesevelam or dialkylaminoalkyl derivatives of a cross-linked dextran; LDL receptor inducers; fibrates, including, but not limited to, clofibrate, bezafibrate, fenofibrate and gemfibrozil; vitamin B6 (pyridoxine) and the pharmaceutically acceptable salts thereof, such as the HCl salt; vitamin B12 (cyanocobalamin); vitamin B3 (nicotinic acid and niacinamide); anti-oxidant vitamins, including, but not limited to, vitamin C and E and beta carotene; beta blockers; angiotensin II receptor (ATI) antagonist; angiotensin-converting enzyme inhibitors, renin inhibitors; platelet aggregation inhibitors, including, but not limited to, fibrinogen receptor antagonists, i.e., glycoprotein IIb/IIIa fibrinogen receptor antagonists; hormones, including but not limited to, estrogen; insulin; ion exchange resins; omega-3 oils; benfluorex; ethyl icosapentate; and amlodipine. Adjunctive therapies may also include increase in exercise, surgery, and changes in diet (e.g., to a low cholesterol diet). Some herbal remedies may also be employed effectively in combinatorial formulations and coordinate therapies for treating hyperlipidemia, for example curcumin, gugulipid, garlic, soy, soluble fiber, fish oil, green tea, carnitine, chromium, coenzyme Q10, grape seed extract, pantothine, red yeast rice, and royal jelly.

Berberine and related compounds also can be employed as second therapeutic agents together with the *Corydalis* lipid lowering agents of the present technology. For example, berberine sulfate, berberine hydrochloride, berberine chloride, oxyberberine, dihydroberberine, 8-cyanodihydroberberine, tetrahydroberberine N-oxide, tetrahydroberberine, 6-protoberberine, 9-ethoxycarbonyl berberine, 9-N,N-dimethylcarbamoyl berberine and 12-bromo berberine, berberine azide, and berberine betaine can be used. Berberine compounds that are effective in raising the expression level of LDLR are described in US 2006/0223838, which is hereby incorporated by reference in its entirety.

Another class of compounds that can be used as second therapeutic agents together with the *Corydalis* lipid lowering agents of the present technology is the SCAP antagonists. These compounds bind to SREBP-cleavage activating protein and prevent its physical interaction with SREBP, resulting in activation of the LDLR promoter and increased expression of LDLR. Suitable compounds are described in U.S. Pat. No. 6,673,555 (which is hereby incorporated by reference in its entirety).

In some embodiments a *Corydalis* lipid lowering agent is combined with one or more sterol 14-reductase inhibitors as second agents. Such inhibitors will reduce the synthesis of cholesterol in the liver, and consequently contribute to the reduction of total cholesterol and LDL-cholesterol. A series of suitable 14-reductase inhibitors based on *Corydalis* alkaloids is described in U.S. Pat. No. 6,255,317 and U.S. Pat. No. 6,239,139, both of which are incorporated by reference in their entirety. It is noteworthy that the *Corydalis* alkaloids which function as 14-reductase inhibitors differ from the *Corydalis* lipid lowering agents of the present technology in having a double bond at the 13-14 position. In some embodiments of the present technology, however, the additional effect of inhibiting cholesterol synthesis may be undesired. In such cases, 14-reductase inhibitors, particularly those *Corydalis* alkaloids having a double bond at the 13-14 position, are specifically excluded from use with a *Corydalis* lipid lowering agent of the present technology.

A compound of the present technology can bind to one or more targets of interest with a dissociation constant (for example, an equilibrium dissociation constant, $K_d$) from, for example, about 0.0001 to 10 µM (or from 0.0001 to 7 µM, 0.0001 to 5 µM, 0.0001 to 1 µM, 0.001 to 5 µM, 0.01 to 5 µM and/or 0.1 to 5 µM) as measured by any suitable techniques routine to those of ordinary skill in the art. The present technology contemplates measurement of a dissociation constant (for example, $K_d$ and $K_i$) or performing competition, saturation and kinetics experiments by conventional techniques routine to one of ordinary skill in the art. Moreover, a compound of the present technology can compete with a reference compound for binding to and/or with targets of interest with a dissociation constant of inhibition (for example, $K_i$) from, for example, about 0.01 nM to >10,000 nM (or from 0.001 to 7,000 nM, 0.001 to 5,000 nM, 0.001 to 1,000 nM, 0.01 to 5,000 nM, 0.01 to 2,000 nM and/or 0.1 to 5,000 nM).

A compound or probe of the present technology can bind to one or more targets of interest with a dissociation constant (for example, an equilibrium dissociation constant, $K_d$) from, for example, about 0.0001 to 10 µM as measured by binding to a synthetic peptide or tissue associated with a target of interest. The present technology contemplates measurement of a dissociation constant (for example, $K_d$ and $K_i$) or performing competition, saturation and kinetics experiments by conventional techniques routine to one of ordinary skill in the art. Moreover, a compound or probe of the present technology can compete with a reference compound for binding to a target of interest with a dissociation constant of inhibition (for example, K) from, for example, about 0.01 nM to >10,000 nM.

In one aspect, binding, interaction or association with can mean the contact between a compound (or analogs, salts, pharmaceutical compositions, derivatives, metabolites, prodrugs or racemic, tautomers mixtures thereof) and a target of interest with a binding affinity of at least $10^{-6}$ M, preferably, at least about $10^{-7}$ M, and more preferably $10^{-8}$ M to $10^{-9}$ M, $10^{-10}$ M, $10^{-11}$ M, or $10^{12}$ M. In one aspect, binding affinities include those with a dissociation constant or $K_d$ less than, but not limited to, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

A compound of the present technology can also be modified, for example, by the covalent attachment of an organic moiety or conjugate to improve pharmacokinetic properties, toxicity or bioavailability (e.g., increased in vivo half-life). The conjugate can be a linear or branched hydrophilic polymeric group, fatty acid group or fatty acid ester group. A polymeric group can comprise a molecular weight that can be adjusted by one of ordinary skill in the art to improve, for example, pharmacokinetic properties, toxicity or bioavailability. Exemplary conjugates can include a polyalkane glycol (e.g., polyethylene glycol (PEG), polypropylene glycol (PPG)), carbohydrate polymer, amino acid polymer or polyvinyl pyrolidone and a fatty acid or fatty acid ester group, each of which can independently comprise from about eight to about seventy carbon atoms. Conjugates for use with a compound of the present technology can also serve as linkers to, for example, any suitable substituents or groups, radiolabels (marker or tags), halogens, proteins, enzymes, polypeptides, other therapeutic agents (for example, a pharmaceutical or drug), nucleosides, dyes, oligonucleotides, lipids, phospholipids and/or liposomes. In one aspect, conjugates can include polyethylene amine (PEI), polyglycine, hybrids of PEI and polyglycine, polyethylene glycol (PEG) or methoxypolyethylene glycol (mPEG). A conjugate can also link a compound of the present technology to, for example, a label (fluorescent or luminescent) or marker (radionuclide, radioisotope and/or isotope) to comprise a probe of the present technology. Conjugates for use with a compound of the present technology can, in one aspect, improve in vivo half-life. Other exemplary conjugates for use with a compound of the present technology as well as applications thereof and related techniques include those generally described by U.S. Pat. No. 5,672,662, which is hereby incorporated by reference herein.

In another aspect, the present technology provides methods of identifying a target of interest including contacting the target of interest with a detectable or imaging effective quantity of a labeled compound of the present technology. A detectable or imaging effective quantity is a quantity of a labeled compound of the present technology necessary to be detected by the detection method chosen. For example, a detectable quantity can be an administered amount sufficient to enable detection of binding of the labeled compound to a target of interest including, but not limited to, one or more cellular proteins. Suitable labels are known by those skilled in the art and can include, for example, radioisotopes, radionuclides, isotopes, fluorescent groups, biotin (in conjunction with streptavidin complexation), and chemoluminescent groups. Upon binding of the labeled compound to the target of interest, the target may be isolated, purified and further characterized such as by determining the amino acid sequence.

The terms "associated" and/or "binding" can mean a chemical or physical interaction, for example, between a compound of the present technology and a target of interest. Examples of associations or interactions include covalent bonds, ionic bonds, hydrophilic-hydrophilic interactions, hydrophobic-hydrophobic interactions and complexes. Associated can also refer generally to "binding" or "affinity" as each can be used to describe various chemical or physical interactions. Measuring binding or affinity is also routine to those skilled in the art. For example, compounds of the present technology can bind to or interact with a target of interest or precursors, portions, fragments and peptides thereof and/or their deposits.

The examples herein are provided to illustrate advantages of the present technology and to further assist a person of ordinary skill in the art with preparing or using the compounds of the present technology or salts, pharmaceutical compositions, derivatives, metabolites, prodrugs, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

Example 1

Isolation and Purification of 13S,14R-Corydaline

All chemicals were purchased from the Sigma-Aldrich Chemical Company (Milwaukee, Wis.). Solvents were purchased from VWR International (Brisbane, Calif.) and were all of HPLC purity standard or higher. Proton and $^{13}$C NMR spectra were performed on a 300 MHz Bruker AC-300 plus NMR spectrometer with a TCPLink PC upgrade (INAC Computer, GmbH, Malsch, Germany). The NMR solvent was CDCl$_3$ unless otherwise specified. HPLC was performed using Waters 600 pumps and controller with a Waters 996 photodiode array detector. Solvent A was 0.05% trifluoroacetic acid in water. Solvent B was 0.04% trifluoroacetic acid in acetonitrile. The gradient was 0 to 100% B over 30 minutes, 2 mL/min. flow rate. The column was a C-18 reverse phase Vydac 254TP18 column of 25×0.46 cm. Flash chromatography was performed on a Teledyne Isco (Lincoln, Nebr.) CombiFlash Companion automated workstation. FT-IR spectra were obtained on a Perkin-Elmer FT-1600 spectrophotometer, and melting points were determined on a Cole Palmer Kofler block melting point apparatus. X-ray crystallography for absolute configuration was performed at the Center for Chemical Characterization and Analysis, Texas A&M University (College Stations, Tex.).

Figure 4:
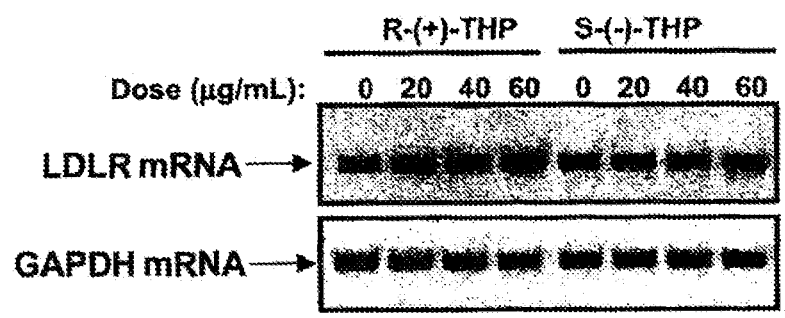
FIG. 4 shows the determination of the specific stereochemical requirements of +/−THP in the upregulation of LDLR mRNA expression.
Figure 5:
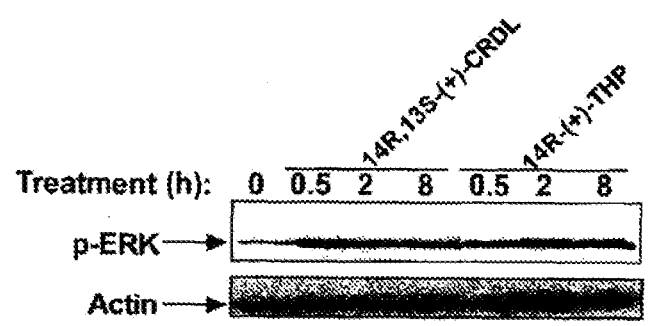
FIG. 5 shows Western blot analysis of the activation of ERK in HepG2 cells by 14R,13S-(+)-CRDL and 14R-(+)-THP.

It was determined by thin layer chromatography (1:1 hexane/ethyl acetate on normal phase silica plates then stained with iodine) that crude corydaline purchased from Sigma-Aldrich Corporation was in fact, a mixture of mainly corydaline ($R_f$=0.7) and a small amount of an unknown impurity ($R_f$=0.3) (see FIG. 5). Crude corydaline (250 mg) was then subjected to normal phase preparative flash chromatography. The crude material was loaded onto a 12 g Isco pre-packed silica column, eluted with 1:1 hexane/ethyl acetate, and 20 mL fractions were collected. Fractions 14 to 16 were pooled and collected. Removal of the eluting solvent in vacuo, afforded an off-white powder (100 mg), which was recrystallized from ethyl acetate/hexane to give 13S,14R-corydaline as off-white needles (m.p. 135 to 137° C.). This material was shown to be greater than 99% pure by reverse-phase HPLC (see FIG. 4). The proton NMR, $^{13}$C NMR, and mass spectra of this material were consistent with the structure of corydaline, and X-ray crystallography demonstrated that the absolute stereochemistry of this material was in fact 13S,14R-corydaline (see Example 5).

Example 2

Isolation and Purification of 14R-Tetrahydropalmatine (14R-THP)

From the silica column of Example 1, the later eluting fractions 22 to 26 containing the unknown impurity were pooled and collected. The solvent was removed in vacuo to afford 3 mg of a yellow powder. This was recrystallized from ethyl acetate/hexane to afford yellow crystals of 14R-tetrahydropalmatine (2 mg). This material was shown to be greater than 95% pure by reverse-phase HPLC. The proton NMR spectrum of this material showed that it was tetrahydropalmatine (THP), and X-ray crystallography demonstrated that the absolute stereochemistry was 14R-THP (see Example 6).

Example 3

Synthesis of 14R-Tetrahydropalmatine (THP) from Berberine (BBR)

14R-THP was prepared from BBR in four steps (see scheme below) starting by treating BBR with boron trichloride in methylene chloride. This deprotected only the methylene bridged catechol leaving the methoxy groups untouched. Methylation with methyl iodide and potassium carbonate in dry acetone then afforded the tetra-O-Me compound that was subsequently subjected to asymmetric hydrogenation with a suitable asymmetric hydrogenation catalyst to afford 14R-THP. The S-enantiomer may be similarly obtained. In addition, acid addition salts of 14R-THP may be prepared by exposure to acid during the hydrogenation or afterwards as a separate step.

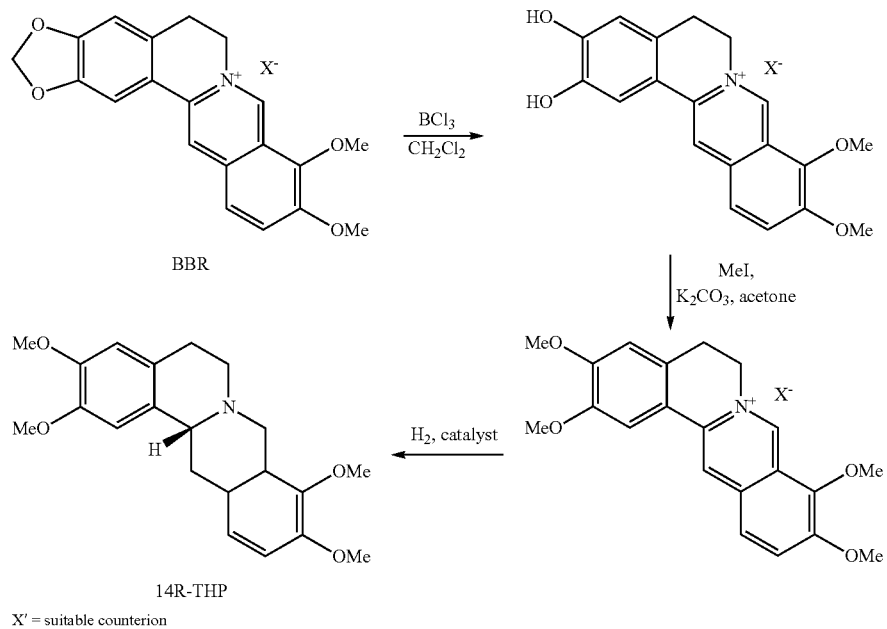

X' = suitable counterion

Exemplary catalysts that can be used for the synthesis are generally described by: Bunlaksananusorn, T., Polborn, K., Knochel, P., "New P,N ligands for asymmetric Ir-catalyzed reactions," Angew. Chemie, Intl. Ed. (2003), 42(33), 941-3943; Lu, S.-M. Han, X.-W., Zhou, Y.-G., "Asymmetric hydrogenation of quinolines catalyzed by iridium with chiral ferrocenyloxazoline derived N,P ligands," Advanced Synthesis & Catalysis (2004), 346(8), 909-912; Lu, S.-M., Wang, Y.-Q., Han, X.-W., Zhou, Y.-G., "Asymmetric hydrogenation of quinolines and isoquinolines activated by chloroforinates," Angew. Chemie, Intl. Ed. (2006), 45(33), 2260-2263; Wang, D.-W. Zeng, W.; Zhou, Y.-G., "Iridium-catalyzed asymmetric transfer hydrogenation of quinolines with Hantzsch esters," Tetrahedron: Asymmetry (2007), 18(9), 1103-1107; Xu Lijin; Lam Kim Hung; Ji Jianxin; Wu Jing; Fan Qing-Hua; Lo Wai-Hung; Chan Albert S C "Air-stable Ir—(P-Phos) complex for highly enantioselective hydrogenation of quinolines and their immobilization in poly(ethylene glycol) dimethyl ether (DMPEG)," Chem. Comm. (Cambridge, England) (2005), (11), 1390-2; and Wang, Y., Weissensteiner, W., Spindler, F., Anon, V. B., and Mereiter, K., "Synthesis and Use in Asymmetric Hydrogenations of Solely Planar Chiral 1,2-Disubstituted and 1,2,3-Trisubstituted Ferrocenyl Diphosphines: A Comparative Study," Organometallics, 2007, each of which is incorporated herein by reference in their entirety.

Example 4

Specific Rotation of *Corydalis* Compounds

The specific rotations of several substantially pure *Corydalis* compounds were determined by dissolving the compounds in ethanol and measuring their specific rotations using a Perkin-Elmer 241 Polarimeter. The results are shown in Table 2 below.

TABLE 2

| Chemical Name | Specific Rotation | MS: m/z (M$^+$ + 1)* |
| --- | --- | --- |
| (+)-CLMD | +21 | 370.1 |
| 14R,13S-(+)-CRDL | +312 | 370 |
| 14R-(+)-THP | +294 | 356 |
| 14S-(−)-THP | −256 | 356 |
| (+)-CRPM | +345 | 342.2 |

Example 5

X-Ray Diffraction of 14R, 13S-*Corydaline*

Crysalline 14R,13 S-corydaline prepared as in Example 1 was examined by X-ray diffraction as follows.

Data Collection.

A Leica MZ7 polarizing microscope was used to identify a suitable specimen from a representative sampling of materials. The chosen sample was then fixed to a nylon loop which in turn was mounted to a copper mounting pin. The mounted powder was then placed in a cold nitrogen stream (Oxford) maintained at 110K.

A BRUKER D8 GADDS general purpose three-circle X-ray diffractometer was employed for sample screening and data collection. The goniometer was controlled using the GADDS software suite (Microsoft Win 2000 operating system). The sample was optically centered with the aid of a video camera such that no translations were observed as the crystal was rotated through all positions. The detector was set at 5.0 cm from the crystal sample (MWPC Hi-Star Detector, 512×512 pixel). The X-ray radiation employed was generated from a Cu sealed X-ray tube ($K_\alpha$=1.54184 Å with a potential of 40 kV and a current of 40 mA) and filtered with a graphite monochromator in the parallel mode (175 mm collimator with 0.5 mm pinholes).

A rotation exposure was taken to determine crystal quality and the X-ray beam intersection with the detector. The beam intersection coordinates were compared to the configured coordinates and changes were made accordingly. The rotation exposure indicated acceptable crystal quality and the unit cell determination was undertaken. Sixty data frames were taken at widths of 0.5° with an exposure time of 10 seconds. Over 200 reflections were centered and their positions were determined. These reflections were used in the auto-indexing procedure to determine the unit cell. A suitable cell was found and refined by nonlinear least squares and Bravais lattice procedures and reported here in Tables 3 (14R, 13S-corydaline) and 4 (14R-tetrahydropalmitine). The unit cell was verified by examination of the hkl overlays on several frames of data, including zone photographs. No super-cell or erroneous reflections were observed.

After careful examination of the unit cell, a standard data collection procedure was initiated. This procedure consists of collection of one hemisphere of data collected using omega scans, involving the collection over 9000 0.5° frames at fixed angles for φ, 2θ, and χ (2θ=−28°, χ=54.73°, 2θ=−90°, χ=54.73°), while varying omega. Addition data frames were collected to complete the data set and collect Fiedel pairs. Each frame was exposed for 10 sec. The total data collection was performed for duration of approximately 24 hours at 110 K. No significant intensity fluctuations of equivalent reflections were observed.

After data collection, the crystal was measured carefully for size, morphology and color. Findings are reported in Table 3 and the structure is shown in FIG. 1.

TABLE 3

Crystal data and structure refinement for 14R,13S-Corydaline

| | |
|---|---|
| Empirical formula | C22 H27 N O4 |
| Formula weight | 369.45 |
| Temperature | 110(2) K |
| Wavelength | 1.54178 Å |
| Crystal system | Monoclinic |
| Space group | P2(1) |
| Unit cell dimensions | a = 8.9648(5) Å  α = 90°. |
| | b = 7.2517(4) Å  β = 92.903(4)°. |
| Volume | 970.46(9) Å³ |
| Z | 2 |
| Density (calculated) | 1.264 Mg/m³ |
| Absorption coefficient | 0.697 mm⁻¹ |
| F(000) | 396 |
| Crystal size | 0.10 × 0.05 × 0.05 mm³ |
| Theta range for data collection | 2.96 to 59.96°. |
| Index ranges | −10 <= h <= 9, −8 <= k <= 8, −16 <= l <= 16 |
| Reflections collected | 11406 |
| Independent reflections | 11406 [R(int) = 0.0000] |
| Completeness to theta = 59.96° | 99.5% |
| Absorption correction | Semi-empirical from equivalents |
| Max and min. transmission | 0.9660 and 0.9335 |
| Refinement method | Full-matrix least-squares on F² |
| Data/restraints/parameters | 11406/1/245 |
| Goodness-of-fit on F² | 1.032 |
| Final R indices [I > 2sigma(I)] | R1 = 0.0397, wR2 = 0.0983 |
| R indices (all data) | R1 = 0.0412, wR2 = 0.1097 |
| Absolute structure parameter | 0.032(75) |
| Extinction coefficient | 0.0331(9) |
| Largest diff. peak and hole | 0.365 and −0.455 e.Å⁻³ |

Example 6

X-Ray Diffraction of 14R-Tetrahydropalmatine

Figure 2:
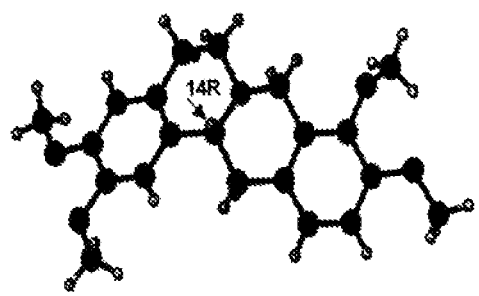
FIG. 2 shows the determination of the stereochemical configuration of THP by x-ray diffraction.

Crystalline 14R-tetrahydropalmatine prepared as in Example 2 was examined by X-ray diffraction by the procedure of Example 5. Findings are presented in Table 4 and the structure is shown in FIG. 2.

TABLE 4

Crystal data and structure refinement for 14R-Tetrahydropalmitine

| | |
|---|---|
| Empirical formula | C21 H25 N O4 |
| Formula weight | 355.42 |
| Temperature | 110(2) K |
| Wavelength | 1.54178 Å |
| Crystal system | Monoclinic |
| Space group | P2(1) |
| Unit cell dimensions | a = 15.1499(8) Å  α = 90°. |
| | b = 7.8440(4) Å  β = 98.770(3)°. |
| Volume | 1806.95(16) Å³ |
| Z | 4 |
| Density (calculated) | 1.306 Mg/m³ |
| Absorption coefficient | 0.729 mm⁻¹ |
| F(000) | 760 |
| Crystal size | 0.10 × 0.10 × 0.01 mm³ |
| Theta range for data collection | 2.91 to 59.97°. |
| Index ranges | −16 <= h <= 17, −8 <= k <= 8, −17 <= l <= 17 |
| Reflections collected | 13614 |
| Independent reflections | 13614 [R(int) = 0.0000] |
| Completeness to theta = 59.97° | 99.8% |
| Absorption correction | Semi-empirical from equivalents |
| Max and min. transmission | 0.9927 and 0.9307 |
| Refinement method | Full-matrix least-squares on F² |
| Data/restraints/parameters | 13614/1/477 |
| Goodness-of-fit on F² | 1.099 |
| Final R indices [I > 2sigma(I)] | R1 = 0.0430, wR2 = 0.0984 |
| R indices (all data) | R1 = 0.0627, wR2 = 0.1282 |
| Absolute structure parameter | 0.00(13) |
| Largest diff. peak and hole | 0.201 and −0.183 e.A⁻³ |

Example 7

Synthesis, Extraction and/or Plant Sources

Exemplary syntheses and identification related to isolation of a compound of the present technology are also generally described by Boudou et al., J. Org. Chem., 70, 9486-94 (2005), and Shaath et al. J. Org. Chem., 40, 1987-88 (1975), each of which are incorporated by reference herein.

Example 8

Design and Synthesis of Compounds

1. Preparation of Berberrubine from Berberine.

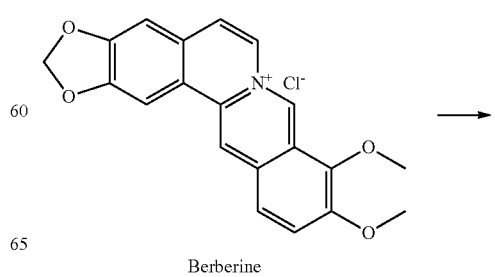

Berberine

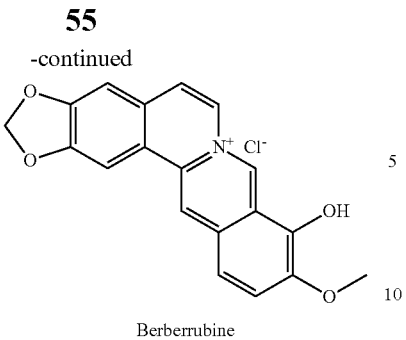

Berberrubine

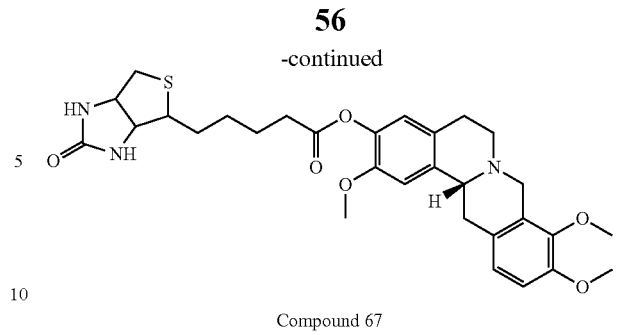

Compound 67

Berberine (1.0 g, 2.68 mmol) was heated at 190° in a dry oven under vacuum for 30 minutes. The crude product was recrystallized from EtOH to give berberrubine (0.6 g, yield 60%, confirmed by $^1$HNMR).

2. Preparation of Compound I1 from Berberrubine.

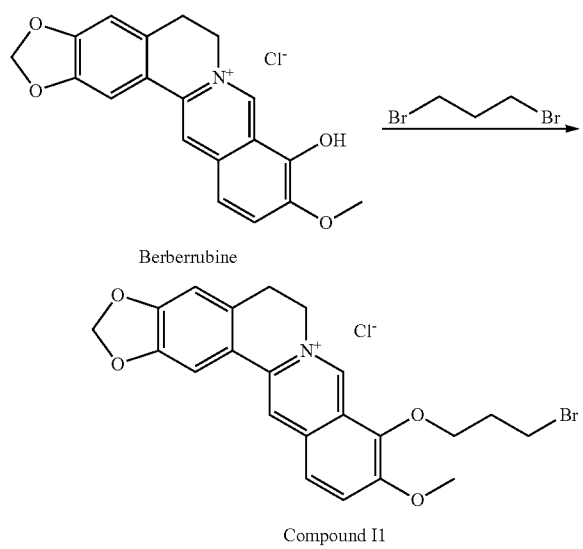

A suspension of berberrubine chloride (0.2 g, 0.5 mmol) and 1,3-dibromopropane (0.58 g, 2.8 mmol) in dry DMF was heat at 60°. The suspension was cooled to room temperature and ethyl ether was added. The precipitate was collected by filtration, rinsed with ethyl ether and dried under vacuum to give compound I1 as yellow solid (confirmed by $^1$H NMR). The reaction was rerun on 0.5 g scale (berberrubine), giving 0.55 g of crude compound I1 (yield 82%).

3. Preparation of Compound 67 from Corypalmine.

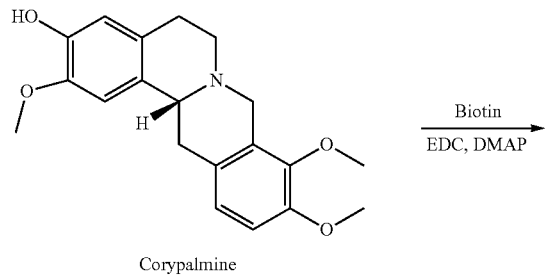

D-Biotin (105 mg, 0.43 mmol), EDC HCl (125 mg, 0.65 mmol) and DMAP (19 mg, 0.16 mmol) were dissolved together in a flask with a minimum volume of DMF (4.5 mL). Then corypalmine (25 mg, 0.073 mmol) was dissolved in this solution. After stirring for 3 hours, 0.5 mL sample of the reaction solution was taken out for testing. The sample was added to 10 mL H$_2$O and extracted with 10 mL EtOAc. The organic layer was dried with MgSO$_4$, filtered, and concentrated under vacuum. The product was subjected to LC-MS. The LC-MS information suggested formation of compound 67. The remaining reaction mixture was stirred overnight. The reaction mixture was subsequently extracted with EtOAc. The organic layer was dried with MgSO$_4$ and evaporated in vacuo. The yellow residue was isolated by preparative TLC to afford compound 67. Preparative HPLC was used to purify compound, 67. The purified product was confirmed by MS and HPLC to confirm the structure and the purity (92.1% and 93.1%).

4. Preparation of Compound I2 from Corypalmine.

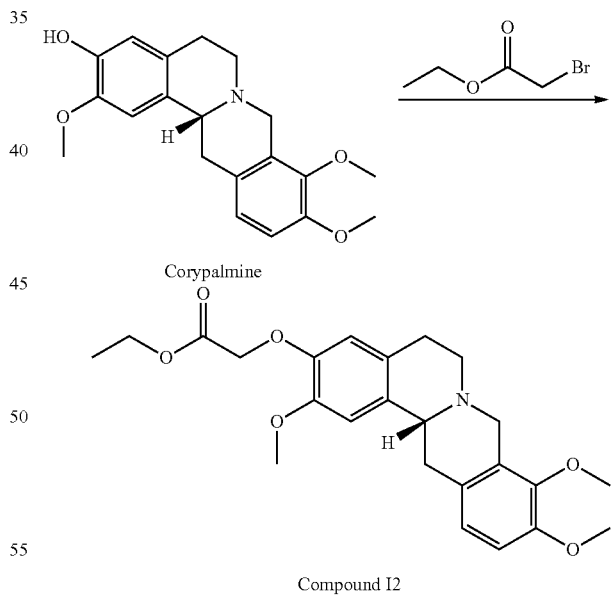

Corypalmine (0.068 g, 0.2 mmol) was added to 20 mL acetone and 5 mL ethanol. The suspension was refluxed for 1 hour to dissolve the starting material. Then 0.068 mg K$_2$CO$_3$ was added and the suspension was refluxed for 1 hour. Ethyl 2-bromoacetate (0.0244 mL, 0.22 mmol) was dissolved in 1 mL acetone and added into the reaction suspension in portions over 30 minutes. The resulting suspension was refluxed for 2 hours. The reaction was monitored by LC-MS. Part of the product was purified by preparative TLC.

5. Preparation of Compound 68 from Compound I2.

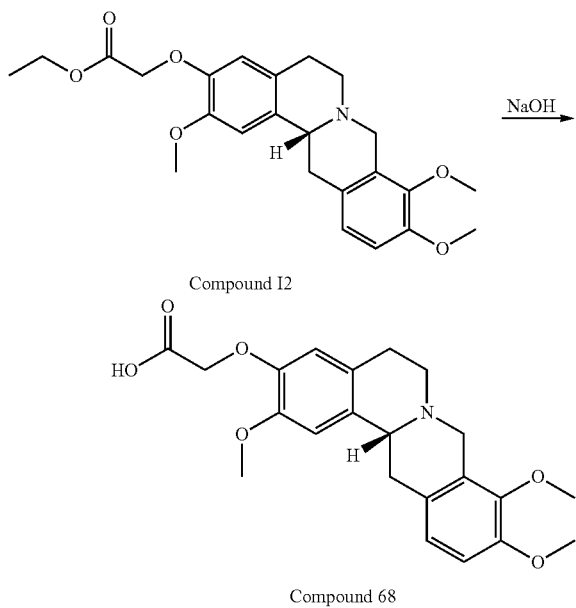

Compound I2

Compound 68

Compound I2, prepared according to procedure 4 was used without purification, and saponified with NaOH to prepare compound 68. This reaction was monitored by LC-MS. After standard workup.

6. Preparation for Compound I3 from Berberrubine.

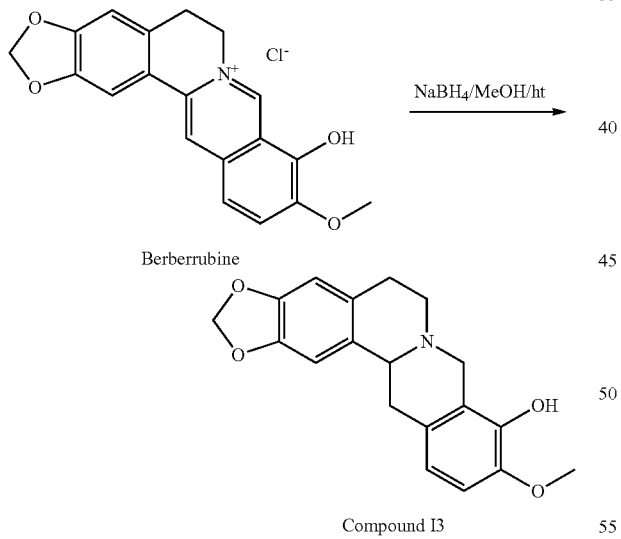

Berberrubine

Compound I3

Berberrubine (60 mg, 0.1 mmol) was added to 7 mL hot MeOH and stirred for 15 minutes at 60° C. Then NaBH$_4$ (8 mg, 0.21 mmol) was added to the mixture and the mixture was stirred at 60° for 15 minutes. Five mL H$_2$O was added to the solution to quench the reaction. The product I3 was extracted from the solution with CHCl$_3$ (10 mL×3). 10 mg grey solid was obtained, yield 20%. The isolated material gave the expected peak in MS and confirmed the structure. HPLC analysis suggested the purity was satisfactory for use without further purification.

7. Preparation for Compound 74 from Compound I1.

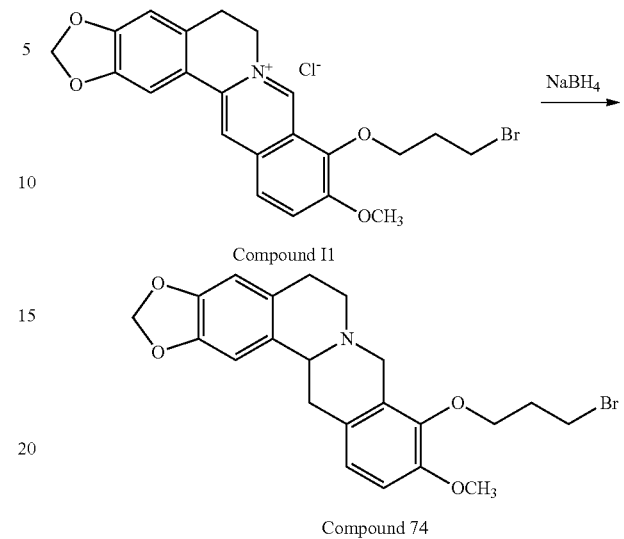

Compound I1

Compound 74

Compound I1 (80 mg, 0.168 mmol) was dissolved in CH$_3$OH (5 mL) in a 25 mL flask at rt. The color of the solution was dark red. Sodium borohydride (8 mg, 0.210 mmol) was added to this flask. The reaction solution became light yellow soon thereafter. The reaction was maintained at rf for 2 hours. Then H$_2$O (20 mL) was added to the solution to quench the reaction.

The solvent was evaporated under reduced pressure to remove all of the CH$_3$OH. Then 30 mL water were added to the residue and the solution was extracted with chloroform 3 times. The combined organic extracts were dried over anhydrous MgSO$_4$, filtered, and concentrated under vacuum. 40 mg product was obtained as yellow oil. (yield: 54.4%). The MS analysis confirmed the structure of compound 74. The HPLC analysis suggested the purity was 86%.

8. Preparation for Compound 77 from 14R-(+)-THP.

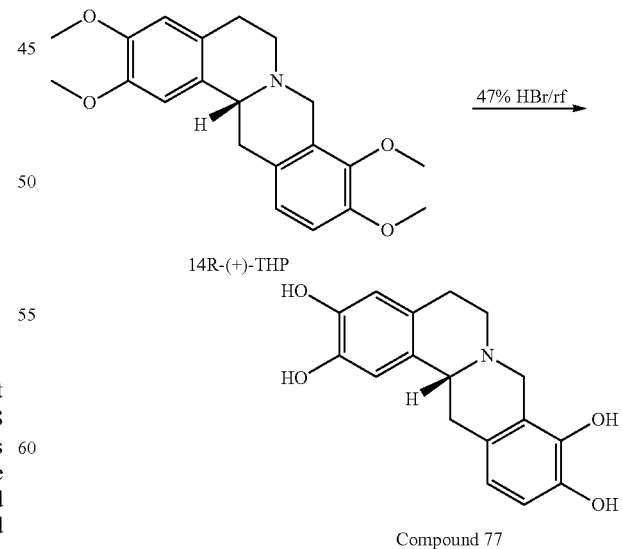

14R-(+)-THP

Compound 77

14R-(+)-THP (250 mg, 0.70 mmol) was added to 15 mL 47% HBr and stirred overnight at 100° C. Then the solution was cooled to room temperature, and the product was filtered off to give compound 77 as the hydrobromide salt.

9. Preparation for Compound 78 from 14R,13S-(+)-CDRL.

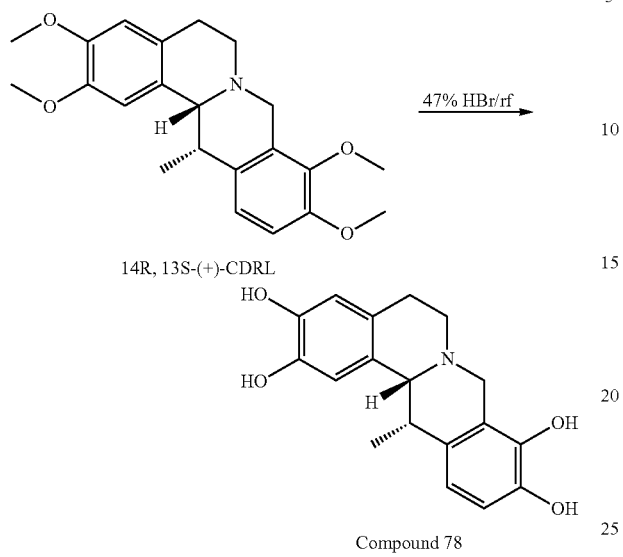

14R,13S-CDRL (200 mg, 0.54 mmol) was added to 10 mL 47% HBr and stirred overnight at 100° C. Then the solution was cooled to rt, and the product was filtered off to give compound 78 as the hydrobromide salt.

10. Preparation for Compound 79 from Berberrubine.

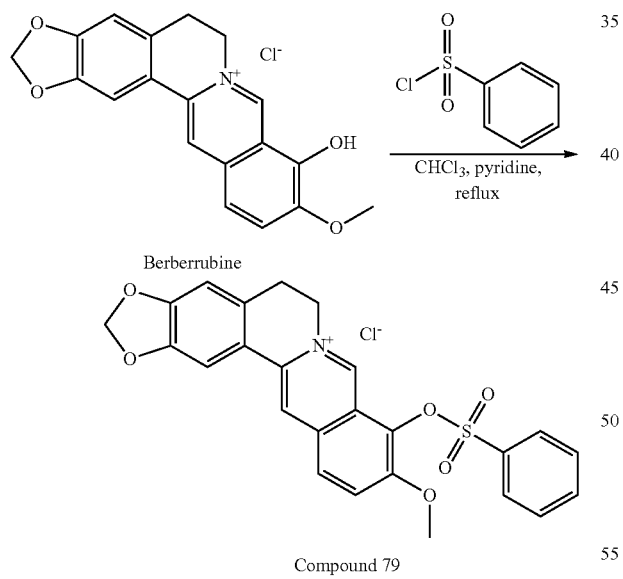

Berberrubine (248 mg, 0.693 mmol) was added to 5 mL CHCl₃ in a flask. The mixture was stirred and refluxed. Then benzenesulfonyl chloride (760 mg, 4.30 mmol) and pyridine (0.1 mL) were slowly added in. The reaction mixture was stirred at the same temperature for 2 hours, and subsequently cooled down to room temperature. The mixture was filtered to afford a yellow solid. The solid was washed with CHCl₃ 3 times and dried under vacuum to provide the final product, compound 79, (yellow solid, 204 mg). Compound 79 was used directly for the next step without purification.

11. Preparation for Compound 69 from Compound 79.

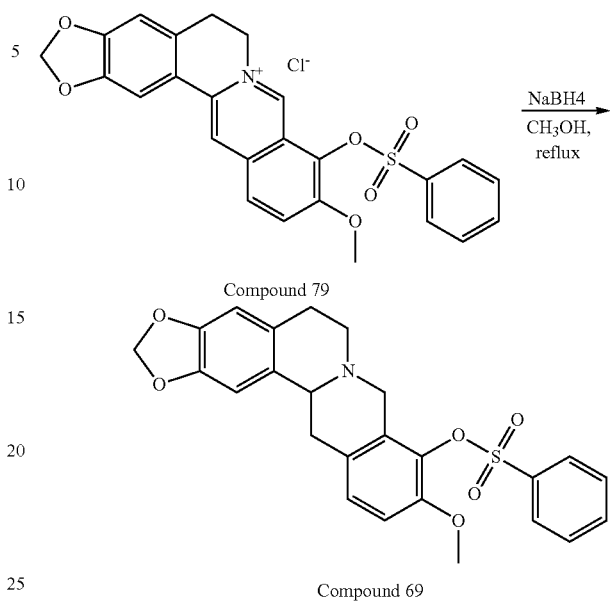

Compound 79 (132 mg, 0.265 mmol) was added in a flask with methanol (5 mL). Then the reaction mixture was heated to reflux to dissolve the starting material. Then NaBH₄ (42 mg, 1.11 mmol) was added slowly to the flask. The reaction mixture was stirred at the same temperature for 1 hour. Then it was cooled down to room temperature and then cooled in refrigerator for 4 hours. The mixture was filtered to afford light yellow crystals. The crystals were washed with H₂O 3 times and then dried under vacuum to provide the final product compound 69 (light yellow solid, 28.7 mg). NMR & MS analyses were consistent with the structure of compound 69.

Analogs of compound 69 may be readily made using commercially available substituted phenyl sulfonyl chlorides.

12. Preparation for Compound 80 from Berberrubine.

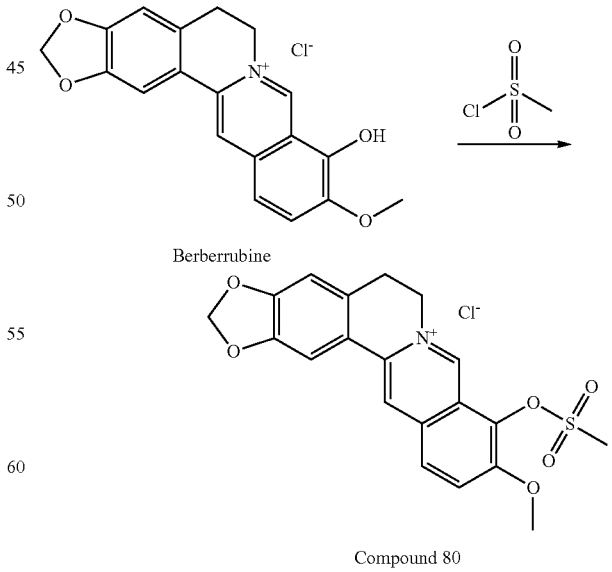

Berberrubine (0.5 g, 1.4 mmol) was dissolved in 40 mL CHCl₃ by refluxing. After stirring for about 30 minutes, the methanesulfonyl chloride (0.33 mL, 4.2 mmol) was added to the solution dropwise over 30 seconds. 10 minutes later, yellow solid appeared. The suspension was refluxed for 3 hours. After cooling, the suspension was filtered to provide a yellow solid. This intermediate (compound 80) was used directly for the next step without purification.

13. Preparation for Compound 71 from Compound 80.

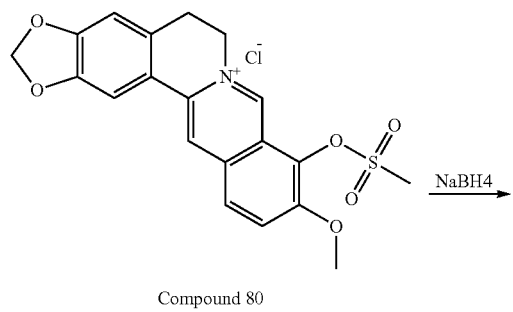

Compound 80

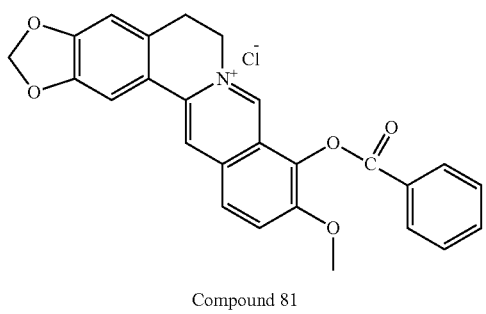

Compound 81

Berberrubine (300 mg, 0.84 mmol) was added to 15 mL CHCl$_3$ and stirred for 20 minutes at reflux. Benzoyl chloride (1180 mg, 8.4 mmol) and 0.1 mL pyridine were added to the solution. The mixture was stirred for 2 hours at reflux. Then product was filtered, washing with CHCl$_3$. The structure of compound 81w as confirmed by $^1$H NMR and MS.

15. Preparation for Compound 70 from Compound 81.

The reaction mixture of the previous reaction was continued by addition of NaBH$_4$ (8 mg, 0.21 mmol). Then the mixture stirred at 60° C. for 15 minutes. 5 mL H$_2$O was added to the solution to quench the reaction. The product was filtered from the solution. MS information suggested it was the desired structure.

16. Preparation for Compound I4 from Berberrubine.

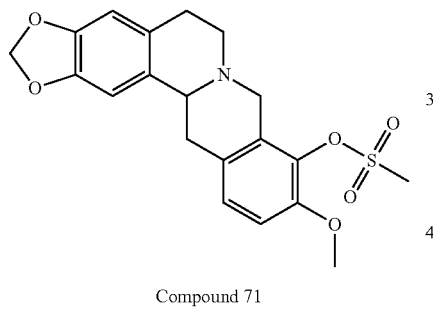

Compound 71

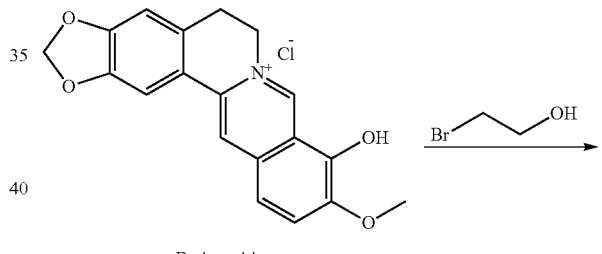

Berberrubine

Compound 80 was dissolved in 30 mL MeOH at reflux. NaBH$_4$ (0.052 g, 1.3 mmol) was added to the reaction. The reaction occurred immediately. The solution was refluxed for 2 hours and cooled down. Analysis by TLC suggested the transformation was complete. The reaction was left overnight, and a gray solid appeared the next morning. The suspension was filtered to afford the gray solid. NMR & MS were consistent with the structure of the compound 71.

14. Preparation for Compound 81 from Berberrubine.

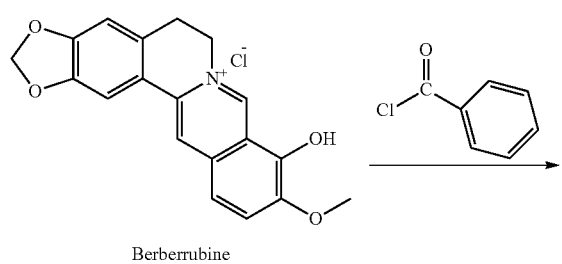

Berberrubine

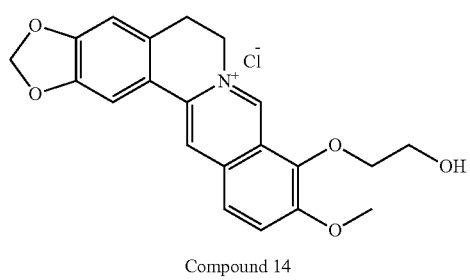

Compound 14

Berberrubine (100 mg, 0.279 mmol) was dissolved in 5 mL acetone. Then 2-bromoethanol (182 mg, 1.40 mmol) was added to the solution and stirred overnight at 60°. The anticipated yellow solid was appeared. Then the product was filtered from the reaction and used without further purification.

17. Preparation for Compound 82 from Compound I4.

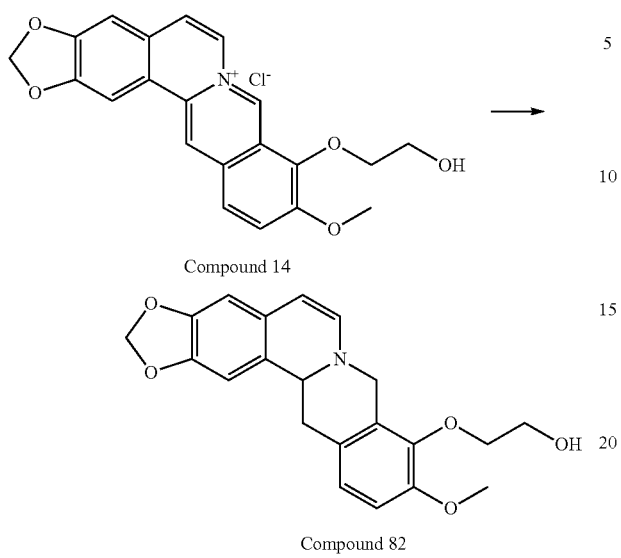

Compound 14

Compound 82

Compound I4 (60 mg, 0.186 mmol) was added to 5 mL hot MeOH and stirred for 15 minutes at 60°. Then NaBH₄ (9 mg, 0.24 mmol) was added to the solution. The color of the solution changed immediately. Then the mixture stirred at 60° for 15 minutes, then worked up and isolated as before.

18. Preparation for Compound I5 from Berberrubine.

Berberrubine

Compound 15

Berberrubine (400 mg, 1.12 mmol) was dissolved in CHCl₃ (14 mL) at reflux in a 50 mL flask. Then ethyl bromoacetate (1.5 g, 8.96 mmol) was added dropwise to the reaction. After the ethyl brommoacetate had been added entirely, the red solution changed into yellow. The reaction was maintained at reflux.

The solution was filtered and the solid was refluxed in CHCl₃ (15 mL) for 2 hours and filtered. $^1$H NMR information suggested the product was the desired structure I5.

19. Preparation for Compound 83 from Compound I5.

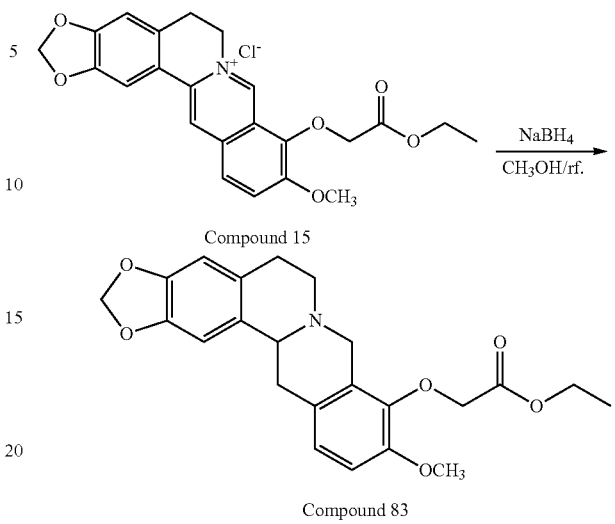

Compound 15

Compound 83

Compound I5 (250 mg, 0.563 mmol) was placed in 50 mL flask and CH₃OH (12 mL) was added in. The solution became clear after refluxing for a while. Then sodium boro-hydride (27.7 mg, 0.732 mmol) was added carefully into the same flask. TLC showed that the material has been disappeared. The reaction continued and was held at the same temperature for 40 minutes.

Water (30 mL) was added to the solution, stirred for half an hour. Then the solution was evaporated under vacuum until the CH₃OH was removed. Water (30 mL) was added into the solution, and the solution was extracted by chloroform for 3 times. The organic phase was washed by water and brine, the dried by anhydrous sodium sulfate, evaporated under vacuum to give compound 83.

20. Preparation for Compound I6 from Berberrubine.

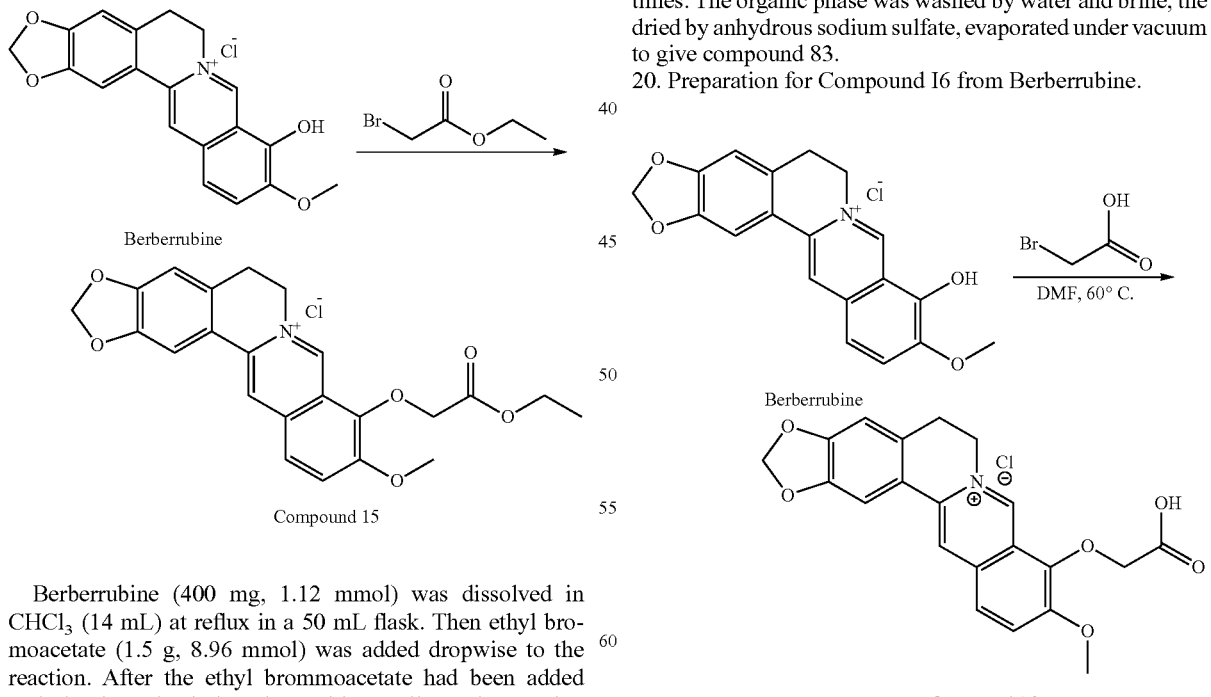

Berberrubine

Compound 16

Berberrubine (648 mg, 1.81 mmol) was added in a flask with 15 mL N,N-dimethylformamide in it. The mixture was stirred and heated to dissolve under 60° C. Then 2-bromoacetic acid (724 mg, 5.21 mmol) was slowly added in. The reaction mixture was stirred under the same temperature for 2 hours. Then it was cooled down to room temperature. The mixture was filtered to show the yellow solid. Then the solid was wash with CHCl₃ for 3 times and then dried in vacuum to show the product.

21. Preparation for Compound 111 from Compound I6.

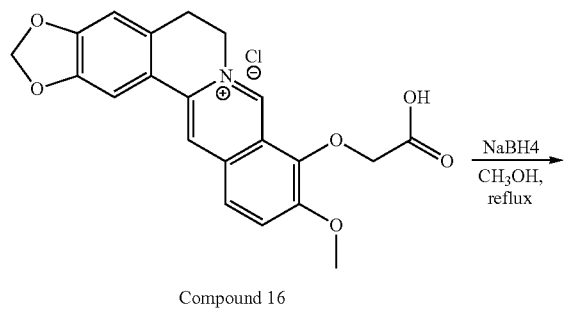

Compound 16

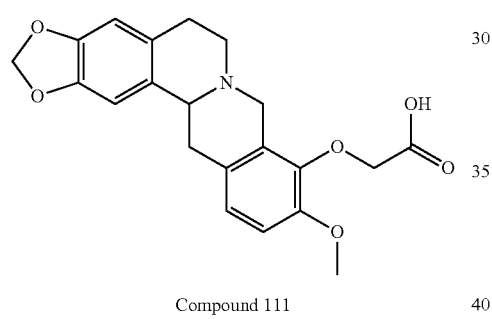

Compound 111

The compound I6 (109 mg, 0.262 mmol) was added in a flask with methanol (5 mL). Then the reaction mixture was heated to dissolve under reflux conditions. NaBH₄ (42 mg, 1.11 mmol) was added to the reaction slowly. The reaction mixture was stirred at the same temperature for 1 hour. Then it was cooled first to room temperature and then cooled in a refrigerator for 4 hours. The mixture was filtered to give clear crystals. The crystals were washed with Et₂O for 3 times and dried in vacuum to give the final product, compound 111.

22. Preparation for Compound I7 from Berberrubine.

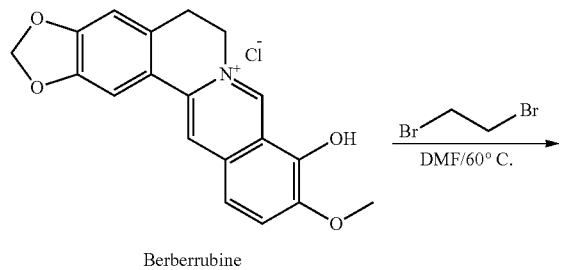

Berberrubine

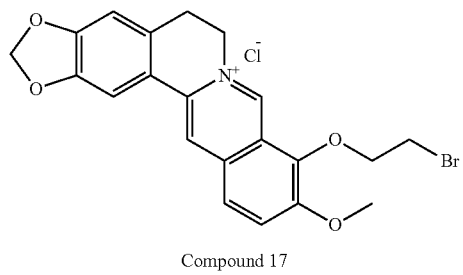

Compound 17

Berberrubine (1.0 g, 2.79 mmol) was dissolved in 5 mL DMF. Then 1,2-dibromoethane (5.3 g, 27.9 mmol) was added to the solution and stirred overnight at 60° C. Then 5 mL Et₂O was added to the solution. The product was filtered from the reaction and used directly for the next reaction.

23. Preparation for Compound I8 from Compound I7.

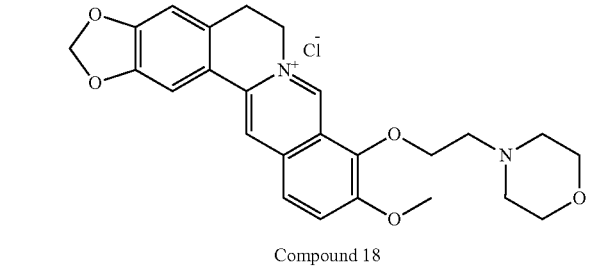

Compound 17

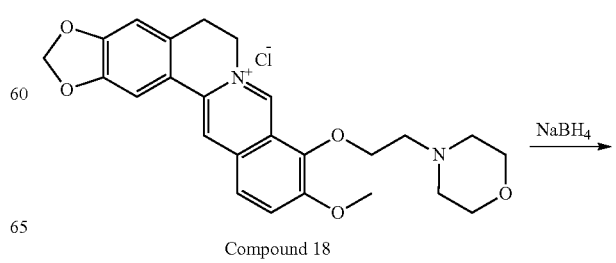

Compound 18

A solution of compound I7 (460 mg, 1 mmol), morpholine (870 mg, 10 mmol). K₂CO₃ (1.38 g, 10 mmol), DMF (30 mL) was heated at 60° C.

24. Preparation for Compound 88 from Compound I8.

Compound 18

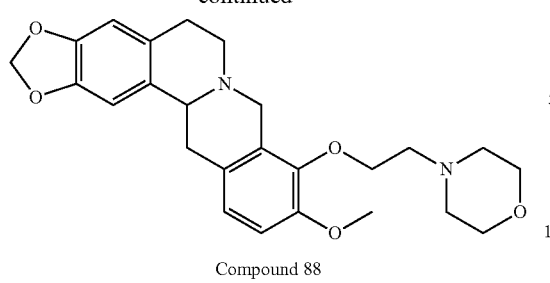

Compound 88

Compound I8 was dissolved in 50 mL methanol and heated to reflux. NaBH$_4$ was added to the refluxing solution. The reaction was monitored by TLC and was refluxed for 4 hours. The methanol was removed by vacuum distillation. The resulting residue was mixed with water and extracted with chloroform (3×). The organic layer was dried over NaSO$_4$. Then the chloroform was removed by vacuum distillation. The product was purified by silica gel column chromatography (acetone:CH$_2$Cl$_2$, from 4:1 to 1:1). The MS analysis was consistent with the desired product and the HPLC assay showed the purity was 96%. $^1$H NMR confirmed the structure was the desired one, compound 88.

25. Preparation for Compound 72 from Compound 78.

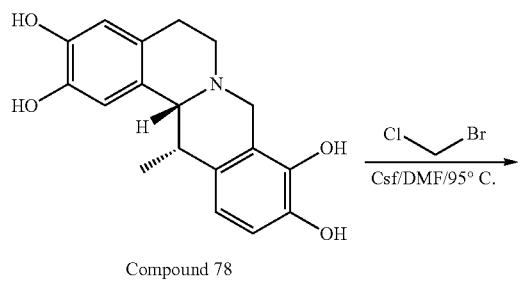

Compound 78

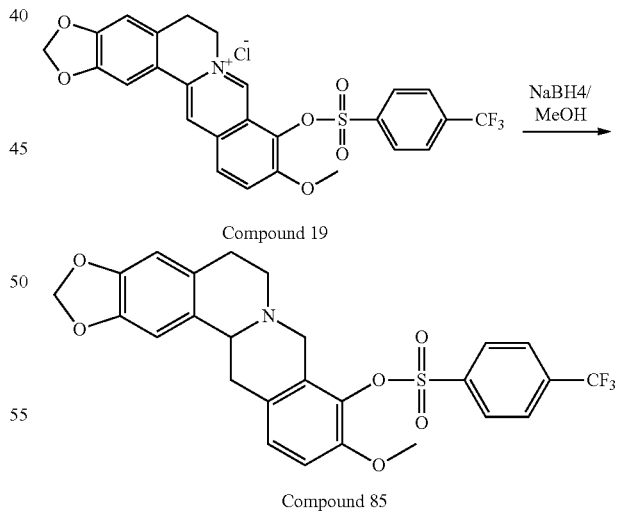

Compound 72

A solution of compound 78 (100 mg, 0.32 mmol) in 5 mL dry DMF under Ar was heated to 60° C. and a solution of CH$_2$BrCl (84 mg, 0.64 mmol) was added. The temperature of the reaction was raised to 95° C. 4 hours later, the reaction was analyzed by LC-MS and confirmed that the product was compound 72.

26. Preparation of Compound I9 from Berberrubine.

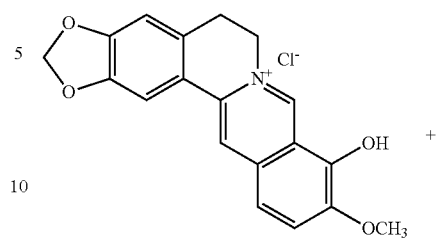

Berberrubine

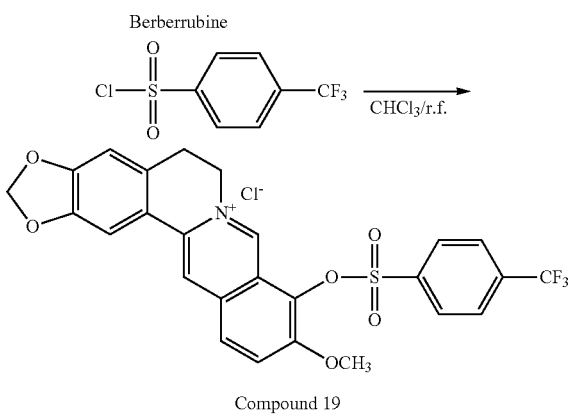

Compound 19

Berberrubine (300 mg, 0.84 mmol) was dissolved in 30 mL CHCl$_3$ at reflux. Then 4-(trifluoromethyl)benzene-1-sulfonyl chloride (300 mg, 1.23 mmol) was added to the solution and stirred for 7 hours. Then product was filtered, washed with CHCl$_3$ and dried. 400 mg product was obtained as yellow solid (yield: 84.2%). The intermediate was used directly without further purification.

27. Preparation of Compound 85 from Compound I9.

Compound 19

Compound 85

Compound I9 (140 mg, 0.247 mmol) was dissolved in 80 mL MeOH at reflux. NaBH$_4$ (50 mg, 1.322 mmol) was added to the solution and stirred for 1 hour. Then product was filtered, washed with MeOH, H$_2$O and hexane. 45 mg product was obtained as gray solid (yield: 34%). The MS & $^1$H NMR analysis of the product was consistent with the structure of compound 85.

28. Preparation of Compound I10 from Berberrubine.

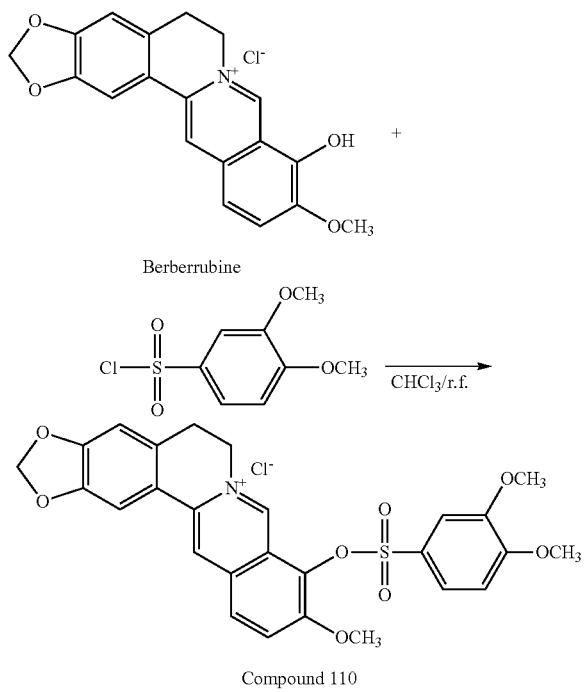

Compound I10

Berberrubine (300 mg, 0.84 mmol) was dissolved in 30 mL CHCl₃ at 70° C. Then 3,4-dimethoxybenzene-1-sulfonyl chloride (300 mg, 1.27 mmol) was added to the solution and stirred for 7 hours. Then product was filtered, washed by CHCl₃ and dried, 40 mg product was obtained as yellow solid. (yield: 17%). The intermediate was used directly without further purification.

29. Preparation of Compound 86 from Compound I10.

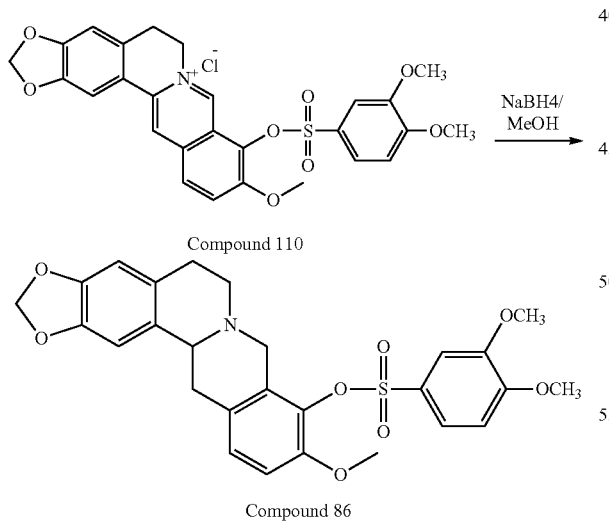

Compound 86

Compound I10 (80 mg, 0.14 mmol) was dissolved in 80 mL MeOH at 70° C. NaBH₄ (50 mg, 1.32 mmol) was added to the solution and stirred for 1 hours. Then product was filtered, washed with MeOH, H₂O and hexane. 25 mg product was obtained as gray solid. (MC0236-38-1; yield: 34%). The MS & ¹H NMR information suggested the product was the desired structure, compound 86.

30. Preparation of Compound I11 from Berberrubine.

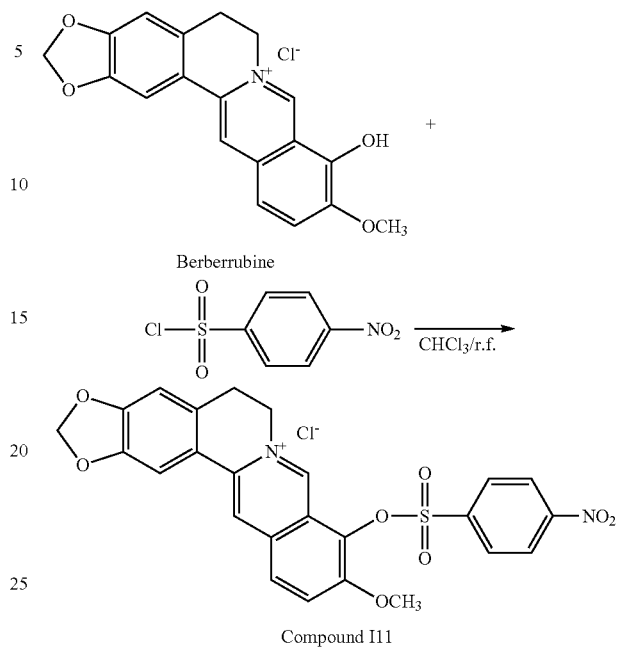

Compound I11

Berberrubine (300 mg, 0.84 mmol) was dissolved in 30 mL CHCl₃ at 70° C. Then 4-nitrobenzene-1-sulfonyl chloride (300 mg, 1.35 mmol) was added to the solution and stirred for 7 hours. Then product was filtered, washed by CHCl₃ and dried. 400 mg product was obtained as yellow solid. (yield: 87.7%) The intermediate was used directly without further purification.

31. Preparation of Compound 106 from Compound I11.

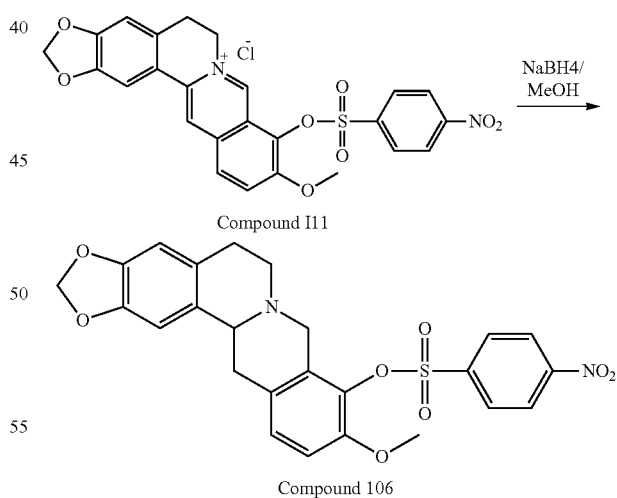

Compound 106

Compound I11 (110 mg, 0.202 mmol) was dissolved in CH₃OH (150 mL) at reflux in a 250 mL three-neck flask. Then sodium borohydride (100 mg, 2.64 mmol) was added carefully to the reaction. The mixture was refluxed for 3 hours. The solution was concentrated to 10 mL in vacuum, cooled in refrigerator, filtered, washed by water and n-hexane, dried in vacuum. 35 mg product was obtained as cyan solid. (yield: 33.9%)

32. Preparation of Compound 107 from Compound I12.

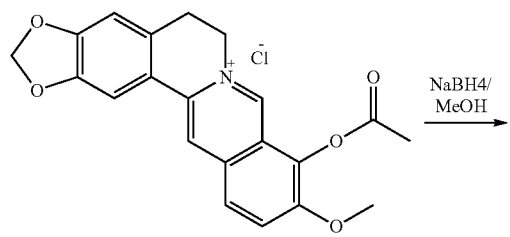

Compound I12

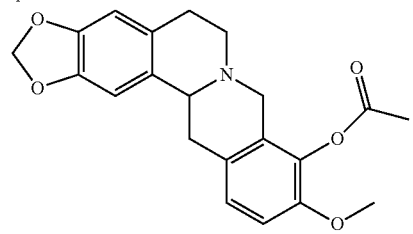

Compound 107

Compound I12 (130 mg, 0.325 mmol) was dissolved in CH₃OH (150 mL) at reflux in a 250 mL three-neck flask. Then sodium borohydride (120 mg, 3.17 mmol) was added carefully. The reaction continued for 3 hours. The solution was concentrated to 10 mL in vacuum, cooled in refrigerator, filtered, washed by water and n-hexane, dried in vacuum.

33. Preparation of Compound I13 from Berberrubine.

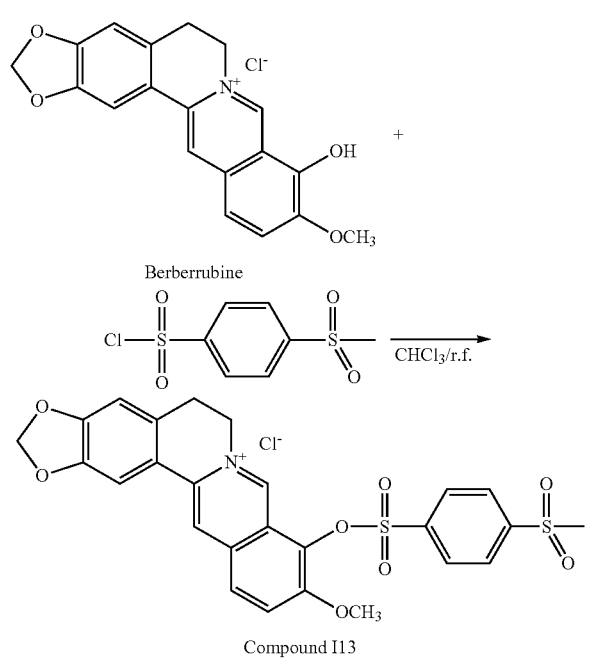

Berberrubine (200 mg, 0.56 mmol) was dissolved in 30 mL CHCl₃ at 70° C. Then 4-(methylsulfonyl)benzene-1-sulfonyl chloride (350 mg, 1.37 mmol) was added to the solution and stirred for 7 hours at 70° C. Then product was filtered, washed by CHCl₃ and dried. 200 mg product was obtained as yellow solid. (yield: 62%) The intermediate compound I13 was used directly without further purification.

34. Preparation of Compound 87 from Compound I13.

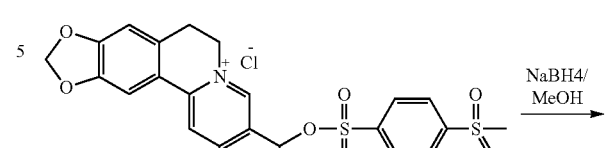

Compound I13

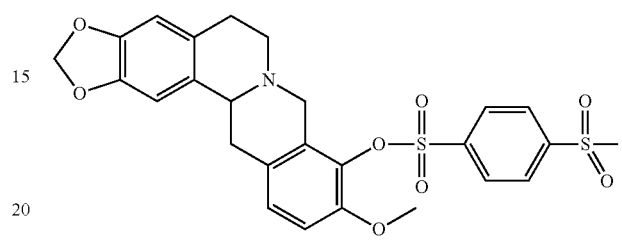

Compound 87

Compound I13 (110 mg, 0.19 mmol) was dissolved in 80 mL MeOH at reflux. Then NaBH₄ (70 mg, 1.85 mmol) was added to the solution and stirred for 1 hour at 70° C. Then most of solvent was removed, and product was filtered, washed by MeOH, H₂O and hexane. 40 mg product was obtained as gray solid (yield: 38.8%).

35. Preparation of Compound I14 from Berberrubine.

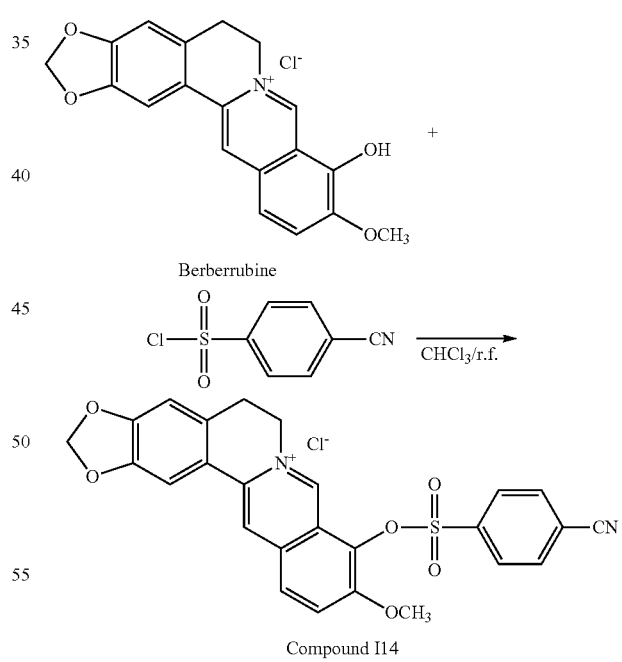

Berberrubine (220 mg, 0.61 mmol) was dissolved in 30 mL CHCl₃ at 70° C. Then 4-cyanobenzene-1-sulfonyl chloride (340 mg, 1.68 mmol) was added to the solution and stirred for 7 hours at 70° C. Then product was filtered, washed by CHCl₃ and dried. 110 mg product was obtained as yellow solid. (yield: 35%) The interniediate compound I14 was used directly without further purification.

36. Preparation of Compound 108 from Compound I14.

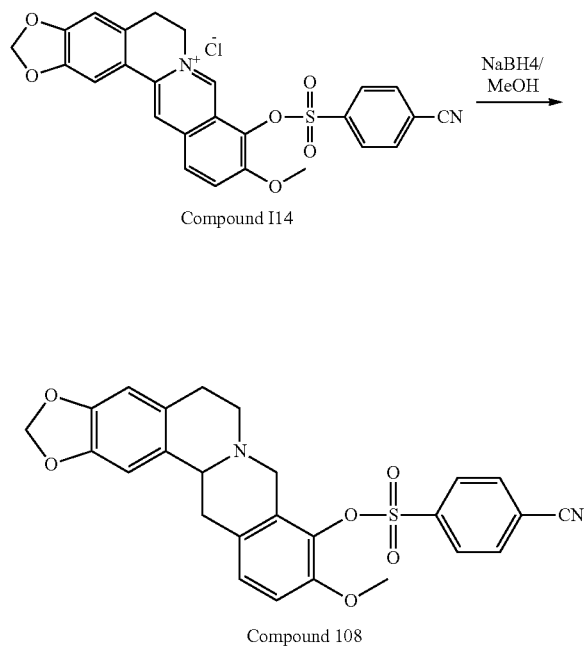

Compound I14

Compound 108

37. Preparation of Compound 109 from Compound I15.

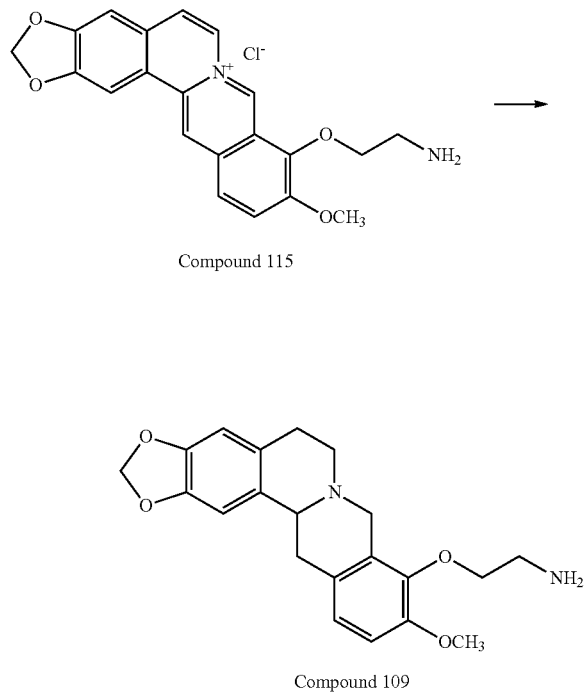

Compound I15

Compound 109

The Compound I15 (150 mg, 0.449 mmol) was added in a flask with methanol (15 mL). Then the reaction mixture was heated to dissolve under reflux condition. Then NaBH₄ (276 mg, 7.30 mmol) was added in slowly. The reaction mixture was stirred under the same temperature for 2 hours. Then it was evaporated in vacuum and the solid was washed with water for 24 hours. The mixture was filtered and then dried to obtain 112 mg compound 109 as red solid. (Yield: 81.2%) The ¹H NMR & MS information suggested the product was the desired structure.

38. Preparation of Compound 110 from Compound 109.

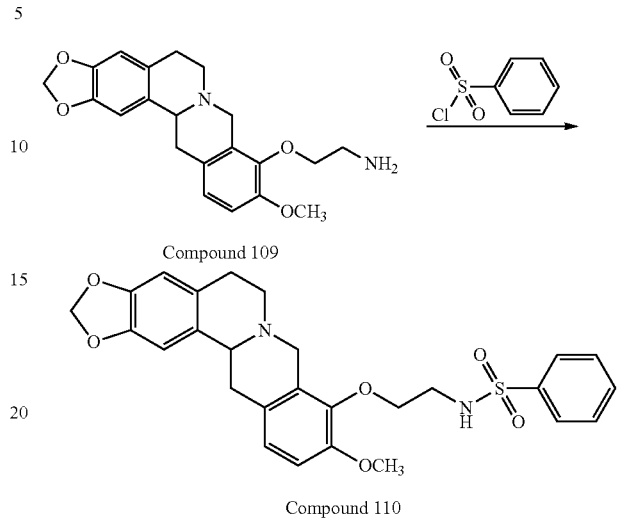

Compound 109

Compound 110

Compound 109 (17 mg, 0.0461 mmol) was added to a flask with 13 mL CHCl₃ in it. The mixture was stirred and heated to reflux to dissolve it. Then benzenesulfonyl chloride (55 mg, 0.311 mmol) and pyridine (0.3 mL) were slowly added in. The reaction mixture was stirred at the same temperature for 2 hours. Then the reaction was cooled down to room temperature. The MS assay suggested the compound 110 was formed.

39. Preparation of Compound I17 from Compound I16.

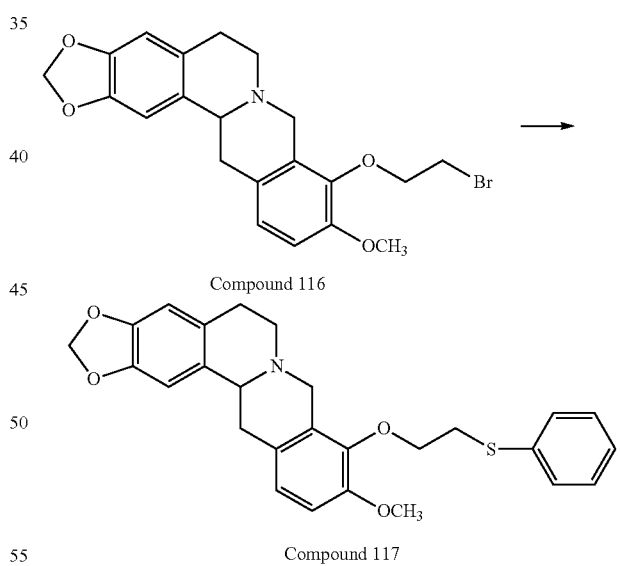

Compound 116

Compound 117

A solution of thiophenol (229 mg, 1.8 mmol) in 5 mL toluene was treated with DBU (317 mg, 1.8 mmol). 5 minutes later, 15 mL of toluene solution, which contained compound I16 (300 mg, 0.6 mmol), was added to the reaction solution. The reaction was stirred overnight. The LC-MS information suggested the desired product compound I17 was formed. Then product was purified by silica gel column chromatogram. (300 mL CH₂Cl₂, then 300 mL CH₂Cl₂: acetone=3:1). 200 mg product was obtained. (Yield: 62.3%) The ¹H NMR & MS information suggested the product was the desired structure.

40. Preparation of Compound 105 from Compound I17.

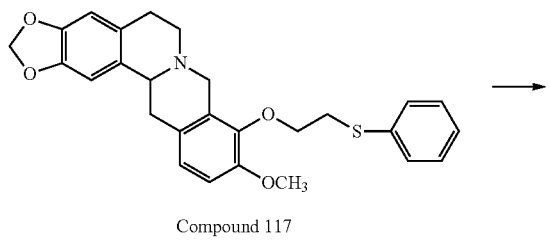

Compound 117

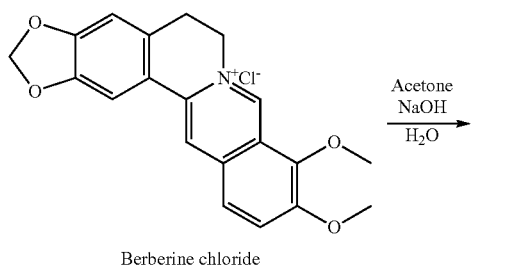

Compound 105

The compound I17 (80 mg, 0.17 mmol) was dissolved in 5 mL AcOH and heated at 60° C. 10 minutes later, the 2 mL 30% H₂O₂ was added in. 1.5 hours later, the reaction was sent to LC-MS assay.

41. Preparation of Compound 1.

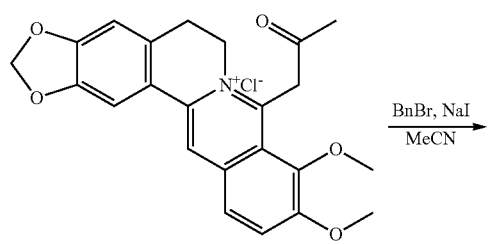

Berberine chloride

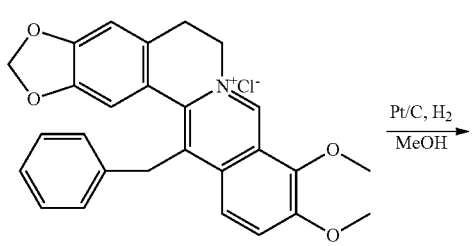

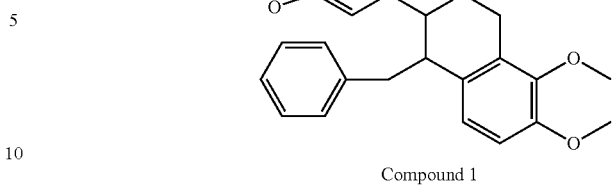

Compound 1

Berberine chloride→B

To a stirred solution of NaOH (4 g, 100 mmol) in water (20 mL) was added berberine chloride (2.0 g, 5.4 mmol) at room temperature. Then acetone (1.6 mL) was added slowly at same temperature and stirred for 1 hour. TLC analysis indicated the completion of the reaction. The reaction solution was filtered, sufficiently washed with 80% methanol and dried to give 1.7 g of B.

B→C

To a stirred solution of B (1.7 g, 4.3 mmol) in MeCN (20 mL) was added KI (450 mg, 2.7 mmol) at room temperature. The reaction mixture was heated to reflux and BnBr (1.5 mL, 12.7 mmol) was added. Then the reaction was refluxed for 4 hours with stirring. TLC analysis indicated the completion of the reaction. The solvent was removed and residue was purified by column chromatography to give 1.6 g of C.

C→Compound 1

To a stirred solution of C (1.6 g, 3.7 mmol) in MeOH was added Pt/C (200 mg) and stirred overnight under H₂ at ambient temperature. After filtering, the filtrate was concentrated to give crude product. The solid was washed with MeOH to give 500 mg of pure Compound 1. $^1$H NMR (CDCl$_3$): δ 7.20-7.14 (m, 3H); 6.88-6.85 (m, 2H); 6.76 (s, 1H); 6.61 (s, 1H); 6.52 (d, 1H, J=8.4 Hz); 6.00 (d, 1H, J=8.4 Hz); 5.94 (s, 2H); 4.28 (d, 11-1, J=16.2 Hz); 3.86 (s, 3H); 3.80 (s, 3H); 3.77 (br, 1H); 3.56 (d, 11-1, J=16.2 Hz); 3.25-3.07 (m, 3H); 2.73-2.57 (m, 4H). MS: m/z (APCI-ESI) 430.2 (M$^+$+1).

42. Preparation of Compounds, Salt Formation.

General Procedure:

14R,13S-(+)-CRDL or 14R-(+)-THP was dissolved in solvent and mixed with a suitable amount of acid to form the corresponding acid addition salt.

Hydrochloride Salts (Compounds 2 and 6)

To a stirred solution of MeOH (2 mL) and DCM (2 mL) contained HCl (2 mmol) was added 14R-(+)-THP (100 mg, 0.28 mmol) or 14R,13S-(+)-CDRL (100 mg, 0.27 mmol) at room temperature and stirred for 2 hours. The solvent was removed to give 110 mg of the salt.

Sulfate Salts (Compounds 3 and 7)

To a stirred solution of MeOH (2 mL) and DCM (2 mL) contained H₂SO₄ (15 μL, 0.28 mmol) was added 14R-(+)-THP (100 mg, 0.28 mmol) or 14R,13S-(+)-CDRL (100 mg, 0.27 mmol) at room temperature and stirred for 2 hours. The solvent was removed to give 110 mg of the salt.

Citrate Salts (Compounds 4 and 8)

To a stirred solution of MeOH (2 mL) and DCM (2 mL) contained citric acid (19.6 mg, 0.093 mmol) was added 14R-(+)-THP (100 mg, 0.28 mmol) or 14R,13S-(+)-CDRL (100 mg, 0.27 mmol) at room temperature and stirred for 2 hours. The solvent was removed to give 110 mg of the salt.

Maleate Salts (Compounds 5 and 9)

To a stirred solution of MeOH (2 mL) and DCM (2 mL) contained maleic acid (16.2 mg, 0.14 mmol) was added 14R-(+)-THP (100 mg, 0.28 mmol) or 14R,13S-(+)-CDRL (100 mg, 0.27 mmol) at room temperature and stirred for 2 hours. The solvent was removed to give 110 mg of the salt.

43. Preparation of Compound 10.

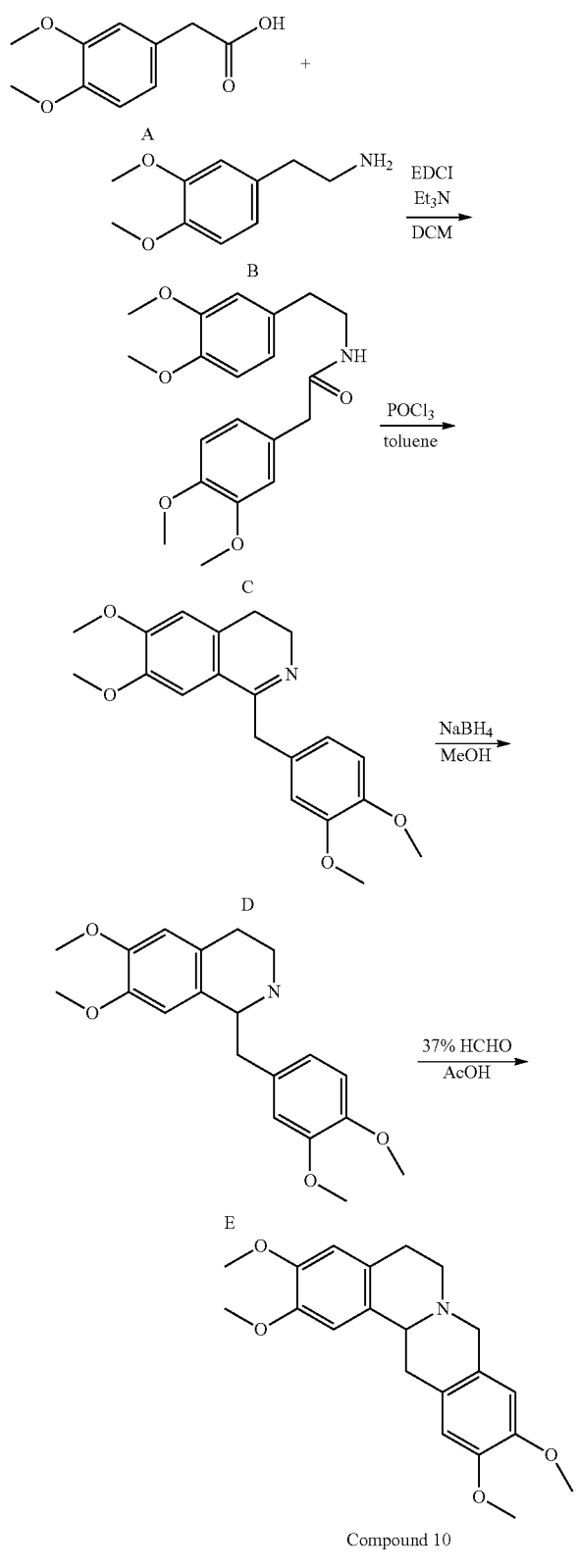

A+B→C

To the solution of A (650 mg, 3.31 mmol), B (630 mg, 3.48 mmol) in DCM (30 mL) was added EDCI (1.27 g, 6.62 mmol) and Et$_3$N (1.0 g, 9.93 mmol) at 20° C. and the solution was stirred overnight. TLC analysis indicated the completion of the reaction. Water was added, and the organic layer was collected, dried and concentrated to give 1.0 g of C.

C→D

To a stirred solution of C (1.0 g. 2.78 mmol) in toluene (10 mL) was added POCl$_3$ (3 mL) at ambient temperature. The reaction mixture was refluxed for 4 hours with stirring. When the reaction was completed, the solvent and excess POCl$_3$ were evaporated off. The residue was poured into ice water and adjusted pH>7 with Na$_2$CO$_3$. The solution was extracted with EtOAc, and the organic layer was dried and concentrated to give the crude product, which was directly used in the next step without further purification.

D→E

To a stirred solution of D in MeOH (15 mL) was added NaBH$_4$ (130 mg, 3.42 mmol) at 10° C. The reaction mixture was stirred for 6 hours at room temperature. TLC analysis indicated the completion of the reaction. The solvent was removed and the residue was extracted with EtOAc and water. The organic layer was dried and concentrated to give crude E.

E→Compound 10

Crude E was added to 37% HCHO (5 mL) and AcOH (10 mL). The reaction mixture was heated to 100° C. and stirred for 8 hours. TLC analysis indicated the completion of the reaction. The water and AcOH was removed. The residue was extracted with Na$_2$CO$_3$ aqueous and EtOAc. The organic phase was dried and concentrated to crude product. The crude material was further purified by column chromatography to give 200 mg of compound 10. $^1$H NMR (CDCl$_3$): δ 6.74 (s, 1H); 6.67 (s, 1H); 6.62 (s, 1H); 6.58 (s, 1H); 3.97-3.92 (m, 1H,); 3.89-3.85 (m, 12H); 3.71 (5, 1H); 3.65-3.56 (m, 1H); 3.27-3.22 (m, 1H); 3.18-3.14 (m, 2H); 2.87-2.78 (m, 1H); 2.68-2.63 (m, 2H). MS: m/z (APCI-ESI) 356.1 (M$^+$+1).

44. Preparation of Compound 11.

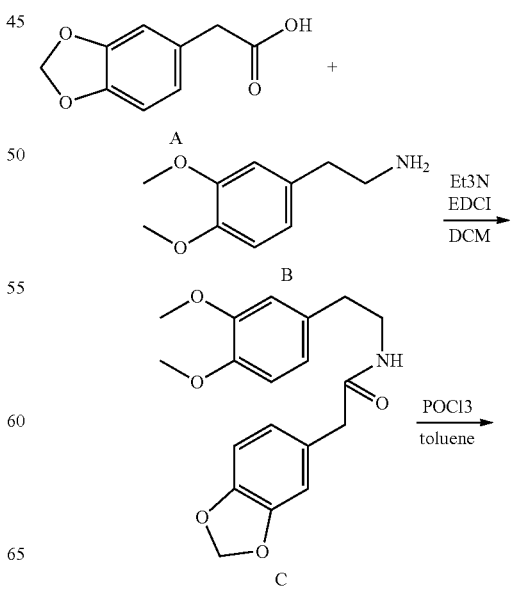

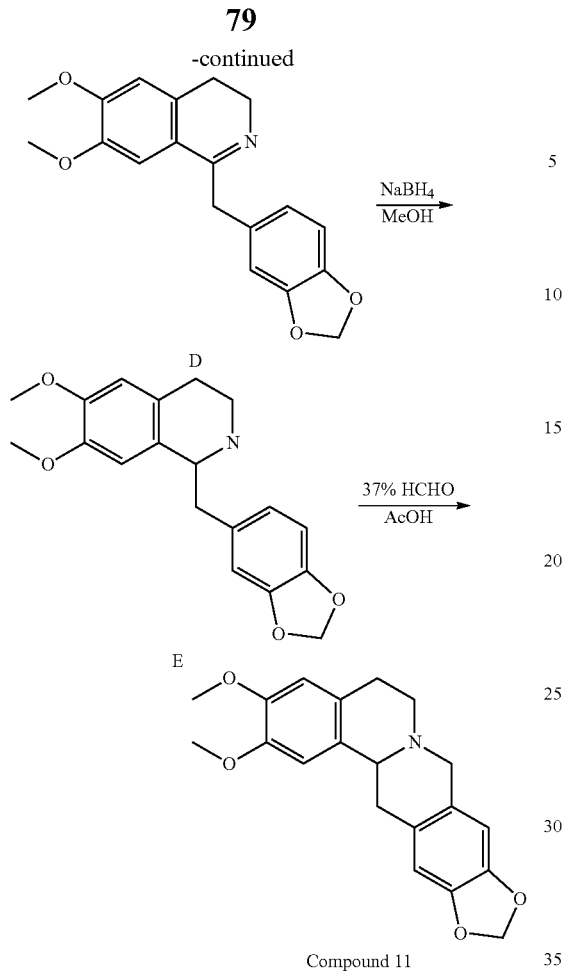

Compound 11

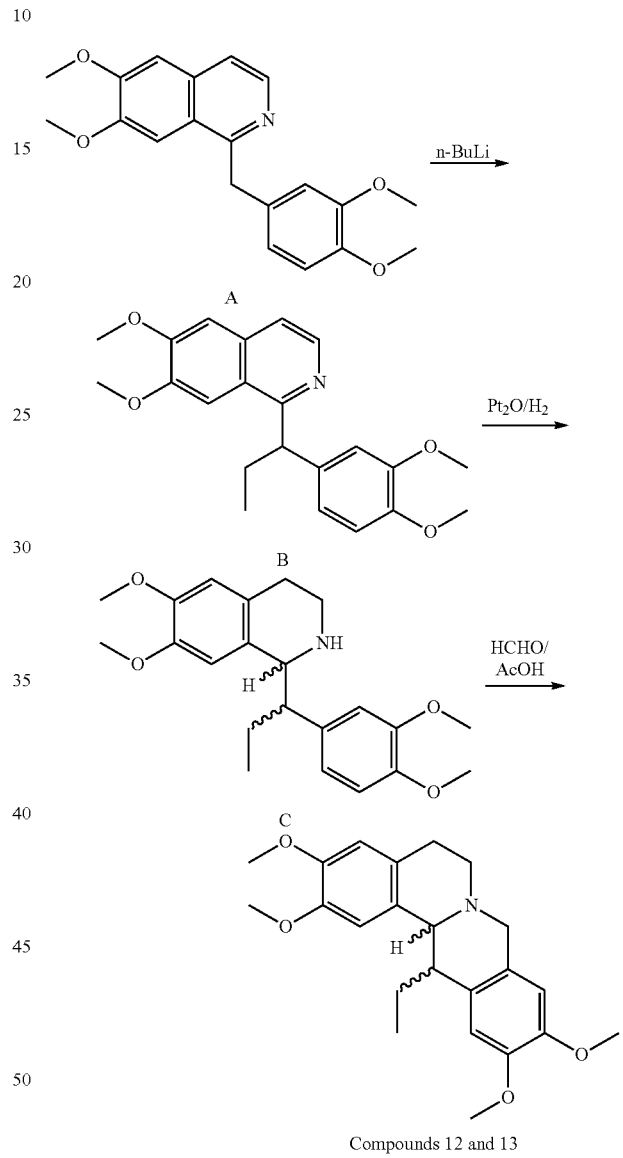

Compounds 12 and 13

A+B→C

To the solution of A (1.8 g, 10 mmol), B (1.81 g, 10 mmol) in DCM (20 mL) was added EDCI (2.83 g, 12 mmol) and Et$_3$N (1.0 g, 9.93 mmol) at 20° C. and the solution was stirred overnight. TLC analysis indicated the completion of the reaction. Water was added, and the organic layer was collected, dried and concentrated to give 1.9 g of C.

C→D

To a stirred solution of C (0.3 g, 0.88 mmol) in toluene (10 mL) was added POCl$_3$ (1.5 mL) at ambient temperature. The reaction mixture was refluxed for 4 hours with stirring. When the reaction was completed, the solvent and excess POCl$_3$ were evaporated off. The residue was poured into ice water and adjusted pH>7 with Na$_2$CO$_3$. The solution was extracted with EtOAc, and the organic layer was dried and concentrated to give the crude product, which was directly used in the next step without further purification.

D→E

To a stirred solution of D in MeOH (8 mL) was added NaBH$_4$ (130 mg, 3.42 mmol) at 10° C. The reaction mixture was stirred for 6 hours at room temperature. TLC analysis indicated the completion of the reaction. The solvent was removed and the residue was extracted with EtOAc and water. The organic layer was dried and concentrated to give crude E (123 mg).

E→Compound 11

Crude E was added to 37% HCHO (10 mL) and AcOH (10 mL). The reaction mixture was heated to 100° C. and stirred for 8 hours. TLC analysis indicated the completion of the reaction. The water and AcOH was removed. The residue was extracted with Na$_2$CO$_3$ aqueous and EtOAc. The organic phase was dried and concentrated to crude product. The crude material was further purified by column chromatography to give 78 mg of compound 11. MS (M$^+$+1): 340.1. $^1$H NMR (CDCl$_3$) δ=6.73 (s, 1H), 6.61-6.63 (s, 2H), 6.55 (s, 1H), 6.70-5.91 (s, 2H), 3.89-3.94 (m, 1H), 3.87-3.90 (s, 6H), 3.54-3.670 (m, 2H), 3.10-3.25 (m, 3H), 2.80-2.86 (t, 1H), 2.60-2.70 (m, 2H).

45. Preparation of Compounds 12 and 13.

A→B

To the solution of A (1.0 g, 2.95 mmol) in dry THF was added n-BuLi (2.5 M, 3.25 mmol) dropwise at the protection of N$_2$ under the temperature of −30° C., stirring for 1 hour, then CH$_3$CH$_2$Br (386 mg, 3.54 mmol) was added dropwise. After the addition was finished, the solution was stirring at room temperature for 1.5 hours. NH$_4$Cl was added and the resolution was removed in vacuo. Water was added and the product was extracted with CH$_2$Cl$_2$, purified by flash chromatography to afford 968 mg, yield: 89.5%.

B→C

To the solution of B (500 mg) in AcOH was added PtO$_2$ (45 mg), stirring overnight under an atmosphere of H$_2$ (8 atm) at 25° C. When the reaction was finished, the solution was concentrated in vacuo. Then water was added, and the solution was adjusted to PH=7 using $Na_2CO_3$. The solution was extracted with $CH_2Cl_2$ and the crude product was purified by flash chromatography to afford 300 mg of product, yield: 59.3%.

C→Compounds 12 and 13

C (300 mg) was dissolved in the solution of HCHO (37%, 20 mL) and AcOH (20 mL). The reaction mixture was heated to reflux for 6 hours and then concentrated in vacuo and extracted by $CH_2Cl_2$. The residue was purified by flash chromatography and TLC to afford two products, one is compound 12 (15.6 mg), and another is compound 13 (19.6 mg). Compound 12. $^1$H NMR (CDCl$_3$) δ=6.71 (s, 1H), 6.66 (s, 1H), 6.60 (s, 1H), 6.51 (s, 1H), 4.41-4.05 (m, 1H), 4.01-3.95 (m, 1H), 3.85 (s, 6H), 3.83 (s, 6H), 3.76-3.71 (m, 1H), 3.10-3.05 (m, 1H), 2.95-2.94 (m, 2H), 2.10-1.90 (m, 2H), 1.24 (m, 1H), 0.95-0.90 (t, 3H). MS: Ink (APCI-ESI): 384.2 (M$^+$+1). Compound 13. $^1$H NMR (CDCl$_3$) δ=6.70 (s, 1H), 6.68 (s, 1H), 6.60 (s, 1H), 6.58 (s, 1H), 4.40-3.98 (m, 1H), 3.88 (s, 6H), 3.85 (s, 6H), 3.74 (s, 1H), 3.10-3.08 (m, 1H), 3.10-3.08 (m, 1H), 2.98-2.92 (m, 1H), 2.60-2.54 (m, 2H), 1.42-1.37 (m, 2H), 0.83-0.78 (t, 3H). MS: m/z (APCI-ESI): 384.2 (M$^+$+1).

46. Preparation of Compounds 14 and 15.

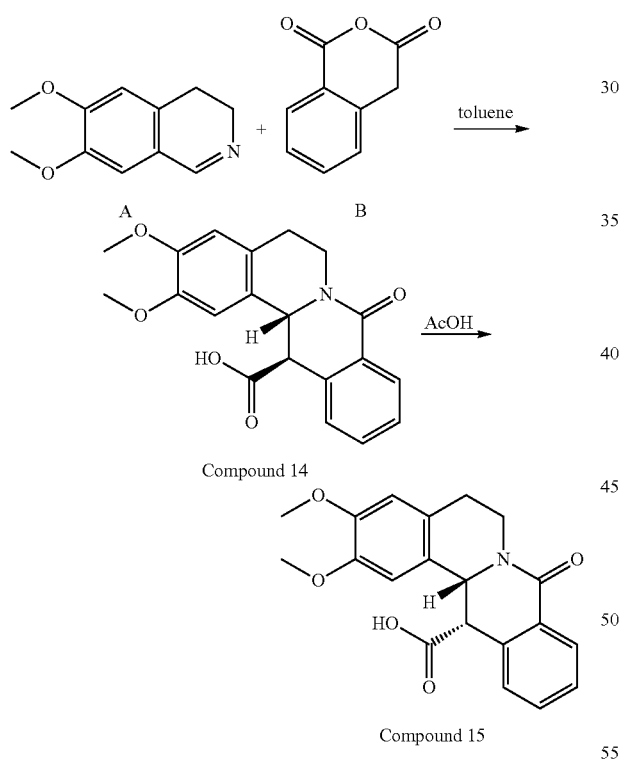

Compound 14

Compound 15

To a solution of 210 mg (1.10 mmol) of A in 10 mL of toluene, 180 mg (1.11 mmol) of B was added and the mixture was heated at reflux for 2 hours. The mixture was allowed to cool to room temperature and was left to stand overnight. The crystals formed was collected, washed with diethyl ether and dried under vacuum. 350 mg of crude product 14 was obtained. $^1$H NMR (300 MHz, DMSO-d$_6$) δ=7.88 (d, J=8.7 Hz, 1H), 7.56-7.51 (m, 1H), 7.41-7.39 (m, 2H). 6.94 (s, 1H), 6.75 (s, 1H), 5.27 (d, J=6.0 Hz, 1H), 4.6-4.58 (m, 2H), 3.69 (s, 3H), 3.68 (s, 3H), 3.18-3.09 (m, 1H), 3.01-2.90 (m, 1H), 2.72-2.67 (br, 1H). MS: m/z (APCI-ESI): 354.1 (M$^+$+1).

A solution of 200 mg (0.57 mmol) of compound 14 in AcOH was heated at reflux for 24 hours. The solvent was evaporated, and the residue was purified by washed with PE and EtOAc to yield 90 mg of compound 15. $^1$H NMR (300 MHz, DMSO-d$_6$) δ=7.97 (d, J=7.6 Hz, 1H), 7.59-7.43 (m, 3H), 7.12 (s, 1H), 6.78 (s, 1H), 5.19 (d, J=4.4 Hz), 4.80 (d, 5.7 Hz), 4.45 (d, J=4.5 Hz), 3.77 (s, 3H), 3.75 (s, 3H), 2.90-2.66 (m, 3H). MS: m/z (APCI-ESI): 354.1 (M$^+$+1).

47. Preparation of Compound 16.

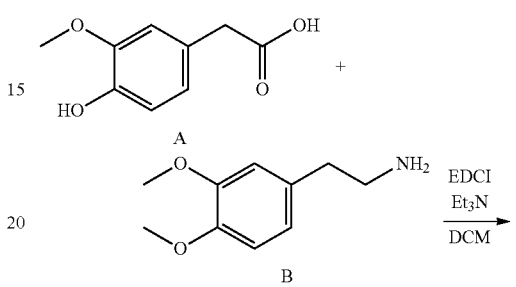

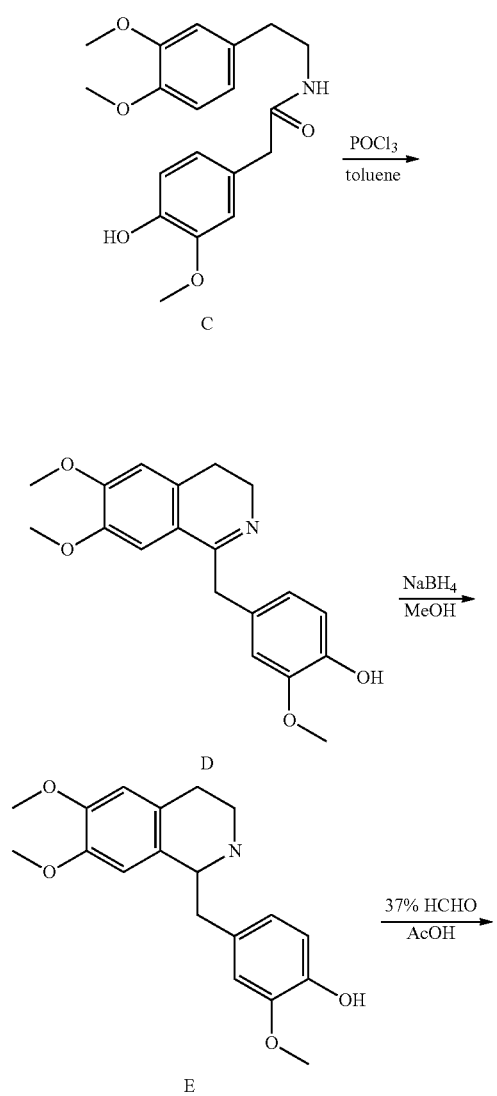

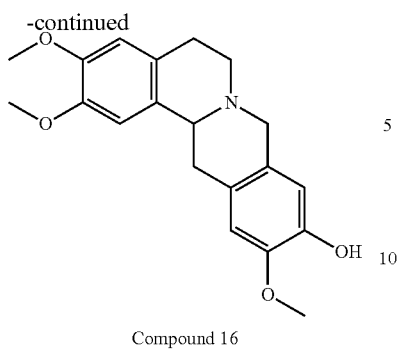

Compound 16

A+B→C

To the solution of A (1.82 g, 10 mmol), B (1.81 g, 10 mmol) in DCM (30 mL) was added EDCI (2.83 g, 12 mmol) and Et₃N (1.0 g, 9.93 mmol) at 20° C. and the solution was stirred overnight. TLC analysis indicated the completion of the reaction. Water was added, and the organic layer was collected, dried and concentrated to give 2.85 g of C.

C→D

To a stirred solution of C (2.55 g, 7.2 mmol) in toluene (20 mL) was added POCl₃ (8 mL) at ambient temperature. The reaction mixture was refluxed for 4 hours with stirring. When the reaction was completed, the solvent and excess POCl₃ were evaporated off. The residue was poured into ice water and adjusted pH>7 with Na₂CO₃. The solution was extracted with EtOAc, and the organic layer was dried and concentrated to give the crude product, which was directly used in the next step without further purification.

D→E

To a stirred solution of D in MeOH (30 mL) was added NaBH₄ (1.0 g) at 10° C. The reaction mixture was stirred for 6 hours at room temperature. TLC analysis indicated the completion of the reaction. The solvent was removed and the residue was extracted with EtOAc and water. The organic layer was dried and concentrated to give crude E (1.3 g).

E→Compound 16

Crude E (0.6 g) was added to 37% HCHO (15 mL) and AcOH (15 mL). The reaction mixture was heated to 100° C. and stirred for 8 hours. TLC analysis indicated the completion of the reaction. The water and AcOH was removed. The residue was extracted with Na₂CO₃ aqueous and EtOAc. The organic phase was dried and concentrated to crude product. The crude material was further purified by column chromatography to give 160 mg of compound 16. MS (M+1): 342.1. ¹HNMR (CDCl₃) δ (ppm) 6.64 (s, 1H), 6.62-6.63 (s, 2H), 6.73 (s, 1H), 3.89-3.94 (m, 1H), 3.86-3.94 (s, 3×3H), 3.55-3.66 (m, 2H), 3.11-3.27 (m, 3H), 2.84-2.88 (t, 1H), 2.60-2.69 (m, 2H).

48. Preparation of Compound 17.

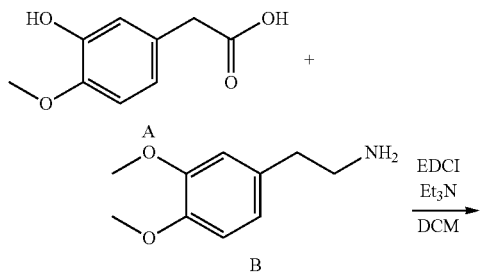

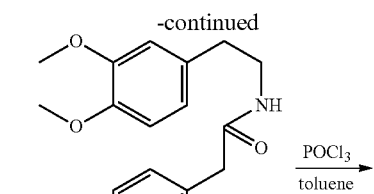

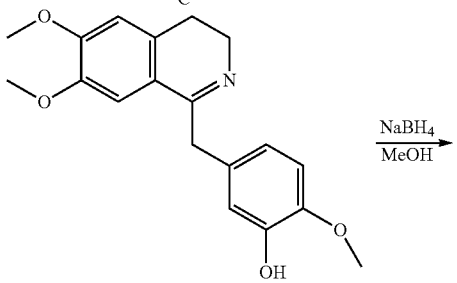

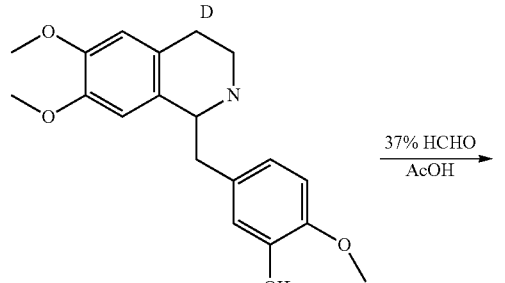

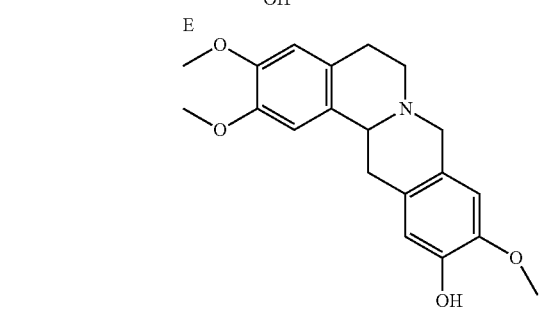

Compound 17

A+B→C

To the solution of A (1.82 g, 10 mmol), B (1.81 g, 10 mmol) in DCM (30 mL) was added EDCI (2.83 g, 12 mmol) and Et₃N (1.0 g, 9.93 mmol) at 20° C. and the solution was stirred overnight. TLC analysis indicated the completion of the reaction. Water was added, and the organic layer was collected, dried and concentrated to give 2.3 g of C.

C→D

To a stirred solution of C (0.25 g, 0.72 mmol) in toluene (10 mL) was added POCl₃ (1.5 mL) at ambient temperature. The reaction mixture was refluxed for 4 hours with stirring. When the reaction was completed, the solvent and excess POCE were evaporated off. The residue was poured into ice water and adjusted pH>7 with Na₂CO₃. The solution was extracted with EtOAc, and the organic layer was dried and concentrated to give the crude product, which was directly used in the next step without further purification.

D→E

To a stirred solution of D in MeOH (8 mL) was added NaBH$_4$ (130 mg, 3.42 mmol) at 10° C. The reaction mixture was stirred for 6 hours at room temperature. TLC analysis indicated the completion of the reaction. The solvent was removed and the residue was extracted with EtOAc and water. The organic layer was dried and concentrated to give crude E (140 mg).

E→Compound 17

Crude F, (120 mg) was added to 37% HCHO (5 mL) and AcOH (5 mL). The reaction mixture was heated to 100° C. and stirred for 8 hours. TLC analysis indicated the completion of the reaction. The water and AcOH was removed. The residue was extracted with Na$_2$CO$_3$ aqueous and EtOAc. The organic phase was dried and concentrated to crude product. The crude material was further purified by column chromatography to give 200 mg of compound 17. MS (M+1): 342.1. $^1$H NMR (CDCl$_3$) δ (ppm) 6.72-6.73 (s, 2H), 6.611 (s, 1H), 6.554 (s, 1H), 3.89-3.94 (m, 1H), 3.87-3.90 (s, 3×3H), 3.55-3.69 (m, 2H), 3.11-3.24 (m, 3H), 2.79-2.84 (t, 1H), 2.60-2.68 (m, 2H).

49. Preparation of Compounds 19 and 20.

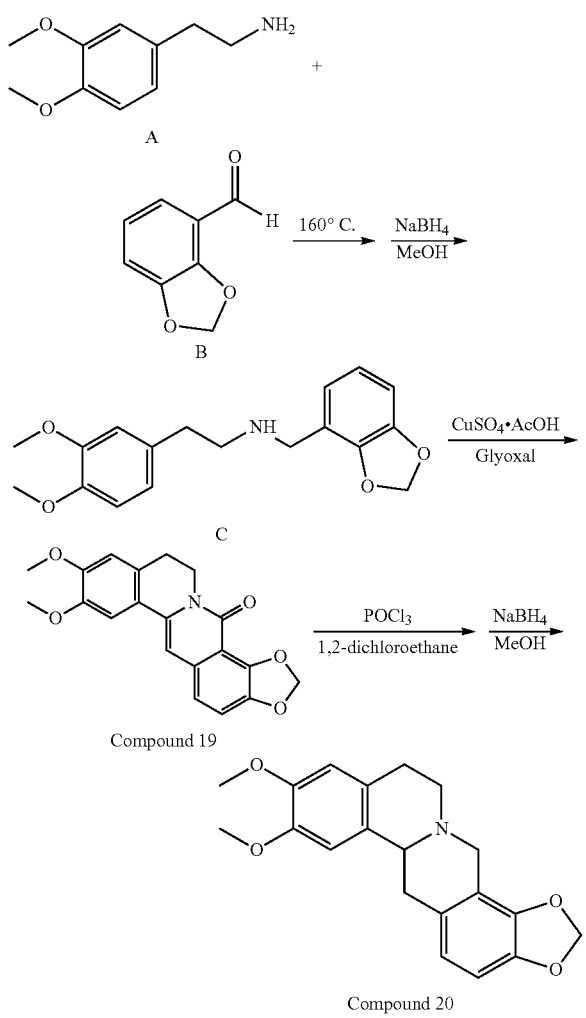

Compound 19

Compound 20

A+B→C

A mixture of 200 mg (1.10 mmol) of A and 165 mg (1.10 mmol) of B was heated to 160° C. for 1 hour, and then cooled; the oil was dissolved in 2 mL of MeOH. 50 mg (1.32 mmol) of NaBH$_4$ was added in portions. After 1 hour at room temperature, the reaction was completed, and the solvent was removed under vacuum. The residue was dissolved with ethyl acetate, washed with water, brine, and dried over anhydrous sodium sulfate. 320 mg of pure product was obtained. Yield: 92.4%.

C→Compound 19

To a solution of 150 mg (0.48 mmol) of C in 2 mL of AcOH was added 1.0 g of CuSO$_4$, followed 2 mL of aqueous (30%) glyoxal. The reaction mixture was heated to reflux for 3 hours. The most solvent was removed under vacuum, and then extracted with EtOAc. The organic phase was washed with water, brine and dried over anhydrous NaSO$_4$. The solvent was removed under vacuum, the crude product was purified with column chromatograph eluting with EA: MeOH=20: 1.35 mg of the title compound was obtained. Yield: 21.0%. $^1$H NMR (CDCl$_3$, 300 MHz) δ=8.81 (s, 1H), 8.41 (br, 1H), 7.99 (d, J=8.7 Hz), 7.51 (d, J=8.7 Hz), 6.94 (s, 1H), 6.35 (s, 2H), 4.66 (t, J=5.7 Hz, 2H), 3.81 (s, 3H), 3.78 (s, 3H), 3.06 (t, J=6.2 Hz, 2H). MS: m/z (APCI-ESI): 352.1 (M$^+$+1).

Compound 19→Compound 20

To a suspension of 14 mg (0.04 mmol) of compound 19 in 2 mL of 1,2-dichloroethane was added 1 mL of POCl$_3$. The mixture was stirred for 30 minutes at 80° C., and then the solvent was removed in vacuo. The residue was dissolved in MeOH, then NaBH$_4$ was added in portions at 0° C. After 30 minutes, the reaction was completed. The solvent was removed under vacuum, the residue was extracted with CH$_2$Cl$_2$, washed with water, brine and dried over anhydrous NaSO$_4$. The product was purified with preparative TLC. 3 mg of the title compound was obtained. Yield: 22.2%. $^1$H NMR (CDCl$_3$, 300 MHz) δ=6.73-6.61 (m, 4H), 5.95 (d, J=11.0 Hz 2H), 4.11 (d, J=15.3 Hz, 1H), 3.89 (s, 3H), 3.87 (s, 3H), 3.66-3.52 (m, 2H), 3.31-3.06 (m, 3H), 2.86-2.60 (m, 3H). MS: trtiz (APCI-ESI): 340.1 (M$^+$+1).

50. Chiral Separation of Compound 1.

Compound 1 was subjected to chiral HPLC using the following HPLC system:

| | |
|---|---|
| Column | CHIRALCEL OJ-H |
| Column size | 0.46 cm I.D. × 15 cm L |
| Injection | 10 μl |
| Mobile phase | Hexane/IPA/DEA = 95/5/0.1 (v/v/v) |
| Flow rate | 1.0 mL/min. |
| Wave length | UV 220 nm |
| Temperature | 35° C. |
| Sample solution | x mg/mL in Mobile phase |
| HPLC equipment | Shimadzu LC 20 with UV detector SPD-20A |
| Solvent Brand | Tedia, HPLC grade |

The (R,S) and (S,R) enantiomers of compound 1 were separated and assigned as shown in the scheme. Under these conditions, the 13S,14R-enantiomer (compound 3H) exhibited a retention time of about 7 minutes and the 13R,14S-enantiomer (compound 32) exhibited a retention time of about 13 minutes.

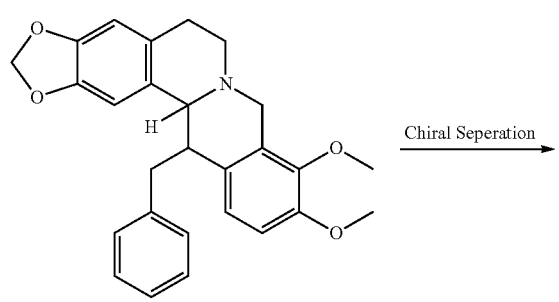

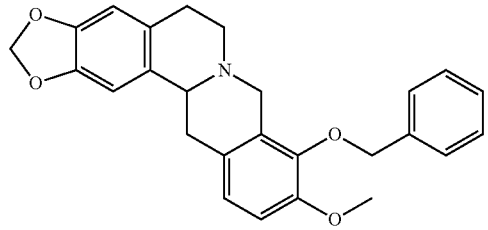

Compound 23

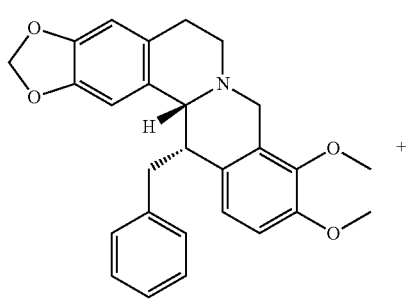

Compound 31

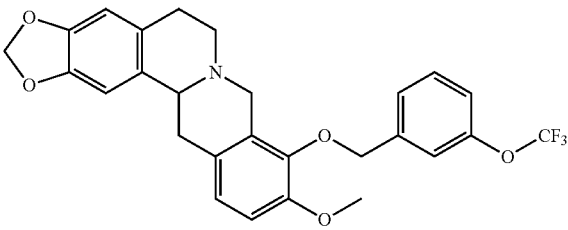

Compound 24

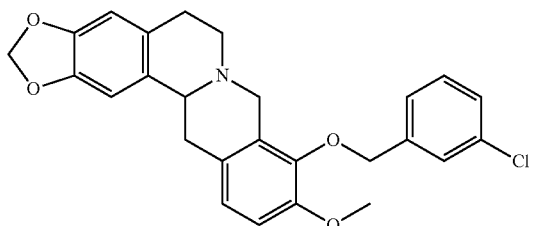

Compound 25

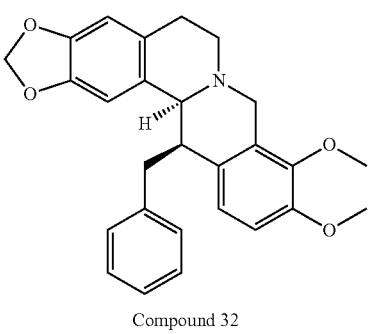

Compound 32

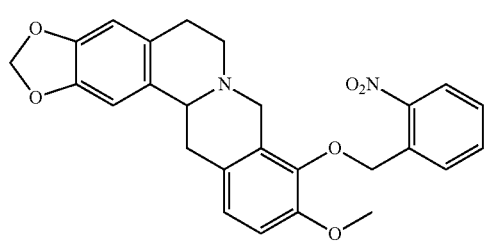

Compound 26

51. Preparation of Compounds 23-26, 29.

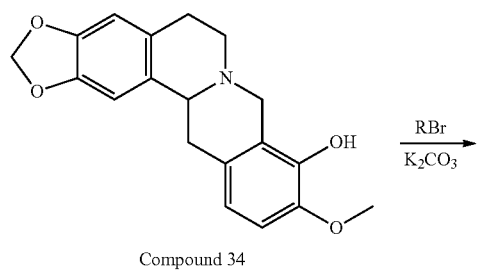

Compound 34

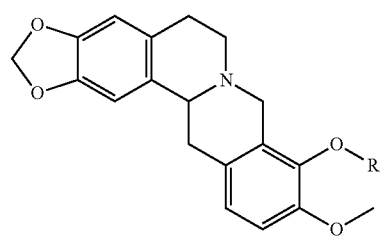

Compound 29

To a solution of compound 34 (50 mg, 0.154 mmol) in acetone was added R—Br (0.308 mmol), and $K_2CO_3$ (63.7 mg, 0.462 mmol), then the mixture was heated for 3 hours at about 70° C. in small ampoule. Then it was purified by preparative TLC to afford the product.

Compound 23: $^1$H NMR (CDCl$_3$): δ 7.50-7.46 (m, 2H), 7.42-7.33 (m, 3H), 6.90-6.80 (m, 2H), 6.72 (s, 1H), 6.58 (s, 1H), 5.92-5.91 (m, 2H), 5.03 (dd, 2H, $J_1$=11.1 Hz, $J_2$=31.2 Hz), 4.20 (d, 1H, J=15.9 Hz), 3.87 (s, 3H), 3.50-3.40 (m, 2H), 3.30-3.09 (m, 3H), 2.90-2.75 (m, 1H), 2.65-2.55 (m, 2H). MS: m/z=416.0 (M$^+$+1).

Compound 24: $^1$H NMR (CDCl$_3$, 300 MHz): δ 7.43-7.35 (m, 3H), 7.19-7.16 (m, 1H), 691-6.80 (m, 2H), 6.72 (s, 1H), 6.58 (s, 1H), 5.92-5.91 (m, 2H), 5.03 (dd, 2H, $J_1$=11.1 Hz, $J_2$=31.2 Hz), 4.20 (d, 1H, J=15.9 Hz), 3.86 (s, 3H), 3.52-3.47 (m, 2H), 3.30-3.05 (m, 3H), 2.90-2.75 (m, 1H), 2.65-2.55 (m, 2H). MS: m/z=500.0 (M$^+$+1).

Compound 25: $^1$H NMR (CDCl$_3$): δ 7.50 (s, 1H), 7.35-7.29 (m, 3H), 6.91-6.80 (m, 2H), 6.72 (s, 1H), 6.58 (s, 1H), 5.92-5.91 (m, 2H), 5.00 (dd, 2H, $J_1$=11.1 Hz, $J_2$=31.2 Hz), 4.20 (d, 1H, J=15.9 Hz), 3.86 (s, 3H), 3.55-3.40 (m, 2H), 3.30-3.05 (m, 3H), 2.90-2.75 (m, 1H), 2.65-2.55 (m, 2H). MS: m/z=450.0 (M$^+$+1).

Compound 26: $^1$H NMR (CDCl$_3$, 300 MHz): δ 8.16-8.11 (m, 2H), 7.76-7.71 (m, 2H), 7.75-7.46 (m, 2H), 7.93-7.80 (m, 2H), 6.73 (s, 1H), 6.58 (s, 1H), 5.92-5.91 (m, 2H), 5.42-5.41 (m, 2H), 4.96 (s, 1H), 2.23 (d, 1H, J=15.9 Hz), 3.80 (s, 3H), 3.60-3.50 (m, 2H), 3.30-3.05 (m, 3H), 2.90-2.75 (m, 1H), 2.65-2.55 (m, 2H). MS: m/z=461.0 (M$^+$+1).

Compound 29: $^1$H NMR (CDCl$_3$, 300 MHz): δ 6.85-6.76 (m, 2H), 6.72 (s, 1H), 6.58 (s, 1H), 5.59 (m, 1H), 5.92 (s, 2H), 4.27-4.26 (m, 2H), 4.22-4.03 (m, 2H), 3.83 (s, 3H), 3.56-3.49 (m, 2H), 3.30-3.05 (m, 3H), 2.90-2.65 (m, 3H), 1.38 (t, 3H, J=6.9 Hz). MS: m/z=354.1 (M$^+$+1).

52. Preparation of Compounds 27 and 28.

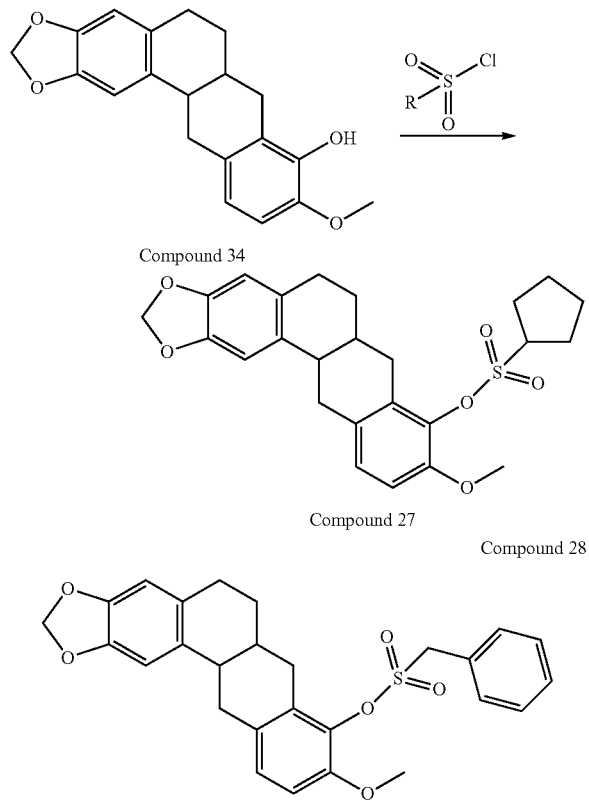

To a solution of compound 34 (50 mg, 0.154 mmol) in CH$_2$Cl$_2$ was added sulfonyl chloride (0.185 mmol), and Na$_2$CO$_3$ (20 mg), then the mixture was stirred overnight at room temperature in small ampoule. Then it was purified by preparative TLC to afford the product.

Compound 27: $^1$H NMR (CD$_3$OH, 300 MHz): δ 7.03 (d, J=8.4 Hz, 1H), 6.83 (d, J=8.7 Hz, 1H), 6.71 (s, 1H), 6.59 (s, 1H), 5.91 (dd, J=1.5, 2.1 Hz, 2H), 4.27 (d, J=16.2 Hz, 1H), 4.00-3.89 (m, 1H), 3.87 (s, 3H), 3.83-3.60 (m, 2H), 3.27-3.16 (m, 3H), 2.85-2.64 (m, 3H), 2.32-2.10 (m, 4H), 2.95-2.65 (m, 4H); MS: m/z=326.1 (M$^+$+1).

Compound 28: $^1$H NMR (CDCl$_3$, 300 MHz): δ 7.55-7.7.51 (m, 5H), 7.06 (d. J=8.4 Hz, 1H), 6.87 (d, J=8.4 Hz, 1H), 6.70 (s, 1H), 6.57 (s, 1H), 5.08 (dd, J=1.2, 2.1 Hz, 2H), 4.75 (q, J=16.5 Hz, 2H), 4.19 (d, J=15.9 Hz, 3H), 3.64-3.54 (m, 2H), 3.26-3.3.02 (m, 3H), 2.86-2.77 (m, 1H), 2.65-2.55 (m, 2H); MS: m/z=480.0 (M$^+$+1), 53. Preparation of Compound 30.

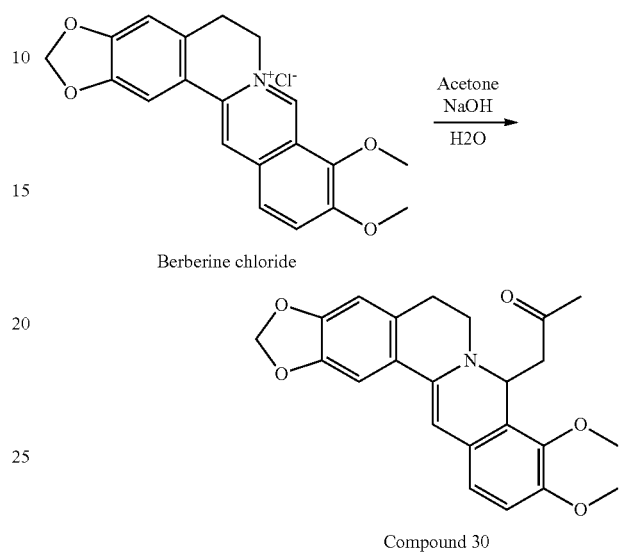

To a stirred solution of NaOH (4 g, 100 mmol) in water (20 mL) was added berberine chloride (2.0 g, 5.4 mmol) at room temperature. Then acetone (1.6 mL) was added slowly at same temperature and stirred for 1 hour. TLC analysis indicated the completion of the reaction. The reaction solution was filtered, sufficiently washed with 80% methanol and dried to give 1.7 g of compound 30. $^1$H NMR (CDCl$_3$): δ 7.13 (s, 1H); 6.77-6.75 (m, 2H); 6.57 (s, 1H); 5.94-5.93 (m, 2H); 5.89 (s, 1H,); 5.34-5.30 (m, 1H); 3.89 (s, 3H); 3.84 (s, 3H); 3.36-3.30 (m, 2H); 3.11-3.04 (m, 1H); 2.84-2.76 (m, 2H); 2.44-2.38 (m, 1H,); 2.04 (s, 3H). MS: m/z (APCI-ESI) 336.0 (M+H)$^+$.

54. Preparation of Compounds 33 and 37.

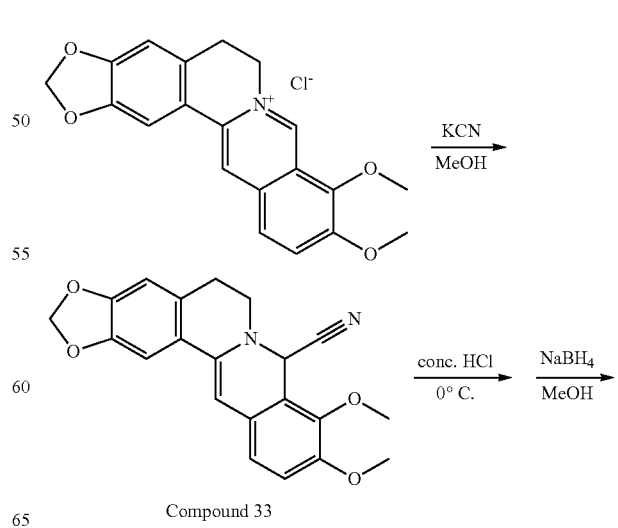

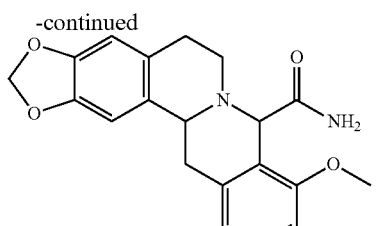

Compound 37

To a solution of 1.0 g (2.7 mmol) of berberine chloride in 50 mL of MeOH was added KCN (175 mg, dissolved in the minimum amount of water). The yellow precipitate that immediately appeared was filtered and washed with methanol. The solid was dried under vacuum. 810 mg of compound 33 was obtained, Yield: 82.9%

¹H NMR (CDCl₃, 300 MHz): δ 7.17 (s, 1H), 6.86 (dd, J=8.7, 15.3 Hz, 2H), 6.60 (s, 1H), 6.15 (s, 1H), 5.97 (dd, J=1.4, 5.1 Hz, 2H), 5.75 (s, 1H), 3.97 (s, 1H), 3.87 (s, 1H), 3.49-3.38 (m, 1H), 3.30-3.24 (m, 1H), 3.05-2.80 (m, 2H); MS: m/z=336.0 (M⁺−CN).

200 mg of compound 33 was dissolved in 1.0 mL of conc.HCl at 0° C. for 30 minutes, then the mixture was dissolved in 15 mL of methnol. NaBH₄ was added in portions until the yellow solution turned to colorless. The reaction was quenched with water, extracted with DCM. The organic phase was washed with water, brine and dried over anhydrous NaSO₄. The solvent was removed in vacuo, the residue was purified by column chromatography to give compound 37. Yield: 78 mg (37.0%).

¹H NMR (CDCl₃, 300 MHz): −7.06 (s, 1H), 6.97 (s, 1H), 6.95-6.85 (m, 3H), 6.65 (s, 1H), 5.94 (q, J=0.9 Hz, 2H), 4.01 (s, 1H), 3.77 (s, 3H), 3.68 (s, 3H), 3.43-3.19 (m, 3H), 2.89-2.56 (m, 3H), 2.46-2.38 (m, 1H); MS: m/z=383.0 (Mtf-1)

55. Preparation of Compound 35.

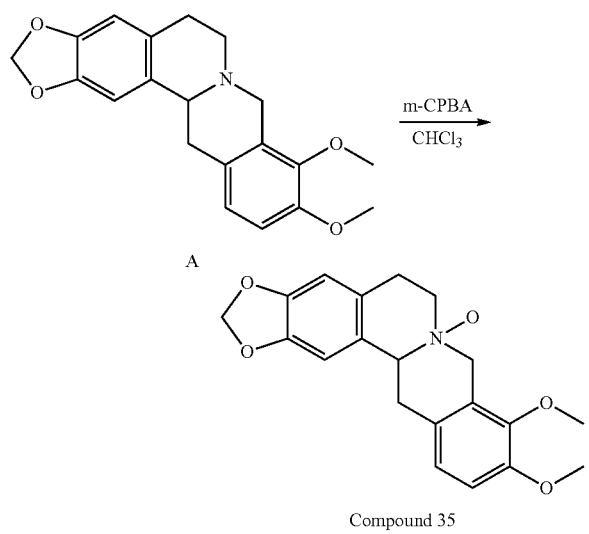

Compound 35

A solution of 200 mg (0.59 mmol) of A (tetrahydroberberine) in 3 mL of CHCl₃ was stirred with 110 mg (0.64 mmol) of m-CPBA at room temperature overnight. The reaction mixture was diluted with 10 mL of DCM, washed with 10% aqueous Na₂CO₃, dried and the solvent was evaporated. The residue was purified by column chromatography to give 185 mg of compound 35. Yield: 85.2%.

¹H NMR (CDCl₃, 300 MHz): 6.98 (d, J=8.4 Hz, 1H), 6.87 (d, J=8.7 Hz, 1H), 6.71 (s, 1H), 6.65 (s, 1H), 5.92 (dd, J=1.5, 4.8 Hz, 2H), 4.70-4.43 (m, 3H), 3.93-3.89 (m, 1H), 3.86 (s, 3H), 3.85 (s, 3H), 3.83-3.80 (m, 1H), 3.66-3.52 (m, 2H), 3.23 (dd, J=3.9, 16.2 Hz, 1H), 2.68 (dd, J=3.6, 16.5 Hz, 1H); MS: m/z=356.0 (M⁺+1).

56. Preparation of Compounds 37, 38 and 42.

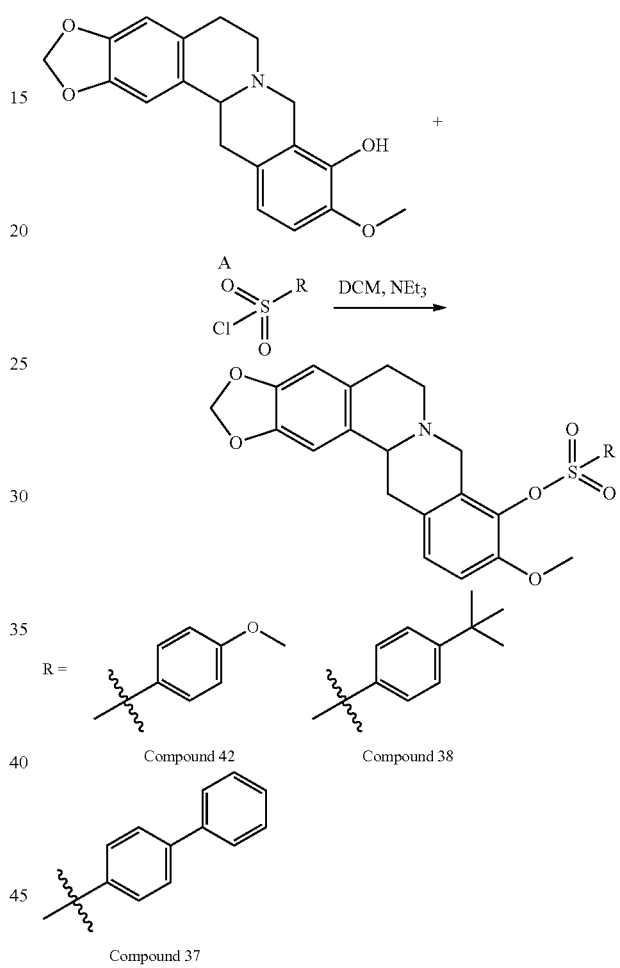

To a solution of A (50 mg, 0.15 mmol) in CH₂Cl₂ was added chlorosulfone (0.20 mmol), and two drops of Et₃N, then the mixture was stirred for 3 hours at room temperature in a small ampoule. Then it was purified by preparative TLC to afford the title compounds.

Compound 37: ¹H NMR (CDCl₃, 300 MHz): δ 8.09-7.44 (m, 9H), 7.02 (d, J=8.4 Hz, 1H), 6.72 (d, J=8.4 Hz, 1H), 6.71 (s, 1H), 6.59 (s, 1H), 5.92 (s, 2H), 4.25 (d, J=15.9 Hz, 1H), 3.68-3.56 (m, 2H), 3.45 (s, 3H), 3.28-3.08 (m, 3H), 2.87-2.60 (m, 3H); MS: m/z=542.1 (M⁺+1).

Compound 38: ¹H NMR (CDCl₃, 300 MHz): δ 7.93-7.55 (m, 4H), 7.01 (d, J=8.4 Hz, 1H), 6.72-6.69 (m, 3H), 5.91 (s, 2H), 4.19 (d, J=19.5 Hz, 1H), 3.61-3.54 (m, 2H), 3.43 (s, 3H), 3.24 (dd, J=3.9, 15.9 Hz, 1H), 3.12-3.02 (m, 2H), 2.86-2.51 (m, 3H); MS: m/z=522.1 (M⁺+1).

Compound 42: ¹H NMR (CDCl₃, 300 MHz): δ 7.93 (d, J=2.1 Hz, 1H), 7.91-7.90 (d, J=2.4 Hz, 1H), 7.02-6.99 (m, 3H), 6.72 (d, J=9.6 Hz, 2H), 6.58 (s, 1H), 5.91 (s, 2H), 4.23 (d, J=17.1 Hz, 1H), 3.90 (s, 3H), 3.64-3.59 (m, 2H), 3.50 (s, 3H), 3.27-3.21 (m, 1H), 3.15-3.10 (m, 2H), 2.85-2.59 (m, 3H); MS: m/z=490.0 (M$^4$+1).

57. Preparation of Compound 39.

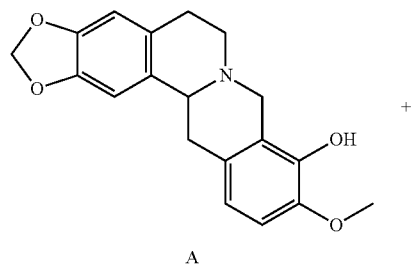

A

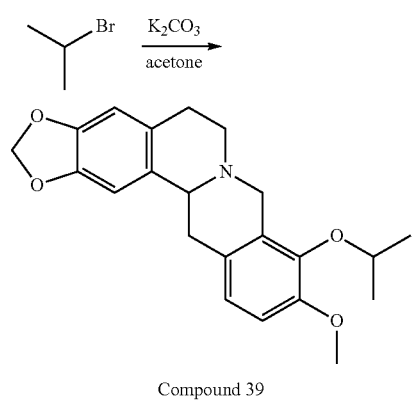

Compound 39

To a solution of A (50 mg, 0.15 mmol) in acetone was added 2-bromopropane (38 mg, 0.31 mmol), and K$_2$CO$_3$ (63.7 mg, 0.46 mmol), then the mixture was heated for 3 hours at about 70° C. in a small ampoule. Then it was purified by preparative TLC to afford the title compound 39. $^1$H NMR (CDCl$_3$, 300 MHz): δ 6.79 (dd, 0.1=8.1, 19.8 Hz, 2H), 6.72 (s, 1H), 6.58 (s, 1H), 5.91 (s, 2H), 4.61-4.53 (m, 1H), 4.24 (d, J=15.9 Hz, 1H), 3.81 (s, 3H), 3.53-3.50 (m, 2H), 3.24-3.10 (m, 3H), 2.86-2.80 (m, H), 2.67-2.57 (m, 2H), 1.30 (d, J=2.7 Hz, 3H), 1.28 (d, J=2.4 Hz, 3H); MS: m/z=368.1 (1-4'+1).

58. Preparation of Compounds 41, 44, 45 and 46.

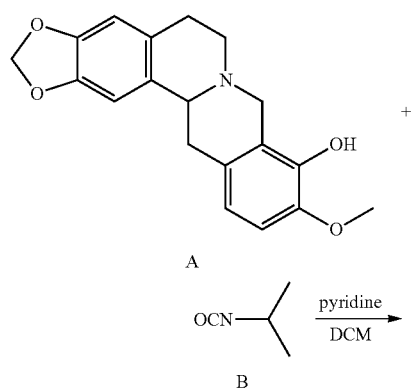

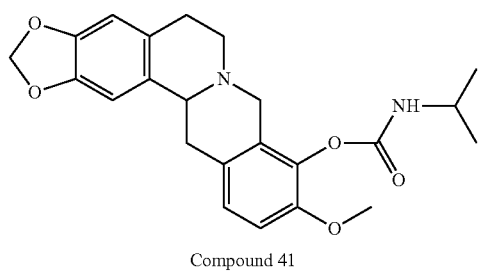

Compound 41

To a stirred solution of A (100 mg, 0.31 mmol) in DCM (1.5 mL) and pyridine (1.5 mL) was added B (33 μL, 0.34 mmol) at room temperature. Then the reaction mixture was heated to 40° C. and stirred for 8 hours. TLC analysis indicated the completion of the reaction. The solvent was removed in reduce pressure. The residue was extracted with EtOAc and water, dried and concentrated to give crude product. The crude material sufficiently washed with Et$_2$O and dried to give 35 mg of compound 41. $^1$H NMR (CDCl$_3$): δ 6.97 (d, J=8.7 Hz, 1H); 6.81 d, J=8.7 Hz, 1H); 6.72 (s, 1H); 6.58 (s, 1H); 5.91 (s, 2H); 5.01 (d, J=8.1 Hz, 1H); 4.07 (d, J=15.6 Hz, 1H); 3.90-3.86 (m, 1H); 3.82 (s, 3H); 3.60-3.48 (m, 2H); 3.25-3.04 (m, 3H); 2.86-2.77 (m, 1H,); 2.66-2.55 (m, 2H); 1.24-1.12 (m, 6H). MS: m/z (APCI-ESI) 411.1 (M+H)$^+$.

The compounds 44, 45 and 46 were prepared analogously using the appropriate isocyanate.

Compound 44: $^1$H NMR (CDCl$_3$): δ 7.46 (dd, J=4.8 Hz, 2H), 7.16 (dd, J=8.4 Hz, 2H), 7.04 (dd, J=8.4 Hz, 1H), 6.85 (dd, J=8.4 Hz, 1H), 6.73 (s, 1H), 6.58 (m, 1H), 5.92 (s, 2H), 4.12-4.17 (m, 1H), 3.82 (s, 3H), 3.55-3.56 (m, 2H), 3.14-3.25 (m, 3H), 2.98-2.75 (m, 1H), 2.61-2.61 (m, 2H). MS: m/z=529.0 (M$^+$+1).

Compound 45: $^1$H NMR (CDCl$_3$): δ 7.48 (m, 1H), 7.03 (dd, J=8.1 Hz, 1H), 6.85 (dd, J=8.4 Hz, 1H), 6.75 (s, 1H), 6.67 (s, 2H), 6.59 (s, 1H), 6.19 (s, 1H), 5.92 (s, 2H), 4.16-4.21 (m, 1H), 3.83 (s, 3H), 3.70 (s, 6H), 3.48-3.64 (m, 2H), 3.13-3.31 (m, 3H), 2.83-2.92 (m, 1H), 2.57-2.83 (m, 2H). MS: m/z=505.1 (M$^+$+1).

Compound 46: $^1$H NMR (CDCl$_3$): δ 7.4 (m, 1H), 7.16-7.23 (m, 2H), 7.03 (dd, 1H, J=8.4 Hz), 6.83-6.90 (m, 2H), 6.75 (s, 2H), 6.58 (s, 1H), 6.19 (s, 1H), 5.92 (s, 2H), 4.14-4.19 (m, 1H), 3.83 (s, 3H), 3.49-3.63 (m, 2H), 3.08-3.31 (m, 3H), 2.81-2.90 (m, 1H), 2.57-2.67 (m, 2H), 2.29 (s, 3H). MS: m/z=459.1 (M$^+$+1).

59. Preparation of Compound 43.

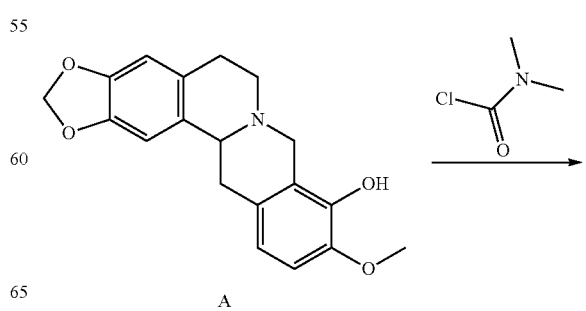

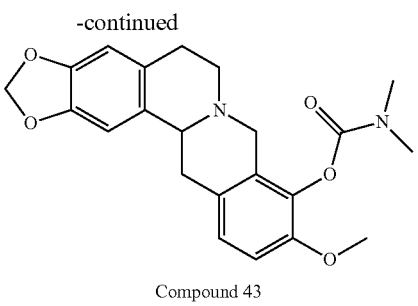

Compound 43

100 mg of A (0.31 mmol) was dissolved in 5.0 mL of DCM, and the solution turned yellow. Then 0.5 mL of chloro-N,N-dimethylamide, 59 mg (0.307 mmol) of EDCI and 1.0 mL of Et$_3$N were added and kept stirring overnight at reflux point. Cooled down and washed with water three times. Purified by silica gel chromatography to afford 45.0 mg of compound 43. $^1$H NMR (CDCl$_3$): δ 6.97 (dd, J=8.4 Hz, 1H), 6.81 (dd, J=8.4 Hz, 1H), 6.71 (m, 1H), 6.58 (s, 1H), 4.04-4.09 (m, 1H), 3.80 (m, 3H), 3.55-3.56 (m, 2H), 3.02-3.25 (m, 8H), 2.61-2.79 (m, 4H). MS: m/z=397.1 (M$^+$+1).

60. Preparation of Compounds 49-53 and 56-60.

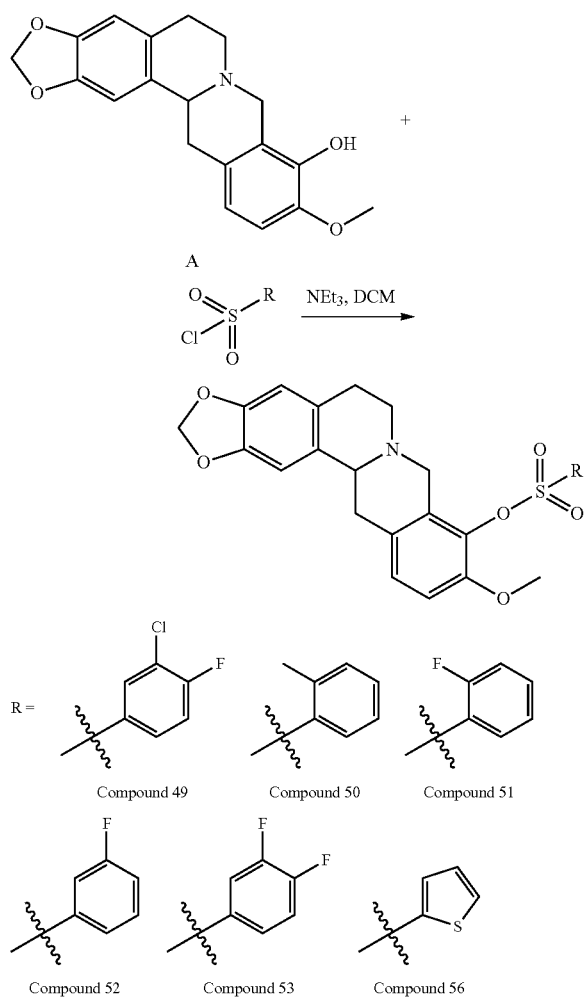

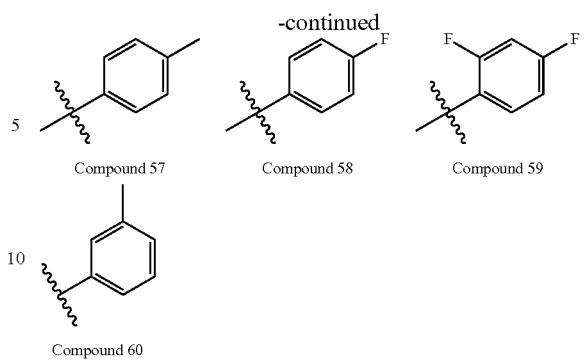

Compound 57   Compound 58   Compound 59

Compound 60

To a solution of A (50 mg, 0.15 mmol) in CH$_2$Cl$_2$ was added chlorosulfone (0.20 mmol), and two drops of Et$_3$N; then the mixture was stirred for 3 hours at room temperature in a small ampoule. The reaction mixture was purified by prepreparative TLC to afford the title compounds.

Compound 49: $^1$H NMR (CDCl$_3$, 300 MHz): δ 8.00 (dd, J=5.7, 9.0 Hz, 1H), 7.38 (dd, J=2.4, 8.4 Hz, 1H), 7.13-7.07 (m, 1H), 7.05 (d, J=8.4 Hz, 1H), 6.71-6.68 (m, 2H), 6.59 (s, 1H), 5.91 (s, 2H), 4.26 (d, J=15.6 Hz, 1H), 3.65-3.56 (m, 2H), 3.39 (s, 3H), 3.26-3.09 (m, 3H), 2.69-2.61 (m, 3H); MS: m/z=517.9 (M$^+$+1).

Compound 50: $^1$H NMR (CDCl$_3$, 300 MHz): δ 7.89-7.86 (dd, J=1.2, 7.6 Hz, 1H), 7.55-7.50 (m, 1H), 7.41 (d, J=7.5 Hz, 1H), 7.32-7.27 (m, 1H), 6.99 (d, J=8.4 Hz, 1H), 6.70-6.66 (m, 2H), 6.58 (s, 1H), 5.91 (s, 2H), 4.18 (d, J=15.9 Hz, 1H), 3.59-3.54 (m, 2H), 3.32 (s, 3H), 3.26-3.07 (m, 3H), 2.82 (s, 3H), 2.66-2.56 (m, 3H); MS: m/z=480.0 (M$^+$+1).

Compound 51: $^1$H NMR (CDCl$_3$, 300 MHz): δ 7.88-7.82 (m, 1H), 7.71-7.63 (m, 1H), 7.34-7.28 (m, 2H), 7.01 (d, J=8.7 Hz, 1H), 6.68 (s, 1H), 6.68 (d, J=8.1 Hz, 1H), 6.59 (s, 1H), 5.91 (s, 2H), 4.27 (d, J=15.9 Hz, 1H), 3.68-3.56 (m, 2H), 3.35 (s, 3H), 3.26-3.08 (m, 3H), 2.86-2.58 (m, 3H); MS: m/z=484.0 (M$^+$+1).

Compound 52: $^1$H NMR (CDCl$_3$, 300 MHz): δ 7.82-7.78 (m, 1H), 7.74-7.70 (m, 1H), 7.59-7.52 (m, 1H), 7.42-7.36 (m, 1H), 7.03 (d, J=8.1 Hz, 1H), 6.74-6.70 (m, 2H), 6.59 (s, 1H), 5.91 (s, 2H), 4.24 (d, J=15.9 Hz, 1H), 3.67-3.57 (m, 2H), 3.45 (s, 3H), 3.28-3.09 (m, 3H), 2.86-2.59 (m, 3H); MS: m/z=484.0 (M$^+$+1).

Compound 53: $^1$H NMR (CDCl$_3$, 300 MHz): δ 7.91-7.77 (m, 2H), 7.40-7.32 (m, 1H), 7.05 (d, J=8.4 Hz, 1H), 6.75-6.71 (m, 2H), 6.59 (s, 1H), 5.91 (s, 2H), 4.25 (d, J=15.6 Hz, 1H), 3.70-3.58 (m, 2H), 3.50 (s, 3H), 3.27-3.05 (m, 3H), 2.88-2.61 (m, 3H); MS: m/z=502.0 (M$^+$+1).

Compound 56: $^1$H NMR (CDCl$_3$, 300 MHz): δ 7.78-7.73 (m, 2H), 7.16-7.13 (m, 1H), 7.04 (d, J=8.4 Hz, 1H), 6.77-6.70 (m, 2H), 6.59 (s, 1H), 5.91 (s, 2H), 4.22 (d, J=15.9 Hz, 1H), 3.63-3.55 (m, 2H), 3.59 (s, 3H), 3.27-3.04 (m, 3H), 2.86-2.60 (m, 3H); MS: m/z=472.0 (M$^+$+1)

Compound 57: $^1$H NMR (CDCl$_3$, 300 MHz): δ 7.89-7.85 (m, 2H), 7.36-7.33 (m, 2H), 7.01 (d, J=8.7 Hz, 1H), 6.71 (d, J=7.2 Hz, 1H), 6.70 (s, 1H), 6.58 (s, 1H), 5.91 (s, 2H), 4.20 (d, J=15.9 Hz, 1H), 3.62-3.54 (m, 2H), 3.45 (s, 3H), 3.28-3.02 (m, 3H), 2.85-2.53 (m, 3H), 2.47 (s, 3H); MS: m/z=480.0 (M$^+$+1)

Compound 58: $^1$H NMR (CDCl$_3$, 300 MHz): δ 8.04-7.99 (m, 2H), 7.27-7.21 (m, 2H), 7.02 (d, J=8.4 Hz, 1H), 6.71 (d, J=7.5 Hz, 1H), 6.70 (s, 1H), 6.59 (s, 1H), 5.91 (s, 2H), 4.24 (d, J=15.9 Hz, 1H), 3.67-3.56 (m, 2H), 3.46 (s, 3H), 3.28-3.03 (m, 3H), 2.86-2.59 (m, 3H); MS: m/z=484.0 (M$^+$+1)

Compound 59: ¹H NMR (CDCl₃, 300 MHz): δ 7.90-7.82 (m, 1H), 7.08-6.97 (m, 3H), 6.71-6.68 (m, 2H), 6.59 (s, 1H), 5.91 (s, 2H), 4.27 (d, J=15.9 Hz, 1H), 3.69-3.55 (m, 2H), 3.40 (s, 3H), 3.26-3.05 (m, 3H), 2.85-2.59 (m, 3H); MS: m/z=502.0 (M⁺+1)

Compound 60: ¹H NMR (CDCl₃, 300 MHz): δ 7.82-7.76 (m, 2H), 7.49-7.41 (m, 2H), 7.01 (d, J=8.7 Hz, 1H), 6.72 (d, J=9.0 Hz, 1H), 6.70 (s, 1H), 6.58 (s, 1H), 5.91 (s, 2H), 4.20 (d, J=15.9 Hz, 1H), 3.61-3.54 (m, 2H), 3.46 (s, 3H), 3.27-3.04 (m, 3H), 2.85-2.55 (m, 3H), 2.45 (s, 3H); MS: m/z=480.0 (M⁺+1)

61. Preparation of Compound 47.

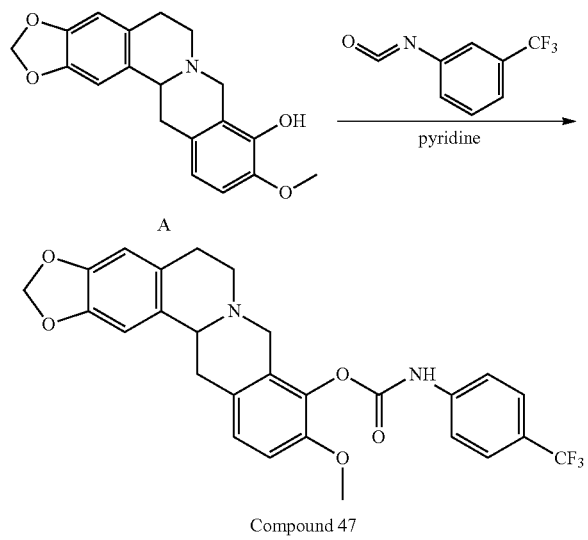

Compound 47

To a solution of 65.0 mg (0.2 mmol) of A in 2 mL of DCM and 1 mL of pyridine was added 0.22 mmol of RNCO. The mixture was stirred at 40° C. for 6 hours. Then it was purified by preparative TLC to afford the title compound.

Compound 47: ¹H NMR (CDCl₃): δ 8.12 (br, 1H), 7.70-7.58 (m, 2H), 7.41-7.28 (m, 2H), 7.04 (d, J=8.7 Hz, 1H), 6.86 (d, J=8.4 Hz, 1H), 6.76 (s, 1H), 6.58 (m, 1H), 5.94 (s, 2H), 4.26 (d, J=15.9 Hz, 1H), 3.85 (s, 3H), 3.71-3.3.57 (m, 2H), 3.36-3.14 (m, 3H), 2.96-2.69 (m, 3H). MS: m/z=513.0 (M⁺+1).

62. Preparation of Compound 48.

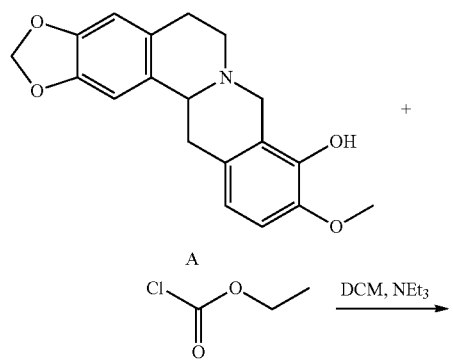

Compound 48

To a solution of A (50 mg, 0.15 mmol) in CH₂Cl₂ was added ethyl chloroformate (0.20 mmol), and two drops of Et₃N, then the mixture was stirred for 3 hours at room temperature in a small ampoule. Then it was purified by preparative TLC to afford the title compound.

Compound 48: ¹H NMR (CDCl₃, 300 MHz): δ 7.01 (d, J=8.1 Hz, 1H), 6.83 (d, J=8.4 Hz, 1H), 6.58 (s, 1H), 5.91 (s, 2H), 4.36-4.29 (m, 2H), 4.12 (d, J=15.9 Hz, 1H), 3.83 (s, 3H), 3.57-3.48 (m, 2H), 3.26-3.11 (m, 3H), 3.68-2.62 (m, 3H), 1.41-1.37 (m, 3H); MS: m/z=398.1 (M⁺+1).

63. Preparation of Compound 54.

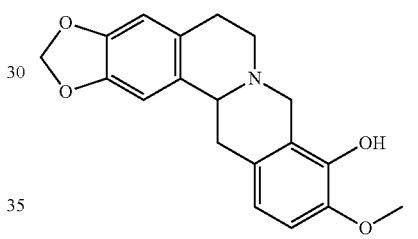

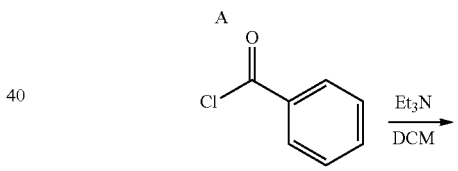

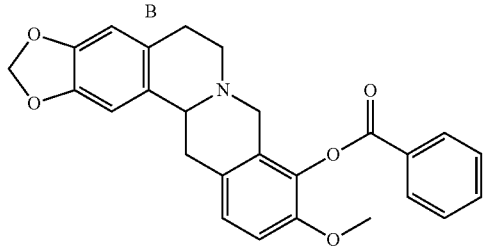

Compound 54

To a stirred solution of A (50 mg, 0.15 mmol) in DCM (2 mL) and Et₃N (3 drops) was added B (40 μL) at room temperature. Then the reaction mixture was heated to 40° C. and stirred for 3 hours. When TLC analysis indicated the completion of the reaction, the solvent was removed in reduced pressure. The residue was dissovled with EtOAc, This solution was washed with water, dried and concentrated to give crude product. The crude material was further purified by preparative TLC to give 20 mg of compound 54.

Compound 54: ¹H NMR (CDCl₃, 300 MHz): δ 8.26-8.23 (m, 2H), 7.68-7.63 (m, 1H), 7.56-7.50 (m, 2H), 7.06 (d, J=9.3 Hz, 1H), 6.88 (d, J=8.4 Hz, 1H), 6.74 (s, 1H), 6.57 (s, 1H), 5.92 (s, 2H), 4.08 (d, J=14.1 Hz, 1H), 3.79 (s, 3H), 3.61-3.47 (m, 2H), 3.28-3.24 (m, 1H), 3.09-3.06 (m, 2H), 2.91-2.81 (m, 1H), 2.64-2.56 (m, 2H); MS: m/z=430.0 (M⁺+1).

64. Preparation of Compound 55.

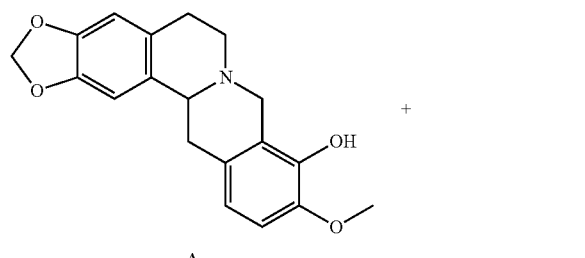

A

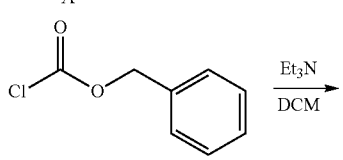

B

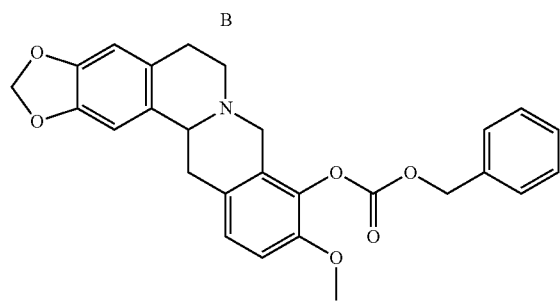

Compound 55

To a stirred solution of A (50 mg, 0.15 mmol) and Et₃N (3 drops) in DCM (2 mL) was added B (40 µL) at room temperature. Then the reaction mixture was heated to 40° C. and stirred for 3 hours. When TLC analysis indicated the completion of the reaction, the solvent was removed in reduced pressure. The residue was dissolved with EtOAc. This solution was washed with water, dried and concentrated to give crude product. The crude material was further purified by preparative TLC to give 26 mg of compound 55.

Compound 55: ¹H NMR (CDCl₃, 300 MHz) δ 7.46-7.39 (m, 5H), 7.01 (d, J=8.4 Hz, 1H), 6.83 (d, J=8.4 Hz, 1H), 6.69 (s, 1H), 6.58 (s, 1H), 5.91 (s, 2H), 5.29 (s, 2H), 4.18 (d, J=12.6 Hz, 2H), 3.81-3.53 (m, 2H), 3.76 (s, 3H), 3.28-3.18 (m, 3H), 2.94-2.68 (m, 3H); MS: m/z=460.1 (M⁺1).

65. Preparation of Compound 61.

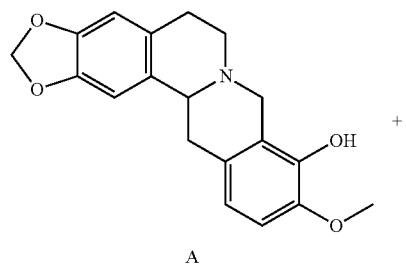

A

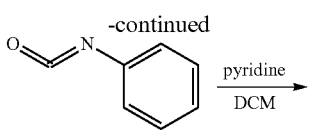

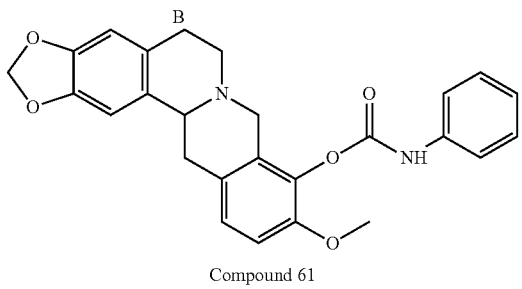

Compound 61

To a stirred solution of A (50 mg, 0.15 mmol) and pyridine (0.5 mL) in DCM (2 mL) was added B (20 mg, 0.17 mmol) at room temperature. Then the reaction mixture was heated to 40° C. and stirred for 6 hours. When TLC analysis indicated the completion of the reaction, the solvent was removed in reduced pressure. The residue was dissolved with EtOAc. This solution was washed with water, dried and concentrated to give crude product. The crude material was further purified by preparative TLC to give 50 mg of compound 61. ¹H NMR (CDCl₃, 300 MHz) δ 7.45 (d, J=7.8 Hz, 2H), 7.30 (t, J=7.5 Hz, 2H), 7.10-7.01 (m, 2H), 6.86 (d, J=8.4 Hz, 1H), 6.70 (s, 1H), 6.58 (s, 1H), 5.93-5.92 (m, 2H), 4.32 (d, J=16.5 Hz, 1H), 3.83 (s, 3H), 3.72 (br, 2H), 3.30-3.23 (m, 2H), 2.95-2.70 (m, 4H); MS: m/z=445.0 (M⁺+1).

66. Preparation of Compound 62.

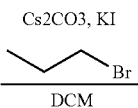

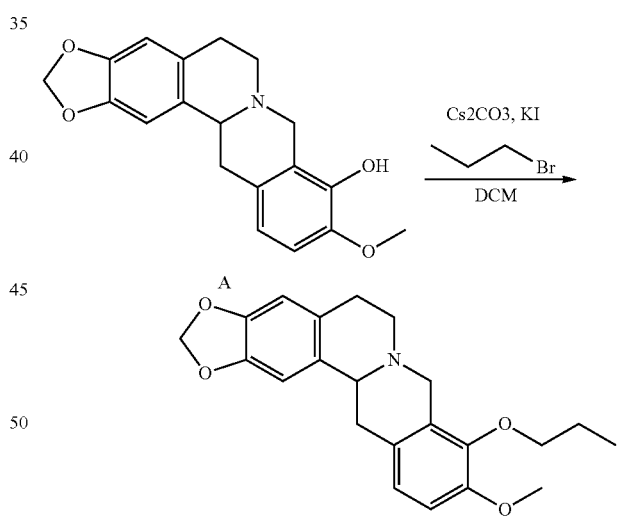

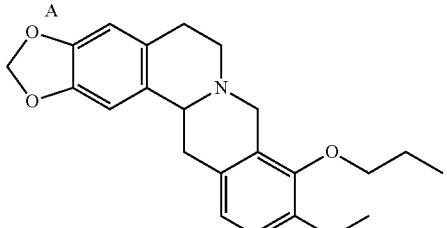

Compound 62

To a stirred solution of A (50 mg, 0.15 mmol) in DCM (2 mL) was added bromopropane (21 mg, 0.17 mmol), Cs₂CO₃ (65 mg, 0.20 mmol) and KI (25 mg, 0.15 mmol) at room temperature. Then the reaction mixture was heated to 40° C. and stirred for 6 hours. When TLC analysis indicated the completion of the reaction, the solvent was removed in reduced pressure. The residue was dissolved with EtOAc. This solution was washed with water, dried and concentrated to give crude product. The crude material was further purified by preparative TLC to give 20 mg of compound 62. ¹H NMR (CDCl₃, 300 MHz) δ 6.81 (dd, J=8.4 Hz, 21 Hz, 2H), 6.72 (s, 1H), 6.59 (s, 1H), 5.91 (t, J=1.5 Hz, 2H), 4.27 (d, J=15.6 Hz, 1H), 4.0-3.89 (m, 2H), 3.82 (s, 3H), 3.59-3.55 (m, 2H), 3.25-3.19 (m, 3H), 2.88-2.80 (m, 1H), 2.70-2.66 (m, 2H), 1.83-1.76 (m, 2H), 1.04 (t, J=7.2 Hz, 3H). MS: m/z=368.1 (M$^+$+1).

67. Preparation of Compounds 63, 65 and 66.

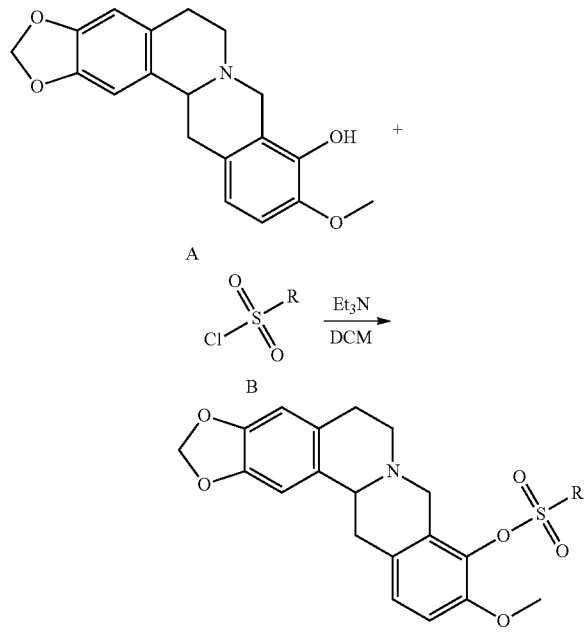

-continued

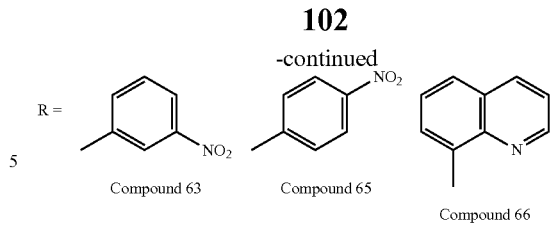

To a stirred solution of A (50 mg, 0.15 mmol) in DCM (2 mL) was added B (0.17 mmol) at room temperature, Et$_3$N (0.1 mL) was added and stirred for 4 hours. When TLC analysis indicated the completion of the reaction, the solvent was removed in reduced pressure. The residue was further purified by preparative TLC to provide title compounds.

Compound 63: $^1$H NMR (CDCl$_3$, 300 MHz) δ 8.92 (t, J=2.1 Hz, 1H), 8.56-8.54 (m, 1H), 8.39-8.34 (m, 1H), 7.80 (t, J=8.4 Hz, 1H), 7.38 (d, J=8.7 Hz, 1H), 6.76-6.72 (m, 2H), 6.60 (s, 1H), 5.92 (s, 2H), 4.30 (d, J=15.6 Hz, 1H), 3.72 (d, J=15.3 Hz, 1H), 3.62-3.59 (m, 1H), 3.50 (s, 3H), 3.28-3.05 (m, 3H), 2.89-2.79 (m, 1H), 2.69-2.60 (m, 2H). MS: m/z=511.0 (M$^+$+1).

Compound 65: $^1$H NMR (CDCl$_3$, 300 MHz) δ 8.52-8.47 (m, 2H), 8.24-8.20 (m, 2H), 7.11 (d, J=8.4 Hz, 1H), 6.94 (d, J=8.4 Hz, 1H), 6.92 (s, 1H), 6.68 (s, 1H), 5.96 (s, 2H), 4.05 (d, J=15.9 Hz, 1H), 3.50-3.42 (m, 2H), 3.36 (s, 3H), 3.06-2.84 (m, 2H), 2.67-2.42 (m, 4H); MS: m/z=511.0 (M$^+$=1).

Compound 66: $^1$H NMR (CDCl$_3$, 300 MHz) δ 9.26-9.24 (m, 1H), 8.41-8.12 (m, 3H), 7.65-7.57 (m, 2H), 6.96 (d, J=8.4 Hz, 1H), 6.68 (s, Hi), 6.58 (d, J=9.9 Hz, 1H), 6.57 (s, 1H), 5.90 (s, 2H), 4.30 (d, J=15.9 Hz, 1H), 3.64-3.52 (m, 2H), 3.23-3.00 (m, 3H), 3.02 (s, 3H), 2.83-2.49 (m, 3H); MS: m/z=517.0 (M$^+$+1).

68. Preparation of Compound 64.

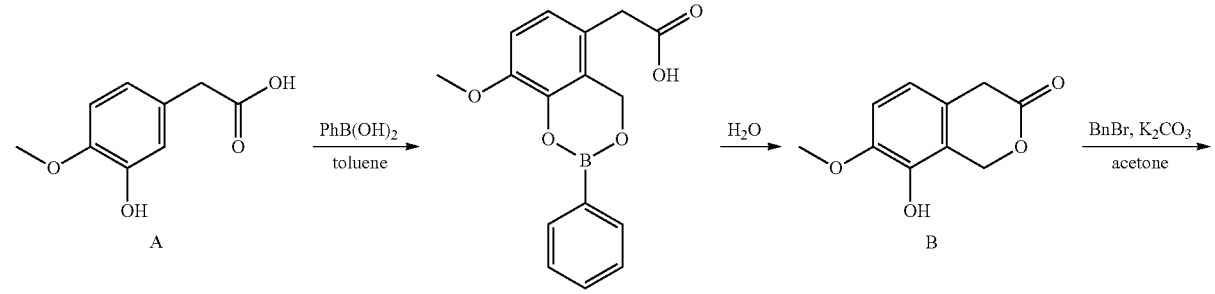

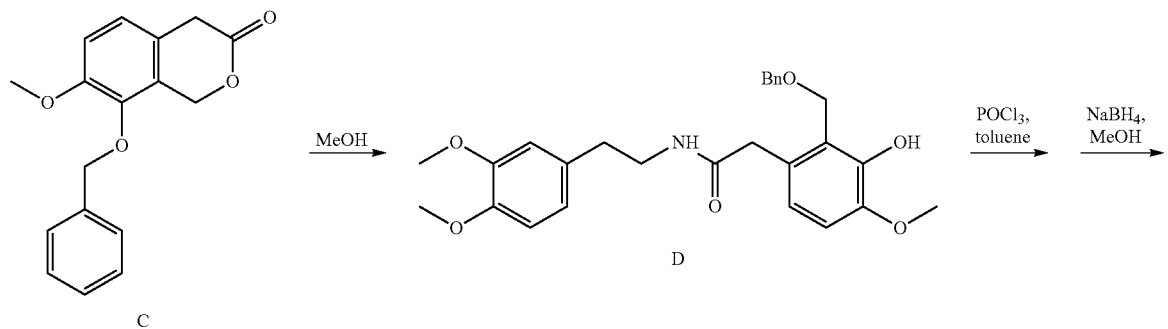

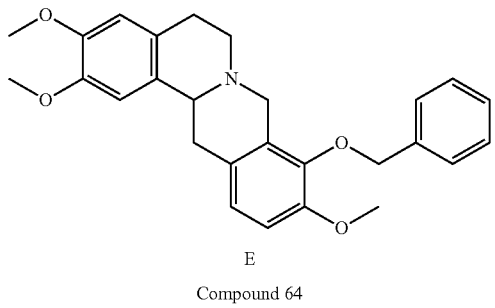

Compound 64

To 5.2 g of A was added phenylboric acid and toluene. The mixture was heated at reflux for 1 hour, and water was collected in a Dean-stark trap. The hot solution was poured over molecular sieves (3.7 g) in a stainless steel bomb. Paraformaldehyde (6.4 g) was added. The bomb was sealed and heated on an oil-bath at 110° C. for 48 hours. The bomb was opened and the hot solution filtered. The toluene was evaporated, and water was added to the residue. After heating at reflux for 2 hours, the mixture was cooled to room temperature and extracted with DCM. The solution was dried and the solvent was removed. The residue was washed with ether to obtained 2.5 g of B.

To a solution of B (1.0 g, 5.2 mmol) in 20 mL of acetone was added $K_2CO_3$ (810 mg, 5.8 mmol), followed by BnBr (0.7 mL, 5.8 mmol). The mixture was stirred at room temperature overnight. Then the mixture was diluted with EtOAc, washed with water, brine, and dried over anhydrous $Na_2SO_4$. The solvent was removed under vacuum. The residue was purified by flash chromatography to provide 1.2 g of C.

To a solution of C (200 mg, 0.7 mmol) in 6 mL of MeOH was added 3,4-dimethoxy phenethylamine (0.3 mL, 1.8 mmol) dropwise. The mixture was stirred at room temperature for 3 hours. The reaction mixture was diluted with EtOAc, washed with $H_2O$, brine, dried over anhydrous $Na_2SO_4$. Then the solvent was removed under vacuum. The residue was purified with flash chromatography to give 310 mg of D.

Compound D (101 mg, 0.25 mmol) was suspended in 2 mL of toluene. The mixture was stirred under nitrogen. Then 0.15 mL of phosphoryl chloride was added in one portion, and the mixture was heated under reflux for 2 hours. The reaction mixture was cooled under nitrogen. Excess phosphoryl chloride and toluene was evaporated under vacuum. The residue was dissolved in methanol, then 100 mg of $NaBH_4$ was added in portions. The mixture was stirred at room temperature for 30 minutes. Then the solvent was removed, the residue was diluted with EtOAc, washed with $H_2O$, brine, dried over anhydrous $Na_2SO_4$. Then the solvent was removed under vacuum. The residue was purified with flash chromatography to give 42 mg of E (compound 64).

Compound 64: $^1$H NMR (CDCl$_3$, 300 MHz), δ 7.50-7.30 (m, 5H), 6.86 (dd, J=8.4, 23.7 Hz, 2H), 6.73 (s, 1H), 6.61 (s, 1H), 5.04 (dd, J=11.4, 33.9 Hz, 2H), 4.22 (d, J=15.9 Hz, 1H), 3.89 (s, 3H), 3.87 (s, 3H), 3.86 (s, 3H), 3.55-3.42 (m, 2H), 3.30-3.11 (m, 3H), 2.89-2.58 (m, 3H); MS: m/z=432.1 (M$^+$+1).

69. Preparation of Biotin-Labeled Compounds Including 156, and 120.

(1) Synthesis of 156

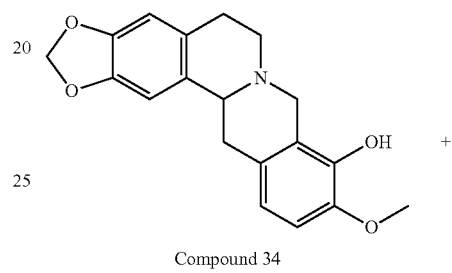

Compound 34

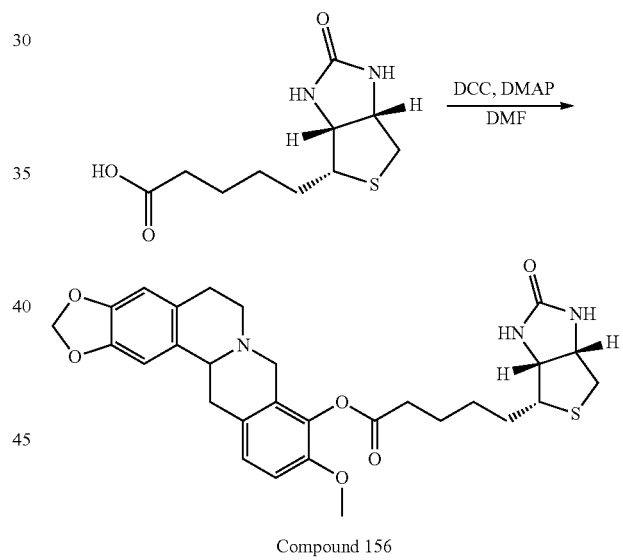

Compound 156

A solution of 34 (325 mg, 1.0 mmol), Biotin (245 mg, 1.0 mmol), DCC (210 mg, 1.0 mmol), and DMAP (125 mg, 1.0 mmol) in DMF was stirred at room temperature overnight. Then the reaction mixture was diluted with DCM, washed with water (3 times), brine, and dried over anhydrous $Na_2SO_4$. The solvent was removed under vacuum. The residue was purified by flash column silica gel chromatography, then preparative TLC to afford 15 mg of the title compound.

Compound 156: $^1$H NMR (CDCl$_3$, 300 MHz) δ 6.99 (d, J=8.4 Hz, 1H), 6.81 (d, J=8.4 Hz, 1H), 6.70 (s, 1H), 6.57 (s, 1H), 6.00 (d, J=8.1 Hz, 1H), 5.90 (s, 2H), 5.35 (s, 1H), 4.47-4.45 (m, 1H), 4.33-4.30 (m, 1H), 3.98 (d, J=15.6 Hz, 1H), 3.79 (s, 3H), 3.57-3.54 (m, 1H), 3.43 (d, J=15.6 Hz, 1H), 3.24-2.59 (m, 9H), 2.15-1.95 (m, 2H), 1.86-1.53 (m, 6H); MS: m/z=552.1 (M$^+$+1).

(4) Preparation of Compound 120

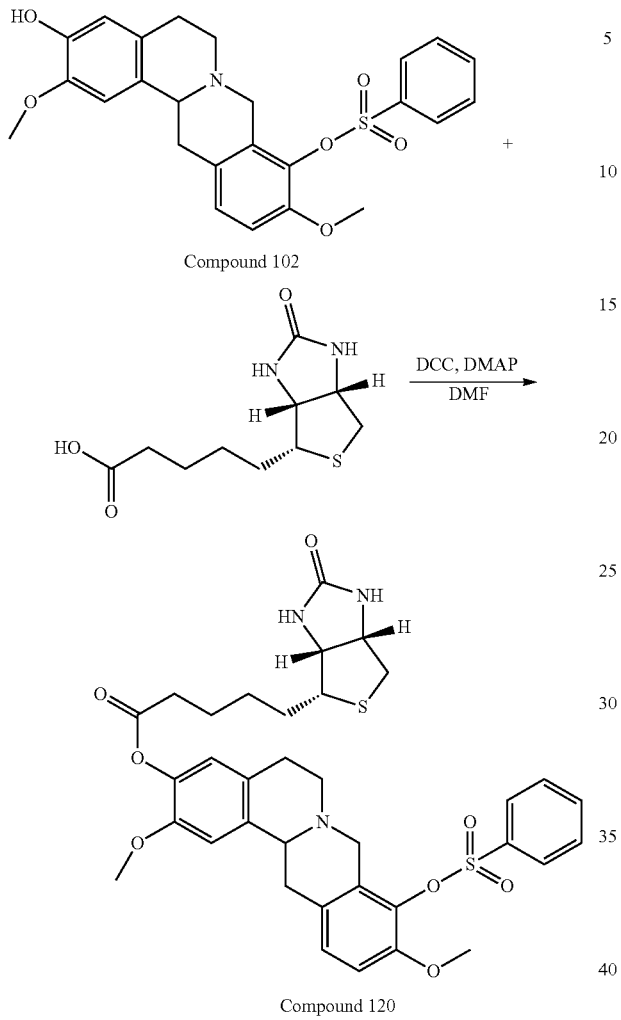

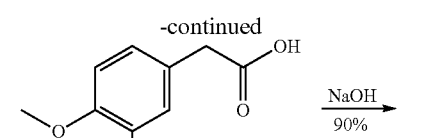

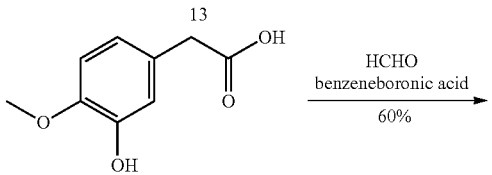

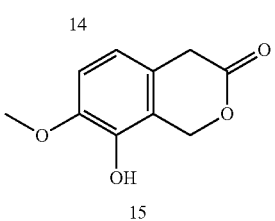

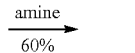

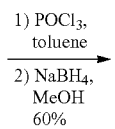

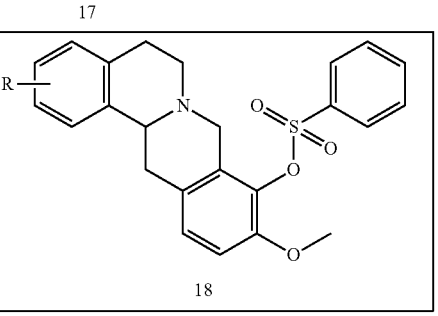

A solution of 102 (30 mg, 0.06 mmol), Biotin (15 mg, 0.06 mmol), DCC (15 mg, 0.06 mmol), and DMAP (10 mg, 0.08 mmol) in DMF was stirred at room temperature overnight. Then the reaction mixture was diluted with DCM, washed with water (3 times), brine, and dried over anhydrous Na$_2$SO$_4$. The solvent was removed under vacuum. The residue was purified by flash column silica gel chromatography, then preparative TLC to afford 10 mg of the title compound.

Compound 120: $^1$H NMR (CDCl$_3$, 300 MHz) δ 8.01-7.53 (m, 5H), 7.03 (d, J=8.7 Hz, 1H), 6.79 (s, 2H), 6.72 (d, J=8.7 Hz, 1H), 5.78 (s, 1H), 5.20 (s, 1H), 4.48-4.46 (m, 1H), 4.34-4.30 (m, 1H), 4.20 (d, J=16.2 Hz, 1H), 3.83 (s, 3H), 3.65-3.57 (m, 2H), 3.44 (s, 1H), 3.33-2.58 (m, 11H), 1.89-1.53 (m, 6H); MS: m/z=694.1 (M$^+$+1).

70. Preparation of R$_1$/R$_2$ Analogs.

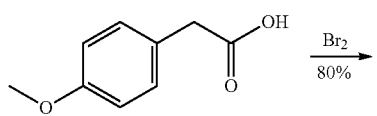

The most important of this part of work is the preparation of various intermediates. The preparation of several intermediates amines and the synthetic routes of desired compounds are shown in Scheme 2.

Scheme 2
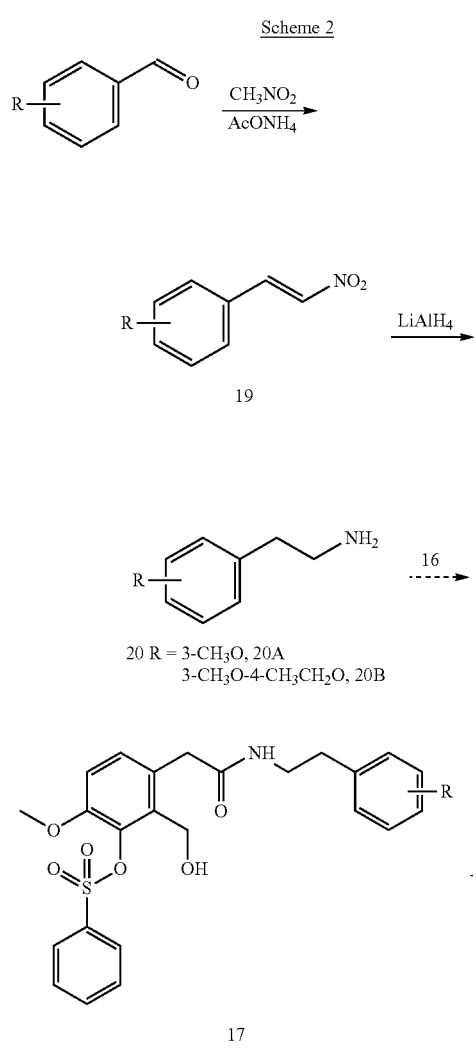
20 R = 3-CH₃O, 20A
3-CH₃O-4-CH₃CH₂O, 20B
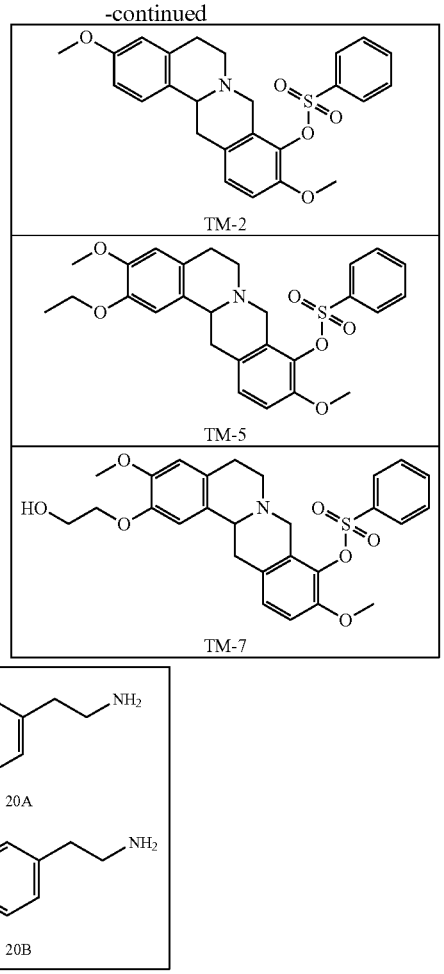
For analog TM-6, different synthetic route was developed as shown in Scheme 3.
Scheme 3
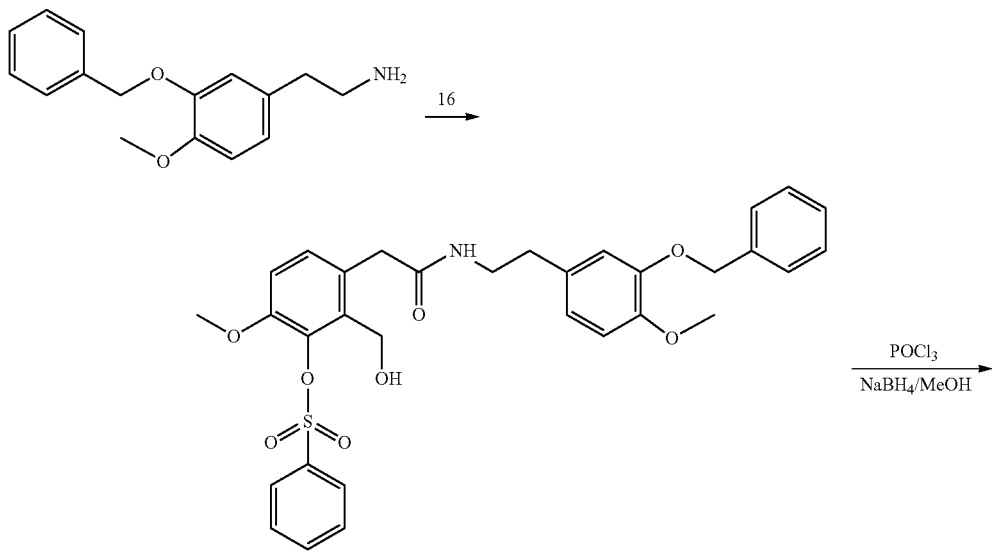

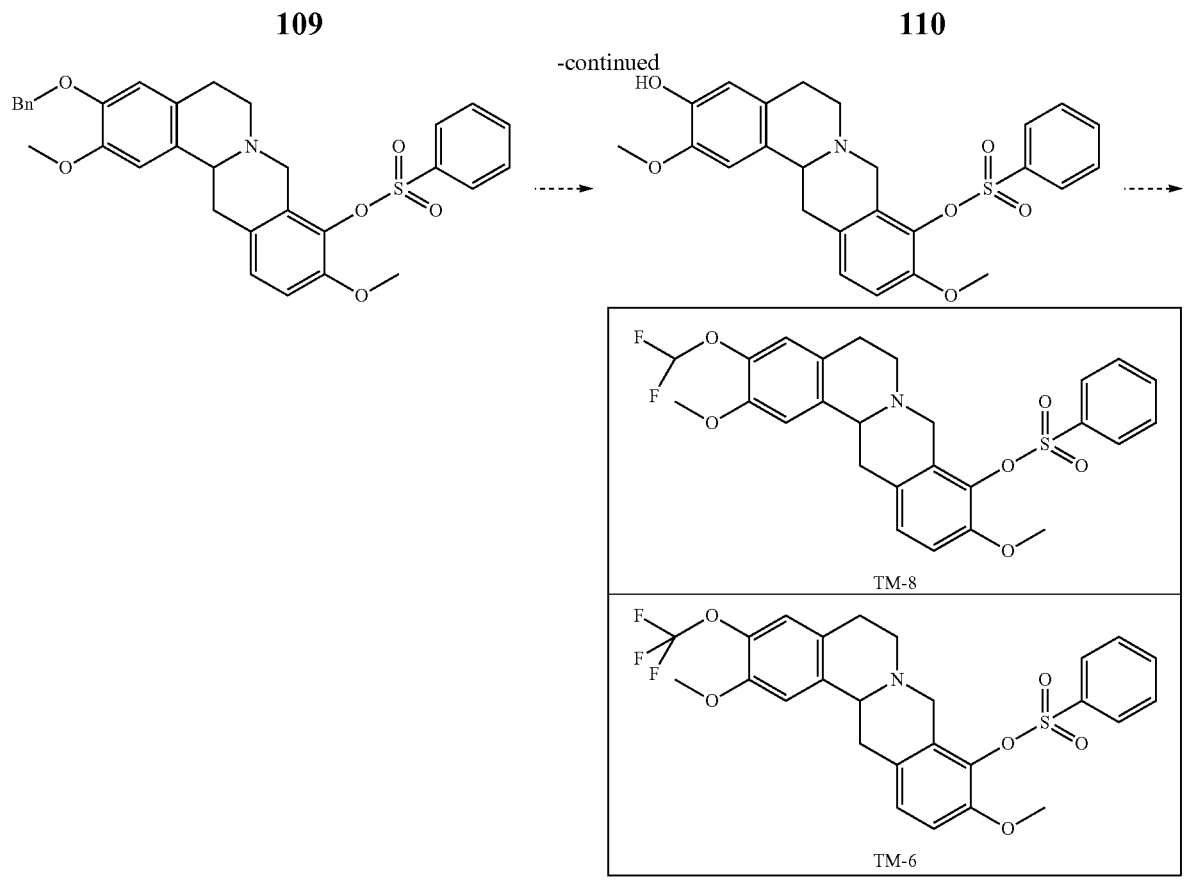
In addition, the COOH group was introduced into the desired compounds to improve the solubility of this series compounds. Some intermediates with the amines such as 21 and 22 were prepared with carboxyl acid group, as shown in Scheme 4.
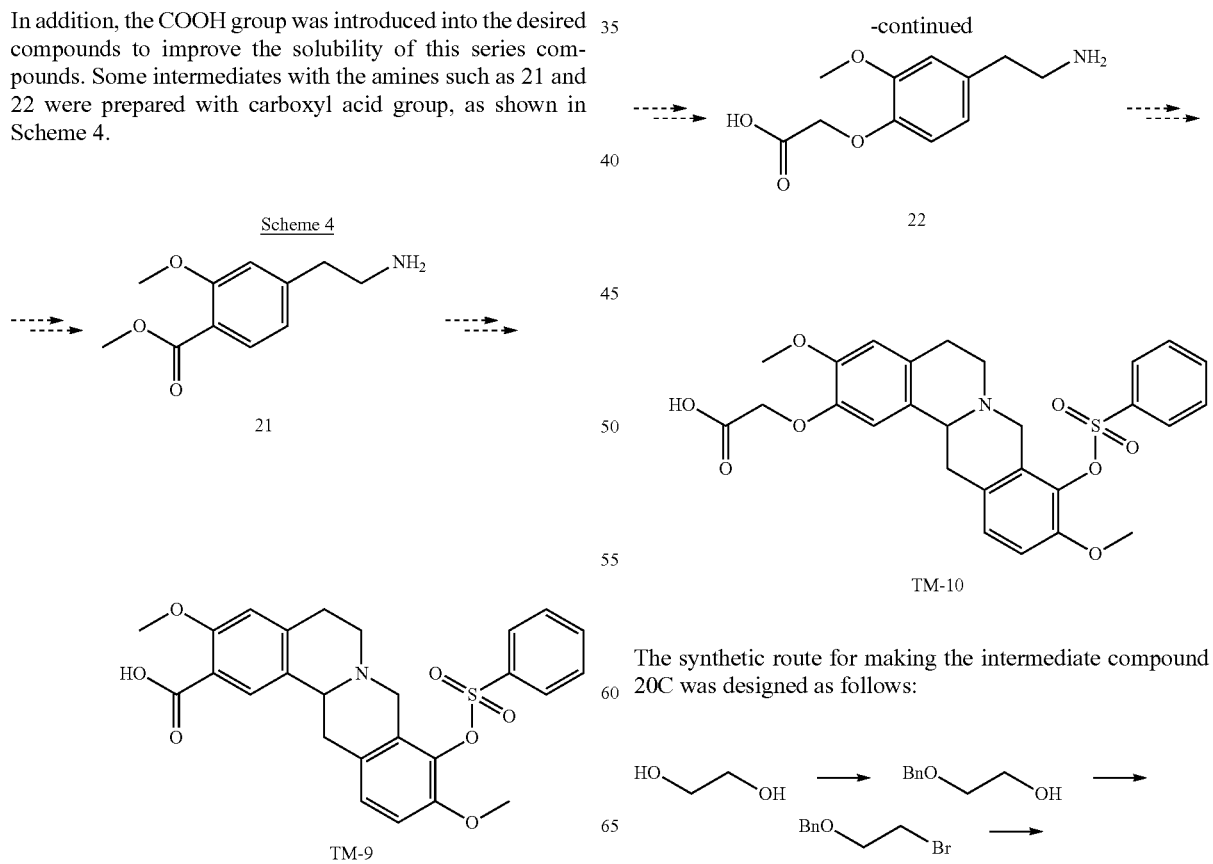
The synthetic route for making the intermediate compound 20C was designed as follows:

111
-continued
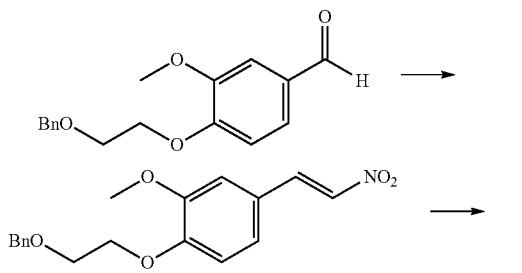
112
-continued
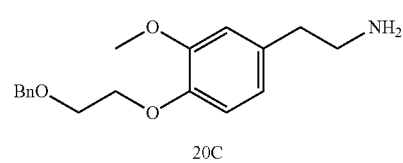
(1) Preparation of Compound 113
Scheme:
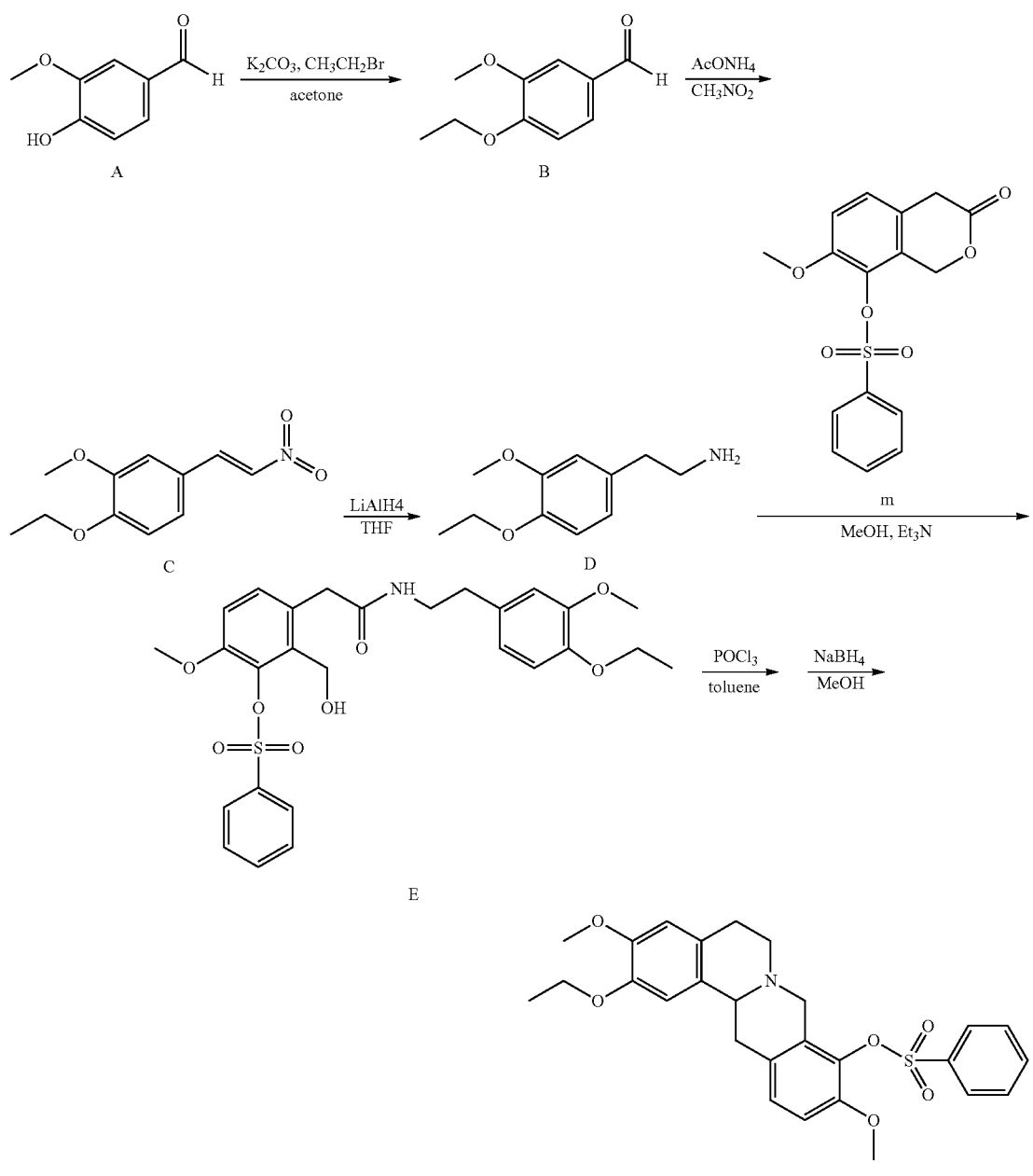
Compound 113

A to B

To a mixture of A (2.0 g, 13.1 mmol) and K₂CO₃ (2.17 g, 15.7 mmol) in 100 mL of acetone, CH₃CH₂Br (1.5 mL, 20.0 mmol) was added. After heating at reflux temperature for one day, the reaction mixture was cooled down. Acetone was removed. Then the reaction mixture was diluted with DCM, washed with water, dried over anhydrous Na₂SO₄, the solvent evaporated and the residue purified on silica chromatography with eluent (EtOAc: PE=1:8) to afford 2.49 g of B.

B to C

B (2.49 g, 13.8 mmol) and AcONH₄ (0.16 g, 1.4 mmol) was dissolved in 20 mL CH₃NO₂. The mixture was stirred at reflux temperature for 2 h. Upon completion, the reaction mixture was cooled to rt. The solvent was removed under vacuum, and the residue was diluted with DCM, washed with water, dried over anhydrous Na₂SO₄. Solvent was removed to afford 1.60 g of C.

C to D

C (1.60 g, 7.2 mmol) in 50 mL THF was added to a solution of LiAlH₄ (1.36 g, 35.9 mmol) in 80 mL THF. The mixture was stirred ar reflux temperature for 8 h. Upon completion, the reaction mixture was cooled to rt. 1.4 mL water, 1.4 mL 15% NaOH (aq) and 4.0 mL water was added. The solid was filtered. Solvent was removed and purified on silica chromatography with eluent (MeOH:DCM=1:12) to afford 0.8 g of D.

D to E

MeOH 20 mL was added to a mixture of m (300 mg, 0.9 mmol), D (193 mg, 1.0 mmol) and 1 mL Et₃N. The resulting solution was stirred at reflux temperature for 8 h. Then the reaction mixture was diluted with DCM, washed with water, aq.NaCl, dried over anhydrous Na₂SO₄. The solvent was removed under vacuum; the residue was purified by silica gel chromatography to afford 300 mg of E.

E to Compound 113

A mixture of E (150 mg, 0.3 mmol) and POCl₃ (1 mL) in toluene (5 mL) was stirred at 120° C. for 2 h. The reaction was monitored by TLC (DCM: MeOH=10:1, v/v). Upon completion, the reaction mixture was cooled to rt. The solvent was removed under vacuum. 53 mg of NaBH₄ was added in portions under 5° C. The reaction mixture was stirred at room temperature for another 30 minutes. The solvent was removed, and the residue was diluted with DCM. The solution was washed with aq.NaCl, water, dried over anhydrous Na₂SO₄. The solvent was removed under vacuum; the residue was purified by silica gel chromatography to afford 20 mg of compound 113.

Compound 113: ¹H NMR (CDCl₃, 300 MHz) δ 7.99-8.02 (m, 2H), 7.65-7.71 (m, 1H), 7.54-7.60 (m, 2H), 7.03 (d, J=8.4 Hz, 1H), 6.70-6.73 (m, 2H), 6.62 (s, 1H), 4.21 (d, J=15.9 Hz, 1H), 4.05-4.15 (m, 2H), 3.86 (s, 3H), 3.56-3.63 (m, 2H), 3.44 (s, 3H), 3.23-3.30 (m, 1H), 3.07-3.16 (m, 2H), 2.78-2.89 (m, 1H), 2.56-2.68 (m, 2H), 1.47-1.49 (t, 3H). MS: m/z=496.1 (M⁺+1).

(2) Preparation of Compound 114

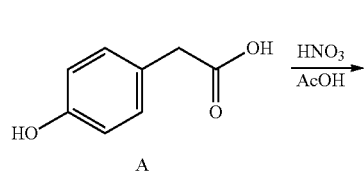

A

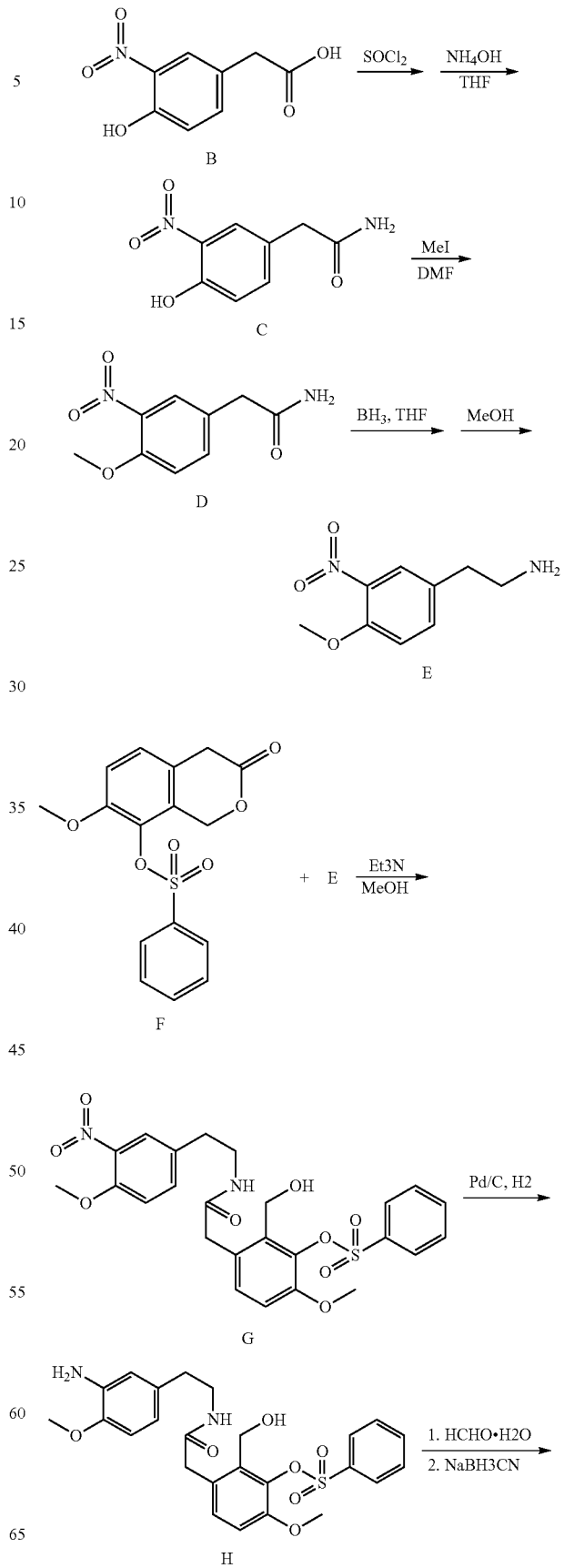

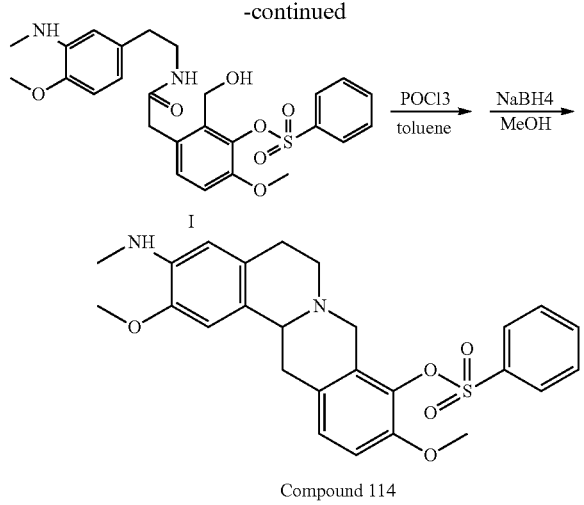

Compound 114

A→B

A solution of nitric acid (2.5 mL, 40 mmol) in acetic acid (2 mL) was slowly added drop-wise to a solution of (4-hydroxyphenyl)acetic acid (5.0 g, 33 mmol) in acetic acid (23 mL) cooled in an ice-bath such that the temperature of the reaction solution did not exceed 20° C. After the reaction solution was stirred for 2 h, water (100 mL) was added drop-wise and the precipitated crystals were collected by filtration. The solid was re-crystallized from EA/PE to afford B (5.0 g).

B→C (4-Hydroxy-3-nitrophenyl)acetic acid (1.3 g, 6.6 mmol) was dissolved in $SOCl_2$ (15 mL) at room temperature and stirred for 10 min. Then the reaction solution was heated to reflux and stirred for 2 hours. The solvent was removed and the residue was dissolved in THF and again concentrated. Aqueous ammonia solution (10 mL of 25% solution) and THF (5 mL) was added to the residue and the mixture was stirred for 30 min at room temperature. The obtained suspension was diluted with water and THF was evaporated under reduced pressure. The precipitate was collected by filtration, washed with water and dried under reduced pressure To give 1.1 g of C.

C→D

C (1.1 g, 5.1 mmol) and potassium carbonate (1.1 g, 8.0 mmol) were suspended in DMF (20 mL) and methyl iodide (0.44 mL, 7.1 mL) was added at room temperature. The mixture was stirred for 3 h. The reaction mixture was diluted with EtOAc and washed with water. The organic layer was concentrated to give 1.0 g of D.

D→E

To a solution of D (1.0 g, 4.8 mmol) in THF (5 mL) was slowly added 1.0 M borane-THF solution (15 mL) at room temperature, and the mixture was refluxed for 5 h. The reaction mixture was concentrated, the residue cooled to room temperature and methanol (20 mL) was added. The mixture was further refluxed overnight. The reaction mixture was extracted with EtOAc and water, the organic layer was collected and concentrated to give 700 mg of E.

E+F→G

To the solution of E (1.6 g, 8.2 mmol), F (3.0 g, 9.0 mmol) in MeOH (40 mL) was added $Et_3N$ (1.4 mL, 9.8 mmol) at 20° C. and the solution was stirred overnight. When TLC analysis indicated the completion of the reaction, the reaction mixture was diluted with EtOAc, and washed with water. The organic layer was collected, dried, concentrated and purified by chromatography to give 3.0 g of G.

G→H

The reaction mixture of G (200 mg, 0.4 mmol) and Pd/C (50 mg) in MeOH (4 mL) was stirred at room temperature under $H_2$ for 8 h. Then the solid was filtered off, and the filtrate was concentrated to give crude product. The residue was further purified by preparative TLC to give 150 mg of H.

H→I

To a stirred solution of H (150 mg, 0.3 mmol) in MeOH was added $HCHO \cdot H_2O$ (96 mg, 1.2 mmol) at room temperature for 1 h. The reaction solution was cooled to 0° C., $NaBH_3CN$ (96 mg, 1.5 mmol) was added and stirred for 30 min at room temperature. When TLC analysis indicated the completion of the reaction, water and EtOAc were added, and the organic layer was collected, dried, concentrated and purified by chromatography to give 50 mg of I.

I→Compound 114

To a stirred solution of I (50 mg, 0.1 mmol) in toluene (3 mL) was added $POCl_3$ (20 μL) at ambient temperature. The reaction mixture was refluxed for 2 h with stirring. When the reaction was completed, the solvent and excess $POCl_3$ were evaporated off. The residue was poured into ice-water and adjusted pH>7 with $Na_2CO_3$. The solution was extracted with EtOAc, and the organic layer was dried, and concentrated. The resulting residue was dissolved in MeOH (3 mL) and $NaBH_4$ (7.6 mg, 0.2 mmol) was added at 0° C. The reaction mixture was stirred for 30 min at this temperature. TLC analysis indicated the completion of the reaction. The solvent was removed and the residue was extracted with EtOAc and water. The organic layer was dried, concentrated and purified by chromatography to give 15 mg of compound 114.

Compound 114: $^1H$ NMR ($CDCl_3$, 300 MHz) δ 8.02-7.98 (m, 2H), 7.72-7.65 (m, 1H), 7.59-7.54 (m, 2H), 7.04 (d, J=8.4 Hz, 1H), 7.03 (d, J=8.4 Hz, 1H), 6.57 (s, 1H), 6.32 (s, 1H), 4.28 (d, J=18.3 Hz, 1H), 3.84 (s, 3H), 3.73 (s, 1H), 3.46 (s, 3H), 3.33-3.26 (m, 1H), 3.19-3.10 (m, 2H), 2.85 (m, 3H), 2.71-2.66 (m, 2H), 2.24-2.17 (m, 1H). MS: m/z=481.1 ($M^+$+1).

(3) Preparation of Compound 115

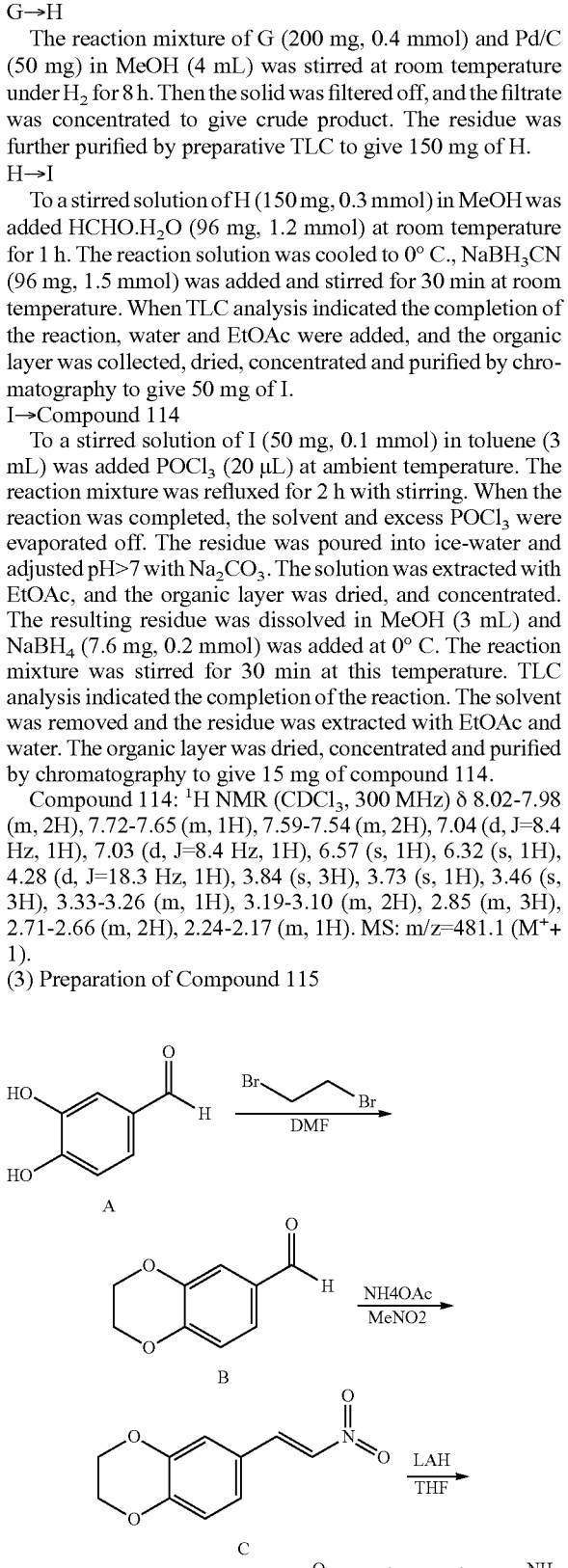

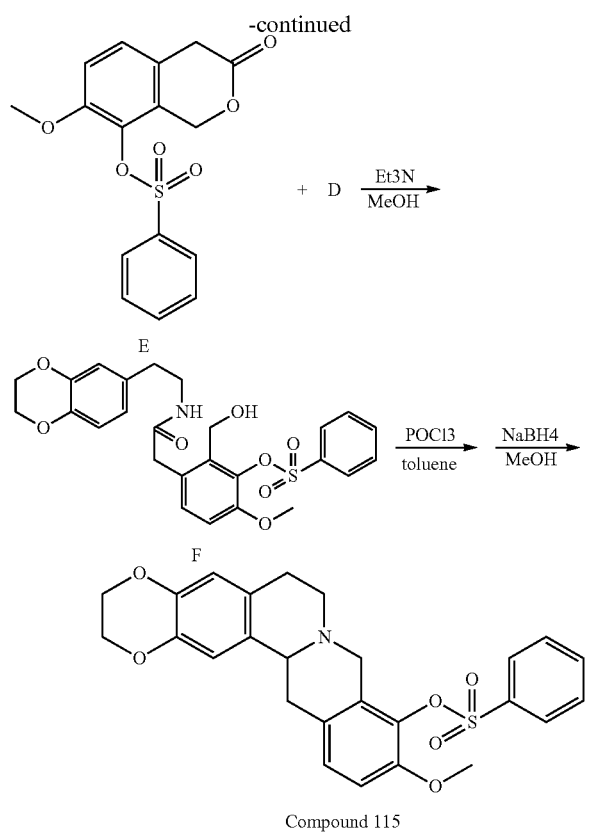

Compound 115

A→B

A (5.0 g, 36.2 mmol), cesium carbonate (26 g, 72.4 mmol), 1,2-dibromoethane (7.0 mL, 72.4 mmol) and anhydrous DMF (50 mL) were stirred at 70° C. for 16 h. After cooling, the solvent was evaporated under reduced pressure and the residue was submitted to flash chromatography (SiO$_2$ column eluted with CH$_2$Cl$_2$), resulting in the isolation of 5.8 g of B.

B→C

B (500 mg, 3.0 mmol) and AcONH$_4$ (23 mg, 0.3 mmol) was dissolved in CH$_3$NO$_2$ (5 mL). The mixture was stirred at reflux temperature for 2 h. Upon completion, the reaction mixture was cooled to rt. The solvent was removed under vacuum, and the residue was diluted with DCM, washed with water, dried over anhydrous Na$_2$SO$_4$. Solvent was removed to afford 600 mg of C.

C→D

C (600 mg, 2.9 mmol) in THF (5 mL) was added to a solution of LiAlH$_4$ (550 mg, 14.5 mmol) in THF (5 mL). The mixture was stirred at reflux temperature for 8 h. Upon completion, the reaction mixture was cooled to rt. 0.5 mL of water, 0.5 mL of 25% NaOH (aq) and 1.5 mL of water was added. The solid was filtered. Solvent was removed and the residue purified on silica chromatography with eluent (MeOH:DCM=1:12) to afford 500 mg of D.

D+E→F

To the solution of D (250 mg, 1.4 mmol), E (520 mg, 1.5 mmol) in MeOH (15 mL) was added Et$_3$N (250 μL, 1.7 mmol) at 20° C. and the solution was stirred overnight. When TLC analysis indicated the completion of the reaction, water was added, and the organic layer was collected, dried, concentrated and purified by chromatography to give 600 mg of F.

F→Compound 115

To a stirred solution of F (100 mg, 0.2 mmol) in toluene (5 mL) was added POCl$_3$ (30 μL) at ambient temperature. The reaction mixture was refluxed for 2 h with stirring. When the reaction was completed, the solvent and excess POCl$_3$ were evaporated off. The residue was poured into ice-water and the pH adjusted to >7 with Na$_2$CO$_3$. The solution was extracted with EtOAc, and the organic layer was dried, concentrated and dissolved in MeOH (5 mL), NaBH$_4$ (15 mg, 0.4 mmol) was added at 0° C. The reaction mixture was stirred for 30 min at this temperature. TLC analysis indicated the completion of the reaction. The solvent was removed and the residue was extracted with EtOAc and water. The organic layer was dried, concentrated and purified by chromatography to give 30 mg of compound 115.

Compound 115: $^1$H NMR (CDCl$_3$, 300 MHz) δ 8.01-7.98 (m, 2H), 7.70-7.65 (m, 1H), 7.59-7.54 (m, 2H), 7.02 (d, J=8.4 Hz, 1H), 6.73-6.70 (m, 2H), 6.63 (s, 1H), 4.28-4.24 (m, 5H), 3.72-3.62 (m, 2H), 3.44 (s, 3H), 3.27 (dd, J=3.9, 16.2 Hz 1H), 3.20-3.07 (m, 2H), 2.95-2.82 (m, 1H), 2.70-2.65 (m, 2H). MS: m/z=480.0 (M$^+$+1).

(4) Preparation of Compound 116

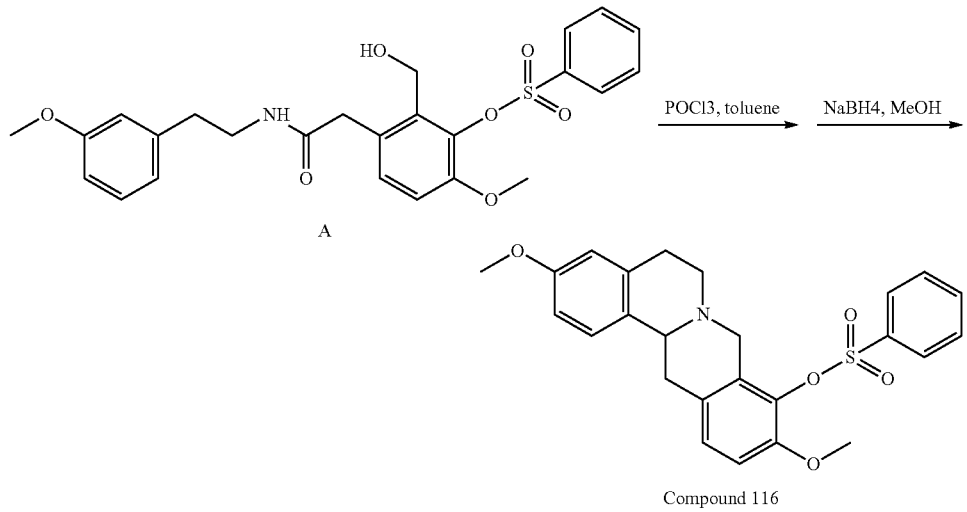

Compound 116

Compound A (200 mg, 0.41 mmol) was suspended in 5 mL of toluene. The mixture was stirred under nitrogen. Then 0.5 mL of phosphoryl chloride was added in one portion, and the mixture was heated under reflux for 2 h. The reaction mixture was cooled under nitrogen. Excess phosphoryl chloride and toluene was evaporated under vacuum. The residue was dissolved in methanol, and 100 mg of $NaBH_4$ was added in portions. The mixture was stirred at room temperature for 30 min. The solvent was removed, and the residue was diluted with EtOAc, washed with $H_2O$ and brine, and dried over anhydrous $Na_2SO_4$. The solvent was removed under vacuum. The residue was purified with flash chromatography to give 120 mg of compound 116.

Compound 116: $^1$H NMR ($CDCl_3$, 300 MHz), δ=8.02-7.99 (m, 1H), 7.70-7.65 (m, 1H), 7.59-7.54 (m, 2H), 7.16 (d, J=8.7 Hz), 7.02 (d, J=8.4 Hz), 6.80-6.65 (m, 3H), 4.22 (d, J=15.9 Hz, 1H), 3.80 (s, 3H), 3.63-3.57 (m, 2H), 3.44 (s, 3H), 3.34-3.12 (m, 3H), 2.87-2.58 (m, 3H); MS: m/z=452.1 ($M^+$+1).

(5) Preparation of Compound 117

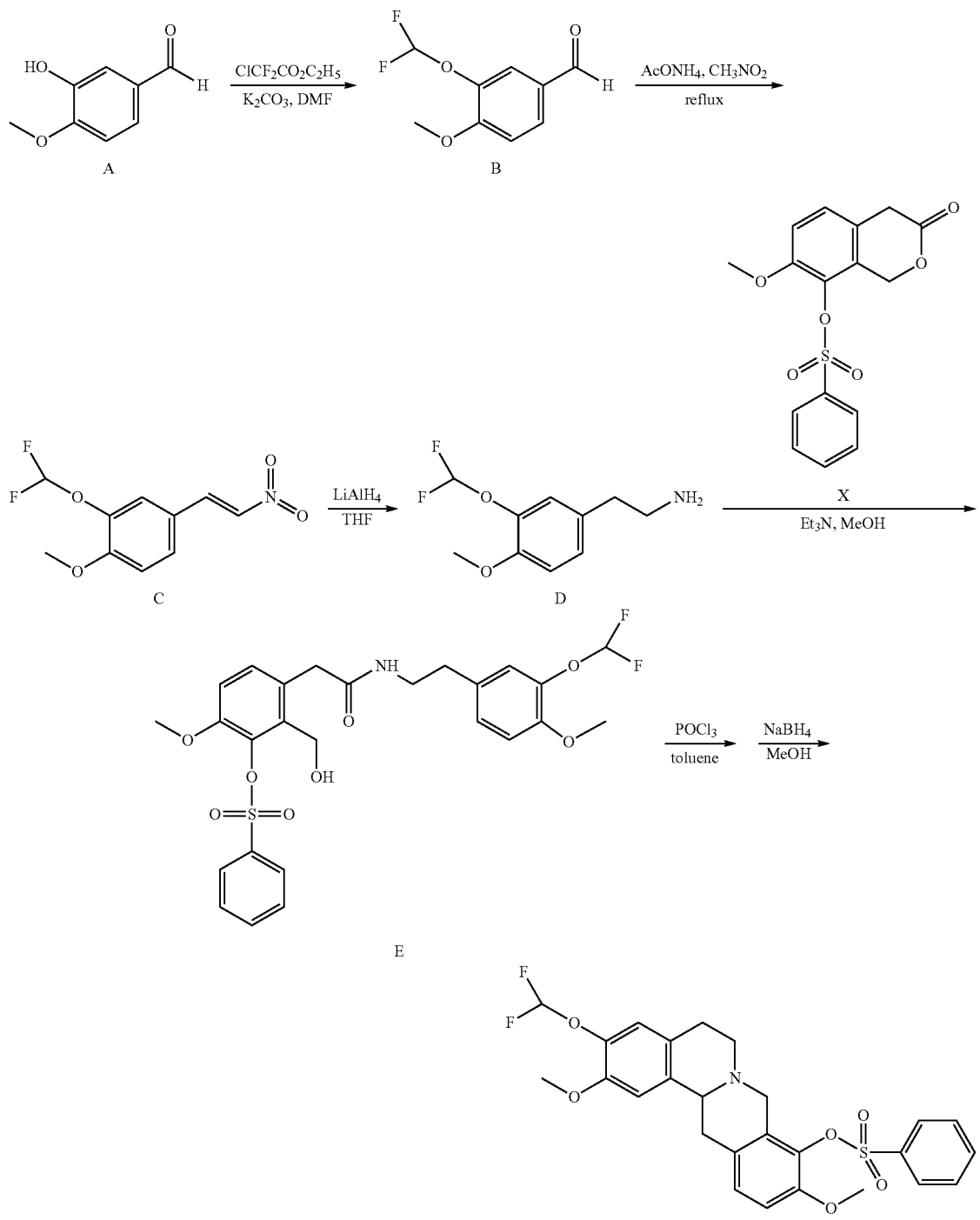

Compound 117

A to B

A mixture of A (5.0 g, 32.9 mmol) and ethyl 2-chloro-2,2-difluoroacetate (5.7 g, 36.0 mmol), potassium carbonate (4.5 g, 32.9 mmol) in dry DMF (90 mL) were stirred at 60° C. for 6 hours under an $N_2$ atmosphere. Then the reaction was stirred at rt. for another 60 hours. Ether (200 mL) was added to the mixture and the layers separated. The organic phase was washed with water (100 mL*3), dried over $Na_2SO_4$, evaporated and purified on silica chromatography with eluent (EtOAc:PE=1:12) to afford B 2.3 g.

B to C

B (500 mg, 2.48 mmol) and $AcONH_4$ (19 mg, 0.25 mmol) was dissolved in 15 mL $CH_3NO_2$. The mixture was stirred at reflux temperature for 2 h. Upon completion, the reaction mixture was cooled to rt. The solvent was removed under vacuum, and the residue was diluted with DCM, washed with water, dried over anhydrous $Na_2SO_4$. Solvent was removed to afford 590 mg of C.

C to D

C (300 mg, 1.2 mmol) in 5 mL THF was added to a solution of LiAlH4 (232 mg, 6.1 mmol) in 10 mL THF. The mixture was stirred at reflux temperature for 8 h. Upon completion, the reaction mixture was cooled to rt. 1.4 mL water, 1.4 mL 15% NaOH (aq) and 4.0 mL water was added. The solid was filtered. Solvent was removed and purified on silica chromatography with eluent (MeOH:DCM=1:10) to afford 85 mg of D.

D to E

MeOH 10 mL was added to a mixture of X (147 mg, 0.4 mmol), D (80 mg, 0.4 mmol) and 1 mL $Et_3N$. The resulting solution was stirred at reflux temperature for 8 h. Then the reaction mixture was diluted with DCM, washed with water, aq.NaCl, dried over anhydrous $Na_2SO_4$. The solvent was removed under vacuum; the residue was purified by silica gel chromatography to afford 132 mg of E.

E to Compound 117

A mixture of E (130 mg, 0.2 mmol) and $POCl_3$ (1 mL) in toluene (10 mL) was stirred at 120° C. for 2 h. The reaction was monitored by TLC (DCM: MeOH=10:1, v/v). Upon completion, the reaction mixture was cooled to rt. The solvent was removed under vacuum. 46 mg of $NaBH_4$ was added in portions under 5° C. The reaction mixture was stirred at room temperature for another 30 minutes. The solvent was removed, and the residue was diluted with DCM. The solution was washed with aq.NaCl, water, dried over anhydrous $Na_2SO_4$. The solvent was removed under vacuum; the residue was purified by silica gel chromatography to afford 20 mg of compound 117.

Compound 117: $^1$H NMR (CDCl$_3$, 300 MHz) δ 7.97-8.02 (m, 2H), 7.54-7.71 (m, 3H), 6.71-7.05 (m, 4H), 6.54 (t, J=75.3, 1H), 4.22 (d, J=159 Hz, 1H), 3.88 (s, 3H), 3.60-3.66 (m, 2H), 3.45 (s, 3H), 3.24-3.31 (m, 1H), 3.04-3.16 (m, 2H), 2.81-2.90 (m, 1H), 2.57-2.72 (m, 2H). MS: m/z=518.1 (M$^+$+1).

(6) Preparation of Compound 118

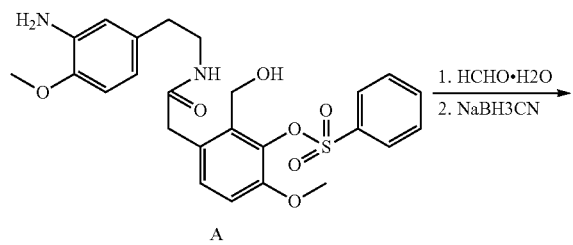

A

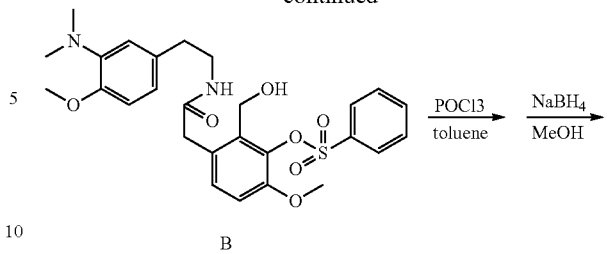

B

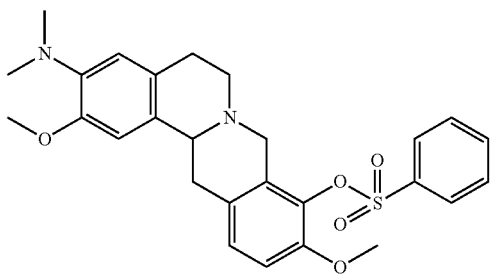

Compound 118

A→B

To a stirred solution of A (150 mg, 0.3 mmol) in MeOH was added HCHO.H$_2$O (96 mg, 1.2 mmol) at room temperature for 3 h. The reaction solution was cooled to 0° C. NaBH$_3$CN (96 mg, 1.5 mmol) was added and stirred for 1 h at room temperature. When TLC analysis indicated the completion of the reaction, water and EtOAc were added, and the organic layer was collected, dried, concentrated and purified by chromatography to give 100 mg of B.

B→Compound 118

To a stirred solution of 1 (100 mg, 0.19 mmol) in toluene (3 mL) was added POCl$_3$ (50 μL) at ambient temperature. The reaction mixture was refluxed for 2 h with stirring. When the reaction was completed, the solvent and excess POCl$_3$ were evaporated off. The residue was poured into ice-water and adjusted to pH>7 with Na$_2$CO$_3$. The solution was extracted with EtOAc, and the organic layer was dried, concentrated and dissolved in MeOH (3 mL), NaBH$_4$ (22.8 mg, 0.6 mmol) was added at 0° C. The reaction mixture was stirred for 30 min at this temperature. TLC analysis indicated the completion of the reaction. The solvent was removed and the residue was extracted with EtOAc and water. The organic layer was dried, concentrated and purified by chromatography to give 10 mg of compound 118.

Compound 118: $^1$H NMR (CDCl$_3$, 300 MHz) δ 8.02-7.99 (m, 2H), 7.68-7.66 (m, 1H), 7.58-7.54 (m, 2H), 7.04 (d, J=8.4 Hz, 1H), 6.73-6.67 (s, 3H), 4.21 (d, J=15.9 Hz, 1H), 3.89 (s, 3H), 3.61-3.56 (m, 2H), 3.45 (s, 3H), 3.32-3.27 (m, 1H), 3.13-3.07 (m, 2H), 2.90-2.83 (m, 1H), 2.78 (s, 6H), 2.67-2.57 (m, 2H). MS: m/z=495.1 (M$^+$+1).

(7) Preparation of Compound 119

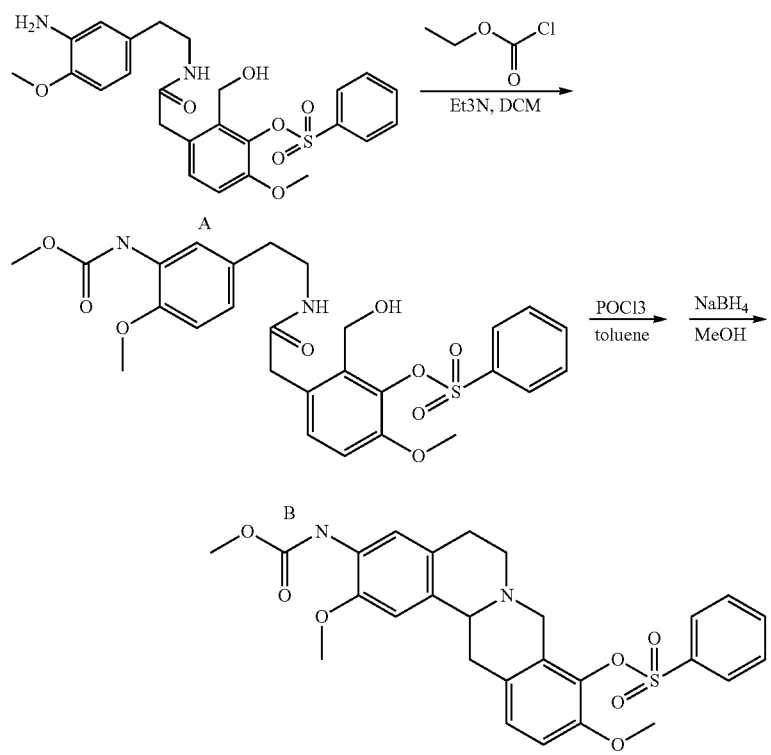

A→B

To a stirred solution of A (150 mg, 0.3 mmol) in DCM (3 mL) was added Et₃N (100 μL), ethyl chloroformate (100 μL) at room temperature for 3 h. When TLC analysis indicated the completion of the reaction, water was added, and the organic layer was collected, dried, concentrated and the resulting residue purified by chromatography to give 100 mg of B.

B→Compound 119

To a stirred solution of 1 (100 mg, 0.17 mmol) in toluene (3 mL) was added $POCl_3$ (50 μL) at ambient temperature. The reaction mixture was refluxed for 2 h with stirring. When the reaction was completed, the solvent and excess $POCl_3$ were evaporated off. The residue was poured into ice-water and adjusted to pH>7 with $Na_2CO_3$. The solution was extracted with EtOAc, and the organic layer was dried, concentrated and dissolved in MeOH (3 mL), $NaBH_4$ (22.8 mg, 0.6 mmol) was added at 0° C. The reaction mixture was stirred for 30 min at this temperature. TLC analysis indicated the completion of the reaction. The solvent was removed and the residue was extracted with EtOAc and water. The organic layer was dried, concentrated and purified by chromatography to give 70 mg of compound 119.

Compound 119: $^1$H NMR ($CDCl_3$, 300 MHz) δ 7.99-7.96 (m, 2H), 7.86 (s, 1H), 7.68-7.66 (m, 1H), 7.59-7.54 (m, 2H), 7.17 (s, 1H), 7.05 (d, J=8.7 Hz, 1H), 6.76 (d, J=8.7 Hz, 1H), 6.68 (s, 1H), 4.40 (d, J=15.3 Hz, 1H), 4.22 (q, J=7.2, 14.1 Hz, 2H), 4.11-4.04 (m, 1H), 3.97-3.91 (m, 1H), 3.85 (s, 3H), 3.47 (s, 3H), 3.43-3.32 (m, 2H), 3.22-3.13 (m, 1H), 3.05-2.84 (m, 3H). MS: m/z=539.1 (M⁺+1).

(8) Preparation of Compound 121

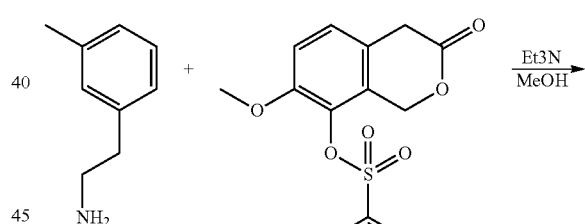

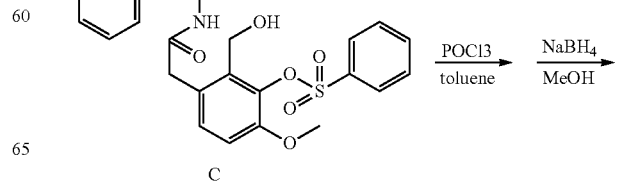

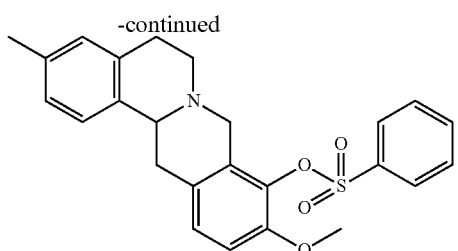

Compound 121

A+B→C

To the solution of A (67.5 mg, 0.5 mmol), B (167 mg, 0.5 mmol) in MeOH (5 mL) was added Et₃N (83 μL, 0.6 mmol) at 20° C. and the solution was heated to reflux overnight. When TLC analysis indicated the completion of the reaction, water and EtOAc were added, and the organic layer was collected, dried, concentrated and the residue purified by chromatography to give 190 mg of C.

C→Compound 121

To a stirred solution of C (94 mg, 0.2 mmol) in toluene (5 mL) was added POCl₃ (30 μL) at ambient temperature. The reaction mixture was refluxed for 2 h with stirring. When the reaction was completed, the solvent and excess POCl₃ were evaporated off. The residue was poured into ice-water and adjusted to pH>7 with Na₂CO₃. The solution was extracted with EtOAc, and the organic layer was dried, concentrated and dissolved in MeOH (5 mL), NaBH₄ (15 mg, 0.4 mmol) was added at 0° C. The reaction mixture was stirred for 10 min at this temperature. TLC analysis indicated the completion of the reaction. The solvent was removed and the residue was extracted with EtOAc and water. The organic layer was dried, concentrated and purified by chromatography to give 30 mg of compound 121.

Compound 121: $^1$H NMR (CDCl₃, 300 MHz) δ 8.02-7.99 (m, 2H), 7.68-7.65 (m, 1H), 7.59-7.54 (m, 2H), 7.14 (d, J=8.1 Hz, 1H), 7.04-6.96 (m, 3H), 6.72 (d, J=8.4 Hz, 1H), 4.22 (d, J=15.9 Hz, 1H), 3.65-3.58 (m, 2H), 3.44 (s, 3H), 3.32 (dd, J=4.2, 16.2 Hz 1H), 3.16-3.11 (m, 2H), 2.88-2.79 (m, 1H), 2.75-2.57 (m, 2H), 2.32 (s, 3H). MS: m/z=436.1 (M⁺+1).

(9) Preparation of Compound 122

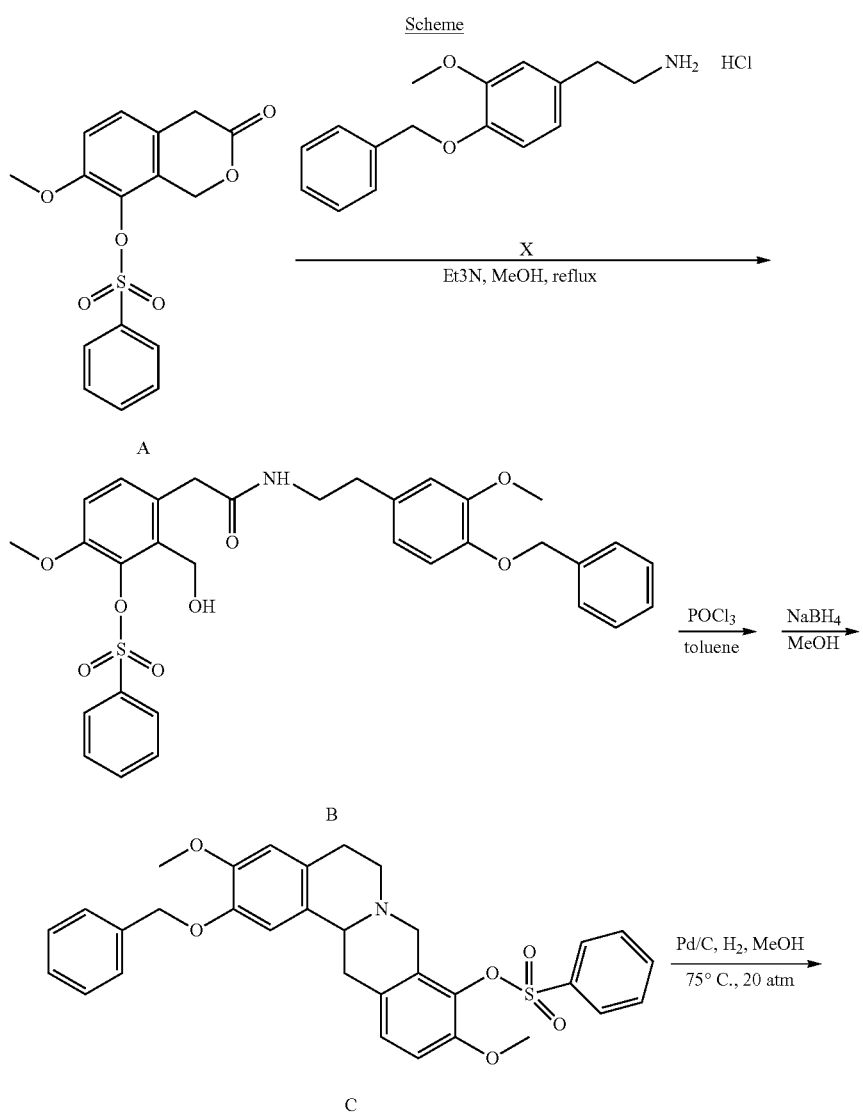

Scheme

-continued

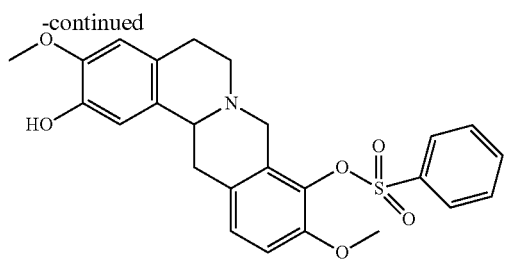

Compound 122

Procedure

A to B

MeOH 100 mL was added to a mixture of A (2.0 g, 6.0 mmol), X (2.1 g, 7.2 mmol) and 3 mL Et₃N. The resulting solution was stirred at reflux temperature for 5 h. Then the reaction mixture was diluted with DCM, washed with water, aq. NaCl, and dried over anhydrous Na₂SO₄. The solvent was removed under vacuum; the residue was purified by silica gel chromatography to afford 3.08 g of B.

B to C

A mixture of B (2.7 g, 4.6 mmol) and POCl₃ (4 mL) in toluene (50 mL) was stirred at 120° C. for 2 h. The reaction was monitored by TLC (DCM: MeOH=10:1, v/v). Upon completion, the reaction mixture was cooled to rt. The solvent was removed under vacuum. 874 mg of NaBH₄ was added in portions under 5° C. The reaction mixture was stirred at room temperature for another 30 minutes. The solvent was removed, and the residue was diluted with DCM. The solution was washed with aq. NaCl, water, and dried over anhydrous Na₂SO₄. The solvent was removed under vacuum; the residue was purified by silica gel chromatography to afford 1 g of C.

C to Compound 122

To a stirred solution of C (600 mg, 1.1 mmol) in MeOH (50 mL) was added Pd/C (120 mg) under 20 atm H₂. The reaction mixture was stirred at 75° C. overnight. Then the solid was filtered off. The solvent was removed under vacuum; the residue was purified by silica gel chromatography to afford 200 mg of compound 122.

Compound 122: $^1$H NMR (CDCl₃, 300 MHz) δ 7.98-8.02 (m, 2H), 7.54-7.71 (m, 3H), 7.02 (d, J=8.4 Hz, 1H), 6.80 (s, 1H), 6.71 (d, J=8.4 Hz, 1H), 6.60 (s, 1H), 5.50 (s, 1H), 4.21 (d, J=15.9 Hz, 1H), 3.88 (s, 3H), 3.54-3.62 (m, 2H), 3.42 (s, 3H), 3.24-3.30 (m, 1H), 3.10-3.15 (m, 2H), 2.80-2.85 (m, 1H), 2.60-2.64 (m, 2H). MS: m/z=468.1 (M⁺+1).

(10) Preparation of Compound 123 and Compound 124

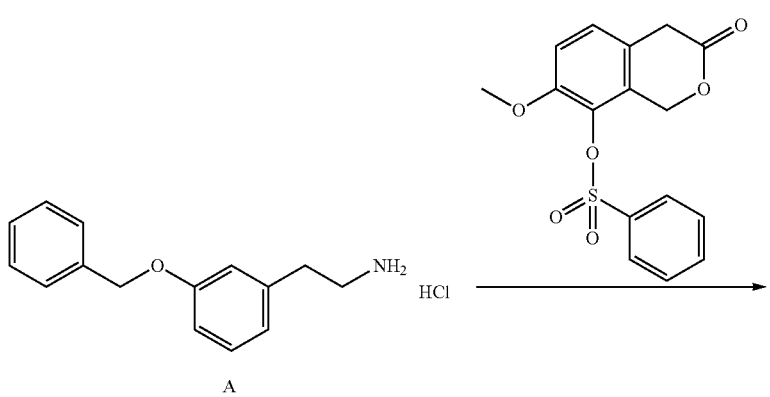

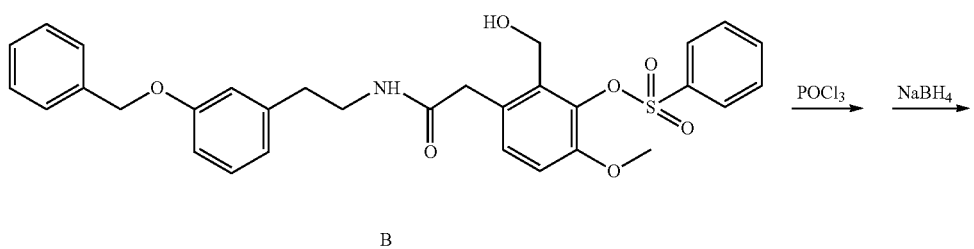

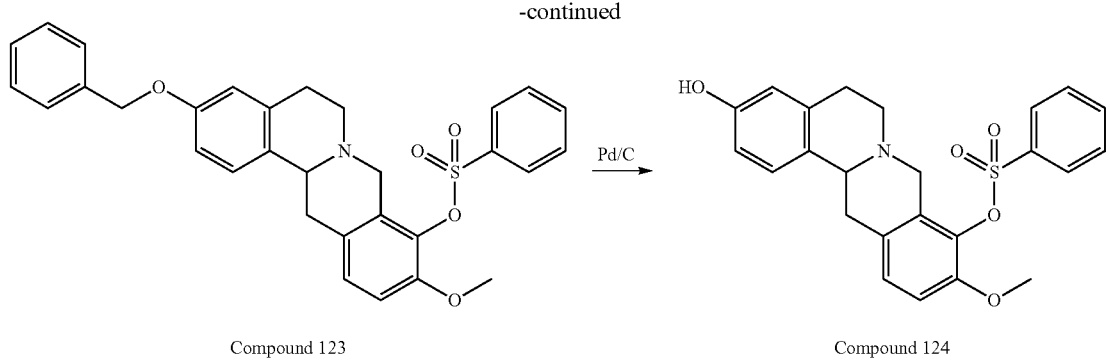

Compound 123 → Compound 124

A to B

To the solution of A (2.4 g, 9.0 mmol) and benzenesulfonate C (2.7 g, 8.1 mmol) in MeOH (20 mL) was added Et₃N (3 mL) at 20° C. and the solution was heated to reflux overnight. When TLC analysis indicated the completion of the reaction, water and EtOAc were added, and the organic layer was collected, dried, concentrated and purified by chromatography to give 3 g of B.

B to Compound 123

To a stirred solution of B (1 g, 1.8 mmol) in toluene (60 mL) was added POCl₃ (3 mL) at ambient temperature. The reaction mixture was refluxed for 2 h with stirring. When the reaction was completed, the solvent and excess POCl₃ were evaporated off. The residue was poured into ice-water and adjusted to pH>7 with Na₂CO₃. The solution was extracted with EtOAc, and the organic layer was dried and concentrated. The resulting residue was dissolved in MeOH (20 mL), and NaBH₄ (400 mg) was added at 0° C. The reaction mixture was stirred for 10 min at this temperature. TLC analysis indicated the completion of the reaction. The solvent was removed and the residue was extracted with EtOAc and water. The organic layer was dried, concentrated and the residue purified by chromatography to give 200 mg of compound 123.

Compound 123 to Compound 124

To a solution of compound 123 (160 mg) in MeOH (50 mL) was added 10% of Pd/C (20 mg). The inner pressure was 2 MPa and the reaction stirred at 70° C. overnight. After stopping the reaction, filter and remove the solvent. Purify by preparative TLC to afford compound 124 about 30 mg.

Compound 123: $^1$H NMR (CDCl₃, 300 MHz) δ 7.99-8.01 (d, J=9 Hz, 1H), 7.68-7.65 (m, 1H), 7.59-7.54 (m, 2H), 7.46-7.32 (m, 5H), 7.18-7.15 (d, J=9 Hz, 1H), 6.01-6.04 (d, J=9 Hz, 1H), 6.87-6.84 (m, 1H), 6.70-6.75 (m, 1H), 5.05 (s, 2H), 4.20-4.26 (d, J=9 Hz, 1H), 3.59-3.64 (m, 2H), 3.44 (s, 3H), 3.32 (dd, J=4.2, 16.2 Hz 1H), 3.16-3.11 (m, 2H), 2.88-2.58 (m, 3H). MS: m/z=528.1 (M⁺+1).

Compound 124: $^1$H NMR (CDCl₃, 300 MHz) δ 7.99-8.01 (d, J=9 Hz, 1H), 7.68-7.65 (m, 1H), 7.59-7.54 (m, 2H), 7.18-7.15 (d, J=9 Hz, 1H), 6.01-6.04 (d, J=9 Hz, 1H), 6.87-6.84 (m, 1H), 6.70-6.75 (m, 1H), 4.20-4.26 (d, J=9 Hz, 1H), 3.59-3.64 (m, 2H), 3.44 (s, 3H), 3.32 (dd, J=4.2, 16.2 Hz 1H), 3.16-3.11 (m, 2H), 2.88-2.58 (m, 3H). MS: m/z=438.1 (M⁺+1).

(11) Preparation of Compound 125

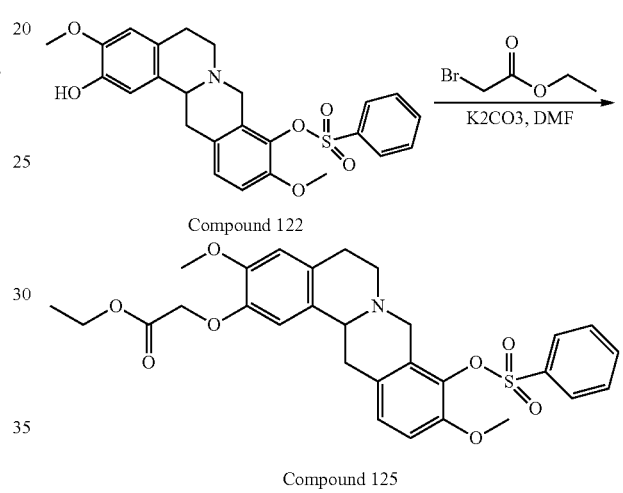

Compound 122

Compound 125

Compound 122 to Compound 125:

To a stirred mixture of compound 122 (30 mg, 0.06 mmol) and K₂CO₃ (8 mg, 0.06 mmol) in DMF (5 mL) was added ethyl 2-bromoacetate (9 µL, 0.08 mmol). The reaction mixture was stirred at rt overnight. The solvent was removed, and the residue was diluted with DCM. The solution was washed with water, aq.NaCl, dried over anhydrous Na₂SO₄. The solvent was removed under vacuum; the residue was purified by silica gel chromatography to afford 10 mg of compound 125.

Compound 125: $^1$HNMR (CDCl₃, 300 MHz) δ 7.98-8.02 (m, 2H), 7.54-7.71 (m, 3H), 7.01 (d, J=8.4 Hz, 1H), 6.64-6.75 (m, 3H), 4.68 (s, 2H), 4.26 (q, J=7.1 Hz, 2H), 4.17 (d, J=15.1 Hz, 1H), 3.57 (s, 3H), 3.54-3.64 (m, 2H), 3.43 (s, 3H), 3.07-3.27 (m, 3H), 2.57-2.85 (m, 3H), 1.31 (t, J=7.2 Hz, 3H). MS: m/z=554.1 (M⁺+1).

(12) Preparation of Compound 126

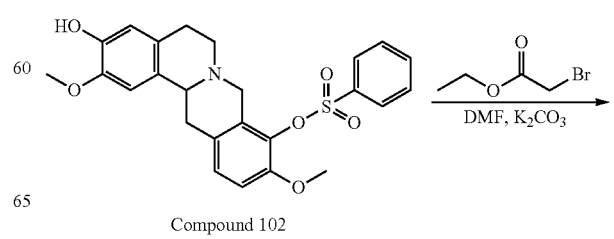

Compound 102

-continued

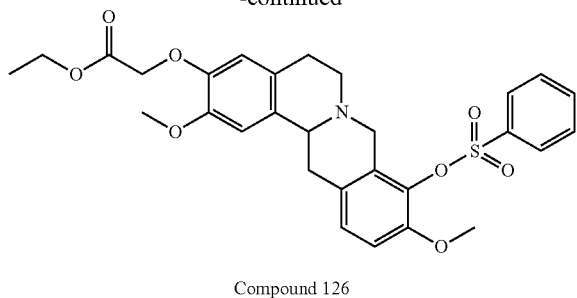

Compound 126

To a stirred mixture of compound 102 (200 mg, 0.43 mmol) and K₂CO₃ (70 mg, 0.50 mmol) in DMF (2 mL) was added ethyl 2-bromoacetate (50 µL, 0.45 mmol). The reaction mixture was stirred at rt. overnight. The solvent was removed under vacuum, and the residue was diluted with DCM. The solution was washed with water, brine, and dried over anhydrous Na₂SO₄. The solvent was removed under vacuum; the residue was purified by silica gel chromatography to afford 160 mg of compound 125.

Compound 125: ¹H NMR (CDCl₃, 300 MHz) δ 8.01-7.98 (m, 2H), 7.67-7.53 (m, 3H), 7.02 (d, J=8.3 Hz, 1H), 6.73-6.70 (m, 2H), 6.56 (s, 1H), 4.66 (s, 2H), 4.26 (q, J=7.1 Hz 2H), 4.17 (d. J=15.1 Hz, 1H), 3.88 (s, 3H), 3.64-3.53 (m, 2H), 3.43 (s, 3H), 3.28-3.01 (m, 3H), 2.85-2.60 (m, 3H), 1.28 (t, J=7.2 Hz, 3H). MS: m/z=554.1 (M⁺+1).

(12) Preparation of Compound 127

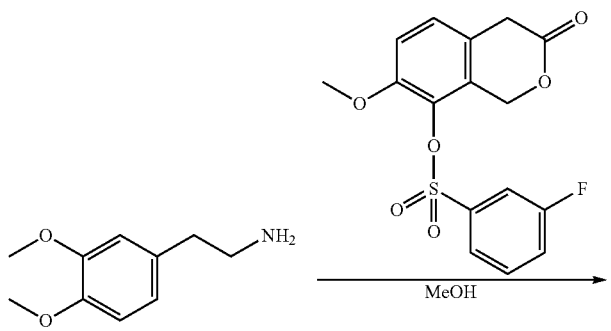

A

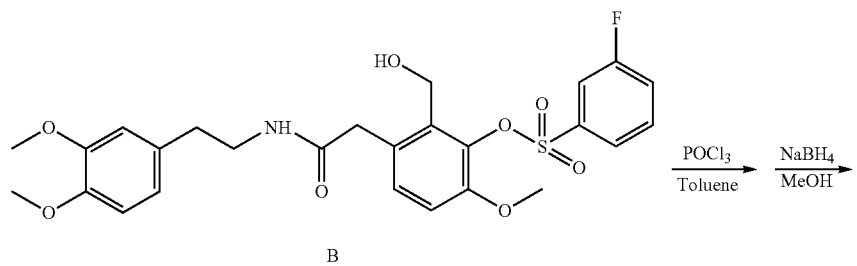

B

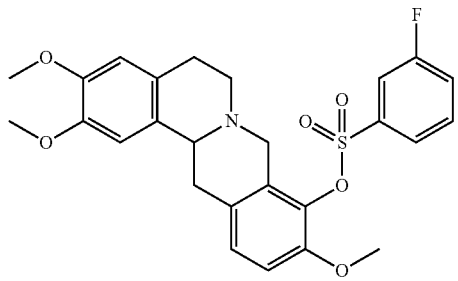

Compound 127

A to B

To the solution of A (240 mg, 1.4 mmol) and the above benzenesulfonate (400 mg, 1.1 mmol) in MeOH (20 mL) was added Et$_3$N (0.5 mL) at 20° C. and then the solution was heated to reflux overnight. When TLC analysis indicated the completion of the reaction, water and EtOAc were added, and the organic layer was collected, dried, concentrated and purified by chromatography to give 500 mg of B.

B to Compound 127

To a stirred solution of B (400 mg, 0.75 mmol) in toluene (60 mL) was added POCl$_3$ (2 mL) at ambient temperature. The reaction mixture was refluxed for 2 h with stirring. When the reaction was completed, the solvent and excess POCl$_3$ were evaporated off. The residue was poured into ice-water and adjusted to pH>7 with Na$_2$CO$_3$. The solution was extracted with EtOAc, and the organic layer was dried, concentrated and dissolved in MeOH (20 mL), NaBH$_4$ (200 mg) was added at 0° C. The reaction mixture was stirred for 10 min at this temperature. TLC analysis indicated the completion of the reaction. The solvent was removed and the residue was extracted with EtOAc and water. The organic layer was dried, concentrated and purified by chromatography to give 130 mg of compound 127.

Compound 127: $^1$H NMR (CDCl$_3$, 300 MHz) δ 7.82-7.79 (m, 2H), 7.75-7.71 (m, 1H), 7.60-7.52 (m, 1H), 7.42-7.36 (m, 1H), 7.07-7.04 (dd, J=9 Hz, 1H), 6.71-6.75 (m, 2H), 6.62 (s, 1H), 4.26-4.22 (d, J=12 Hz, 1H), 3.89 (s, 3H), 3.87 (s, 3H), 3.67-3.59 (m, 2H), 3.49 (s, 3H), 3.32-3.26 (dd, J=12 Hz, 1H), 3.19-3.08 (m, 2H), 2.88-2.79 (m, 1H), 2.70-2.63 (m, 2H). MS: m/z 500.1 (M$^+$+1).

(13) Preparation of Compound 128

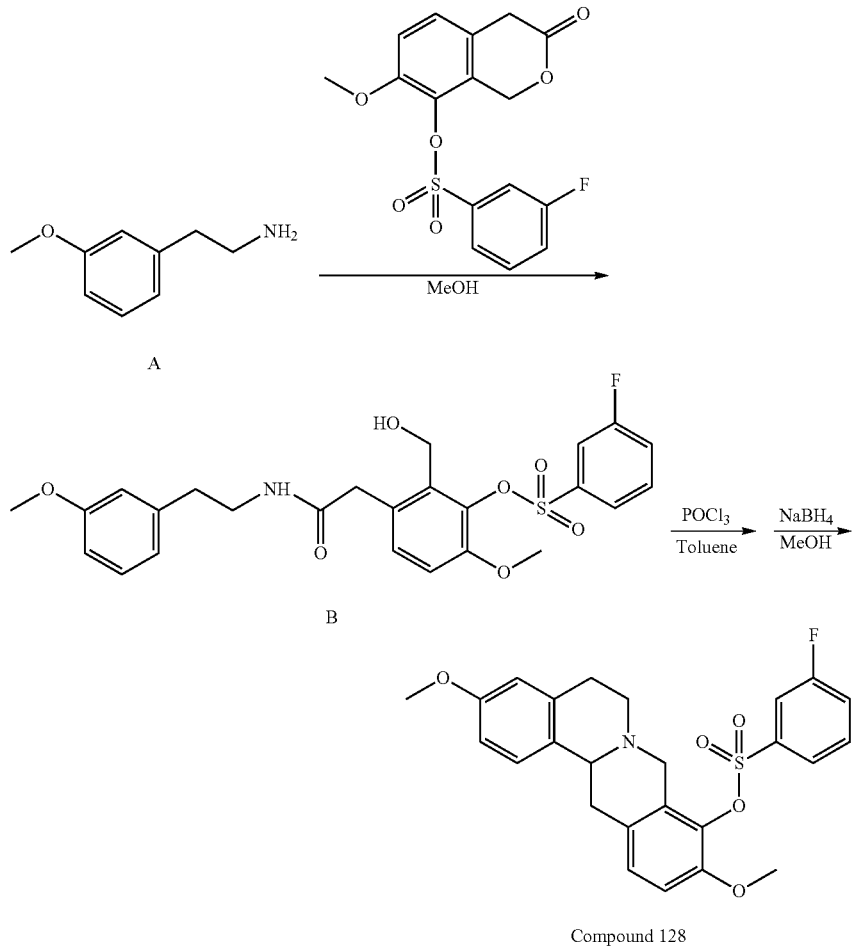

Compound 128

A to B

To the solution of A (96.5 mg, 0.64 mmol) and the above benzenesulfonate (150 mg, 0.43 mmol) in MeOH (10 mL) was added Et$_3$N (0.5 mL) at 20° C. and then the solution was heated to reflux overnight. When TLC analysis indicated the completion of the reaction, water and EtOAc were added, and the organic layer was collected, dried, concentrated and purified by chromatography to give 230 mg of B.

B to Compound 128

To a stirred solution of B (230 mg, 0.46 mmol) in toluene (30 mL) was added POCl$_3$ (105 mL) at ambient temperature. The reaction mixture was refluxed for 2 h with stirring. When the reaction was completed, the solvent and excess POCl$_3$ were evaporated off. The residue was poured into ice-water and adjusted to pH>7 with Na$_2$CO$_3$. The solution was extracted with EtOAc, and the organic layer was dried, concentrated and dissolved in MeOH (20 mL), NaBH$_4$ (200 mg) was added at 0° C. The reaction mixture was stirred for 10 min at this temperature. TLC analysis indicated the completion of the reaction. The solvent was removed and the residue was extracted with EtOAc and water. The organic layer was dried, concentrated and purified by chromatography to give 32 mg of compound 128.

Compound 128: $^1$H NMR (CDCl$_3$, 300 MHz) δ 7.82-7.80 (d, J=6 Hz, 1H), 7.75-7.71 (m, 1H), 7.60-7.52 (m, 1H), 7.42-7.36 (m, 1H), 7.17 (dd, J=9 Hz, 1H), 7.05-7.03 (d, J=9 Hz, 1H), 6.80-6.66 (m, 3H), 4.26-4.22 (d, J=12 Hz, 1H), 3.80 (s, 3H), 3.68-3.63 (m, 2H), 3.48 (s, 3H), 3.35-3.29 (dd, J=12 Hz, 1H), 3.19-3.14 (m, 2H), 2.87-2.77 (m, 3H). MS: m/z=470.1 (M$^+$+1).

(14) Preparation of Compound 129

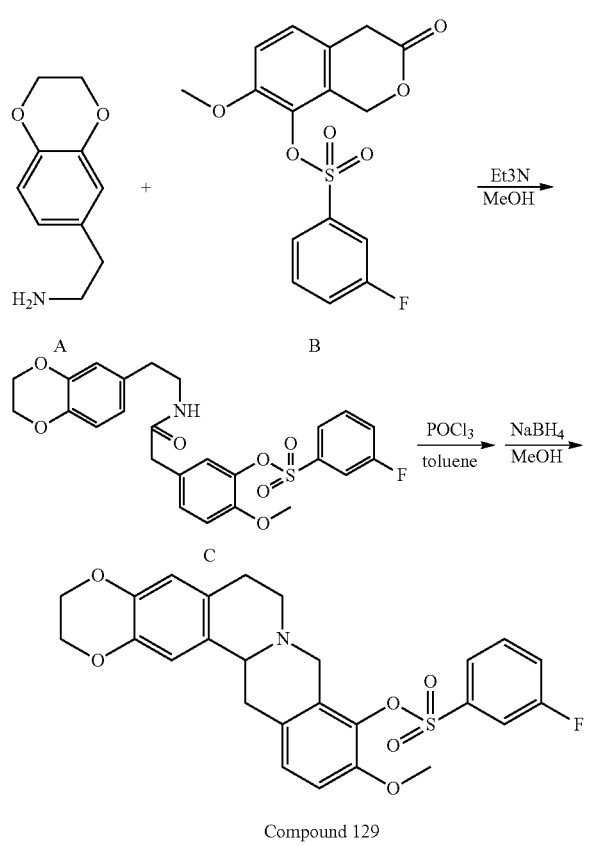

Compound 129

Compound 129: $^1$H NMR (CDCl$_3$, 300 MHz) δ 7.80-7.77 (m, 1H), 7.72-7.69 (m, 1H), 7.59-7.55 (m, 1H), 7.41-7.35 (m, 1H), 7.03 (d, J=8.4 Hz, 1H), 6.76-6.72 (m, 2H), 6.63 (s, 1H), 4.34 (d, J=15.6 Hz, 1H), 4.24-4.20 (m, 4H), 3.78-3.70 (m, 2H), 3.48 (s, 3H), 3.33-3.26 (m, 2H), 3.14-3.08 (m, 1H), 2.96-2.87 (m, 1H), 2.74-2.69 (s, 2H). MS: m/z=498.1 (M$^+$+1).

(15) Preparation of Compound 130

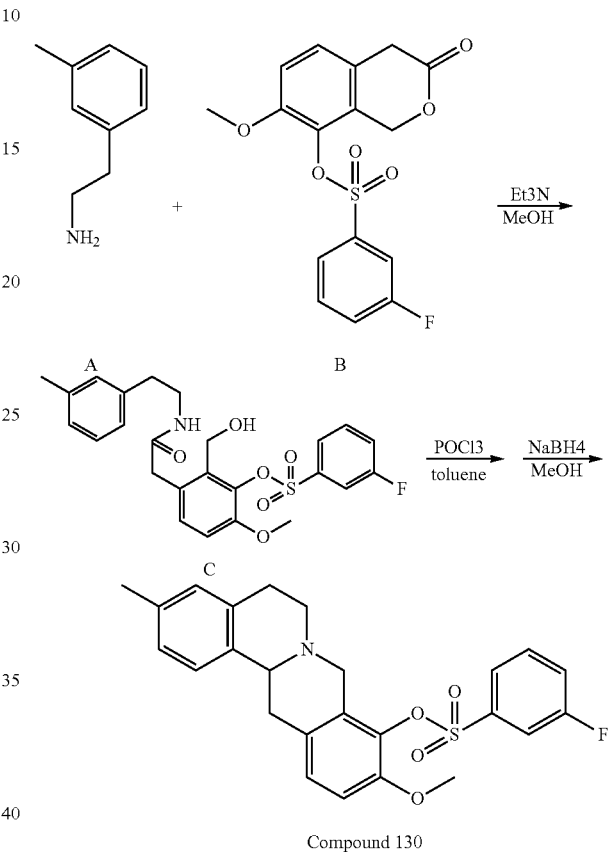

Compound 130

A+B→C

To the solution of A (152 mg, 0.85 mmol), B (300 mg, 0.85 mmol) in MeOH (5 mL) was added Et$_3$N (130 μL, 0.94 mmol) at 20° C., and the solution was heated to reflux overnight. When TLC analysis indicated the completion of the reaction, water was added, and the organic layer was collected, dried, concentrated and purified by chromatography to give 300 mg of C.

C→Compound 129

To a stirred solution of C (300 mg, 0.56 mmol) in toluene (5 mL) was added POCl$_3$ (300 μL) at ambient temperature. The reaction mixture was refluxed for 2 h with stirring. When the reaction was completed, the solvent and excess POCl$_3$ were evaporated off. The residue was poured into ice-water and adjusted to pH>7 with Na$_2$CO$_3$. The solution was extracted with EtOAc, and the organic layer was dried and concentrated. The resulting residue was dissolved in MeOH (5 mL), and NaBH$_4$ (86 mg, 2.26 mmol) was added at 0° C. The reaction mixture was stirred for 30 min at this temperature. TLC analysis indicated the completion of the reaction. The solvent was removed and the residue was extracted with EtOAc and water. The organic layer was dried, concentrated and purified by chromatography to give 70 mg of compound 129.

A+B→C

To the solution of A (115 mg, 0.85 mmol), 13 (300 mg, 0.85 mmol) in MeOH (5 mL) was added Et$_3$N (130 μL, 0.94 mmol) at 20° C. and the solution was heated to reflux overnight. When TLC analysis indicated the completion of the reaction, water and EtOAc were added, and the organic layer was collected, dried, concentrated and purified by chromatography to give 300 mg of C.

C→Compound 130

To a stirred solution of C (300 mg, 0.62 mmol) in toluene (5 mL) was added POCl$_3$ (300 μL) at ambient temperature. The reaction mixture was refluxed for 2 h with stirring. When the reaction was completed, the solvent and excess POCl$_3$ were evaporated off. The residue was poured into ice-water and adjusted to pH>7 with Na$_2$CO$_3$. The solution was extracted with EtOAc, and the organic layer was dried and concentrated. The resulting residue was dissolved in MeOH (5 mL), and NaBH$_4$ (94 mg, 2.48 mmol) was added at 0° C. The reaction mixture was stirred for 10 min at this temperature. TLC analysis indicated the completion of the reaction. The solvent was removed and the residue was extracted with EtOAc and water. The organic layer was dried, concentrated and purified by chromatography to give 180 mg of compound 130.

Compound 130: $^1$H NMR (CDCl$_3$, 300 MHz) δ 7.82-7.84 (m, 1H), 7.73-7.69 (m, 1H), 7.60-7.53 (m, 1H), 7.41-7.35 (m, 1H), 7.26-6.97 (m, 4H), 6.76 (d, J=8.7 Hz, 1H), 4.40 (d, J=15.9 Hz, 1H), 3.94-3.81 (m, 2H), 3.49 (s, 3H), 3.43-3.36 (m, 2H), 3.25-3.21 (m, 1H), 3.01-2.80 (m, 3H), 2.31 (s, 3H). MS: m/z=454.1 (M$^+$+1).

(16) Preparation of Compound 131 and Compound 132

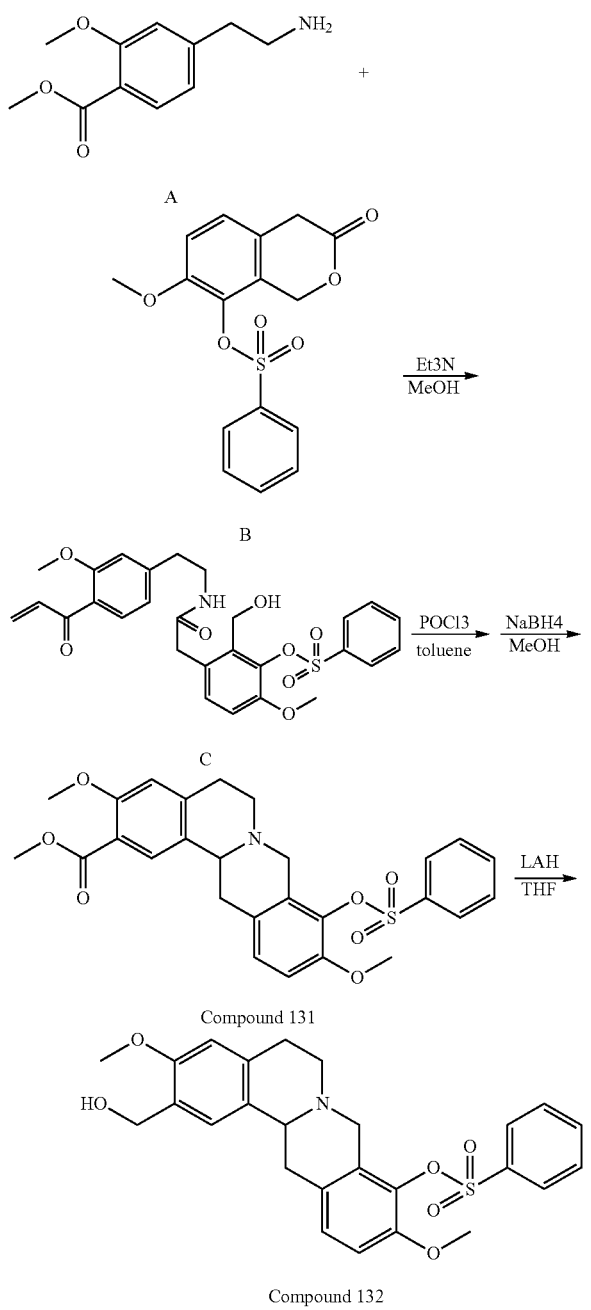

A+B→C

To a solution of A (3.1 g, 15 mmol) and ft (5.0 g, 15 mmol) in MeOH (80 mL) was added Et$_3$N (2.5 mL, 18 mmol) at 20° C. and the solution was heated to reflux overnight. When TLC analysis indicated the completion of the reaction, water and EtOAc were added, and the organic layer was collected, dried, concentrated and purified by chromatography to give 6.5 g of C.

C→Compound 131

To a stirred solution of C (5.4 g, 10 mmol) in toluene (50 mL) was added POCl$_3$ (2 mL) at ambient temperature. The reaction mixture was refluxed for 2 h with stirring. When the reaction was completed, the solvent and excess POCl$_3$ were evaporated off. The residue was poured into ice-water and adjusted to pH>7 with Na$_2$CO$_3$. The solution was extracted with EtOAc, and the organic layer was dried, concentrated and dissolved in MeOH (50 mL), NaBH$_4$ (1.6 g, 40 mmol) was added at 0° C. The reaction mixture was stirred for 10 min at this temperature. TLC analysis indicated the completion of the reaction. The solvent was removed and the residue was extracted with EtOAc and water. The organic layer was dried, concentrated and purified by chromatography to give 4.0 g of compound 131.

Compound 131→Compound 132

To a stirred solution of 131 (509 mg, 1 mmol) in THF (5 mL) was slowly added LAH (114 mg, 3 mmol) at room temperature for 2 h. TLC analysis indicated the completion of the reaction. Water (0.1 mL), NaOH (25% aq, 0.1 mL) and water (0.3 mL) was added one by one, the mixture was filtered, and the solution was concentrated, extracted with EtOAc and water. The organic layer was dried, concentrated and purified by chromatography to give 430 mg of compound 132.

Compound 131: $^1$H NMR (CDCl$_3$, 300 MHz) δ 8.01-7.98 (m, 2H), 7.72-7.65 (m, 2H), 7.59-7.53 (m, 2H), 7.03 (d, J=8.4 Hz, 1H), 6.72-6.70 (m, 2H), 4.24 (d, J=15.9 Hz, 1H), 3.90 (s, 3H), 3.89 (s, 3H), 3.65-3.57 (m, 2H), 3.41 (s, 3H), 3.39-3.33 (m, 1H), 3.23-3.13 (m, 2H), 2.85-2.75 (m, 2H), 2.67-2.58 (m, 1H). MS: m/z=510.1 (M$^+$+1).

Compound 132: $^1$H NMR (CDCl$_3$, 300 MHz) δ 8.01-7.98 (m, 2H), 7.70-7.65 (m, 1H), 7.59-7.54 (m, 2H), 7.14 (s, 1H), 7.02 (d, J=8.7 Hz, 1H), 6.71 (d, J=8.7 Hz, 1H), 6.63 (s, 1H), 4.68-4.66 (m, 2H), 4.22 (d, J=15.9 Hz, 1H), 3.85 (s, 3H), 3.64-3.57 (m, 2H), 3.41 (s, 3H), 3.36-3.30 (m, 1H), 3.17-3.12 (m, 2H), 2.85-2.57 (m, 3H), 2.35-2.29 (m, 1H). MS: m/z=482.1 (M$^+$+1).

(17) Preparation of Compound 133

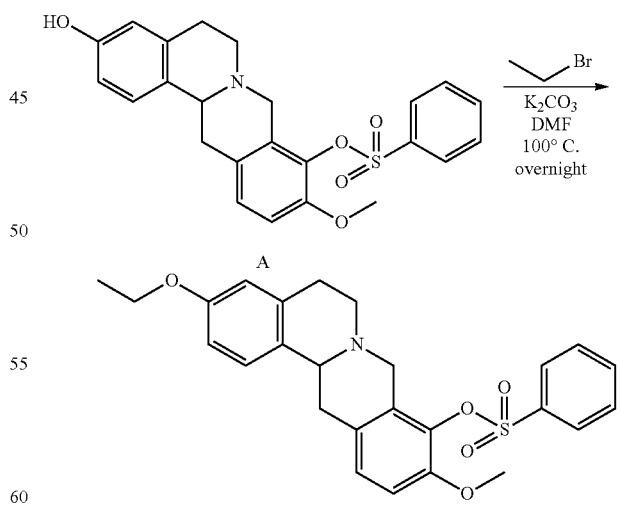

A→133

To a solution of A (88 mg, 0.2 mmol) in 5 mL of dry DMF was added 0.1 mL of bromoethane, and K$_2$CO$_3$ (100 mg) at ambient temperature. The reaction mixture was heated at 100° C. overnight with stirring. When the reaction was completed, reaction mixture was cooled and solvent was removed by vacuum. The residue was extracted by DCM, and purify by preparative TLC to give about 30 mg of compound 133 (PE: EA=3:1).

Compound 133: $^1$H NMR (CDCl$_3$, 300 MHz) δ 8.01-7.98 (d, J=9 Hz, 2H), 7.70-7.65 (m, 1H), 7.59-7.54 (m, 2H), 7.14 (d, J=8.4 Hz, 1H), 7.02 (d, J=8.4 Hz, 1H), 6.79-6.65 (m, 3H), 4.27-4.21 (d, J=18 Hz, 1H), 4.06-3.99 (m, 2H), 3.65-3.60 (m, 2H), 3.44 (s, 3H), 3.29-3.28 (m, 1H), 3.17-3.14 (m, 2H), 2.75-2.63 (m, 3H), 1.43-1.38 (t, 3H). MS: m/z=466.1 (M$^+$+1).

(18) Preparation of Compound 134

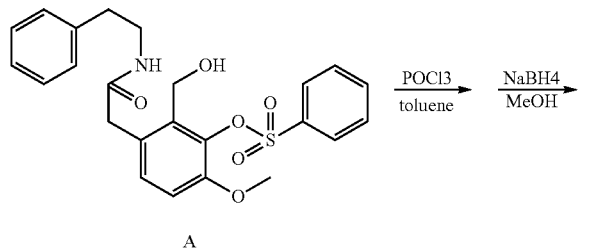

A

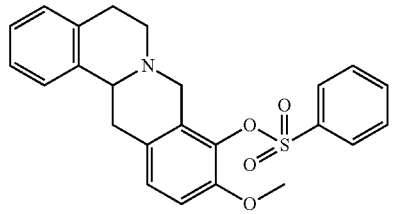

Compound 134

A→Compound 134

To a white solid A (130 mg, 0.28 mmol) was added POCl$_3$ (300 µL) at ambient temperature. The reaction mixture was refluxed for 2 h with stirring. When the reaction was complete, excess POCl$_3$ were evaporated off. The residue was poured into ice-water and adjusted to pH>7 with Na$_2$CO$_3$. The solution was extracted with EtOAc, and the organic layer was dried, concentrated and dissolved in MeOH (5 mL), NaBH$_4$ (86 mg, 2.26 mmol) was then added at 0° C. The reaction mixture was stirred for 30 min at this temperature. TLC analysis indicated the completion of the reaction. The solvent was removed and the residue was extracted with EtOAc and water. The organic layer was dried, concentrated and purified by chromatography to give 10 mg of compound 134.

Compound 134: $^1$H NMR (CDCl$_3$, 300 MHz) δ 8.02-7.99 (d, J=9 Hz, 2H), 7.68-7.66 (m, 1H), 7.59-7.57 (m, 2H), 7.26-7.13 (m, 4H), 7.03 (d, J=8.4 Hz, 1H), 6.74 (m, J=8.4 Hz, 1H), 4.30-4021 (d, J=15.6 Hz, 1H), 3.72-3.65 (m, 2H), 3.44 (s, 3H), 3.37-3.33 (m, 1H), 3.20-3.16 (m, 2H), 2.88-2.74 (m, 3H). MS: m/z=422.1 (M$^+$+1).

(19) Preparation of Compound 135 and Compound 136

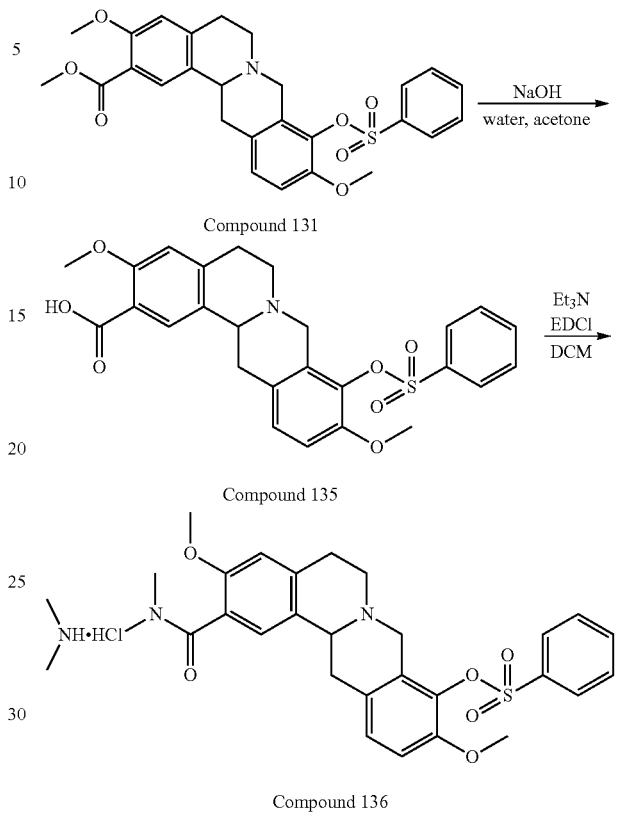

Compound 131→Compound 135

To a stirred solution of NaOH (400 mg, 10 mmol) in water (4 mL) and acetone (2 mL) was added compound 131 (400 mg, 0.78 mmol) at room temperature, then heated to reflux for 2 h. When TLC analysis indicated completion of reaction, the reaction solution was adjusted to pH=3 with conc. HCl at room temperature. The mixture was extracted with EtOAc, dried, concentrated, and purified by silica gel to give 230 mg of compound 135.

Compound 135→Compound 136

A mixture of compound 135 (49.5 mg, 0.1 mmol), dimethylamine hydrochloride (16.3 mg, 0.2 mmol), EDCI (38.4 mg, 0.2 mmol) and triethylamine (55 µL, 0.4 mmol) were added to DCM (5 mL) at room temperature and stirred overnight. When TLC analysis indicated the completion, the mixture was concentrated, extracted with EtOAc, dried, concentrated, and purified by silica gel to give 30 mg of compound 136

Compound 135: $^1$H NMR (DMSO-d$_6$, 300 MHz) δ 11.74 (s, 1H), 7.96 (d, J=7.2 Hz, 2H), 7.89-7.84 (m, 1H), 7.75-7.70 (m, 3H), 7.31 (d, J=8.4 Hz, 1H), 7.12-7.04 (m, 2H), 4.86-4.83 (m, 1H), 4.72 (d, J=15.6 Hz, 1H), 4.54-4.51 (m, 1H), 3.95-3.81 (m, 5H), 3.59-3.43 (m, 2H), 3.38 (s, 3H), 3.16-3.03 (m, 2H). MS: m/z=494.0 (M$^+$−1).

Compound 136: $^1$H NMR (CDCl$_3$, 300 MHz) δ 8.00-7.97 (m, 2H), 7.69-7.64 (m, 1H), 7.58-7.53 (m, 2H), 7.13 (s, 1H), 6.99 (d, J=8.7 Hz, 1H), 6.70 (d, J=8.7 Hz, 1H), 6.63 (s, 1H), 4.24 (6, J=15.9 Hz, 1H), 3.81 (s, 3H), 3.64-3.61 (m, 2H), 3.41 (s, 3H), 3.30 (dd, J=3.9, 16.2 Hz, 1H), 3.19-3.14 (m, 2H), 3.11 (s, 3H), 2.87 (s, 3H), 2.84-2.60 (m, 3H). MS: m/z 523.1 (M$^+$+1).

(20) Preparation of Compound 137

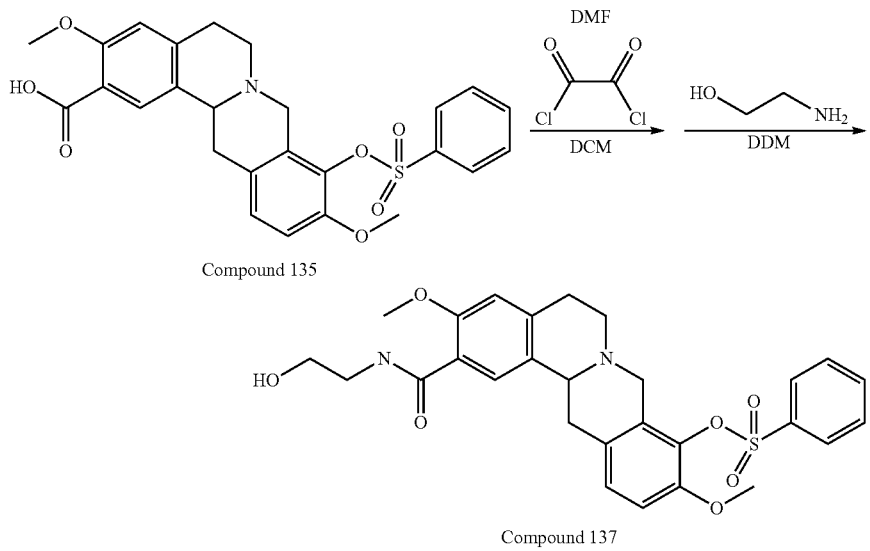

Compound 135→Compound 137

To a stirred solution of 135 (49.5 mg, 0.1 mmol) and DMF (2 drops) in DCM (2 mL) was added drop-wise zeroane (1.0 mL) at ambient temperature, then heated to reflux for 1 h. The reaction solution was concentrated and re-dissolved in DCM (1.5 mL) and added to 2-aminoethan-1-ol (12 μL, 0.2 mmol) in DCM (1.5 mL) and maintained at rt for 2 h. When TLC analysis indicated the completion of reaction, the mixture was extracted with DCM, washed with water, dried, concentrated, and purified by silica gel to give 30 mg of compound 137.

Compound 137: $^1$H NMR (CDCl$_3$, 300 MHz) δ 8.32 (t, J=5.7 Hz, 1H), 8.11 (s, 1H), 7.98 (d, J=7.8 Hz, 2H), 7.67 (t, J=7.5 Hz, 1H), 7.55 (t. J=8.1 Hz, 2H), 7.01 (d, J=8.1 Hz, 1H), 6.71-6.68 (m, 2H), 4.25 (d, J=15.6 Hz, 1H), 3.98 (s, 3H), 3.84-3.80 (m, 2H), 3.65-3.60 (m, 4H), 3.50-3.42 (m, 1H), 3.38 (s, 3H), 3.25-3.14 (m, 2H), 2.84-2.75 (m, 2H), 2.67-2.59 (m, 1H). MS: m/z=539.1 (M$^+$+1).

(21) Preparation of Compound 138

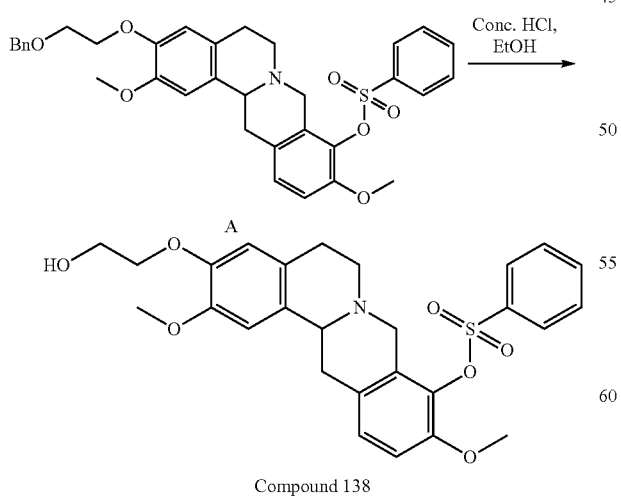

Compound A (0.35 mmol) was dissolved in 5 mL of EtOH and 5 mL of conc. HCl was added to it dropwise. The reaction mixture was refluxed for 2 h. Then it was neutralized with saturated aq. NaHCO$_3$ and extracted with EtOAc. The organic extract was dried with anhydrous Na$_2$SO$_4$ and evaporated to give an oily residue, which was purified with silica gel to furnish compound 138.

Compound 138: $^1$H NMR (CDCl$_3$, 300 MHz) δ=8.02-7.99 (m, 2H), 7.71-7.66 (m, 2H), 7.60-7.54 (m, 2H), 7.03 (d, J=8.4 Hz, 1H), 6.73-6.68 (m, 3H), 4.22 (d, J=16.0 Hz, 1H), 4.13-4.10 (m, 2H), 3.92 (br, 2H), 3.87 (s, 3H), 3.64-3.59 (m, 2H), 3.43 (s, 3H), 3.31-3.05 (m, 3H), 2.88-2.57 (m, 3H); MS: ink=512.1 (M$^+$+1).

(22) Preparation of Compound 141

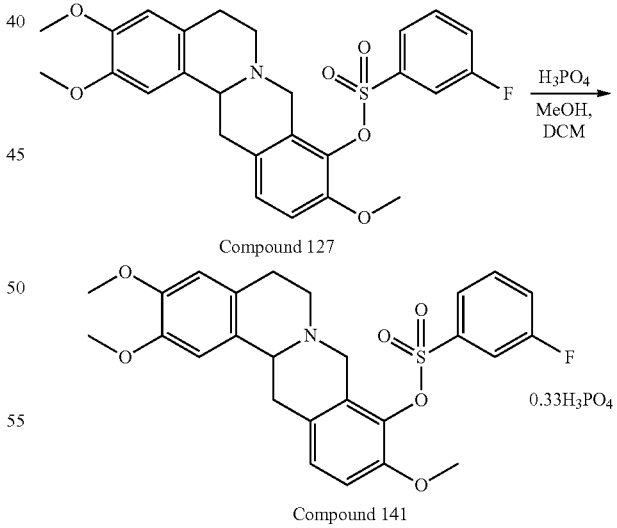

To a stirred solution of compound 127 (1.497 g, 3.0 mmol) in MeOH (10 mL) and DCM (20 mL) was added 85% of H$_3$PO$_4$ (115 mg, 1.0 mmol) at room temperature and stirred for 2 h. The solvent was removed to give compound 141.

Compound 141: $^1$H NMR (DMSO-d6, 300 MHz) δ 7.82-7.70 (m, 4H), 7.13 (d, J=8.7 Hz, 1H), 6.96 (d, J=8.7 Hz, 1H), 6.88 (s, 1H), 6.69 (s, 1H), 4.01 (d, J=15.9 Hz, 1H), 3.75 (s, 3H), 3.73 (s, 3H), 3.48-3.38 (m, 6H), 3.04-2.88 (m, 2H), 2.64-2.58 (m, 2H), 2.53-2.42 (m, 1H). MS: m/z=500.1 (M⁺+1).

(23) Preparation of Compound 142

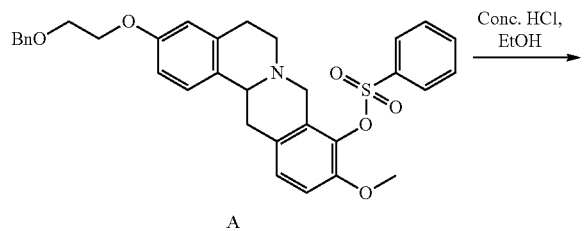

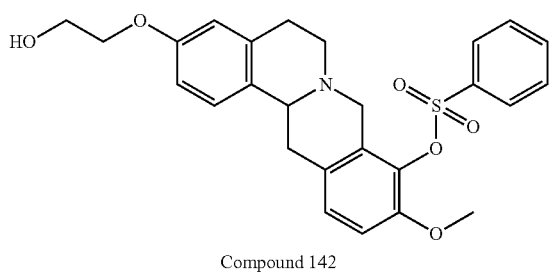

Compound 142

Compound A (200 mg, 0.35 mmol) was dissolved in 5 mL of EtOH, and 5 mL of conc. HCl was added dropwise. The reaction mixture was refluxed for 2 h. Then it was neutralized with saturated aq. NaHCO₃ and extracted with EtOAc. The organic layer was dried with anhydrous Na₂SO₄ and evaporated to give an oily residue, which was purified with silica gel to afford compound 142.

Compound 142: ¹H NMR (CDCl₃, 300 MHz) δ=8.02-7.99 (m, 2H), 7.68-7.66 (m, 1H), 7.59-7.54 (m, 2H), 7.18-7.15 (d, J=8.4 Hz, 1H), 7.04-7.01 (m, 1H), 6.82-6.68 (m, 3H), 4.27 (d, J=16.0 Hz, 1H), 4.10-4.07 (m, 2H), 3.97-3.95 (m, 2H), 3.80-3.66 (m, 2H), 3.44 (s, 3H), 3.34-3.30 (m, 1H), 3.18-3.13 (m, 2H), 2.84-2.64 (m, 3H); MS: m/z=482.1 (M⁺+1).

(24) Preparation of Compound 143

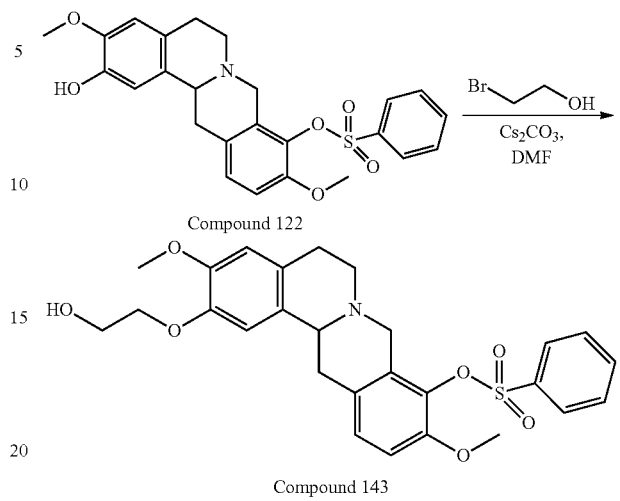

Compound 143

Compound 122 to Compound 143:

To a stirred mixture of compound 122 (100 mg, 0.21 mmol) and Cs₂CO₃ (68 mg, 0.21 mmol) in DMF (10 mL) was added 2-bromoethan-1-ol (31 mg, 0.25 mmol). The reaction mixture was stirred at 80° C. overnight. The solvent was removed, and the residue was diluted with DCM. The solution was washed with water and dried over anhydrous Na₂SO₄. The solvent was removed under vacuum; the residue was purified by silica gel chromatography to afford 10 mg of compound 143.

Compound 143: ¹H NMR (CDCl₃, 300 MHz) δ7.99-8.02 (m, 2H), 7.66-7.71 (m, 1H), 7.55-7.60 (m, 2H), 7.03 (d, J=8.4 Hz, 1H), 6.82 (s, 1H), 6.71 (s, 1H), 6.64 (s, 1H), 4.24 (d, J=−15.9 Hz, 1H), 4.11-4.20 (m, 2H), 3.92 (t, J=4.2 Hz, 2H), 3.86 (s, 3H), 3.58-3.66 (m, 2H), 3.44 (s, 3H), 3.27 (dd, J=15.9 Hz, 1H), 3.12-3.17 (m, 2H), 2.62-2.89 (m, 4H). MS: m/z=512.1 (M⁺+1).

(25) Preparation of Compound 144

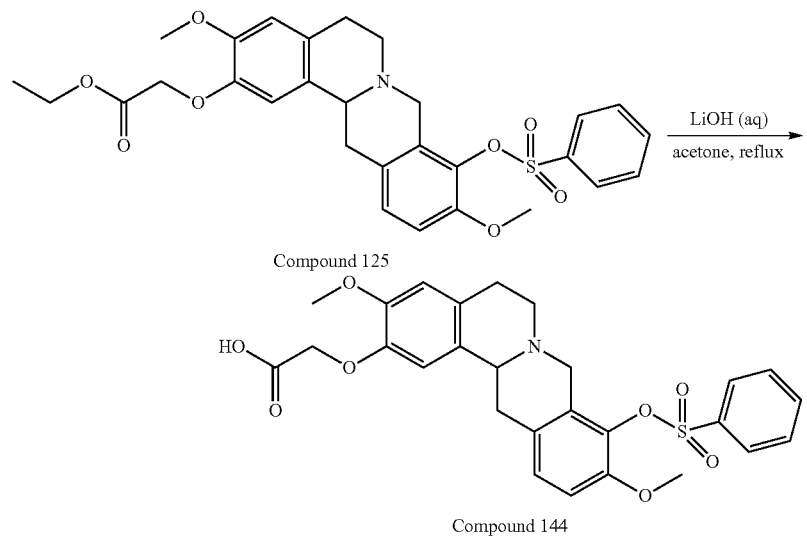

Compound 144

Compound 125 to Compound 144:

To a stirred solution of compound 125 (100 mg, 0.18 mmol) in acetone (5 mL) was added 2N LiOH (0.1 mL, 0.18 mmol) at room temperature, then heated to reflux for 2 h. When TLC analysis indicated completion of reaction, the reaction solution was adjusted pH=3 with conc. HCl at room temperature. The mixture was extracted with DCM, dried, concentrated, and purified by silica gel to give 90 mg of compound 144.

Compound 144: $^1$H NMR (MeOH-d$_4$, 300 MHz) δ7.92-7.95 (m, 2H), 7.74-7.80 (m, 1H), 7.62-7.67 (m, 2H), 7.14 (d, J=8.4 Hz, 1H), 6.90 (s, 1H), 6.87 (s, 1H), 6.79 (s, 1H), 4.39 (s, 2H), 4.26 (d, J=15.9 Hz, 1H), 3.87 (s, 3H), 3.63-3.71 (m, 2H), 3.47-3.53 (m, 2H), 3.40 (s, 3H), 3.10-3.23 (m, 2H), 2.68-2.82 (m, 2H). MS: m/z=524.1 (M$^-$−1).

(26) Preparation of Compound 145 under vacuum and the residue was purified by silica gel chromatography to afford 700 mg of B.

B to Compound 145

To a stirred solution of B (200 mg, 0.4 mmol) in CH$_3$CN (15 mL) was added POCl$_3$ (1 mL) at ambient temperature. The reaction mixture was refluxed for 2 h with stirring. When the reaction was completed, the solvent and excess POCl$_3$ were evaporated off. The residue was poured into ice-water and adjusted to pH>7 with Na$_2$CO$_3$. The solution was extracted with DCM, and the organic layer was dried, con-

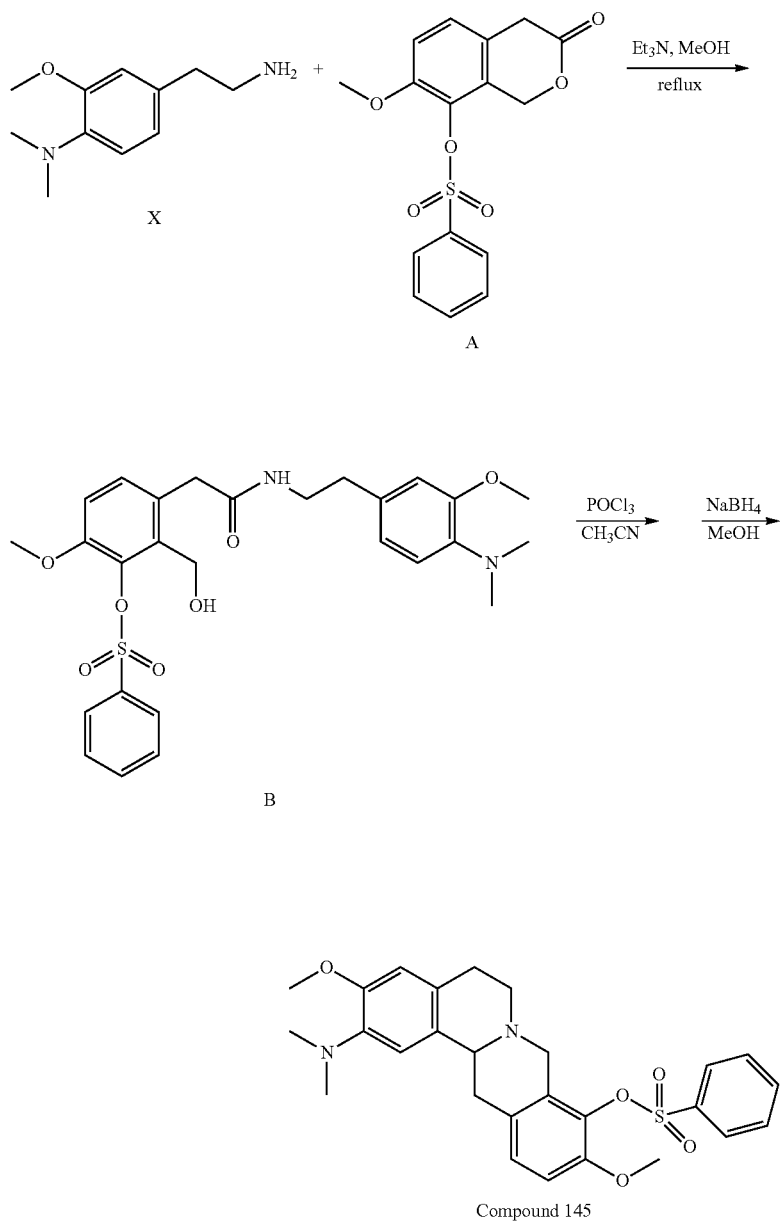

A to B

MeOH 20 mL was added to a mixture of A (500 mg, 1.5 mmol), X (349 mg, 1.8 mmol) and 1 mL Et$_3$N. The resulting solution was stirred at reflux temperature for 2 h. Then the reaction mixture was diluted with DCM, washed with water, dried over anhydrous Na$_2$SO$_4$. The solvent was removed centrated and dissolved in MeOH (20 mL) to which NaBH$_4$ (72 mg, 1.9 mmol) was added at 0° C. The reaction mixture was stirred for 30 min at this temperature. TLC analysis indicated the completion of the reaction. The solvent was removed and the residue was extracted with DCM and water. The organic layer was dried, concentrated and purified by chromatography to give 50 mg of compound 145.

Compound 145: $^1$H NMR (CDCl$_3$, 300 MHz) δ 7.93 (d, J=7.5 Hz, 2H), 7.60 (t, J=7.5 Hz, 1H), 7.50 (t, J=7.5 Hz, 2H), 6.97 (d, J=8.7 Hz, 1H), 6.71 (s, 1H), 6.65 (d, J=8.7 Hz, 1H), 6.52 (s, 1H), 4.15 (d, J=16.2 Hz, 1H), 3.80 (s, 3H), 3.50-3.55 (m, 2H), 3.37 (s, 3H), 3.19-3.25 (m, 1H), 3.01-3.09 (m, 2H), 2.72 (s, 6H), 2.50-2.62 (m, 3H). MS: m/z=495.2 (M$^+$+1).

(27) Preparation of Compound 146 and Compound 147

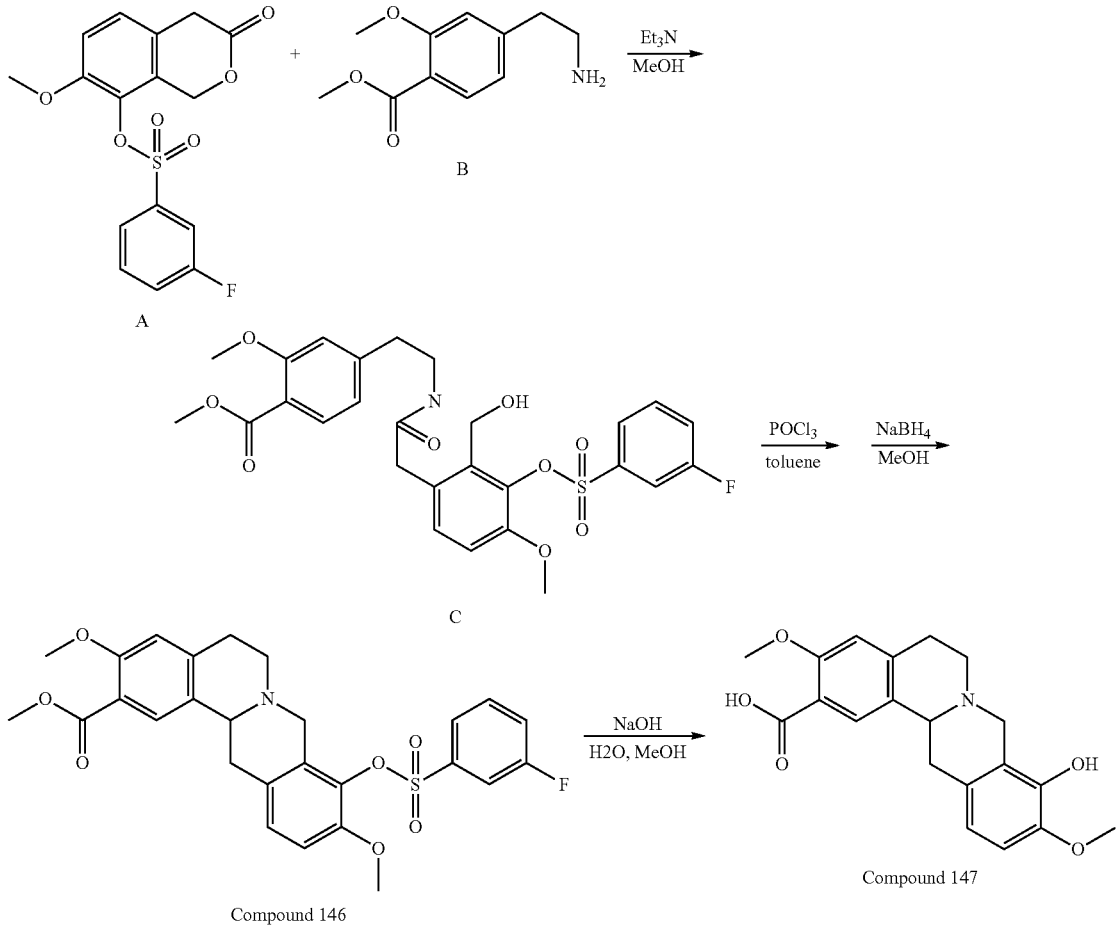

Compound 146

Compound 147

A+B→C

To the solution of A (1.27 g, 3.6 mmol) and B (627 mg, 3.0 mmol) in MeOH (30 mL) was added Et$_3$N (600 μL, 4.5 mmol) at 20° C. and the solution was heated to reflux overnight. When TLC analysis indicated completion of the reaction, water and EtOAc were added, and the organic layer was collected, dried, concentrated and purified by chromatography to give 1.2 g of C.

C→Compound 146

To a stirred solution of C (1.2 g, 2.14 mmol) in toluene (50 mL) was added POCl$_3$ (0.6 mL) at ambient temperature. The reaction mixture was refluxed for 2 h with stirring. When the reaction was completed, the solvent and excess POCl$_3$ were evaporated off. The residue was poured into ice-water and adjusted to pH>7 with Na$_2$CO$_3$. The solution was extracted with EtOAc, and the organic layer was dried, concentrated and dissolved in MeOH (50 mL) to which NaBH$_4$ (244 mg, 6.42 mmol) was added at 0° C. The reaction mixture was stirred for 10 min at this temperature. TLC analysis indicated completion of the reaction. The solvent was removed and the residue was extracted with EtOAc and water. The organic layer was dried, concentrated and purified by preparative TLC to give 800 mg of compound 146.

Compound 146→Compound 147

To a stirred solution of NaOH (600 mg, 15 mmol) in water (4 mL) and MeOH (2 mL) was added 146 (400 mg, 0.76 mmol) at room temperature, then heated to reflux for 4 h. When TLC analysis indicated completion of the reaction, the reaction solution was adjusted pH=3 with conc. HCl at room temperature. The mixture was extracted with EtOAc, dried, concentrated, and purified by silica gel to give 200 mg of compound 147.

Compound 146: $^1$H NMR (CDCl$_3$, 300 MHz) δ 7.82-7.79 (m, 1H), 7.74-7.71 (m, 2H), 7.60-7.53 (m, 1H), 7.43-7.36 (m, 1H), 7.06 (d, J=8.7 Hz, 1H), 6.75-6.72 (m, 2H), 4.26 (d, J=15.9 Hz, 1H), 3.91 (s, 3H), 3.90 (s, 3H), 3.68-3.59 (m, 2H), 3.47 (s, 3H), 3.37 (dd, J=3.9, 15.9 Hz, 1H), 3.23-3.14 (m, 2H), 2.87-2.76 (m, 2H), 2.70-2.61 (m, 1H). MS: m/z=528.2 (M$^+$+1).

Compound 147: $^1$H NMR (DMSO-d6, 300 MHz) δ 12.74 (br, 1H), 12.16-12.14 (m, 1H), 9.22 (s, 1H), 7.72 (s, 1H), 7.03 (s, 1H), 6.95 (d, J=8.7 Hz, 1H), 6.76 (d, J=8.7 Hz, 1H), 4.71 (t, J=9.0 Hz, 1H), 4.50 (d, J=15.0 Hz, 1H), 4.26-4.18 (m, 1H), 3.83 (s, 3H), 3.80 (s, 3H), 3.72-3.42 (m, 4H), 3.18-2.98 (m, 2H). MS: m/z=354.1 (M$^+$−1).

Part 3. Modification on R4

To make R4 deletion, the following synthetic route was developed as shown in Scheme 5.

Scheme 5
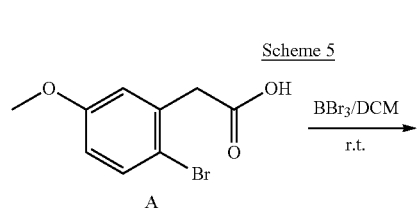
A
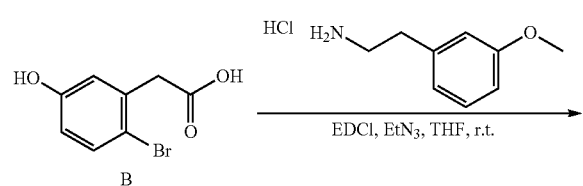
B
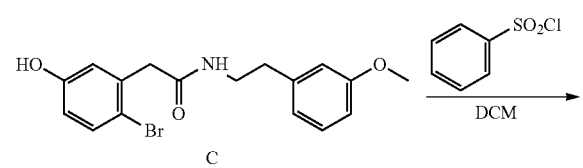
C
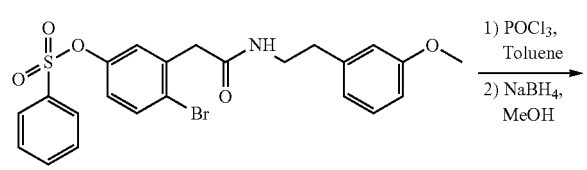
D
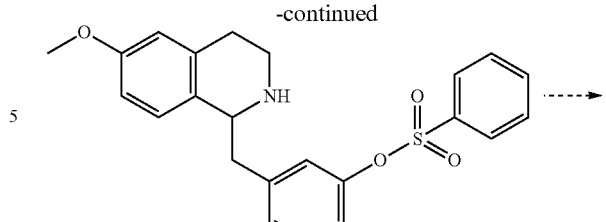
E
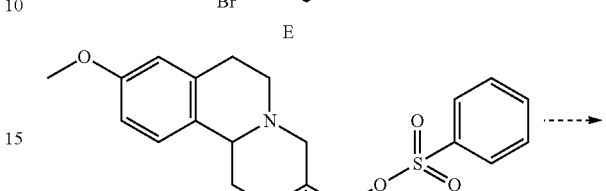
F
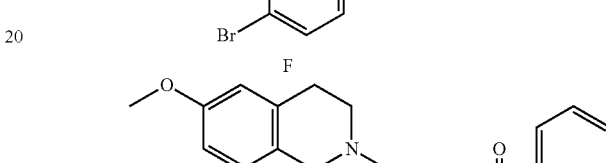
G
(1) Preparation of Compound 149, Compound 150 and Compound 151
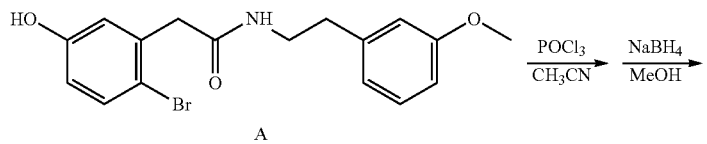
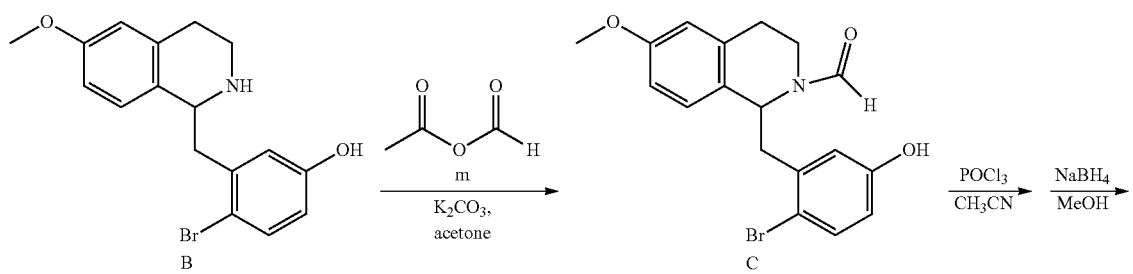
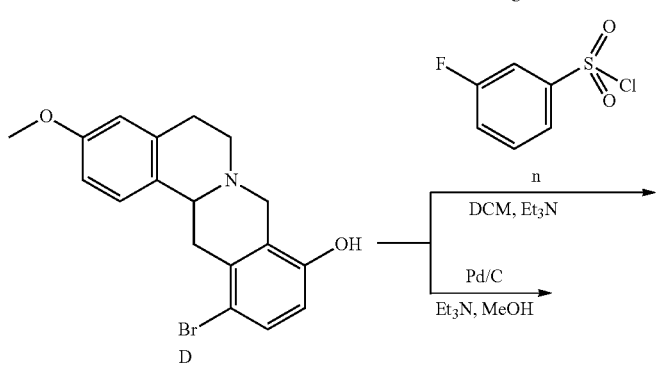

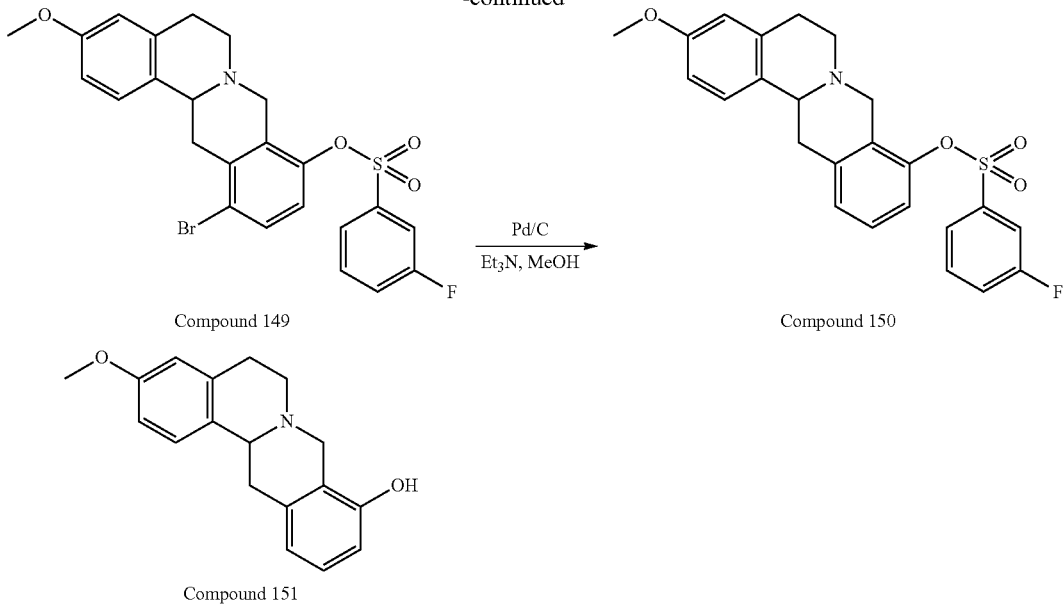

A to B

To a stirred solution of A (5.0 g, 13.7 mmol) in CH₃CN (350 mL) was added POCl₃ (5 mL) at ambient temperature. The reaction mixture was refluxed for 2 h with stirring. When the reaction was complete, the solvent and excess POCl₃ were evaporated off. The solution was extracted with DCM and water, and the organic layer was dried, concentrated and dissolved in MeOH (300 mL) to which NaBH₄ (2.6 g, 68.5 mmol) was added at 0° C. The reaction mixture was stirred for 30 min at this temperature. TLC analysis indicated completion of the reaction. The solvent was removed and the residue was extracted with DCM and water. The organic layer was dried, concentrated and purified by chromatography to g 4.3 g of B.

B to C

To a stirred mixture of B (2.0 g, 5.8 mmol) and K₂CO₃ (2.4 g, 17.3 mmol) in acetone (100 mL) was added m (0.5 g, 5.8 mmol) at rt. The mixture was stirred for 3 h. The solvent was removed and the residue was extracted with DCM and water. The organic layer was dried, concentrated and purified to give 1.3 g of C.

C to D

To a stirred solution of C (1.3 g, 3.5 mmol) in CH₃CN (150 mL) was added POCl₃ (1.5 mL) at ambient temperature. The reaction mixture was refluxed for 2 h with stirring. When the reaction was complete, the solvent and excess POCl₃ were evaporated off. The solution was extracted with DCM and water, and the organic layer was dried, concentrated and dissolved in MeOH (120 mL) to which NaBH₄ (0.67 g, 17.7 mmol) was added at 0° C. The reaction mixture was stirred for 30 min at this temperature. TLC analysis indicated completion of the reaction. The solvent was removed and the residue was extracted with DCM and water. The organic layer was dried, concentrated and purified by chromatography to give 0.78 g of D.

D to Compound 149

To a stirred solution of D (100 mg, 0.3 mmol) in DCM (10 mL) was added n (60 mg, 0.3 mmol) and EoN (0.5 mL) at rt. The mixture was stirred for 2 h. The mixture was washed with water. The organic layer was dried, concentrated and purified to give 120 mg of compound 149.

Compound 149: $^1$H NMR (CDCl₃, 300 MHz) δ 7.70-7.74 (m, 1H), 7.62-7.66 (m, 1H), 7.55-7.61 (m, 1H), 7.40-7.46 (m, 1H), 7.38 (d, J=8.7 Hz, 1H), 7.21 (d, J=8.7 Hz, 1H), 6.81 (dd, J=8.7 Hz, 1H), 6.66-6.70 (m, 2H), 4.07 (d, J=15.6 Hz, 1H), 3.81 (s, 3H), 3.51-3.56 (m, 1H), 3.29-3.41 (m, 2H), 3.10-3.13 (m, 2H), 2.56-2.77 (m, 3H). MS: m/z=518.0 (M⁺+1).

Compound 149 to Compound 150

To a stirred mixture of 149 (50 mg, 0.1 mmol) and Pd/C (20 mg) in MeOH (10 mL) was added EoN (0.5 mL) at rt. The mixture was stirred overnight. Then the solid was filtered off. The solvent was removed under vacuum and the residue was extracted with DCM and water. The organic layer was dried, concentrated and purified to give 30 mg of compound 150.

Compound 150: $^1$H NMR (CDCl₃, 300 MHz) δ 7.72 (d, J=7.8 Hz, 1H), 7.52-7.65 (m, 2H), 7.37-7.44 (m, 1H), 7.09-7.16 (m, 3H), 6.77-6.80 (m, 2H), 7.66 (s, 1H), 4.08 (d, J=15.9 Hz, 1H), 3.80 (s, 3H), 3.51-3.56 (m, 1H), 3.30-3.35 (m, 2H), 3.07-3.20 (m, 2H), 2.53-2.90 (m, 3H). MS: m/z=440.1 (M⁺+1).

D to Compound 151

To a stirred mixture of D (100 mg, 0.3 mmol) and Pd/C (40 mg) in MeOH (15 mL) was added E₁₃N (1 mL) at rt. The mixture was stirred overnight. Then the solid was filtered off. The solvent was removed under vacuum and the residue was extracted with DCM and water. The organic layer was dried, concentrated and purified to give 80 mg of compound 151.

Compound 151: $^1$H NMR (CDCl₃, 300 MHz) δ 7.19 (d, J=8.7 Hz, 1H), 6.99 (t, J=7.8 Hz, 1H), 6.72-6.81 (m, 2H), 6.67 (s, 1H), 6.51 (d, J=7.8 Hz, 1H), 4.19 (d, J=15.6 Hz, 1H), 3.81 (s, 3H), 3.46-3.66 (m, 2H), 3.18-3.36 (m, 3H), 2.64-2.93 (m, 3H). MS: m/z=282.1 (M⁺+1).

Part 4. Approach to 13-Substituted Compound

To synthesis 13-substituted compounds, the following route was developed shown in Scheme 6.

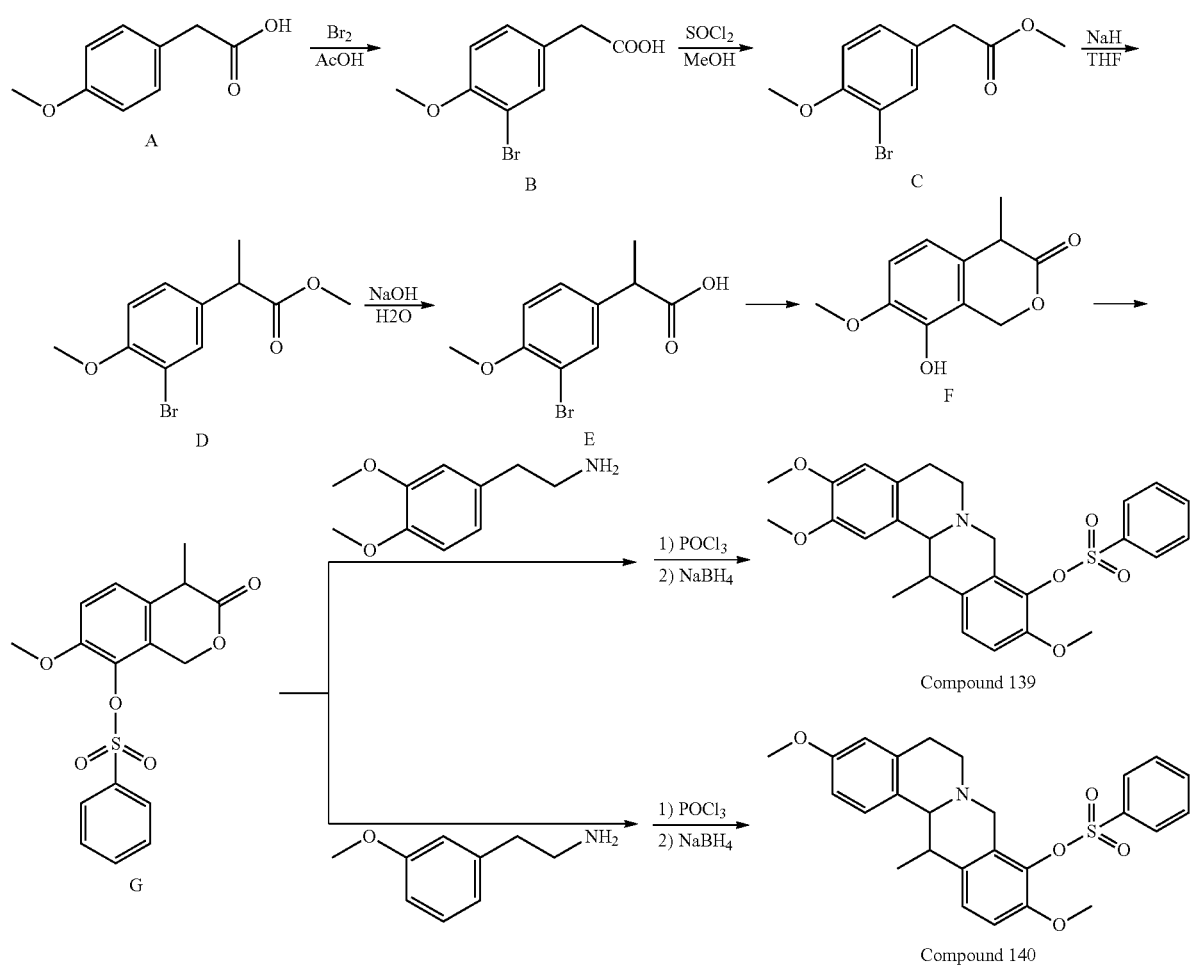
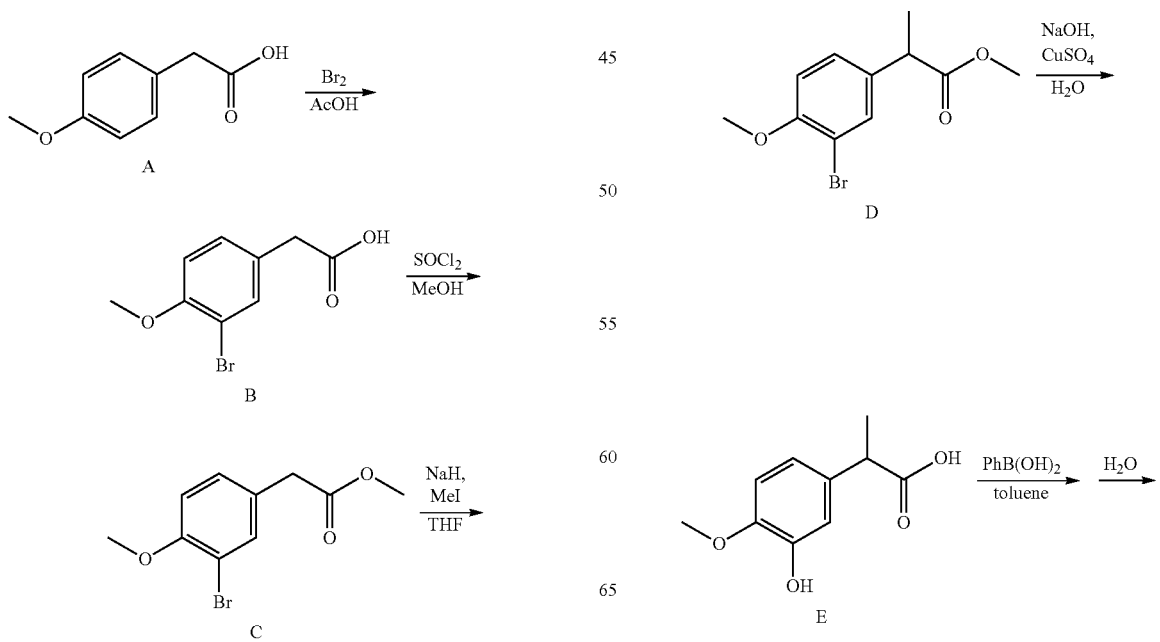
(1) Preparation of Compound 139

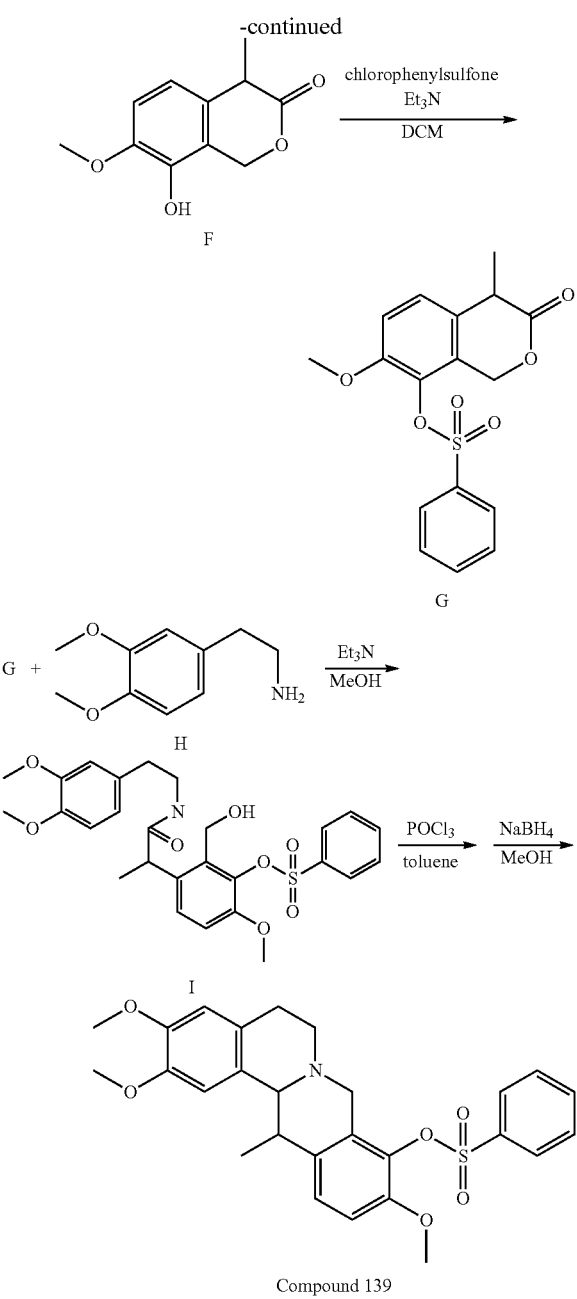

Compound 139

A→B

To a stirred solution of A (166 g, 1.0 mol) in AcOH (2.0 L) was added bromine (56 mL, 1.1 mol) drop-wise at room temperature. The solution was stirred overnight. When the reaction was completed, the solvent was evaporated off. The residue was extracted with EtOAc, washed with water and concentrated to give 225 g of B.

B→C

To a stirred solution of B (150 g, 0.6 mol) in MeOH (1.0 L) was added SOCl$_2$ (87 mL, 1.2 mol) slowly at rt and heated to reflux for 2 h. The solvent and excess SOCl$_2$ were evaporated off to give 150 g of C.

C→D

To a stirred solution of C (51.8 g, 0.2 mol) in THF (700 mL) was added 60% of NaH (8.8 g, 0.22 mol) at room temperature and stirred for 30 min. MeI (13 mL, 0.21 mol) was then added and stirred for 1 h. When TLC analysis indicated completion of the reaction, water was added carefully. The mixture was concentrated, the residue was extracted with water and EtOAc and the organic layer was collected, dried, concentrated and purified to give 46 g of D.

D→E

To a stirred solution of CuSO$_4$ (2.7 g, 17 mmol), NaOH (100 g, 2.5 mol) in water (1.0 L) was added D (46 g, 168 mol) under N$_2$ in a steel bomb at room temperature. Then the solution was heated to 150° C. overnight. When the reaction was complete, the reaction solution was adjusted to pH=3 with conc.HCl at room temperature. The solution was extracted with EtOAc, dried, concentrated, and purified to give 30 g E.

E→F

To 30 g of E (153 mmol) was added phenylboric acid (56 g, 306 mmol) and toluene (1.0 L). The mixture was heated at reflux for 1 h, and water was collected in a dean-stark trap. The hot solution was poured over molecular sieves (10 g) in a stainless steel bomb. Paraformaldehyde (10 g, 306 mmol) was added. The bomb was sealed and heated on an oil-bath at 110° C. for 48 h. The bomb was opened and the hot solution was filtered. Toluene was evaporated and water (500 mL) was added to the residue. After heating at reflux for 2 h, the mixture was cooled to room temperature and extracted with DCM. The solution was dried and the solvent was removed. The residue was washed with ether to obtain 13 g of F.

F→G

To a stirred solution of F (13 g, 62.5 mmol) in DCM (200 mL) was added chlorophenylsulfone (16.2 mL, 125 mmol) at rt: Et$_3$N (25 mL) was then added and stirred for 4 h. When TLC analysis indicated the completion of the reaction, the solvent was removed under reduced pressure. The residue was further purified to give 5 g of G.

G+H→I

To the solution of G (69.6 mg, 0.2 mmol), H (54.3 mg, 0.3 mmol) in MeOH (5 mL) was added Et$_3$N (41.5 µL, 0.3 mmol) at 20° C. and the solution was heated to reflux overnight. When TLC analysis indicated completion of the reaction, water and EtOAc were added, and the organic layer was collected, dried, concentrated and purified by chromatography to give 86 mg of I.

I→Compound 139

To a stirred solution of I (86 mg, 0.16 mmol) in toluene (5 mL) was added POCl$_3$ (0.1 mL) at ambient temperature. The reaction mixture was refluxed for 2 h with stirring. When the reaction was completed, the solvent and excess POCl$_3$ were evaporated off. The residue was poured into ice-water and adjusted to pH>7 with Na$_2$CO$_3$. The solution was extracted with EtOAc, and the organic layer was dried, concentrated and dissolved in MeOH (5 mL) to which NaBH$_4$ (15.2 mg, 0.4 mmol) was added at 0° C. The reaction mixture was stirred for 10 min at this temperature. TLC analysis indicated completion of the reaction. The solvent was removed and the residue was extracted with EtOAc and water. The organic layer was dried, concentrated and purified by preparative TLC to give 50 mg of compound 139.

Compound 139: $^1$H NMR (CDCl$_3$, 300 MHz) δ 7.94 (d, J=7.5 Hz, 2H), 7.69-7.64 (m, 1H), 7.57-7.52 (m, 2H), 7.10 (d, J=8.7 Hz, 1H), 6.78 (m, J=8.7 Hz, 1H), 6.70 (s, 1H), 6.61 (s, 1H), 4.22 (dd, J=16.5, 28.5 Hz, 2H), 3.94 (d, J=7.8 Hz, 1H), 3.84 (s, 3H), 3.82 (s, 3H), 3.47 (s, 3H), 3.15-3.03 (m, 4H), 2.90-2.84 (m, 1H), 1.50 (d, J=6.9 Hz, 3H). MS: m/z—496.1 (M$^+$+1).

(2) Preparation of Compound 140

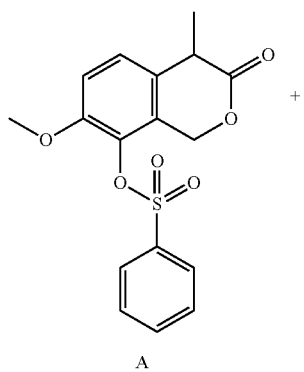

A

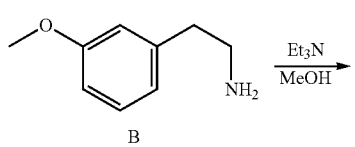

B

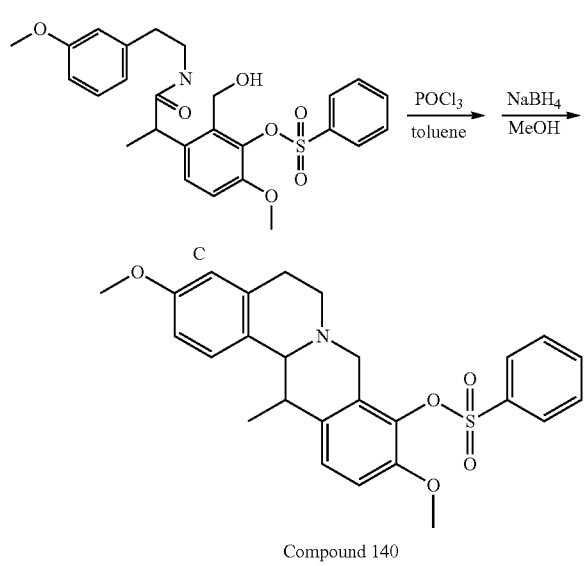

Compound 140

A+B→C

To the solution of A (69.6 mg, 0.2 mmol) and B (45.3 mg, 0.3 mmol) in MeOH (5 mL) was added Et$_3$N (41.5 μL, 0.3 mmol) at 20° C. and the solution was heated to reflux overnight. When TLC analysis indicated completion of the reaction, water and EtOAc were added, and the organic layer was collected, dried, concentrated and purified by chromatography to give 50 mg of C.

C→Compound 140

To a stirred solution of C (50 mg, 0.1 mmol) in toluene (5 mL) was added POCl$_3$ (0.1 mL) at ambient temperature. The reaction mixture was refluxed for 2 h with stirring. When the reaction was completed, the solvent and excess POCl$_3$ were evaporated off. The residue was poured into ice-water and adjusted to pH>7 with Na$_2$CO$_3$. The solution was extracted with EtOAc, and the organic layer was dried, concentrated and dissolved in MeOH (5 mL) to which NaBH$_4$ (11.4 mg, 0.3 mmol) was added at 0° C. The reaction mixture was stirred for 10 min at this temperature. TLC analysis indicated completion of the reaction. The solvent was removed and the residue was extracted with EtOAc and water. The organic layer was dried, concentrated and purified by preparative TLC to give 7.3 mg of compound 140.

Compound 140: $^1$H NMR (CDCl$_3$, 300 MHz) δ 7.99-7.96 (m, 2H), 7.70-7.64 (m, 1H), 7.58-7.53 (m, 2H), 7.15 (d, J=5.6 Hz, 1H), 7.08 (m, J=5.6 Hz, 1H), 6.74-6.65 (m, 3H), 4.08-3.86 (m, 2H), 3.78 (s, 3H), 3.61 (d, J=8.4 Hz, 1H), 3.47 (s, 3H), 3.03-2.89 (m, 4H), 2.76-2.70 (m, 1H), 1.45 (d, J=6.9 Hz, 3H). MS: m/z=466.1 (M$^+$+1).

(3) Preparation of Compound 148

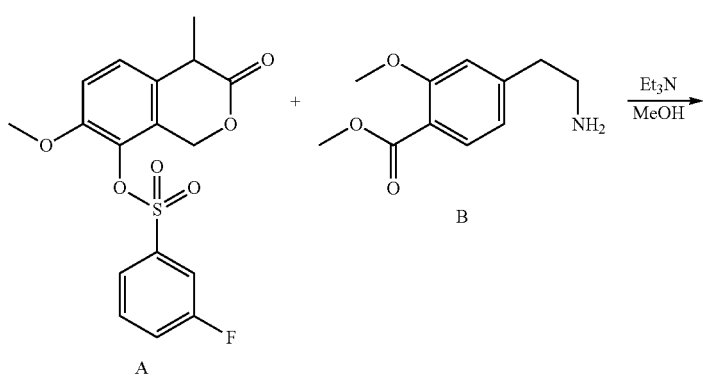

-continued

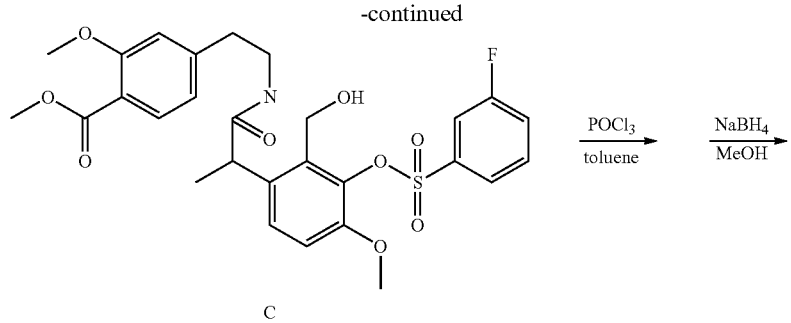

C

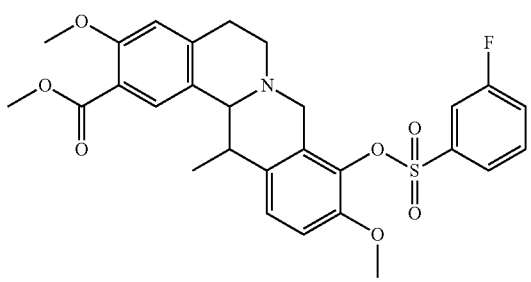

Compound 148

A+B→C

To a solution of A (3.66 g, 10 mmol) and B (2.09 g, 10 mmol) in MeOH (50 mL) was added Et₃N (2.1 mL, 15 mmol) at 20° C. and the solution was heated to reflux overnight. When TLC analysis indicated completion of the reaction, water and EtOAc were added, and the organic layer was collected, dried, concentrated and purified by chromatography to give 4.0 g of C.

C→Compound 148

To a stirred solution of C (4.0 g, 6.96 mmol) in toluene (100 mL) was added POCl₃ (2 mL) at ambient temperature. The reaction mixture was refluxed for 2 h with stirring. When the reaction was complete, the solvent and excess POCl₃ were evaporated off. The residue was poured into ice-water and adjusted to pH>7 with Na₂CO₃. The solution was extracted with EtOAc, and the organic layer was dried, concentrated and dissolved in MeOH (100 mL) to which NaBH₄ (793 mg, 20.87 mmol) was added at 0° C. The reaction mixture was stirred for 10 min at this temperature. TLC analysis indicated completion of the reaction. The solvent was removed and the residue was extracted with EtOAc and water. The organic layer was dried, concentrated and purified by preparative TLC to give 2.0 g of compound 148.

Compound 148: ¹H NMR (CDCl₃, 300 MHz) δ 7.78-7.68 (m, 3H), 7.58-7.51 (m, 1H), 7.40-7.26 (m, 1H), 7.11 (d, J=11.7 Hz, 1H), 4.14-3.94 (m, 2H), 3.88 (s, 3H), 3.87 (s, 3H), 3.62 (d, J=8.4 Hz, 1H), 3.48 (s, 3H), 3.04-2.92 (m, 4H), 2.80-2.74 (m, 1H), 1.47 (d, J=3.9 Hz, 3H). MS: m/z=542.1 (M⁺+1).

(4) Preparation of Compound 152 and Compound 153

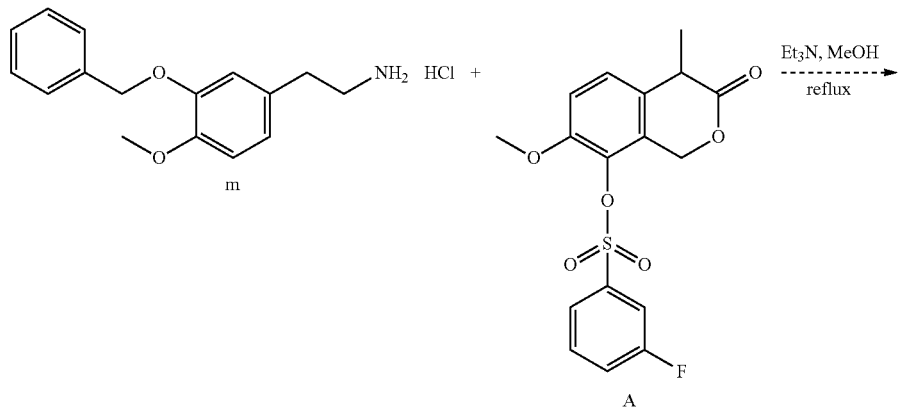

-continued

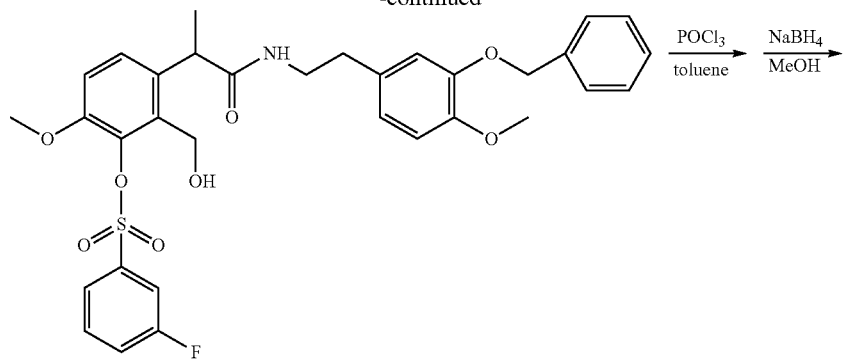

B

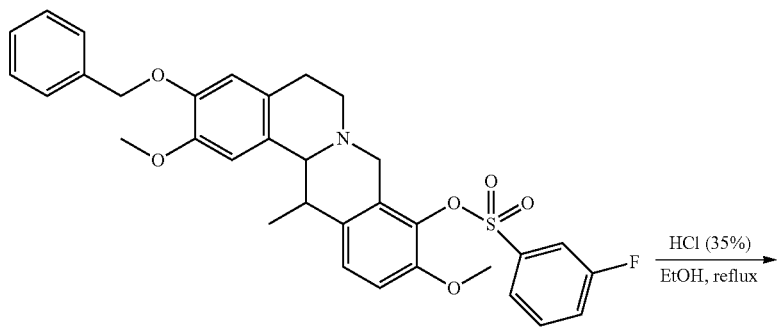

Compound 152

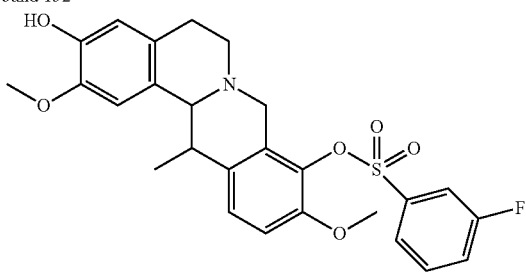

Compound 153

A to B

MeOH 30 mL was added to a mixture of m (0.88 g, 3.0 mmol), A (1.0 g, 2.8 mmol) and 1 mL Et$_3$N. The resulting solution was stirred at reflux temperature for 2 h. Then the solvent was removed, and the residue was diluted with DCM, washed with water and dried over anhydrous Na$_2$SO$_4$. The solvent was removed under vacuum and the residue was purified by silica gel chromatography to afford 930 mg of B.

B to Compound 152

To a stirred solution of B (930 mg, 1.5 mmol) in toluene (60 mL) was added POCl$_3$ (1 mL) at ambient temperature. The reaction mixture was refluxed for 2 h with stirring. When the reaction was completed, the solvent and excess POCl$_3$ were evaporated off. The solution was extracted with DCM and water, and the organic layer was dried, concentrated and dissolved in MeOH (50 mL) to which NaBH$_4$ (283 mg, 7.5 mmol) was added at 0° C. The reaction mixture was stirred for 30 min at this temperature. TLC analysis indicated completion of the reaction. The solvent was removed and the residue was extracted with DCM and water. The organic layer was dried, concentrated and purified by chromatography to give 330 mg of compound 152.

Compound 152: $^1$H NMR (CDCl$_3$, 300 MHz) δ 7.77-7.80 (m, 1H), 7.68-7.73 (m, 1H), 7.51-7.58 (m, 1H), 7.29-7.45 (m, 6H), 7.11 (d, J=9.0 Hz, 1H), 6.74-6.77 (m, 2H), 6.65 (s, 1H), 5.12 (s, 2H), 3.95-4.13 (m, 2H), 3.88 (s, 3H), 3.62 (d, J=8.7 Hz, 1H), 3.51 (s, 3H), 2.73-3.04 (m, 5H), 1.49 (d, J=6.9 Hz, 3H). MS: m/z=590.2 (M$^+$+1).

Compound 152 to Compound 153

10 mL conc. HCl was added dropwise to a solution of 152 (330 mg, 0.6 mmol) in 10 mL EtOH. The reaction mixture was refluxed for 2 h. Then it was neutralized with saturated aq. NaHCO$_3$ and extracted with DCM. The organic layer was dried, concentrated and purified by chromatography to give 130 mg of compound 153.

Compound 153: $^1$H NMR (CDCl$_3$, 300 MHz) δ 7.78-7.81 (m, 1H), 7.67-7.73 (m, 1H), 7.53-7.59 (m, 1H), 7.35-7.41 (m, 1H), 7.11 (d, J=8.7 Hz, 1H), 6.76 (d, J=8.7 Hz, 1H), 6.69 (d, J=7.5 Hz, 2H), 5.56 (s, 1H), 3.96-4.14 (m, 2H), 3.88 (s, 3H), 3.61 (d, 0.7=8.4 Hz, 1H), 3.52 (s, 3H), 2.72-3.03 (m, 5H), 1.48 (d, J=6.9 Hz, 3H). MS: m/z=500.1 (M$^+$+1).

(5) Preparation of Compound 154 and Compound 155

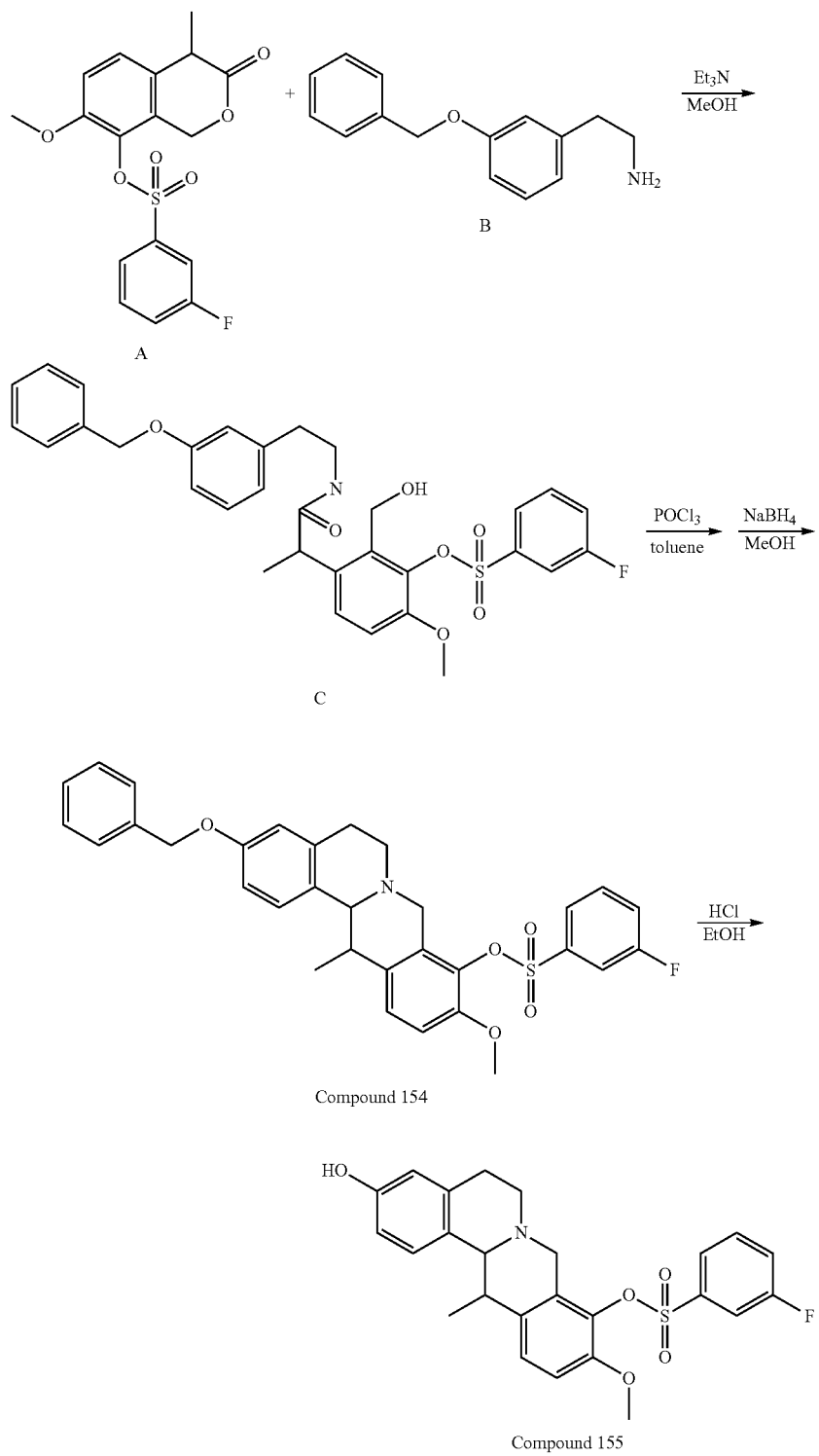

A+B→C

To the solution of A (1.27 g, 3.6 mmol) and B (627 mg, 3.0 mmol) in MeOH (30 mL) was added Et₃N (600 μL, 4.5 mmol) at 20° C. and the solution was heated to reflux overnight. When TLC analysis indicated completion of the reaction, water and EtOAc were added, and the organic layer was collected, dried, concentrated and purified by chromatography to give 1.8 g of C.

C→Compound 154

To a stirred solution of C (1.8 g, 30.4 mmol) in toluene (50 mL) was added POCl₃ (2 mL) at ambient temperature. The reaction mixture was refluxed for 2 h with stirring. When the reaction was complete, the solvent and excess POCl₃ were evaporated off. The residue was poured into ice-water and adjusted to pH>7 with Na₂CO₃. The solution was extracted with EtOAc, and the organic layer was dried, concentrated and dissolved in MeOH (50 mL) to which NaBH₄ (244 mg, 6.42 mmol) was added at 0° C. The reaction mixture was stirred for 10 min at this temperature. TLC analysis indicated completion of the reaction. The solvent was removed and the residue was extracted with EtOAc and water. The organic layer was dried, concentrated and purified by preparative TLC to give 500 mg of compound 154.

Compound 154→Compound 155

Compound 154 (400 mg, 0.71 mmol) was dissolved in 5 mL of EtOH, and 5 mL of conc. HCl was added to it dropwise. The reaction mixture was refluxed for 2 h. Then it was neutralized with saturated aq. NaHCO₃ and extracted with EtOAc. The organic layer was dried with anhydrous Na₂SO₄ and evaporated to give a white residue which was purified with silica gel to afford compound 155.

Compound 154: $^1$H NMR (CDCl₃, 300 MHz) δ 7.84-7.80 (m, 2H), 7.76-7.73 (m, 1H), 7.47-7.33 (m, 6H), 7.12-7.05 (m, 2H), 6.88-6.86 (d, J=8.7 Hz, 1H), 6.75-6.72 (m, 2H), 5.06 (s, 2H), 4.23-4.17 (d, J=15.9 Hz, 1H), 3.76-3.75 (m, 1H), 3.62-3.56 (d, J=18 Hz, 1H), 3.49 (s, 3H), 3.29-3.26 (m, 1H), 3.16-3.05 (m, 2H), 2.64-2.56 (m, 2H), 0.94-0.92 (d, J=6.0 Hz, 1H). MS: m/z=560.1 (M⁺+1).

Compound 155: $^1$H NMR (DMSO-d6, 300 MHz) δ 7.84-7.72 (m, 2H), 7.60-7.52 (m, 1H), 7.38-7.26 (m, 1H), 7.08-7.04 (m, 2H), 6.78-6.69 (m, 2H), 6.58-6.57 (m, 1H), 4.22-4.17 (d, J=15.9 Hz, 1H), 3.74 (m, 1H), 3.61-3.56 (d, J=15 Hz, 1H), 3.50 (s, 3H), 3.12-3.09 (m, 1H), 3.16-3.05 (m, 2H), 2.62-2.56 (m, 2H), 0.93-0.91 (d, J=6.0 Hz, 1H). MS: m/z=470.1 (M⁺+1).

Example 9

The following compounds of Table 5 were synthesized according the above procedures or slight modifications thereof and were characterized by mass spectroscopy. Each compound gave the expected MH⁺ peak in the mass spectrum.

TABLE 5

| Cmpd No. | Structure |
|---|---|
| 1 | 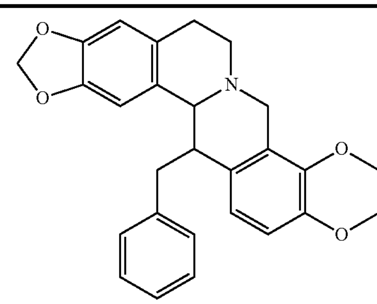 |
| 2 | 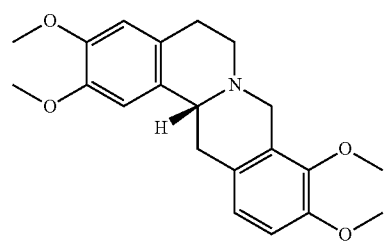 |
| 3 | 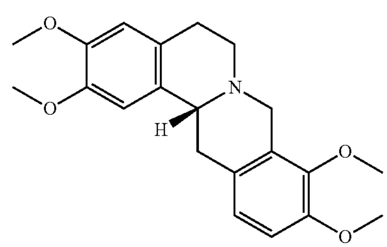 |
| 4 | 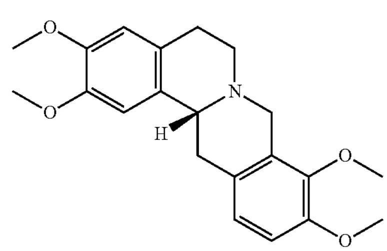 |

TABLE 5-continued
5 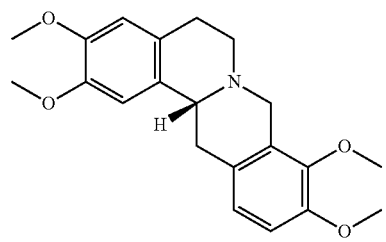
6 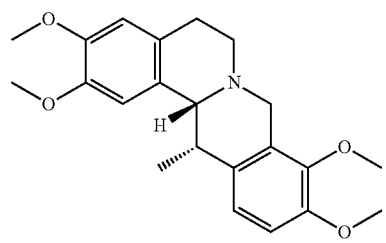
7 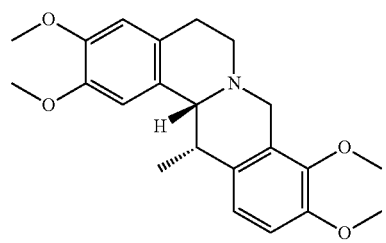
8 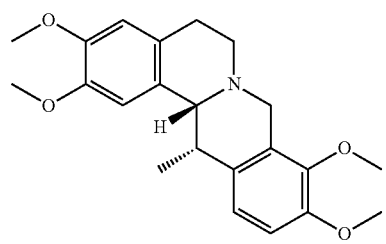
9 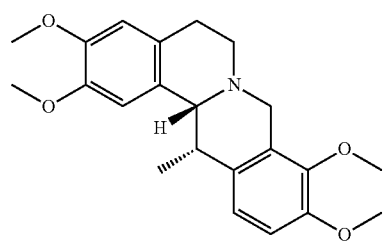
10 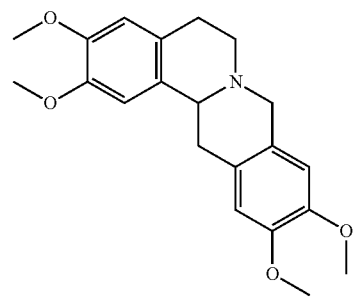

TABLE 5-continued
| | |
|---|---|
| 11 | 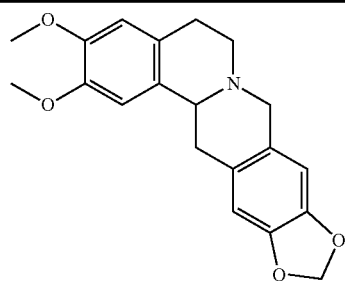 |
| 12 | 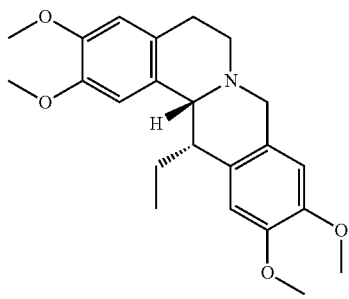 |
| 13 | 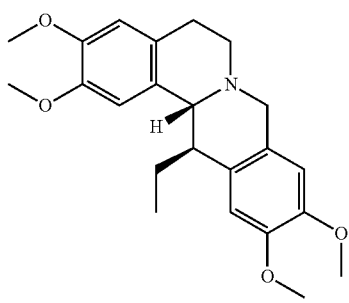 |
| 14 | 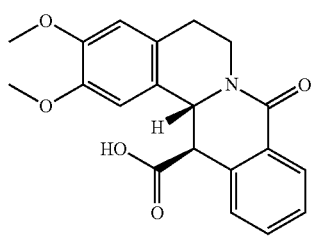 [SMILES: COc1cc2c(cc1OC)[C@H]1[C@H](C(=O)O)c3ccccc3C(=O)N1CC2] |
| 15 | 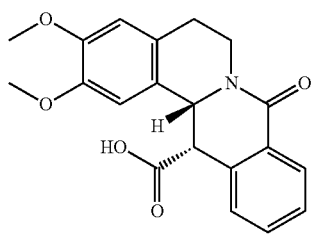 [SMILES: COc1cc2c(cc1OC)[C@H]1[C@@H](C(=O)O)c3ccccc3C(=O)N1CC2] |
| 16 | 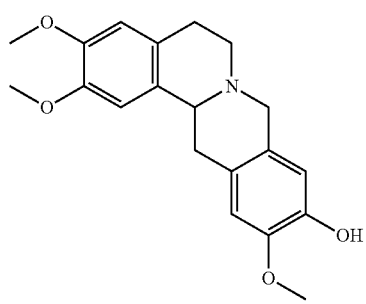 [SMILES: COc1cc2c(cc1O)CN1CCc3cc(OC)c(OC)cc3C1C2] |

TABLE 5-continued
17 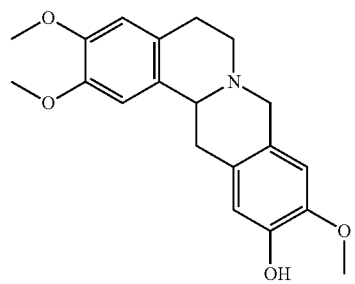
18 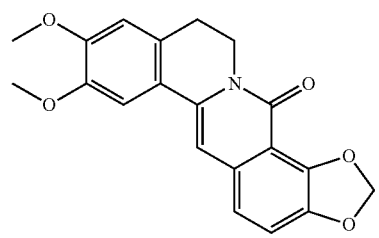 [SMILES: COc1cc2c(cc1OC)-c1cc3ccc4c(c3c(=O)n1CC2)OCO4]
19 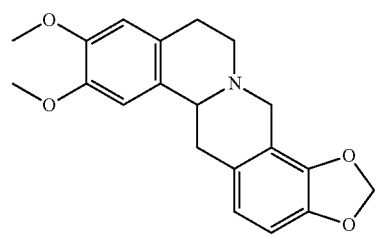 [SMILES: COc1cc2c(cc1OC)C1Cc3ccc4c(c3CN1CC2)OCO4]
20 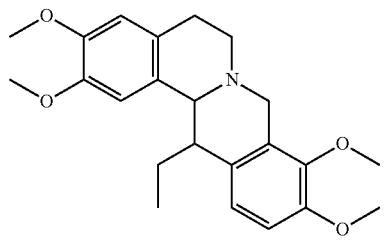
21 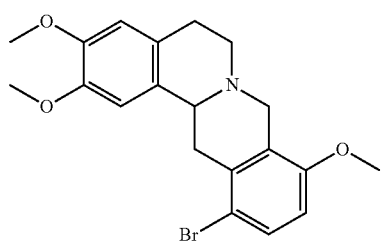
22 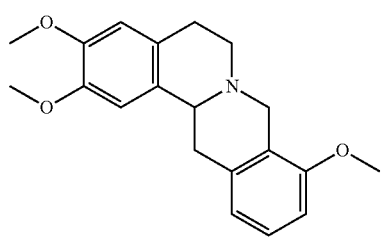

TABLE 5-continued
23 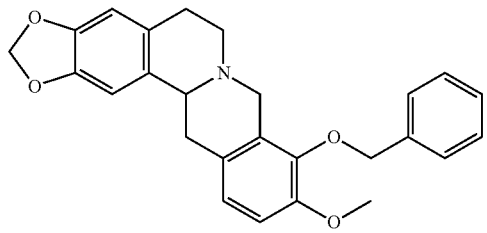 [SMILES: COc1ccc2c(c1OCc1ccccc1)CN1CCc3cc4c(cc3C1C2)OCO4]
24 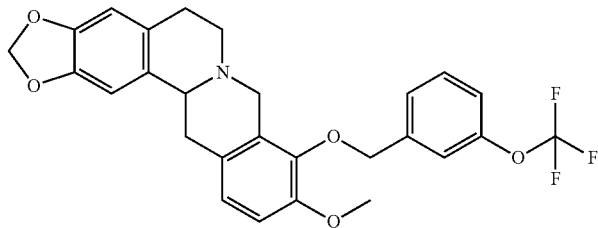 [SMILES: COc1ccc2c(c1OCc1cccc(OC(F)(F)F)c1)CN1CCc3cc4c(cc3C1C2)OCO4]
25 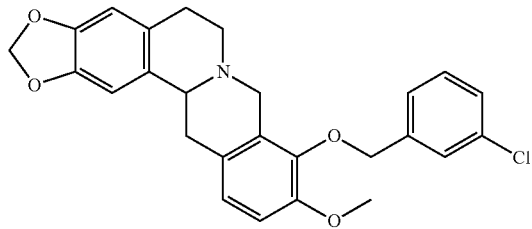 [SMILES: COc1ccc2c(c1OCc1cccc(Cl)c1)CN1CCc3cc4c(cc3C1C2)OCO4]
26 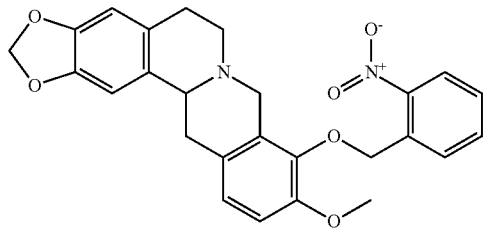 [SMILES: COc1ccc2c(c1OCc1ccccc1[N+](=O)[O-])CN1CCc3cc4c(cc3C1C2)OCO4]
27 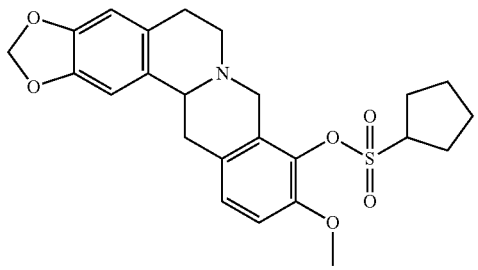 [SMILES: COc1ccc2c(c1OS(=O)(=O)C1CCCC1)CN1CCc3cc4c(cc3C1C2)OCO4]
28 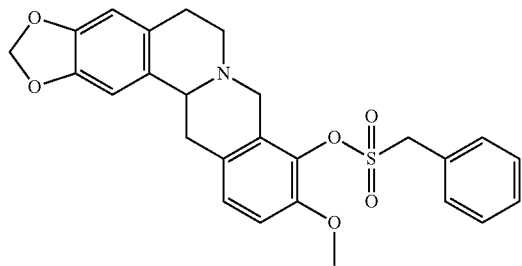 [SMILES: COc1ccc2c(c1OS(=O)(=O)Cc1ccccc1)CN1CCc3cc4c(cc3C1C2)OCO4]

TABLE 5-continued
| 29 | 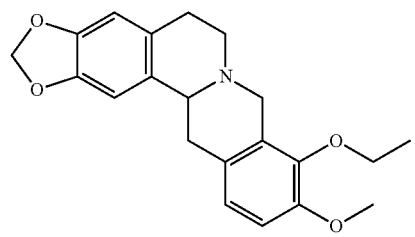 [SMILES: CCOc1c(OC)ccc2c1CN1CCc3cc4c(cc3C1C2)OCO4] |
| 30 | 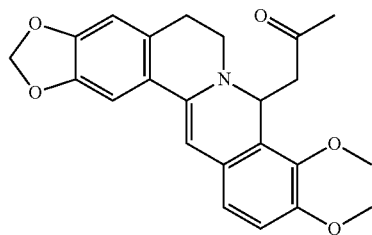 [SMILES: COc1ccc2c(c1OC)C(CC(C)=O)N1CCc3cc4c(cc3C1=C2)OCO4] |
| 31 | 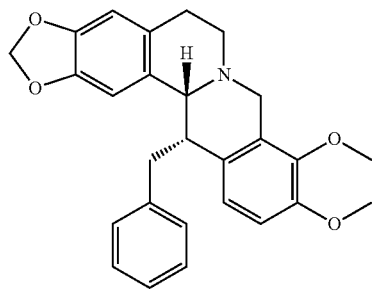 |
| 32 | 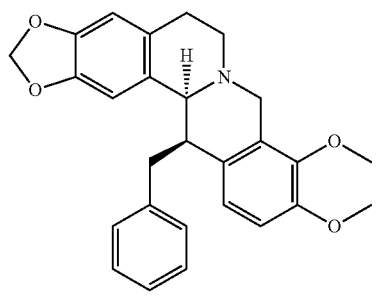 |
| 33 | 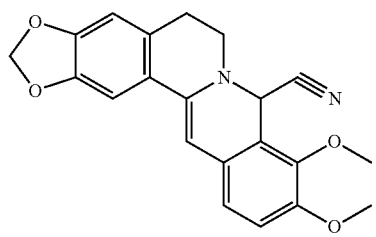 [SMILES: COc1ccc2c(c1OC)C(C#N)N1CCc3cc4c(cc3C1=C2)OCO4] |
| 34 | 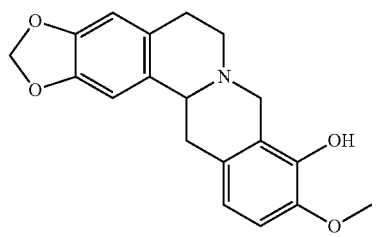 [SMILES: COc1ccc2c(c1O)CN1CCc3cc4c(cc3C1C2)OCO4] |

TABLE 5-continued
35 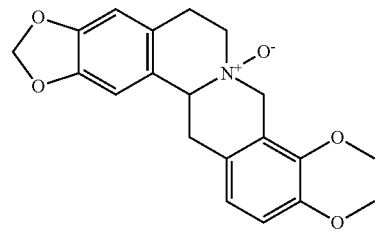 [SMILES: COc1ccc2c(c1OC)C[N+]1([O-])CCc3cc4c(cc3C1C2)OCO4]
36 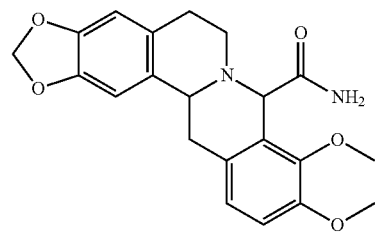 [SMILES: COc1ccc2c(c1OC)C(C(N)=O)N1CCc3cc4c(cc3C1C2)OCO4]
37 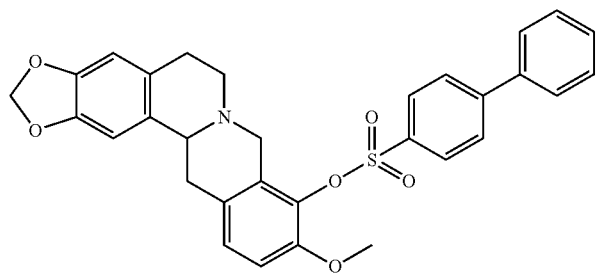 [SMILES: COc1ccc2c(c1OS(=O)(=O)c1ccc(-c3ccccc3)cc1)CN1CCc3cc4c(cc3C1C2)OCO4]
38 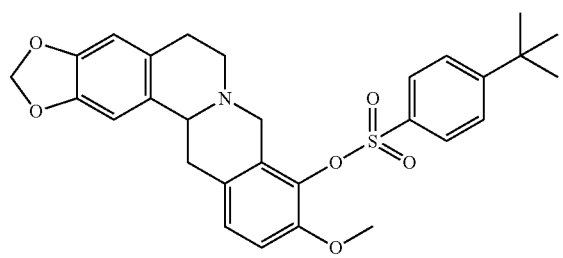 [SMILES: COc1ccc2c(c1OS(=O)(=O)c1ccc(C(C)(C)C)cc1)CN1CCc3cc4c(cc3C1C2)OCO4]
39 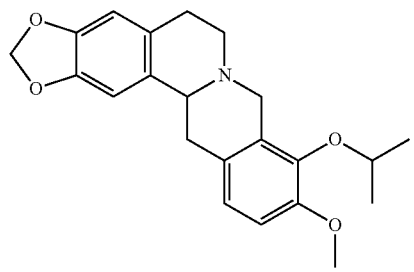 [SMILES: COc1ccc2c(c1OC(C)C)CN1CCc3cc4c(cc3C1C2)OCO4]
41 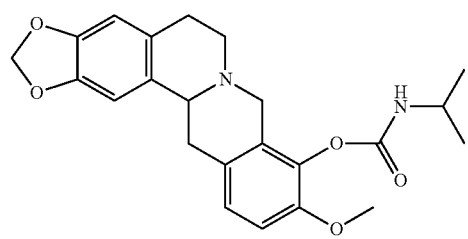 [SMILES: COc1ccc2c(c1OC(=O)NC(C)C)CN1CCc3cc4c(cc3C1C2)OCO4]

TABLE 5-continued
| 42 | 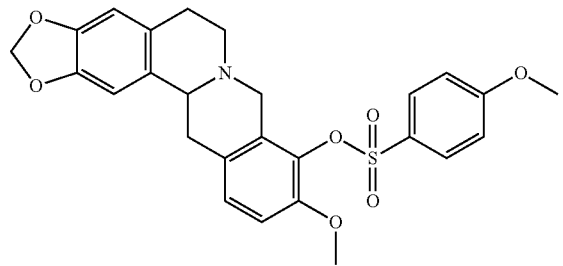 [SMILES: COc1ccc(S(=O)(=O)Oc2c(OC)ccc3c2CN2CCc4cc5c(cc4C2C3)OCO5)cc1] |
| --- | --- |
| 43 | 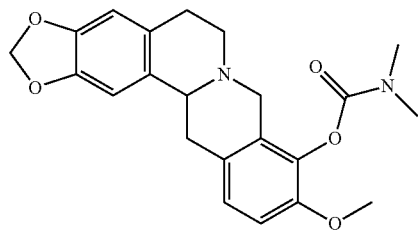 [SMILES: COc1ccc2c(c1OC(=O)N(C)C)CN1CCc3cc4c(cc3C1C2)OCO4] |
| 44 | 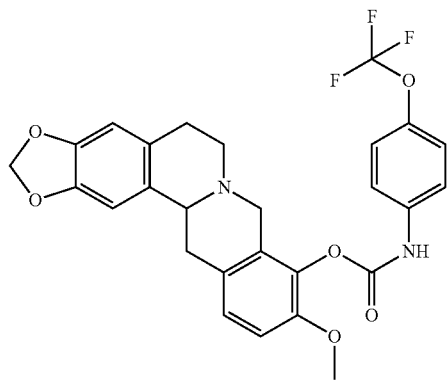 [SMILES: COc1ccc2c(c1OC(=O)Nc1ccc(OC(F)(F)F)cc1)CN1CCc3cc4c(cc3C1C2)OCO4] |
| 45 | 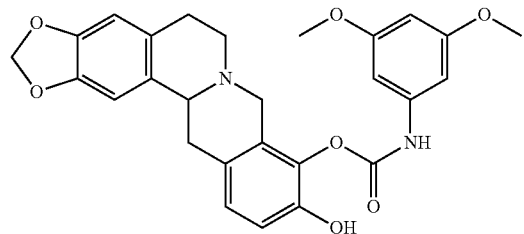 [SMILES: COc1cc(NC(=O)Oc2c(O)ccc3c2CN2CCc4cc5c(cc4C2C3)OCO5)cc(OC)c1] |
| 46 | 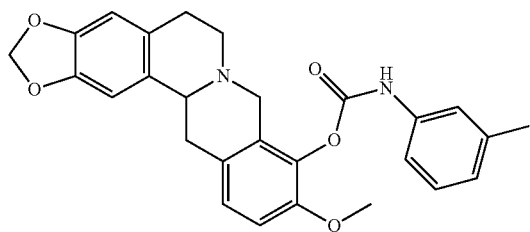 [SMILES: COc1ccc2c(c1OC(=O)Nc1cccc(C)c1)CN1CCc3cc4c(cc3C1C2)OCO4] |

TABLE 5-continued
47 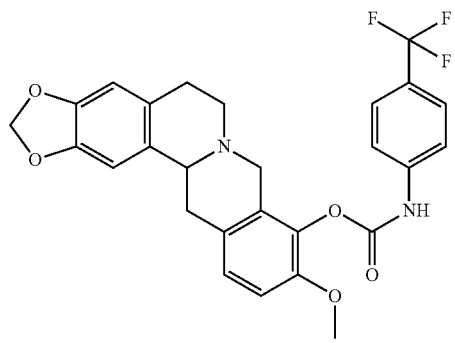 [SMILES: COc1ccc2c(c1OC(=O)Nc1ccc(C(F)(F)F)cc1)CN1CCc3cc4c(cc3C1C2)OCO4]
48 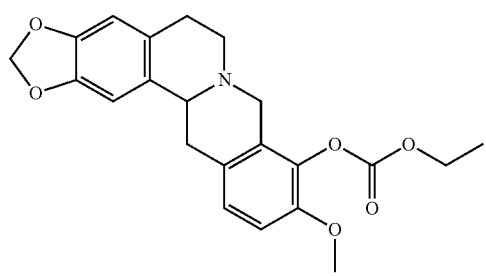 [SMILES: CCOC(=O)Oc1c(OC)ccc2c1CN1CCc3cc4c(cc3C1C2)OCO4]
49 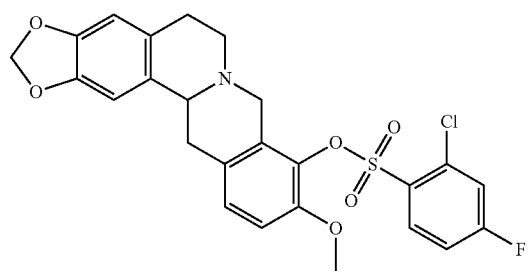 [SMILES: COc1ccc2c(c1OS(=O)(=O)c1ccc(F)cc1Cl)CN1CCc3cc4c(cc3C1C2)OCO4]
50 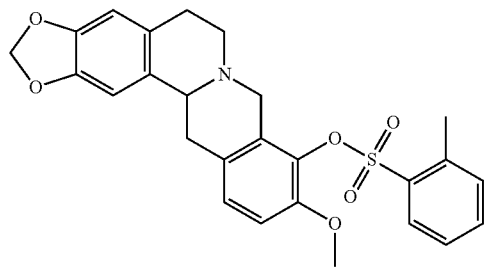 [SMILES: COc1ccc2c(c1OS(=O)(=O)c1ccccc1C)CN1CCc3cc4c(cc3C1C2)OCO4]
51 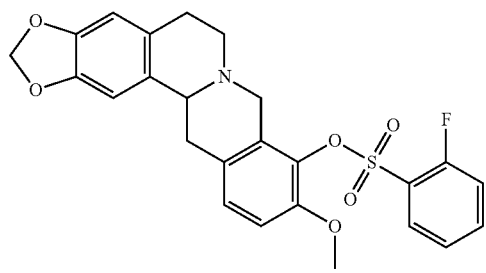 [SMILES: COc1ccc2c(c1OS(=O)(=O)c1ccccc1F)CN1CCc3cc4c(cc3C1C2)OCO4]

TABLE 5-continued
52 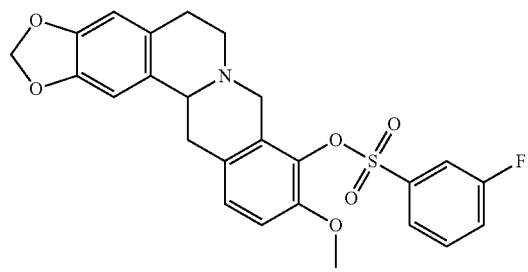 [SMILES: COc1ccc2c(c1OS(=O)(=O)c1cccc(F)c1)CN1CCc3cc4c(cc3C1C2)OCO4]
53 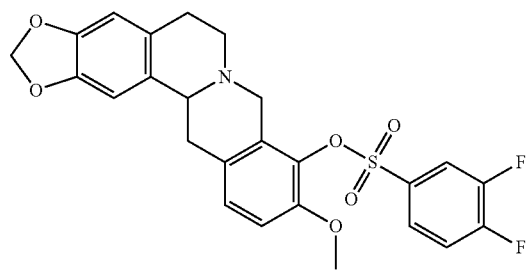 [SMILES: COc1ccc2c(c1OS(=O)(=O)c1ccc(F)c(F)c1)CN1CCc3cc4c(cc3C1C2)OCO4]
54 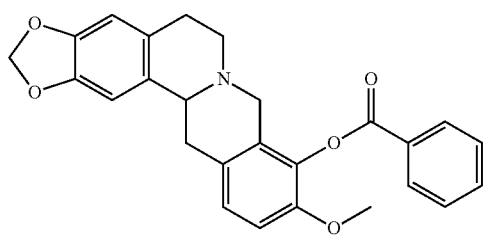 [SMILES: COc1ccc2c(c1OC(=O)c1ccccc1)CN1CCc3cc4c(cc3C1C2)OCO4]
55 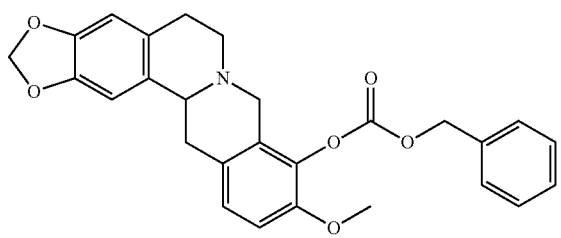 [SMILES: COc1ccc2c(c1OC(=O)OCc1ccccc1)CN1CCc3cc4c(cc3C1C2)OCO4]
56 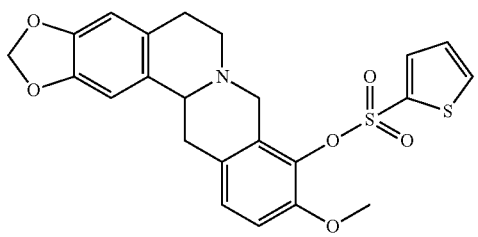 [SMILES: COc1ccc2c(c1OS(=O)(=O)c1cccs1)CN1CCc3cc4c(cc3C1C2)OCO4]
57 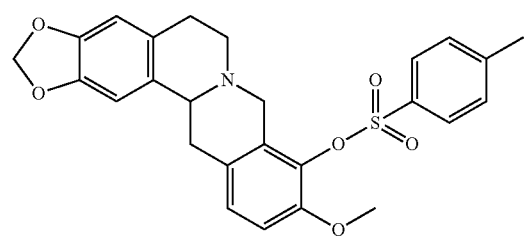 [SMILES: COc1ccc2c(c1OS(=O)(=O)c1ccc(C)cc1)CN1CCc3cc4c(cc3C1C2)OCO4]

TABLE 5-continued
| 58 | 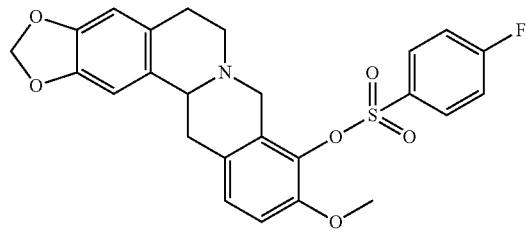 [SMILES: COc1ccc2c(c1OS(=O)(=O)c1ccc(F)cc1)CN1CCc3cc4c(cc3C1C2)OCO4] |
| 59 | 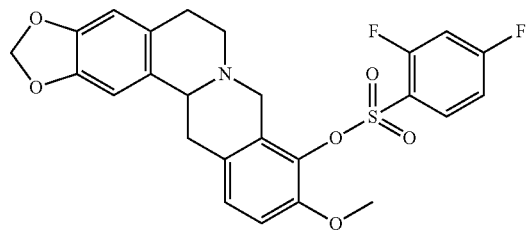 [SMILES: COc1ccc2c(c1OS(=O)(=O)c1ccc(F)cc1F)CN1CCc3cc4c(cc3C1C2)OCO4] |
| 60 | 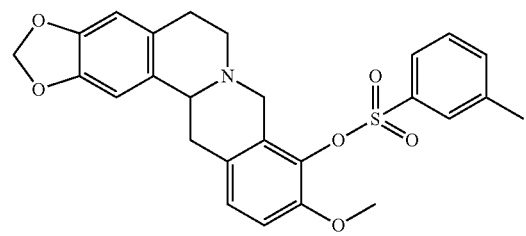 [SMILES: COc1ccc2c(c1OS(=O)(=O)c1cccc(C)c1)CN1CCc3cc4c(cc3C1C2)OCO4] |
| 61 | 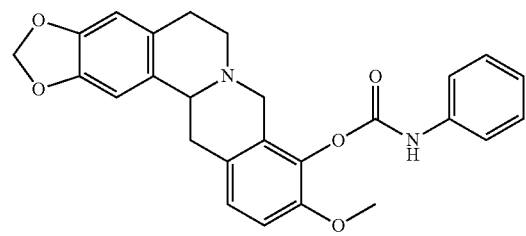 [SMILES: COc1ccc2c(c1OC(=O)Nc1ccccc1)CN1CCc3cc4c(cc3C1C2)OCO4] |
| 62 | 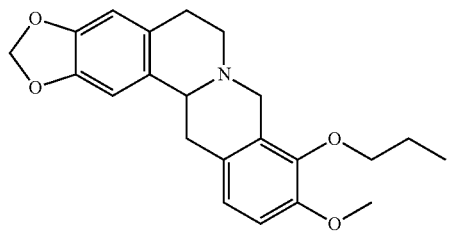 [SMILES: CCCOc1c(OC)ccc2c1CN1CCc3cc4c(cc3C1C2)OCO4] |
| 63 | 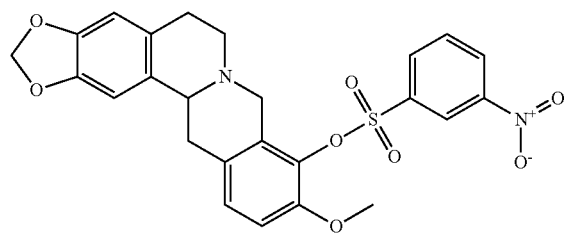 [SMILES: COc1ccc2c(c1OS(=O)(=O)c1cccc([N+](=O)[O-])c1)CN1CCc3cc4c(cc3C1C2)OCO4] |

TABLE 5-continued
| | |
|---|---|
| 64 | 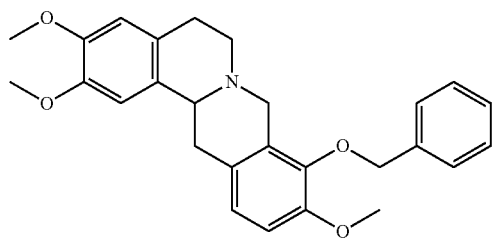 [SMILES: COc1cc2c(cc1OC)C1Cc3ccc(OC)c(OCc4ccccc4)c3CN1CC2] |
| 65 | 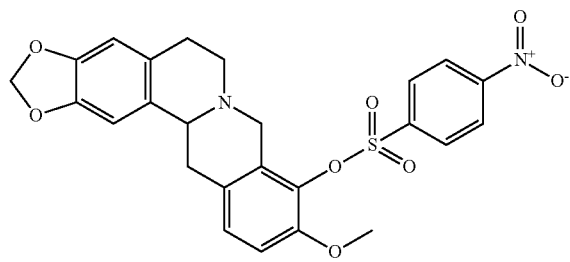 [SMILES: COc1ccc2c(c1OS(=O)(=O)c1ccc([N+](=O)[O-])cc1)CN1CCc3cc4c(cc3C1C2)OCO4] |
| 66 | 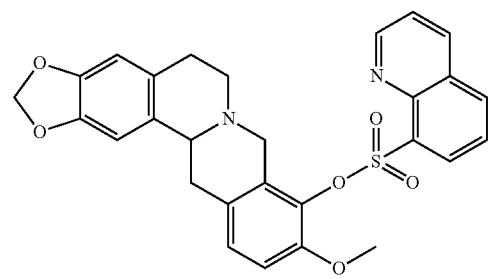 [SMILES: COc1ccc2c(c1OS(=O)(=O)c1cccc3cccnc13)CN1CCc3cc4c(cc3C1C2)OCO4] |
| 67 | 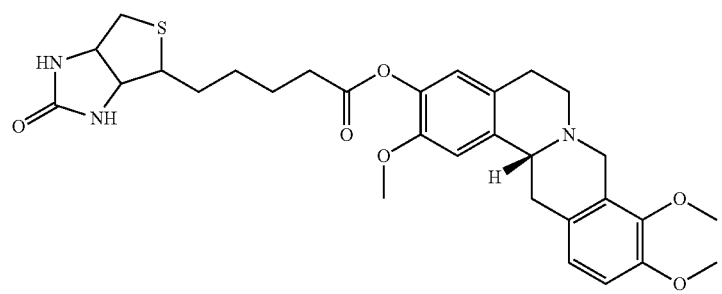 [SMILES: COc1cc2c(cc1OC(=O)CCCCC1SCC3NC(=O)NC31)CCN1Cc3c(ccc(OC)c3OC)C[C@H]21] |
| 68 | 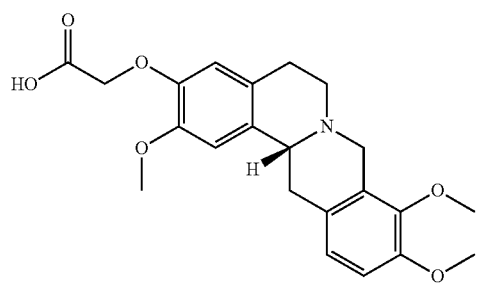 [SMILES: COc1cc2c(cc1OCC(=O)O)CCN1Cc3c(ccc(OC)c3OC)C[C@H]21] |
| 69 | 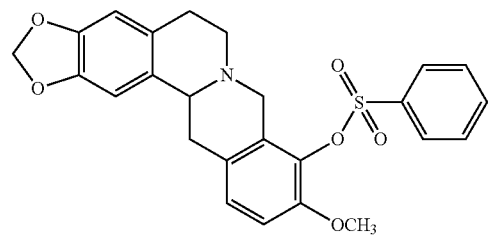 [SMILES: COc1ccc2c(c1OS(=O)(=O)c1ccccc1)CN1CCc3cc4c(cc3C1C2)OCO4] |

TABLE 5-continued
| 70 | 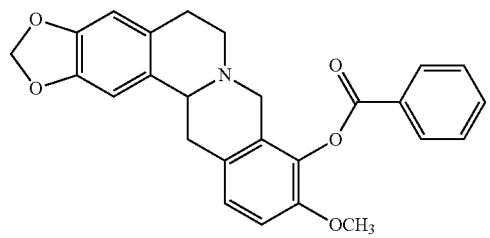 [SMILES: COc1ccc2c(c1OC(=O)c1ccccc1)CN1CCc3cc4c(cc3C1C2)OCO4] |
| 71 | 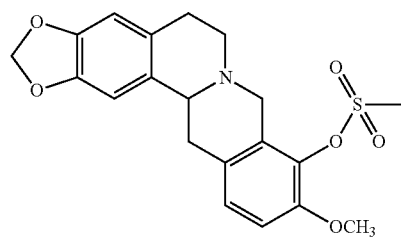 [SMILES: COc1ccc2c(c1OS(C)(=O)=O)CN1CCc3cc4c(cc3C1C2)OCO4] |
| 72 | 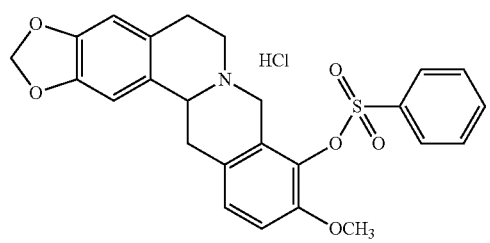 [SMILES: COc1ccc2c(c1OS(=O)(=O)c1ccccc1)CN1CCc3cc4c(cc3C1C2)OCO4 ; Cl] |
| 73 | 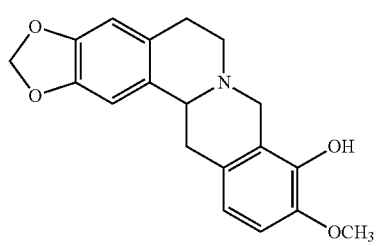 [SMILES: COc1ccc2c(c1O)CN1CCc3cc4c(cc3C1C2)OCO4] |
| 74 | 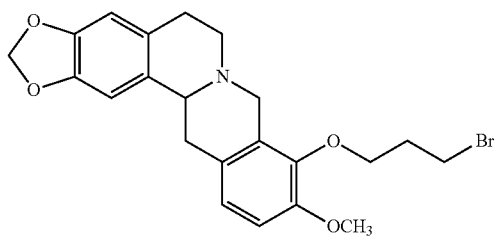 [SMILES: COc1ccc2c(c1OCCCBr)CN1CCc3cc4c(cc3C1C2)OCO4] |
| 75 | 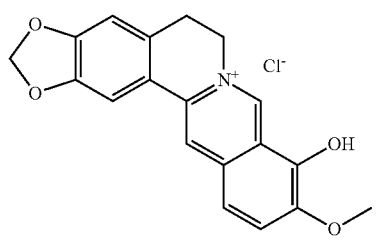 [SMILES: COc1ccc2cc3[n+](cc2c1O)CCc1cc2c(cc1-3)OCO2 ; [Cl-]] |

TABLE 5-continued
| | |
|---|---|
| 76 | 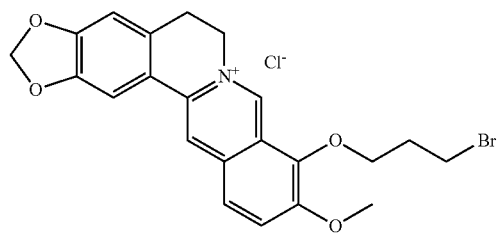 [SMILES: COc1ccc2cc3[n+](cc2c1OCCCBr)CCc1cc2c(cc1-3)OCO2 ; [Cl-]] |
| 77 | 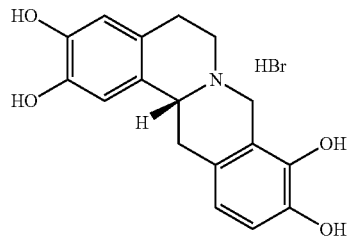 [SMILES: Oc1cc2c(cc1O)[C@H]1Cc3ccc(O)c(O)c3CN1CC2 ; Br] |
| 78 | 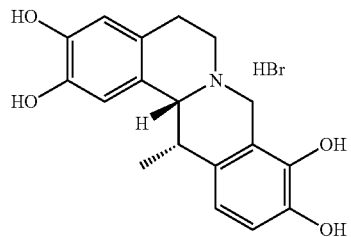 [SMILES: C[C@H]1c2ccc(O)c(O)c2CN2CCc3cc(O)c(O)cc3[C@@H]12 ; Br] |
| 79 | 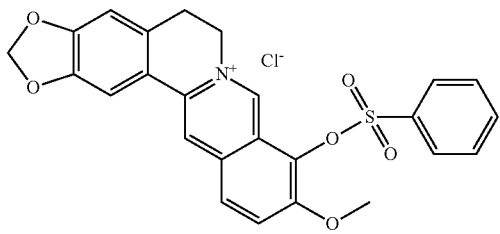 [SMILES: COc1ccc2cc3[n+](cc2c1OS(=O)(=O)c1ccccc1)CCc1cc2c(cc1-3)OCO2 ; [Cl-]] |
| 80 | 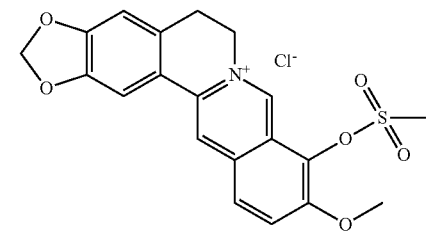 [SMILES: COc1ccc2cc3[n+](cc2c1OS(C)(=O)=O)CCc1cc2c(cc1-3)OCO2 ; [Cl-]] |
| 81 | 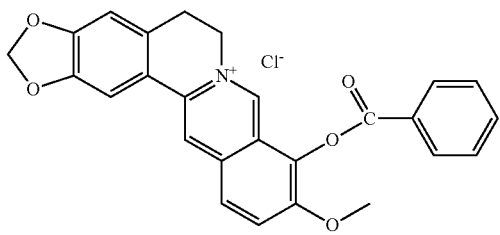 [SMILES: COc1ccc2cc3[n+](cc2c1OC(=O)c1ccccc1)CCc1cc2c(cc1-3)OCO2 ; [Cl-]] |

TABLE 5-continued
82 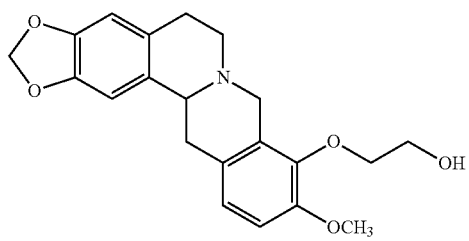 [SMILES: COc1ccc2c(c1OCCO)CN1CCc3cc4c(cc3C1C2)OCO4]
83 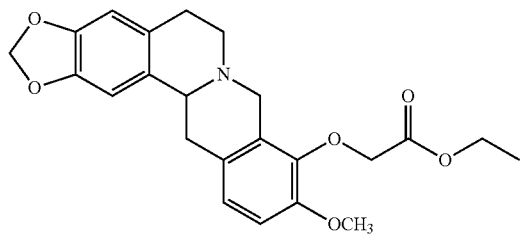 [SMILES: CCOC(=O)COc1c(OC)ccc2c1CN1CCc3cc4c(cc3C1C2)OCO4]
84 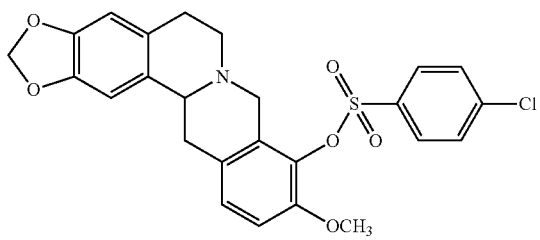 [SMILES: COc1ccc2c(c1OS(=O)(=O)c1ccc(Cl)cc1)CN1CCc3cc4c(cc3C1C2)OCO4]
85 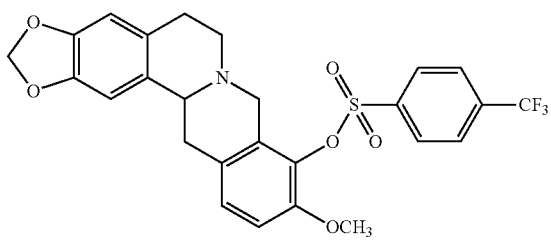 [SMILES: COc1ccc2c(c1OS(=O)(=O)c1ccc(C(F)(F)F)cc1)CN1CCc3cc4c(cc3C1C2)OCO4]
86 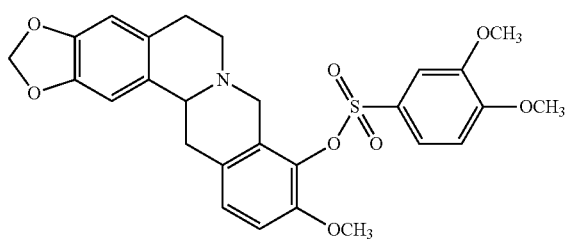 [SMILES: COc1ccc(S(=O)(=O)Oc2c(OC)ccc3c2CN2CCc4cc5c(cc4C2C3)OCO5)cc1OC]
87 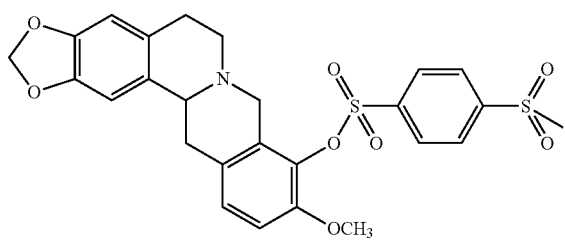 [SMILES: COc1ccc2c(c1OS(=O)(=O)c1ccc(S(C)(=O)=O)cc1)CN1CCc3cc4c(cc3C1C2)OCO4]

TABLE 5-continued
| 88 | 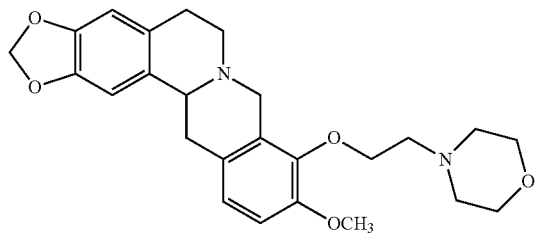 [SMILES: COc1ccc2c(c1OCCN1CCOCC1)CN1CCc3cc4c(cc3C1C2)OCO4] |
| --- | --- |
| 89 | 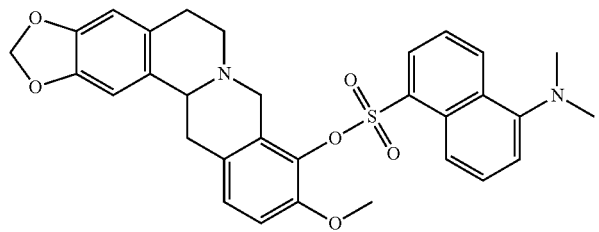 [SMILES: COc1ccc2c(c1OS(=O)(=O)c1cccc3c(N(C)C)cccc13)CN1CCc3cc4c(cc3C1C2)OCO4] |
| 90 | 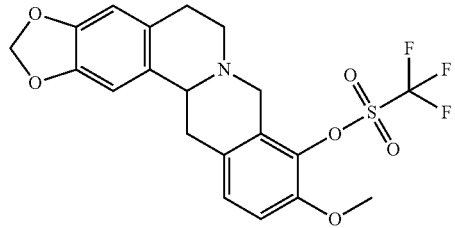 [SMILES: COc1ccc2c(c1OS(=O)(=O)C(F)(F)F)CN1CCc3cc4c(cc3C1C2)OCO4] |
| 91 | 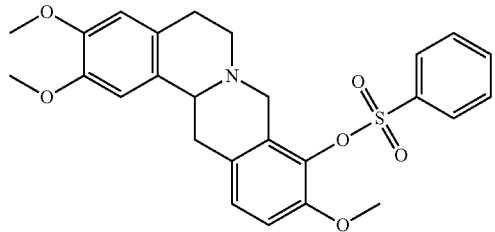 [SMILES: COc1cc2c(cc1OC)C1Cc3ccc(OC)c(OS(=O)(=O)c4ccccc4)c3CN1CC2] |
| 92 | 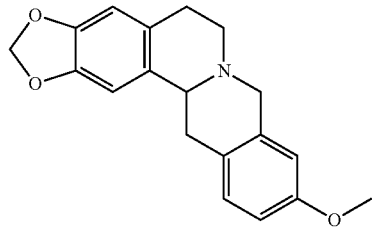 [SMILES: COc1ccc2c(c1)CN1CCc3cc4c(cc3C1C2)OCO4] |
| 93 | 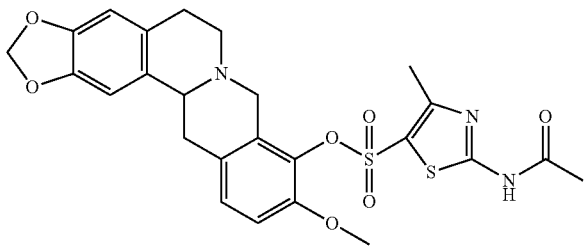 [SMILES: COc1ccc2c(c1OS(=O)(=O)c1sc(NC(C)=O)nc1C)CN1CCc3cc4c(cc3C1C2)OCO4] |

TABLE 5-continued
| 94 | 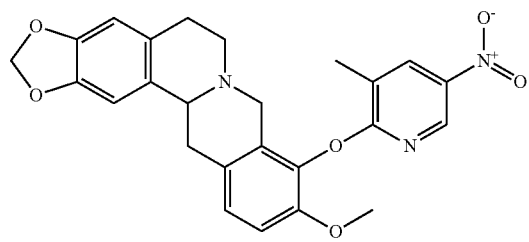 [SMILES: COc1ccc2c(c1Oc1ncc([N+](=O)[O-])cc1C)CN1CCc3cc4c(cc3C1C2)OCO4] |
| 95 | 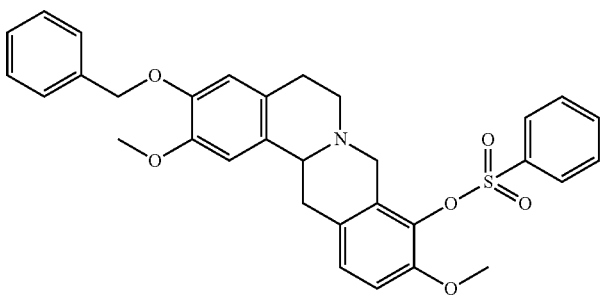 [SMILES: COc1cc2c(cc1OCc1ccccc1)CCN1Cc3c(ccc(OC)c3OS(=O)(=O)c3ccccc3)CC21] |
| 96 | 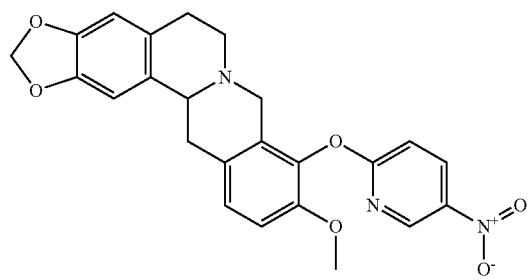 [SMILES: COc1ccc2c(c1Oc1ccc([N+](=O)[O-])cn1)CN1CCc3cc4c(cc3C1C2)OCO4] |
| 97 | 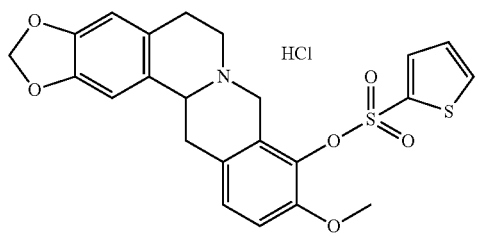 [SMILES: COc1ccc2c(c1OS(=O)(=O)c1cccs1)CN1CCc3cc4c(cc3C1C2)OCO4 ; Cl] |
| 98 | 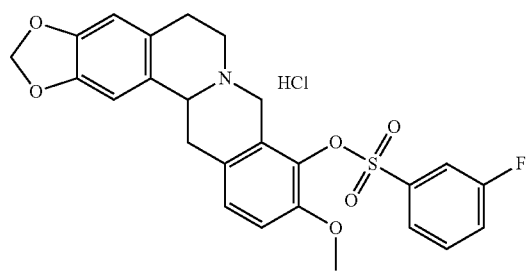 |
| 99 | 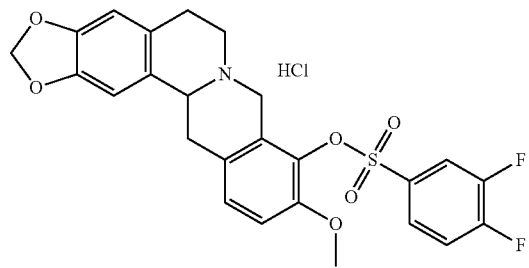 |

TABLE 5-continued
100 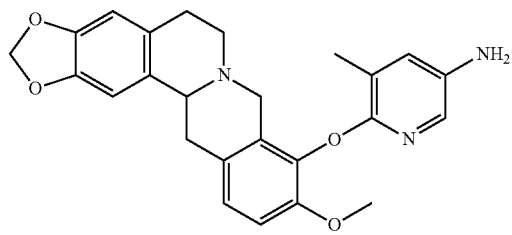 [SMILES: COc1ccc2c(c1Oc1ncc(N)cc1C)CN1CCc3cc4c(cc3C1C2)OCO4]
101 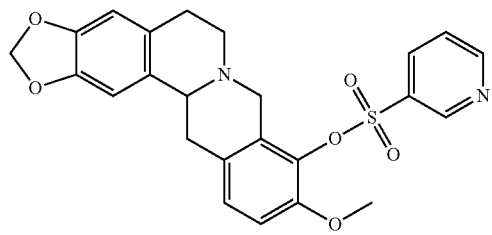 [SMILES: COc1ccc2c(c1OS(=O)(=O)c1cccnc1)CN1CCc3cc4c(cc3C1C2)OCO4]
102 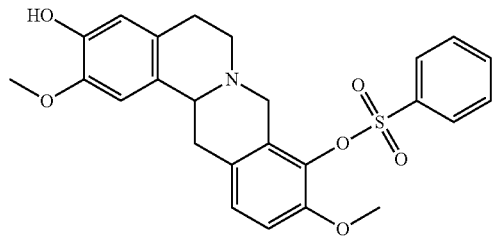 [SMILES: COc1cc2c(cc1O)CCN1Cc3c(ccc(OC)c3OS(=O)(=O)c3ccccc3)CC21]
103 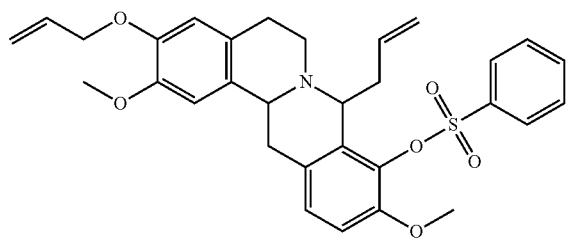 [SMILES: C=CCOc1cc2c(cc1OC)C1Cc3ccc(OC)c(OS(=O)(=O)c4ccccc4)c3C(CC=C)N1CC2]
104 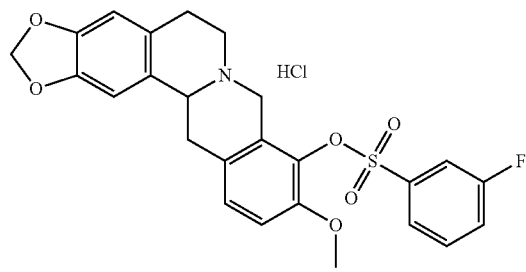 [SMILES: COc1ccc2c(c1OS(=O)(=O)c1cccc(F)c1)CN1CCc3cc4c(cc3C1C2)OCO4 ; Cl]
105 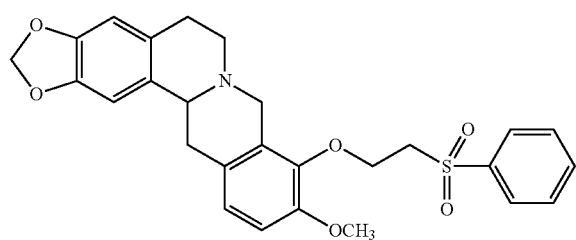 [SMILES: COc1ccc2c(c1OCCS(=O)(=O)c1ccccc1)CN1CCc3cc4c(cc3C1C2)OCO4]

TABLE 5-continued
112 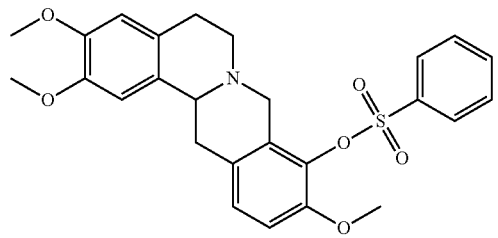 [SMILES: COc1cc2c(cc1OC)C1Cc3ccc(OC)c(OS(=O)(=O)c4ccccc4)c3CN1CC2]
113 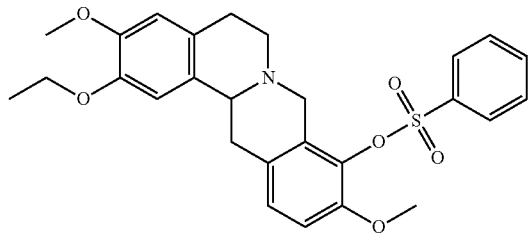 [SMILES: CCOc1cc2c(cc1OC)CCN1Cc3c(ccc(OC)c3OS(=O)(=O)c3ccccc3)CC21]
114 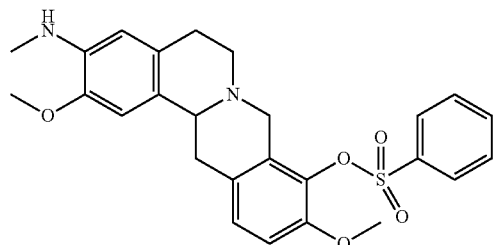
115 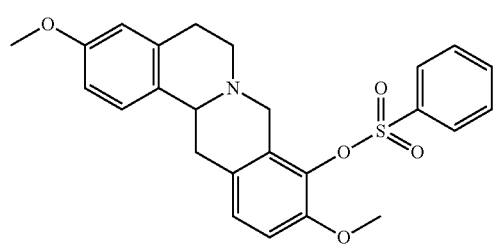 [SMILES: COc1ccc2c(c1)CCN1Cc3c(ccc(OC)c3OS(=O)(=O)c3ccccc3)CC21]
116 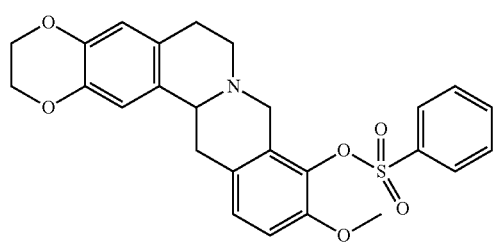 [SMILES: COc1ccc2c(c1OS(=O)(=O)c1ccccc1)CN1CCc3cc4c(cc3C1C2)OCCO4]
117 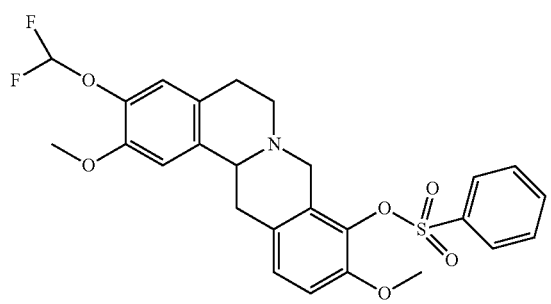 [SMILES: COc1cc2c(cc1OC(F)F)CCN1Cc3c(ccc(OC)c3OS(=O)(=O)c3ccccc3)CC21]

TABLE 5-continued
118
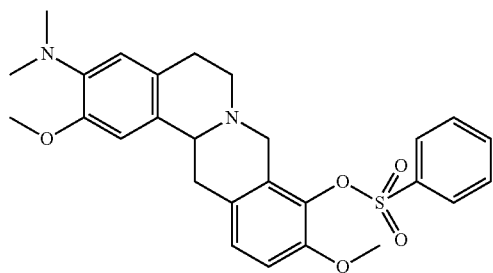 [SMILES: COc1cc2c(cc1N(C)C)CCN1Cc3c(ccc(OC)c3OS(=O)(=O)c3ccccc3)CC21]
119
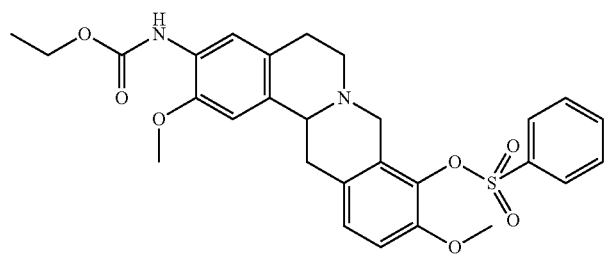 [SMILES: CCOC(=O)Nc1cc2c(cc1OC)C1Cc3ccc(OC)c(OS(=O)(=O)c4ccccc4)c3CN1CC2]
120
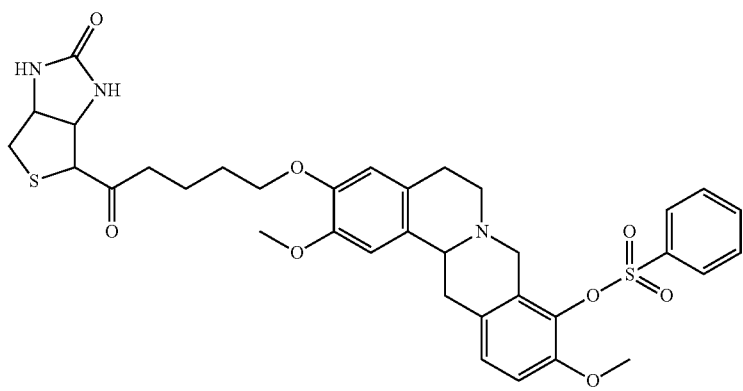 [SMILES: COc1cc2c(cc1OCCCCC(=O)C1SCC3NC(=O)NC31)CCN1Cc3c(ccc(OC)c3OS(=O)(=O)c3ccccc3)CC21]
121
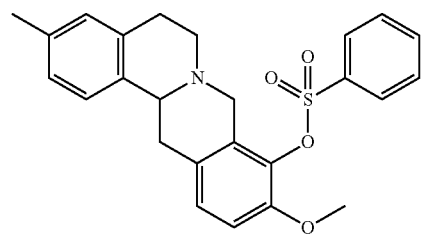 [SMILES: COc1ccc2c(c1OS(=O)(=O)c1ccccc1)CN1CCc3cc(C)ccc3C1C2]
122
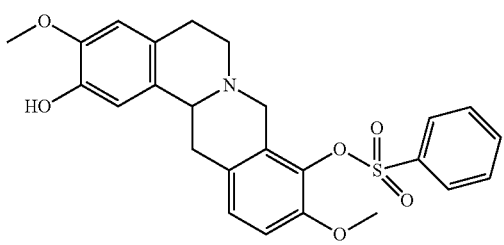 [SMILES: COc1cc2c(cc1O)C1Cc3ccc(OC)c(OS(=O)(=O)c4ccccc4)c3CN1CC2]

TABLE 5-continued
123 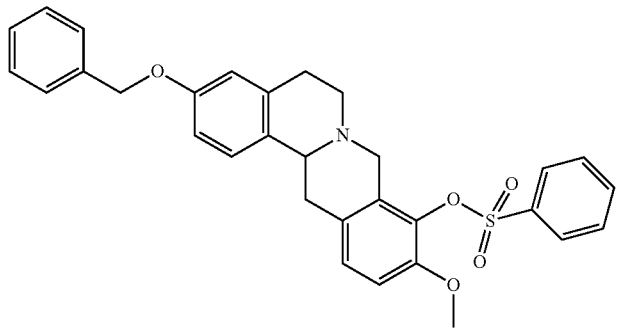 [SMILES: COc1ccc2c(c1OS(=O)(=O)c1ccccc1)CN1CCc3cc(OCc4ccccc4)ccc3C1C2]
124 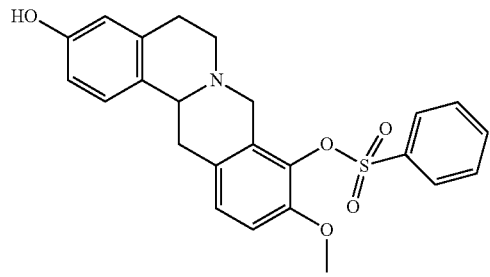 [SMILES: COc1ccc2c(c1OS(=O)(=O)c1ccccc1)CN1CCc3cc(O)ccc3C1C2]
125 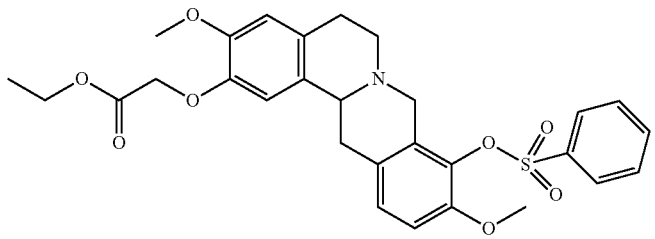 [SMILES: CCOC(=O)COc1cc2c(cc1OC)CCN1Cc3c(ccc(OC)c3OS(=O)(=O)c3ccccc3)CC21]
126 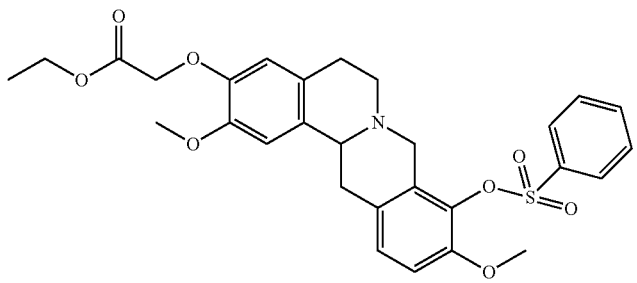 [SMILES: CCOC(=O)COc1cc2c(cc1OC)C1Cc3ccc(OC)c(OS(=O)(=O)c4ccccc4)c3CN1CC2]
127 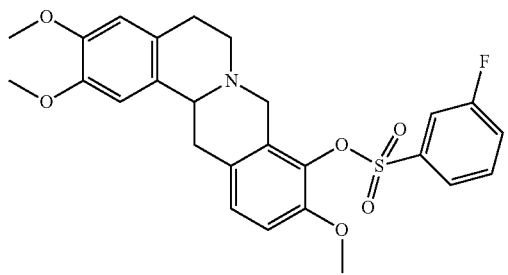 [SMILES: COc1cc2c(cc1OC)C1Cc3ccc(OC)c(OS(=O)(=O)c4cccc(F)c4)c3CN1CC2]

TABLE 5-continued
128 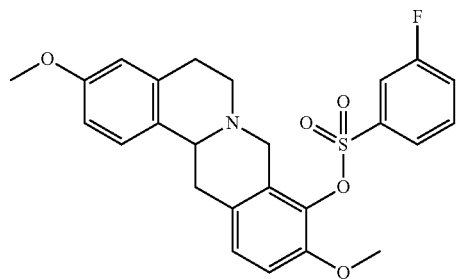 [SMILES: COc1ccc2c(c1)CCN1Cc3c(ccc(OC)c3OS(=O)(=O)c3cccc(F)c3)CC21]
129 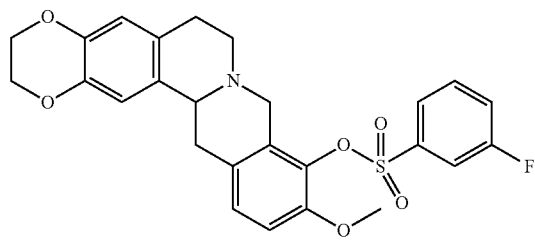 [SMILES: COc1ccc2c(c1OS(=O)(=O)c1cccc(F)c1)CN1CCc3cc4c(cc3C1C2)OCCO4]
130 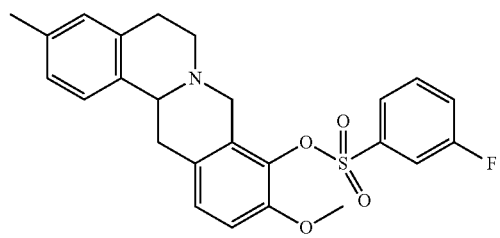 [SMILES: COc1ccc2c(c1OS(=O)(=O)c1cccc(F)c1)CN1CCc3cc(C)ccc3C1C2]
131 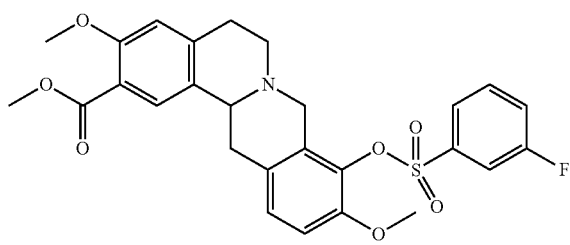 [SMILES: COC(=O)c1cc2c(cc1OC)CCN1Cc3c(ccc(OC)c3OS(=O)(=O)c3cccc(F)c3)CC21]
132 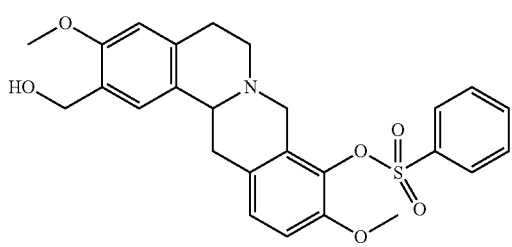 [SMILES: COc1cc2c(cc1CO)C1Cc3ccc(OC)c(OS(=O)(=O)c4ccccc4)c3CN1CC2]
133 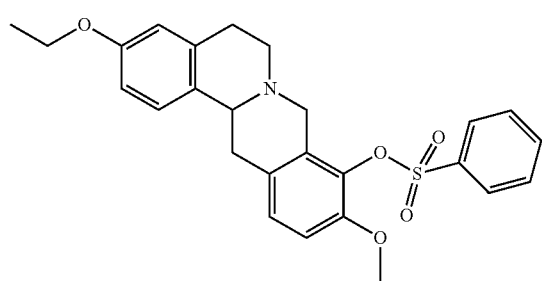 [SMILES: CCOc1ccc2c(c1)CCN1Cc3c(ccc(OC)c3OS(=O)(=O)c3ccccc3)CC21]

TABLE 5-continued
134 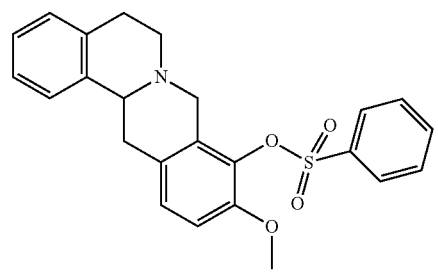 [SMILES: COc1ccc2c(c1OS(=O)(=O)c1ccccc1)CN1CCc3ccccc3C1C2]
135 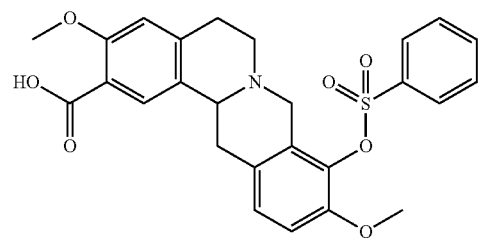 [SMILES: COc1cc2c(cc1C(=O)O)C1Cc3ccc(OC)c(OS(=O)(=O)c4ccccc4)c3CN1CC2]
136 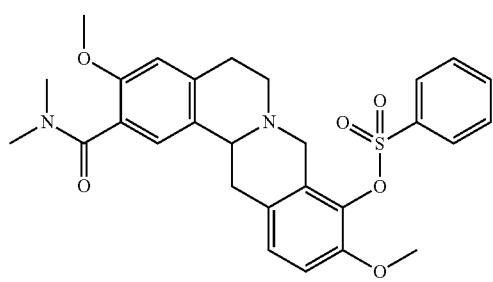 [SMILES: COc1cc2c(cc1C(=O)N(C)C)C1Cc3ccc(OC)c(OS(=O)(=O)c4ccccc4)c3CN1CC2]
137 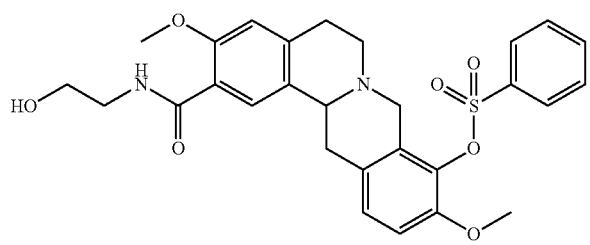 [SMILES: COc1cc2c(cc1C(=O)NCCO)C1Cc3ccc(OC)c(OS(=O)(=O)c4ccccc4)c3CN1CC2]
138 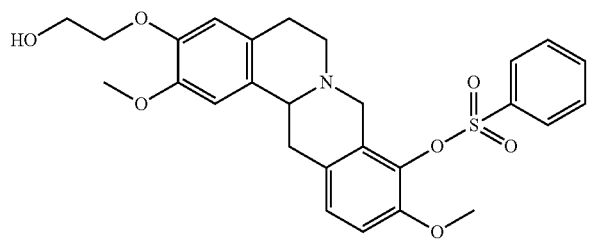 [SMILES: COc1cc2c(cc1OCCO)CCN1Cc3c(ccc(OC)c3OS(=O)(=O)c3ccccc3)CC21]
139 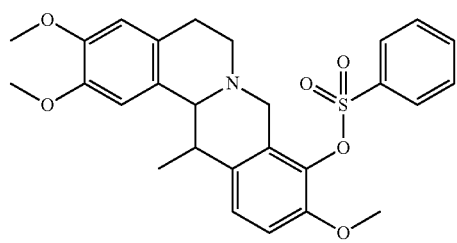 [SMILES: COc1cc2c(cc1OC)C1C(C)c3ccc(OC)c(OS(=O)(=O)c4ccccc4)c3CN1CC2]

TABLE 5-continued
140 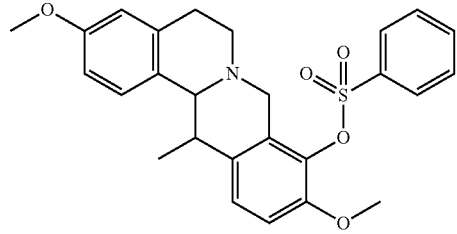 [SMILES: COc1ccc2c(c1)CCN1Cc3c(ccc(OC)c3OS(=O)(=O)c3ccccc3)C(C)C21]
141 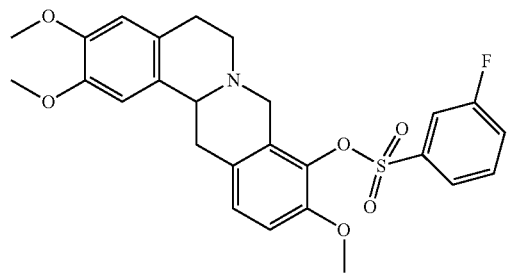 [SMILES: COc1cc2c(cc1OC)C1Cc3ccc(OC)c(OS(=O)(=O)c4cccc(F)c4)c3CN1CC2]
142 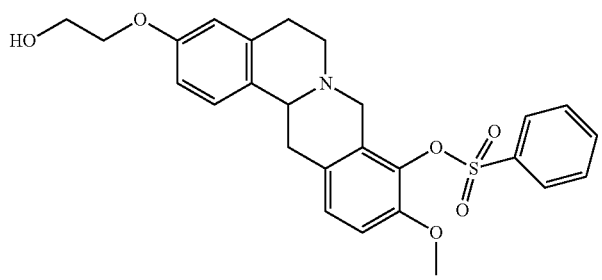 [SMILES: COc1ccc2c(c1OS(=O)(=O)c1ccccc1)CN1CCc3cc(OCCO)ccc3C1C2]
143 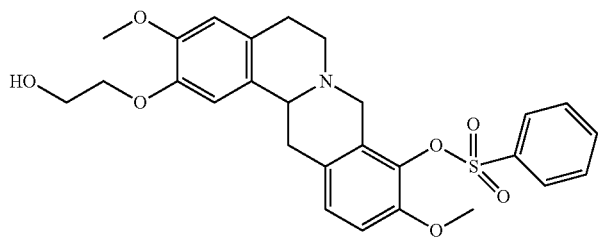 [SMILES: COc1cc2c(cc1OCCO)C1Cc3ccc(OC)c(OS(=O)(=O)c4ccccc4)c3CN1CC2]
144 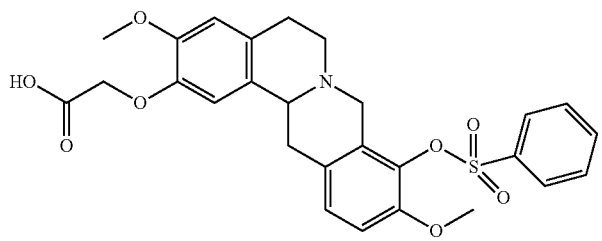 [SMILES: COc1cc2c(cc1OCC(=O)O)C1Cc3ccc(OC)c(OS(=O)(=O)c4ccccc4)c3CN1CC2]
145 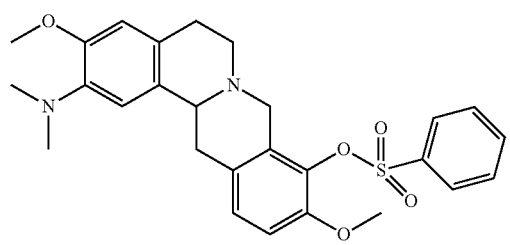 [SMILES: COc1cc2c(cc1N(C)C)C1Cc3ccc(OC)c(OS(=O)(=O)c4ccccc4)c3CN1CC2]

TABLE 5-continued
146 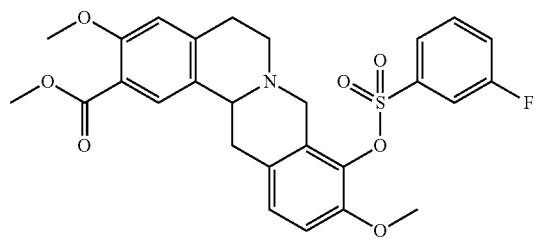 [SMILES: COC(=O)c1cc2c(cc1OC)CCN1Cc3c(ccc(OC)c3OS(=O)(=O)c3cccc(F)c3)CC21]
147 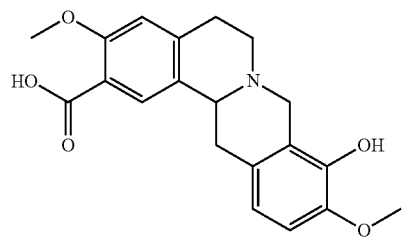
148 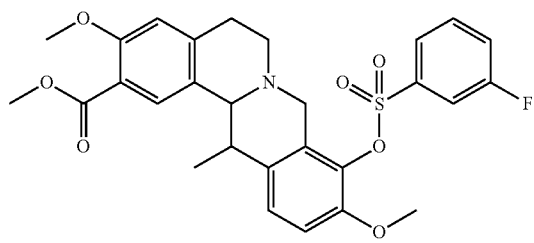 [SMILES: COC(=O)c1cc2c(cc1OC)CCN1Cc3c(ccc(OC)c3OS(=O)(=O)c3cccc(F)c3)C(C)C21]
149 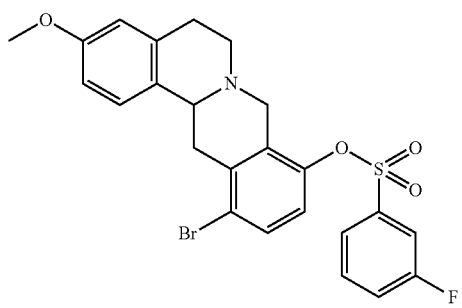 [SMILES: COc1ccc2c(c1)CCN1Cc3c(OS(=O)(=O)c4cccc(F)c4)ccc(Br)c3CC21]
150 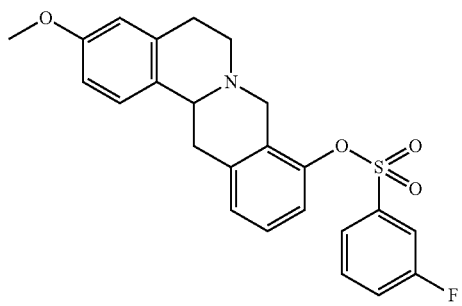 [SMILES: COc1ccc2c(c1)CCN1Cc3c(cccc3OS(=O)(=O)c3cccc(F)c3)CC21]
151 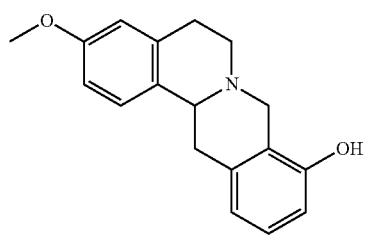 [SMILES: COc1ccc2c(c1)CCN1Cc3c(O)cccc3CC21]

TABLE 5-continued
152 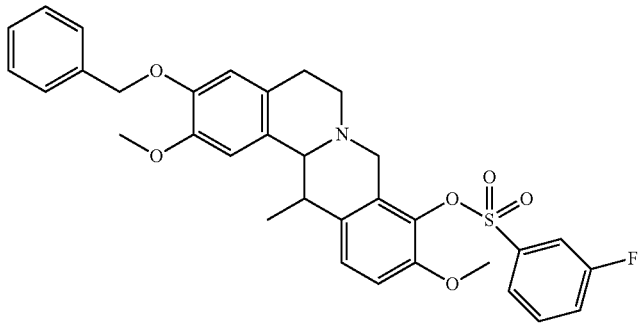 [SMILES: COc1cc2c(cc1OCc1ccccc1)CCN1Cc3c(ccc(OC)c3OS(=O)(=O)c3cccc(F)c3)C(C)C21]
153 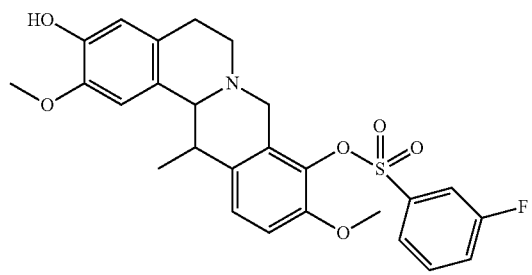 [SMILES: COc1cc2c(cc1O)CCN1Cc3c(ccc(OC)c3OS(=O)(=O)c3cccc(F)c3)C(C)C21]
154 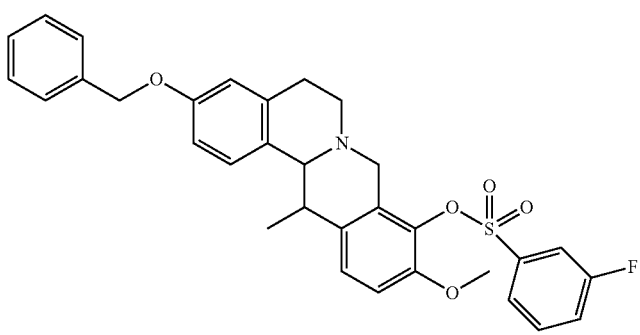 [SMILES: COc1ccc2c(c1OS(=O)(=O)c1cccc(F)c1)CN1CCc3cc(OCc4ccccc4)ccc3C1C2C]
155 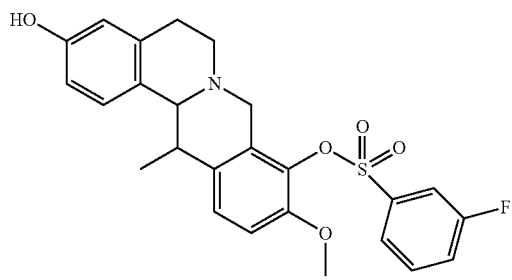 [SMILES: COc1ccc2c(c1OS(=O)(=O)c1cccc(F)c1)CN1CCc3cc(O)ccc3C1C2C]
156 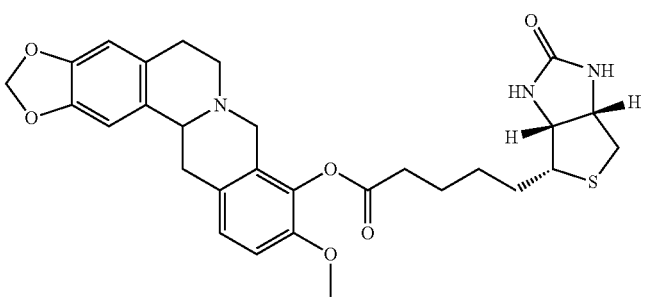 [SMILES: COc1ccc2c(c1OC(=O)CCCC[C@H]1SC[C@H]3NC(=O)N[C@H]31)CN1CCc3cc4c(cc3C1C2)OCO4]

TABLE 5-continued

157 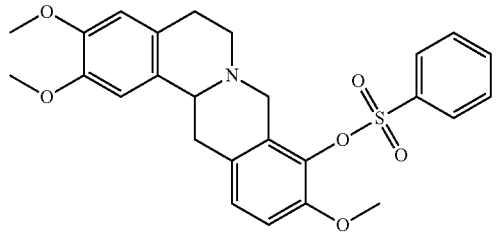 [SMILES: COc1cc2c(cc1OC)C1Cc3ccc(OC)c(OS(=O)(=O)c4ccccc4)c3CN1CC2]

158 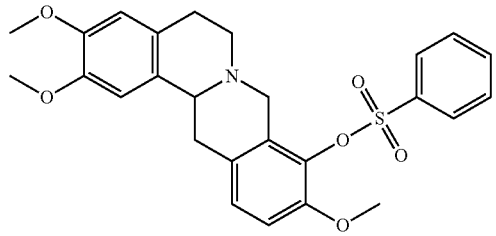 [SMILES: COc1cc2c(cc1OC)C1Cc3ccc(OC)c(OS(=O)(=O)c4ccccc4)c3CN1CC2]

159 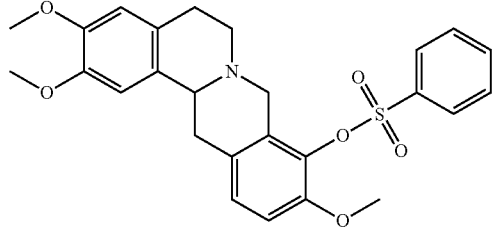 [SMILES: COc1cc2c(cc1OC)C1Cc3ccc(OC)c(OS(=O)(=O)c4ccccc4)c3CN1CC2]

160 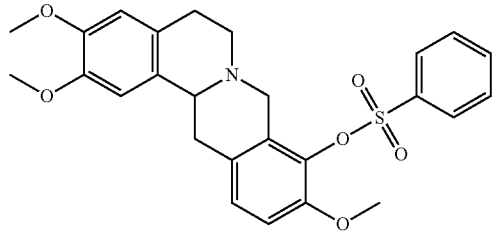 [SMILES: COc1cc2c(cc1OC)C1Cc3ccc(OC)c(OS(=O)(=O)c4ccccc4)c3CN1CC2]

161 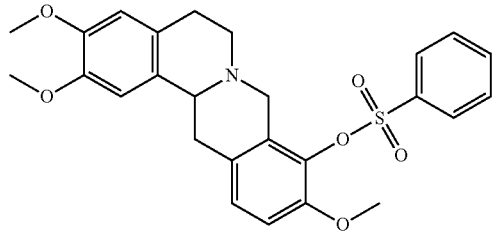 [SMILES: COc1cc2c(cc1OC)C1Cc3ccc(OC)c(OS(=O)(=O)c4ccccc4)c3CN1CC2]

| Cmpd No. | Chemical Name | Molecular Formula | Molecular Weight | MS: m/z [M+ + 1]* |
|---|---|---|---|---|
| 1 | 9,10-dimethoxy-13-benzyl-5,6,7,8,13,13a-hexahydro-2H-1,3-dioxolano[4,5-g]isoquinolino[3,2-a]isoquinoline | C27H27NO4 | 429.51 | 430.2 |
| 2 | (13aR)-2,3,9,10-tetramethoxy-5,6,7,8,13,13a-hexahydroisoquinolino[3,2-a]isoquinoline hydrochloride | C21H25NO4•HCl | 355.43** | 356.2 |
| 3 | (13aR)-2,3,9,10-tetramethoxy-5,6,7,8.13,13a-hexahydroisoquinolino[3,2-a]isoquinoline sulfate | C21H25NO4•H2SO4 | 355.43** | 356.2 |
| 4 | (13aR)-2,3,9,10-tetramethoxy-5,6,7,8,13,13a-hexahydroisoquinolino[3,2-a]isoquinoline citrate | C21H25NO4•citrate | 355.43** | 356.2 |

TABLE 5-continued

| | | | | |
|---|---|---|---|---|
| 5 | (13aR)-2,3,9,10-tetramethoxy-5,6,7,8,13,13a-hexahydroisoquinolino[3,2-a]isoquinoline maleate | C21H25NO4•maleate | 355.43** | 356.2 |
| 6 | (13S,13aR)-2,3,9,10-tetramethoxy-13-methyl-5,6,7,8,13,13a-hexahydroisoquinolino[2,1-b]isoquinoline hydrochloride | C22H27NO4•HCl | 369.45** | 370.2 |
| 7 | (13S,13aR)-2,3,9,10-tetramethoxy-13-methyl-5,6,7,8,13,13a-hexahydroisoquinolino[2,1-b]isoquinoline sulfate | C22H27NO4•H2SO4 | 369.45** | 370.2 |
| 8 | (13S,13aR)-2,3,9,10-tetramethoxy-13-methyl-5,6,7,8,13,13a-hexahydroisoquinolino[2,1-b]isoquinoline citrate | C22H27NO4•citrate | 369.45** | 370.2 |
| 9 | (13S,13aR)-2,3,9,10-tetramethoxy-13-methyl-5,6,7,8,13,13a-hexahydroisoquinolino[2,1-b]isoquinoline maleate | C22H27NO4•maleate | 369.45** | 370.2 |
| 10 | 2,3,10,11-tetramethoxy-5,6,7,8,13,13a-hexahydroisoquinolino[3,2-a]isoquinoline | C21H25NO4 | 355.43 | 356.1 |
| 11 | 2,3-dimethoxy-5,6,7,8,14,14a-hexahydro-11H-1,3-dioxoleno[4,5-g]isoquinolino[2,1-b]isoquinoline | C20H21NO4 | 339.39 | 340.1 |
| 12 | (13S,13aR)-13-ethyl-2,3,10,11-tetramethoxy-5,6,7,8,13,13a-hexahydroisoquinolino[2,1-b]isoquinoline | C23H29NO4 | 383.48 | 384.2 |
| 13 | (13R,13aR)-13-ethyl-2,3,10,11-tetramethoxy-5,6,7,8,13,13a-hexahydroisoquinolino[2,1-b]isoquinoline | C23H29NO4 | 383.48 | 384.2 |
| 14 | (13R,13aR)-2,3-dimethoxy-8-oxo-5,6,7,13,13a-pentahydroisoquinolino[2,1-b]isoquinoline-13-carboxylic acid | C20H19NO5 | 353.37 | 354.1 |
| 15 | (13S,13aR)-2,3-dimethoxy-8-oxo-5,6,7,13,13a-pentahydroisoquinolino[2,1-b]isoquinoline-13-carboxylic acid | C20H19NO5 | 353.37 | 354.1 |
| 16 | 2,3,11-trimethoxy-5,6,7,8,13,13a-hexahydroisoquinolino[2,1-b]isoquinolin-10-ol | C20H23NO4 | 341.40 | 342.1 |
| 17 | 2,3,10-trimethoxy-5,6,7,8,13,13a-hexahydroisoquinolin[2,1-b]isoquinolin-11-ol | C20H23NO4 | 341.40 | 342.1 |
| 18 | 8,9-dimethoxy-6,11,12,13,6a-pentahydro-2H-1,3-dioxoleno[4,5-h]isoquinolino[2,1-b]isoquinolin-14-one | C20H17NO5 | 351.10 | 352.0 |
| 19 | 8,9-dimethoxy-6,11,12,13,14,6a-hexahydro-2H-1,3-dioxoleno[4,5-h]isoquinolino[2,1-b]isoquinoline | C20H21NO4 | 339.14 | 340.1 |
| 20 | 13-ethyl-2,3,9,10-tetramethoxy-5,6,7,8,13,13a-hexahydroisoquinolino[2,1-b]isoquinoiine | C23H29NO4 | 383.49 | 402.1 [M$^+$ + 1 + H$_2$O] |
| 21 | 12-bromo-2,3,9-trimethoxy-5,6,7,8,13,13a-hexahydroisoquinolino[2,1-b]isoquinoline | C20H22BrNO3 | 404.31 | 403.9, 405.9 |
| 22 | 2,3,9-trimethoxy-5,6,7,8,13,13a- | C20H23NO3 | 325.41 | 326.1 |

TABLE 5-continued

| | | | | |
|---|---|---|---|---|
| 23 | hexahydroisoquinolino[3,2-a]isoquinoline 10-methoxy-9-(phenylmethoxy)-5,6,7,8,13,13a-hexahydro-2H-1,3-dioxolano[4,5-g]isoquinolino[3,2-a]isoquinoline | C26H25NO4 | 415.48 | 416.0 |
| 24 | 10-methoxy-9-{[3-(trifluoromethoxy)phenyl]methoxy}-5,6,7,8,13,13a-hexahydro-2H-1,3-dioxolano[4,5-g]isoquinolino[3,2-a]isoquinoline | C27H24F3NO5 | 499.48 | 500.0 |
| 25 | 9-[(3-chlorophenyl)methoxy]-10-methoxy-5,6,7,8,13,13a-hexahydro-2H-1,3-dioxolano[4,5-g]isoquinolino[3,2-a]isoquinoline | C26H24ClNO4 | 449.93 | 450.0, 452.0 |
| 26 | 10-methoxy-9-[(2-nitrophenyl)methoxy]-5,6,7,8,13,13a-hexahydro-2H-1,3-dioxolano[4,5-g]isoquinolino[3,2-a]isoquinoline | C26H25NO6S | 460.48 | 461.0 |
| 27 | 10-methoxy-5,6,7,8,13,13a-hexahydro-2H-1,3-dioxolano[4,5-g]isoquinolino[3,2-a]isoquinolin-9-yl cyclopentanesulfonate | C26H24N2O6 | 457.54 | 458.1 |
| 28 | 10-methoxy-5,6,7,8,13,13a-hexahydro-2H-1,3-dioxolano[4,5-g]isoquinolino[3,2-a]isoquinolin-9-yl benzylsulfonate | C24H27NO6S | 479.54 | 480.0 |
| 29 | 9-ethoxy-10-methoxy-5,6,7,8,13,13a-hexahydro-2H-1,3-dioxolano[4,5-g]isoquinolino[3,2-a]isoquinoline | C21H23NO4 | 353.41 | 354.1 |
| 30 | 1-(9,10-dimethoxy-5,6,7,8-tetrahydro-2H-1,3-dioxolano[4,5-g]isoquinolino[3,2-a]isoquinolin-8-yl)acetone | C23H23NO5 | 393.43 | 336.0 [M+ + 1 - acetone] |
| 31 | (13S,13aR)-9,10-dimethoxy-13-benzyl-5,6,7,8,13,13a-hexahydro-2H-1,3-dioxolano[4,5-g]isoquinolino[3,2-a]isoquinoline | C27H27NO4 | 429.51 | 430.1 |
| 32 | (13aS,13R)-9,10-dimethoxy-13-benzyl-5,6,7,8,13,13a-hexahydro-2H-1,3-dioxolano[4,5-g]isoquinolino[3,2-a]isoquinoline | C27H27NO4 | 429.51 | 430.1 |
| 33 | 9,10-dimethoxy-5,6,7,8-tetrahydro-2H-1,3-dioxolano[4,5-g]isoquinolino[3,2-a]isoquinoline-8-carbonitrile | C21H18N2O4 | 362.38 | 336.0 [M+ − CN] |
| 34 | 10-methoxy-5,6,7,8,13,13a-hexahydro-2H-1,3-dioxolano[4,5-g]isoquinolino[3,2-a]isoquinolin-9-ol | C19H19NO4 | 325.13 | 326.0 |
| 35 | 9,10-dimethoxy-5,6,7,8,13,13a-hexahydro-2H-1,3-dioxolano[4,5-g]isoquinolino[3,2-a]isoquinoline-N-oxide | C20H21NO5 | 355.38 | 356.0 |
| 36 | 9,10-dimethoxy-5,6,7,8,13,13a-hexahydro-2H-1,3-dioxolano[4,5-g] | C21H22N2O5 | 382.41 | 383.0 |

TABLE 5-continued

| | | | | |
|---|---|---|---|---|
| 37 | isoquinolino[3,2-a]isoquinoline-8-carboxamide 10-methoxy-5,6,7,8,13,13a-hexahydro-2H-1,3-dioxolano[4,5-g]isoquinolino[3,2-a]isoquinolin-9-yl 4-phenylbenzenesulfonate | C31H27NO6S | 541.61 | 542.0 |
| 38 | 10-methoxy-5,6,7,8,13,13a-hexahydro-2H-1,3-dioxolano[4,5-g]isoquinolino[3,2-a]isoquinolm-9-yl 4-(tert-butyl)benzenesulfonate | C29H31NO6S | 521.62 | 522.1 |
| 39 | 10-methoxy-9-(methylethoxy)-5,6,7,8,13,13a-hexahydro-2H-1,3-dioxolano[4,5-g]isoquinolino[3,2-a]isoquinoline | C22H25NO4 | 367.44 | 368.1 |
| 41 | (10-methoxy(5,6,7,8,13,13a-hexahydro-2H-1,3-dioxolano[4,5-g]isoquinolino[3,2-a]isoquinolin-9-yloxy))-N-(methylethyl)carboxamide | C23H26N2O5 | 410.46 | 411.1 |
| 42 | 10-methoxy-5,6,7,8,13,13a-hexahydro-2H-1,3-dioxolano[4,5-g]isoquinolino[3,2-a]isoquinolin-9-yl 4-methoxybenzenesulfonate | C26H25NO7S | 495.54 | 496.0 |
| 43 | (10-methoxy(5,6,7,8,13,13a-hexahydro-2H-1,3-dioxolano[4,5-g]isoquinolino[3,2-a]isoquinolin-9-yloxy))-N,N-dimethylcarboxamide | C22H24N2O5 | 396.44 | 397.3 |
| 44 | (10-methoxy(5,6,7,8,13,13a-hexahydro-2H-1,3-dioxolano[4,5-g]isoquinolino[3,2-a]isoquinolin-9-yloxy))-N-[4-(trifluoromethoxy)phenyl]carboxamide | C27H23F3N2O6 | 528.41 | 529.1 |
| 45 | N-(3,5-dimethoxyphenyl)(10-methoxy(5,6,7,8,13,13a-hexahydro-2H-1,3-dioxolano[4,5-g]isoquinolino[3,2-a]isoquinolin-9-yloxy))carboxamide | C28H28N2O7 | 504.53 | 505.1 |
| 46 | (10-methoxy(5,6,7,8,13,13a-hexahydro-2H-1,3-dioxolano[4,5-g]isoquinolino[3,2-a]isoquinolin-9-yloxy))-N-(3-methylphenyl)carboxamide | C27H26N2O5 | 458.51 | 459.1 |
| 47 | (10-methoxy(5,6,7,8,13,13a-hexahydro-2H-1,3-dioxolano[4,5-g]isoquinolino[3,2-a]isoquinolin-9-yloxy))-N-[3-(trifluoromethyl)phenyl]carboxamide | C27H23F3N2O5 | 512.48 | 513.0 |
| 48 | 10-methoxy-5,6,7,8,13,13a-hexahydro-2H-1,3-dioxolano[4,5-g]isoquinolino[3,2-a]isoquinolin-9-yl ethoxyformate | C22H23NO6 | 397.42 | 398.1 |
| 49 | 10-methoxy-5,6,7,8,13.13a-hexahydro-2H-1,3-dioxolano[4,5-g]isoquinolino[3,2-a]isoquinolin-9-yl 2-chloro-4-fluorobenzenesulfonate | C25H21ClFNO6S | 517.95 | 517.9, 519.9 |
| 50 | 10-methoxy-5,6,7,8,13,13a-hexahydro-2H-1,3-dioxolano[4,5-g]isoquinolino[3,2-a] | C26H25NO6S | 479.54 | 480.0 |

TABLE 5-continued

| | | | | |
|---|---|---|---|---|
| 51 | isoquinolin-9-yl 2-methylbenzenesulfonate 10-methoxy-5,6,7,8,13,13a-hexahydro-2H-1,3-dioxolano[4,5-g]isoquinolino[3,2-a]isoquinolin-9-yl 2-fluorobenzenesulfonate | C25H22FNO6S | 483.51 | 484.0 |
| 52 | 10-methoxy-5,6,7,8,13,13a-hexahydro-2H-1,3-dioxolano(4,5-g]isoquinolino[3,2-a]isoquinolin-9-yl 3-fluorobenzenesulfonate | C25H22FNO6S | 483.51 | 484.0 |
| 53 | 10-methoxy-5,6,7,8,13,13a-hexahydro-2H-1,3-dioxolano[4,5-g]isoquinolino[3,2-a]isoquinolin-9-yl 3,4-difluorobenzenesulfonate | C25H21F2NO6S | 501.50 | 502.0 |
| 54 | 10-methoxy-5,6,7,8,13,13a-hexahydro-2H-1,3-dioxolano[4,5-g]isoquinolino[3,2-a]isoquinolin-9-yl benzoate | C26H23NO5 | 429.46 | 430.0 |
| 55 | 10-methoxy-5,6,7,8,13,13a-hexahydro-2H-1,3-dioxolano[4,5-g]isoquinolino[3,2-a]isoquinolin-9-yl (phenylmethoxy)formate | C27H25NO6 | 459.49 | 460.1 |
| 56 | 10-methoxy-5,6,7,8,13,13a-hexahydro-2H-1,3-dioxolano[4,5-g]isoquinolino[3,2-a]isoquinolin-9-yl thiophene-2-sulfonate | C23H21NO6S2 | 471.55 | 472.0 |
| 57 | 10-methoxy-5,6,7,8,13,13a-hexahydro-2H-1,3-dioxolano[4,5-g]isoquinolino[3,2-a]isoquinolin-9-yl 4-methylbenzenesulfonate | C26H25NO6S | 479.54 | 480.0 |
| 58 | 10-methoxy-5,6,7,8,13,13a-hexahydro-2H-1,3-dioxolano[4,5-g]isoquinolino[3,2-a]isoquinolin-9-yl 4-fluorobenzenesulfonate | C25H22FNO6S | 483.51 | 484.0 |
| 59 | 10-methoxy-5,6,7,8,13,13a-hexahydro-2H-1,3-dioxolano[4,5-g]isoquinolino[3,2-a]isoquinolin-9-yl 2,4-difluorobenzenesulfonate | C25H21F2NO6S | 501.50 | 502.0 |
| 60 | 10-methoxy-5,6,7,8,13,13a-hexahydro-2H-1,3-dioxolano[4,5-g]isoquinolino[3,2-a]isoquinolin-9-yl 3-methylbenzenesulfonate | C26H25NO6S | 479.54 | 480.0 |
| 61 | (10-methoxy(5,6,7,8,13,13a-hexahydro-2H-1,3-g]dioxolano[4,5-isoquinolino[3,2-a]isoqiunolin-9-yloxy))-N-benzamide | C26H24N2O5 | 444.48 | 445.0 |
| 62 | 10-methoxy-9-propoxy-5,6,7,8,13,13a-hexahydro-2H-1,3-dioxolano[4,5-g]isoquinolino[3,2-a]isoquinoline | C22H25NO4 | 367.44 | 368.1 |
| 63 | 10-methoxy-5,6,7,8,13,13a-hexahydro-2H-1,3-dioxolano[4,5-g]isoquinolino[3,2-a]isoquinolin-9-yl 3-nitrobenzenesulfonate | C25H22N2O8S | 510.52 | 511.0 |
| 64 | 2,3,10-trimethoxy-9-(phenylmethoxy)- | C27H29NO4 | 431.52 | 432.1 |

TABLE 5-continued

| | | | | |
|---|---|---|---|---|
| | 5,6,7,8,13,13a-hexahydroisoquinolino[3,2-a]isoquinoline | | | |
| 65 | 10-methoxy-5,6,7,8,13,13a-hexahydro-2H-1,3-dioxolano[4,5-g]isoquinoiino[3,2-a]isoquinolin-9-yl 4-nitrobenzenesulfonate | C25H22N2O8S | 510.52 | 511.0 |
| 66 | 10-methoxy-5,6,7,8,13,13a-hexahydro-2H-1,3-dioxolano[4,5-g]isoquinolino[3,2-a]isoquinolin-9-yl quinoline-8-sulfonate | C28H24N2O6S | 516.56 | 517.0 |
| 67 | [3,9,10-trirnethoxy-5,8,13,13a-tetrahydro-6H-isoquino[3,2-a]isoquinolin-3-yl]-5-(2-oxo-hexahydro-1H-thieno[3,4-d]imidazol-4-y])pentanoic ester | C30H37N3O6S | 567.24 | 568.3 |
| 68 | 2-[3,9,10-trimethoxy-5,8,13,13a-tetrahydro-6H-isoquino[3,2-a]isoquinolin-3-yl]-acetic acid | C22H25NO6 | 399.17 | 400.2 |
| 69 | 9-benzenesulfonyloxy-10-methoxy-5,8,13,13a-tetrahydro-6H-[1,3]dioxolo[4,5-g]isoquino[3,2-a]isoquinoline | C25H23NO6S | 465.12 | 466.2 |
| 70 | 9-benzoxy-10-methoxy-5,8,13,13a-tetrahydro-6H-[1,3]dioxolo[4,5-g]isoquino[3,2-a]isoquinoline | C26H23NO5 | 429.16 | 430.1 |
| 71 | 9-methanesulfonyloxy-10-methoxy-5,8,13,13a-tetrahydro-6H-[1,3]dioxolo[4,5-g]isoquino[3,2-a]isoquinoline | C20H21NO6S | 403.11 | 404.1 |
| 72 | 9-benzenesulfonyloxy-10-methoxy-5,8,13,13a-tetrahydro-6H-[1,3]dioxolo[4,5-g]isoquino[3,2-a]isoquinoline hydrochloride | C25H24ClNO6S | 466.13 | 466.2 |
| 73 | 10-methoxy-5,8,13,13a-tetrahydro-6H-[1,3]dioxolo[4,5-g]isoquino[3,2-a]isoquinoline-9-ol | C19H19NO4 | 325.13 | 326.2 |
| 74 | 9-O-3-(1'-bromo-propyl)-10-methoxy-5,8,13,13a-tetrahydro-6H-[1,3]dioxolo[4,5-g]isoquino[3,2-a]isoquinoline | C22H24BrNO4 | 445.09 | 446.2 |
| 75 | 9-hydroxy-10-methoxy-5,6-dihydro-[1,3]dioxolo[4,5-g]isoquino[3,2-a]isoquinolinylium | C19H16C1NO4 | 357.08 | 323.1 |
| 76 | 9-O-3-(1'-bromo-propyl)-10-methoxy-5,6-dihydro-[1,3]dioxolo[4,5-g]isoquino[3,2-a]isoquinolinylium | C22H21BrClNO4 | 479.03 | 443.9 |
| 77 | 5,8,13,13a-Tetrahydro-6H-isoquino[3,2-a]isoquinoline-2,3,9,10-tetraol; hydrobromide | C17H18BrNO4 | 379.04 | 298.3 |
| 78 | 13-methyl-5,8,13,13a-Tetrahydro-6H-isoquino[3,2-a]isoquinoline-2,3,9,10-tetraol; hydrobromide | C18H20BrNO4 | 393.06 | 313.8 |
| 79 | 9-benzenesulfonyloxy-10-methoxy-5,6-dihydro-[1,3]dioxolo[4,5-g]isoquino[3,2-g]isoquinolinylium | C25H20ClNO6S | 497.07 | 462.2 |
| 80 | 9-methanesulfonyloxy-10-methoxy-5,6-dihydro-[1,3]dioxolo[4,5-g]isoquino[3,2-a]isoquinolinylium | C20H18ClNO6S | 435.05 | 399.5 |

TABLE 5-continued

| | | | | |
|---|---|---|---|---|
| 81 | 9-benzoxy-10-methoxy-5,6-dihydro-[1,3]dioxolo[4,5-g]isoquino[3,2-a]isoquinolinylium | C26H20ClNO5 | 461.1 | 426.1 |
| 82 | 9-O-2-(1'-hydroxy-ethyl)-10-methoxy-5,8,13,13a-tetrahydro-6H-[1,3]dioxolo[4,5-g]isoquino[3,2-a]isoquinoline | C21H23NO5 | 369.16 | 370.1 |
| 83 | 2-[10-methoxy-5,8,13,13a-tetrahydro-6H-[1,3]dioxolo[4,5-g]isoquino[3,2-a]isoquinoline-9-yl]-acetic esate | C23H25NO6 | 411.17 | 412.2 |
| 84 | 9-(4-chloro-benzenesulfonyloxy)-10-methoxy-5,8,13,13a-tetrahydro-6H-[1,3]dioxolo[4,5-g]isoquino[3,2-q]isoquinoline | C25H22ClNO6S | 499.09 | 500.3 |
| 85 | 9-(4-trifluoromethyl-benzenesulfonyloxy)-10-methoxy-5,8,13,13a-tetrahydro-6H-[1,3]dioxolo[4,5-g]isoquino[3,2-a]isoquinoline | C26H22F3NO6S | 533.52 | 534.2 |
| 86 | 9-(3,4-dimethoxy-benzenesulfonyloxy)-10-methoxy-5,8,13,13a-tetrahydro-6H-[1,3]dioxolo[4,5-g]isoquino[3,2-a]isoquinoline | C27H27NO8S | 525.57 | 526.3 |
| 87 | 9-(4-methylsulfonyl-benzenesulfonyloxy)-10-methoxy-5,8,13,13a-tetrahydro-6H-[1,3]dioxolo[4,5-g]isoquino[3,2-a]isoquinoline | C26H25NO8S2 | 543.61 | 544.3 |
| 88 | 9-O-2-(1'-morpholine-ethyl)-10-methoxy-5,8,13,13a-tetrahydro-6H-[1,3]dioxolo[4,5-g]isoquino[3,2-a]isoquinoline | C25H30N2O5 | 438.52 | 439.2 |
| 89 | 10-methoxy-5,6,7,8,13,13a-hexahydro-2H-1,3-dioxolano[4,5-g]isoquino)ino[3,2-a]isoquinolin-9-yl 5-(dimethylamino)naphthalene-sulfonate | C31H30N2O6S | 558.64 | 559.1 |
| 90 | 10-methoxy-5,6,7,8,13,13a-hexahydro-2H-1,3-dioxolano[4,5-g]isoquinolino[3,2-a]isoquinolin-9-yl (trifluoromethyl)sulfonate | C20H18F3NO6S | 457.42 | 458.0 |
| 91 | 2,3,10-trimethoxy-5,6,7,8,13,13a-hexahydroisoquinolino[2,1-b]isoquinolin-9-yl benzenesulfonate | C26H27NO6S | 481.56 | 482.0 |
| 92 | 10-methoxy-5,6,7,13,13a-hexahydro-2H-1,3-dioxolano[4,5-g]isoquinolino[3,2-a]isoquinoline | C19H19NO3 | 309.36 | 310.0 |
| 93 | 10-methoxy-5,6,7,8,13,13a-hexahydro-2H-1,3-dioxolano[4,5-g]isoquinolino[3,2-a]isoquinolin-9-yl 2-(acetylamino)-4-methyl-1,3-thiazole-5-sulfonate | C25H25N3O7S2 | 543.61 | 543.9 |
| 94 | 10-methoxy-9-(3-methyl-5-nitro(2-pyridyl)oxy)-5,6,7,8,13,13a-hexahydro-2H-1,3-dioxolano[4,5-g]isoquinolino[3,2-a]isoquinoline | C25H23N3O6 | 461.47 | 462.0 |
| 95 | 2,10-dimethoxy-3-(phenylmethoxy)-5,6,7,8,13,13a- | C32H31NO6S | 557.66 | 558.0 |

TABLE 5-continued

| | | | | |
|---|---|---|---|---|
| 96 | hexahydroisoquinolino[2,1-b]isoquinolin-9-yl benzenesulfonate 10-methoxy-9-(5-nitro(2-pyridyl)oxy)5,6,7,8,13,13a-hexahydro-2H-1,3-dioxolano[4,5-g]isoquinolino[3,2-a]isoquinoline | C24H21N3O6 | 447.40 | 448.0 |
| 97 | 10-methoxy-5,6,7,8,13,13a-hexahydro-2H-1,3-dioxolano[4,5-g]isoquinolino[3,2-a]isoquinolin-9-yl thiophene-2-sulfonate hydrochloride | C23H22ClNO6S2 | 508.00 | 471.9 |
| 98 | 10-methoxy-5,6,7,8,13,13a-hexahydro-2H-1,3-dioxolano[4,5-g]isoquinolino[3,2-a]isoquinolin-9-yl 3-fluorobenzenesulfonate hydrochloride | C25H23ClFNO6S | 519.96 | 484.0 |
| 99 | 10-methoxy-5,6,7,8,13,13a-hexahydro-2H-1,3-dioxolano[4,5-g]isoquinolino[3,2-a]isoquinolin-9-yl 3,4-difluorobenzenesulfonate hydrochloride | C25H22C1F2NO6S | 537.95 | 502.0 |
| 100 | 6-(10-methoxy (5,6,7,8,13,13a-hexahydro-2H-1,3-dioxolano[4,5-g]isoquinolino[3,2-a]isoquinolin-9-yloxy))-5-methyl-3-pyridylamine | C25H25N3O4 | 431.48 | 432.1 |
| 101 | 10-methoxy-5,6,7,8,13,13a-hexahydro-2H-1,3-dioxolano[4,5-g]isoquinolino[3,2-a]isoquinolin-9-yl pyridine-3-sulfonate | C24H22N2O6S | 466.51 | 467.0 |
| 102 | 3-Hydroxy-2,10-dimethoxy-5,6,7,8,13,13a-hexahydroisoquinolino[2,1-b]isoquinoiin-9-yl benzenesulfonate | C25H25NO6S | 467.53 | 468.0 |
| 103 | 2,10-Dimethoxy-8-prop-2-enyl-3-prop-2-enyloxy-5,6,7,8,13,13a-hexahydroisoquinolino[2,1-b]isoquinolin-9-yl benzenesulfonate | C31H33NO6S | 547.66 | 548.1 |
| 104 | 10-methoxy-5,6,7,8,13,13a-hexahydro-2H-1,3-dioxolano[4,5-g]isoquinolino[3,2-a]isoquinolin-9-yl 3-fluorobenzenesulfonate hydrochloride | C25H23ClFNO6S | 519.97 | 512.0 |
| 105 | 9-O-2-(1'-phenylsulfonyl-ethyl)-10-methoxy-5,8,13,13a-tetrahydro-6H-[1,3]dioxolo[4,5-g]isoquino(3,2-a]isoquinoline | C27H27NO6S | 493.57 | 494.3 |
| 112 | 2,3,10-Trimethoxy-5,6,7,8,13,13a-hexahydroisoquinolino[2,1-b]isoquinolin-9-yl benzenesulfonate tartrate | C26H27NO6S | 631.65 | 482.1 |
| 113 | 2-ethoxy-3,10-dimethoxy-5,6,7,8,13,13a-hexahydroisoquinolino[2,1-b]isoquinolin-9-yl benzenesulfonate | C27H29NO6S | 495.59 | 496.1 |
| 114 | 2,10-Dimethoxy-3-(methylamino)-5,6,7,8,13,13a-hexahydroisoquinolino[2,1-b]isoquinolin-9-yl benzenesulfonate | C26H28N2O5S | 480.58 | 481.1 |
| 115 | 3,10-Dimethoxy-5,6,7,8,13,13a-hexahydroisoquinolino[2,1-b]isoquinolin-9-yl benzenesulfonate | C25H25NO5S | 451.53 | 452.1 |
| 116 | 11-Methoxy-6,7,8,9,14,14a-hexahydro-2H,3H-1,4- | C26H25NO6S | 479.54 | 480.0 |

TABLE 5-continued

| | | | | |
|---|---|---|---|---|
| | dioxano[5,6-g]isoquinoluio[3,2-a]isoquinolin-10-yl benzenesulfonate | | | |
| 117 | 3-(Difluoromethoxy)-2,10-dimethoxy-5,6,7,8,13,13a-hexahydroisoquinolino[2,1-b]isoquinolin-9-yl benzenesulfonate | $C_{26}H_{25}F_2NO_6S$ | 517.54 | 518.1 |
| 118 | 3-(Dimethylamino)-2,10-dimethoxy-5,6,7,8,13,13a-hexahydroisoquinolino[2,1-b]isoquinolin-9-yl benzenesulfonate | $C_{27}H_{30}N_2O_5S$ | 494.6 | 495.1 |
| 119 | 3-(Ethoxycarbonylamino)-2,10-dimethoxy-5,6,7,8,13,13a-hexahydroisoquinolino[2,l-b]isoquinolin-9-yl benzenesulfonate | $C_{28}H_{30}N_2O_7S$ | 538.61 | 539.1 |
| 120 | 2,10-Dimethoxy-9-(phenylsulfonyloxy)-5,6,7,8,13,13a-hexahydroisoquinolino[3,2-a]isoquinolin-3-yl 5-((5S,1R,2R)-7-oxo-3-thia-6,8-diazabicyclo[3.3.0]oct-2-yl)pentanoate | C35H39N3O8S2 | 693.83 | 694.1 |
| 121 | 10-Methoxy-3-methyl-5,6,7,8,13,13a-hexahydroisoquinolino[2,1-b]isoquinofin-9-yl benzenesulfonate | $C_{25}H_{25}NO_4S$ | 435.54 | 436.1 |
| 122 | 2-hydroxy-3,10-dimethoxy-5,6,7,8,13,13a-hexahydroisoquinolino[2,1-b]isoquinolm-9-yl benzenesulfonate | $C_{25}H_{25}NO_6S$ | 467.53 | 468.1 |
| 123 | 10-Methoxy-3-(phenylmethoxy)-5,6,7,8,13,13a-hexahydroisoquinolino[2,1-b]isoquinolin-9-yl benzenesulfonate | C31H29NO5S | 527.63 | 528.1 |
| 124 | 3-Hydroxy-10-methoxy-5,6,7,8,13,13a-hexahydroisoquinolino[2,1-b]isoquinolin-9-yl benzenesulfonate | C24H23NO5S | 437.51 | 438.1 |
| 125 | Ethyl 2-[3,10-dimethoxy-9-(phenylsulfonyloxy)-5,6,7,8,13,13a-hexahydro-isoquinolino[3,2-a]isoquinolin-2-yloxy]acetate | C29H31NO8S | 553.62 | 554.1 |
| 126 | Ethyl 2-[2,10-dimethoxy-9-(phenylsulfonyloxy)-5,6,7,8,13,13a-hexahydro-isoquinolino[3,2-a]isoquinolin-3-yloxy]acetate | C29H31NO8S | 553.62 | 554.1 |
| 127 | 2,3,10-Trimethoxy-5,6,7,8,13,13a-hexahydroisoquinolino[2,1-b]isoquinolin-9-yl 3-fluorobenzenesulfonate | $C_{26}H_{26}FNO_6S$ | 499.55 | 500.1 |
| 128 | 3,10-Dimethoxy-5,6,7,8,13,13a-hexahydroisoquinolino[2,1-b]isoquinolin-9-yl 3-fluorobenzenesulfonate | $C_{25}H_{24}FNO_5S$ | 469.53 | 470.1 |
| 129 | 11-Methoxy-6,7,8,9,14,14a-hexahydro-2H,3H-1,4-dioxano[5,6-g]isoquinolino[3,2-a]isoquinolin-10-yl 3-fluorobenzenesulfonate | $C_{26}H_{24}FNO_6S$ | 497.54 | 498.1 |
| 130 | 10-Methoxy-3-methyl-5,6,7,8,13,13a-hexahydroisoquinolino[2,1-b]isoquinolin-9-yl 3-fluorobenzenesulfonate | $C_{25}H_{24}FNO_4S$ | 453.53 | 454.1 |

TABLE 5-continued

| | | | | |
|---|---|---|---|---|
| 131 | Methyl 3,20-dimethoxy-9-(phenylsulfonyloxy)-5,6,7,8,13,13a-hexahydroisoquinolino[3,2-a]isoquinoline-2-carboxylate | C27H27NO7S | 509.57 | 510.1 |
| 132 | 2-(Hydroxymethyl)-3,10-dimethoxy-5,6,7,8,13,13a-hexahydroisoquinolino[2,1-b]isoqninolin-9-yl benzenesulfonate | C26H27NO6S | 481.56 | 482.1 |
| 133 | 3-Ethoxy-10-methoxy-5,6,7,8,13,13a-hexahydroisoquinolino[2,1-b]isoquinolin-9-yl benzenesulfonate | C26H27NO5S | 465.56 | 466.1 |
| 134 | 10-Methoxy-5,6,7,8,13,13a-hexahydroisoquinolino[2,1-b]isoquinolin-9-yl benzenesulfonate | C24H23NO4S | 421.51 | 422.1 |
| 135 | 3,10-Dimethoxy-9-(phenyl-sulfonyloxy)-5,6,7,8,13,13a-hexahydroisoquinolino[3,2-a]isoquinoline-2-carboxylic acid | C26H25NO7S | 495.54 | 494.0 (M$^-$ − 1) |
| 136 | 2-(N,N-dimethylcarbamoyl)-3,10-dimethoxy-5,6,7,8,13,13a-hexahydroisoquinolino[2,1-b]isoquinolin-9-yl benzenesulfonate | C28H30N2O6S | 522.61 | 523.1 |
| 137 | 2-[N-(2-hydroxyethyl)carbamoyl]-3,10-dimethoxy-5,6,7,8,13,13a-hexahydroisoquinolino[2,1-b]isoquinolin-9-yl benzenesulfonate | C28H30N2O7S | 538.61 | 539.1 |
| 138 | 3-(2-Hydroxyethoxy)-2,10-dimethoxy-5,6,7,8,13,13a-hexahydroisoquinolino[2,1-b]isoquinolin-9-yl benzenesulfonate | C27H29NO7S | 511.59 | 512.1 |
| 139 | 2,3,10-Trimethoxy-13-methyl-5,6,7,8,13,13a-hexahydroisoquinolino[2,1-b]isoquinolin-9-yl benzenesulfonate | $C_{27}H_{29}NO_6S$ | 495.59 | 496.1 |
| 140 | 3,10-Dimethoxy-13-methyl-5,6,7,8,13,13a-hexahydroisoquinolino[2,1-b]isoquinolin-9-yl benzenesulfonate | $C_{26}H_{27}NO_5S$ | 465.56 | 466.1 |
| 141 | 2,3,10-Trimethoxy-5,6,7,8,13,13a-hexahydroisoquinolino[2,1-b]isoquinolin-9-yl 3-fluorobenzenesulfonate phosphate Salt | $C_{26}H_{26}FNO_6S$ | 531.89 | 500.1 |
| 142 | 3-(2-Hydroxyethoxy)-10-methoxy-5,6,7,8,13,13a-hexahydroisoquinolino[2,1-b]isoquinolin-9-y] benzenesulfonate | $C_{26}H_{27}NO_6S$ | 481.56 | 482.1 |
| 143 | 2-(2-hydroxyethoxy)-3,10-dimethoxy-5,6,7,8,13,13a-hexahydroisoquinolino[2,1-b]isoquinolin-9-yl benzenesulfonate | $C_{27}H_{29}NO_7S$ | 511.59 | 512.1 |
| 144 | 2-[3,10-dimethoxy-9-(phenylsulfonyloxy)-5,6,7,8,13,13a-hexahydroisoquinolino[3,2-a]isoquinolin-2-yloxy]acetic acid | $C_{27}H_{27}NO_8S$ | 525.57 | 524.1 (M − 1) |
| 145 | 2-(dimethylamino)-3,10-dimethoxy-5,6,7,8,13,13a-hexahydroisoquinolino[2,1-b]isoquinolin-9-yl benzenesulfonate | C27H30N2O5S | 494.6 | 495.2 |
| 146 | Methyl 9-[(3-fluorophenyl)sulfonyloxy]- | C27H26FNO7S | 527.56 | 528.2 |

TABLE 5-continued

| | | | | |
|---|---|---|---|---|
| | 3,10-dimethoxy-5,6,7,8,13,13a-hexahydro-isoquinolino[3,2-a]isoquinoline-2-carboxylate | | | |
| 147 | 9-Hydroxy-3,10-dimethoxy-5,6,7,8,13,13a-hexa-hydroisoquinolino[3,2-a]isoquinoline-2-carboxylic acid | $C_{20}H_{21}NO_5$ | 355.38 | 354.1 |
| 148 | Methyl 9-[(3-fluorophenyl)sulfonyloxy]-3,10-dimethoxy-13-methyl-5,6,7,8,13,13a-hexahydroisoquinolino[3,2-a]isoquinoline-2-carboxylate | C28H28FNO7S | 541.59 | 542.1 |
| 149 | 12-bromo-3-methoxy-5,6,7,8,13,13a-hexahydroisoquinolino[2,1-b]isoquitiolm-9-yl 3-fluorobenzenesulfonate | C24H21BrFNO4S | 518.39 | 518.0 |
| 150 | 3-methoxy-5,6,7,8,13,13a-hexahydroisoquinolino[2,1-b]isoquinolin-9-yl 3-fluorobenzenesulfonate | C24H22FNO4S | 439.5 | 440.1 |
| 151 | 3-methoxy-5,6,7,8,13,13a-hexahydroisoquinolino[2,1-b]isoquinolin-9-ol | C18H19NO2 | 281.35 | 282.1 |
| 152 | 2,10-dimethoxy-13-methyl-3(phenylmethoxy)-5,6,7,8,13,13a-hexahydroisoquinolino[2,1-b]isoquinolin-9-yl 3-fluorobenzenesulfonate | C33H32FNO6S | 589.67 | 590.2 |
| 153 | 3-hydroxy-2,10-dimethoxy-13-methyl-5,6,7,8,13,13a-hexahydroisoquinolino[2,1-b]isoquinolin-9-yl 3-fluorobenzenesulfonate | C26H26FNO6S | 499.55 | 500.1 |
| 154 | 10-Methoxy-13-methyl-3-(phenylmethoxy)-5,6,7,8,13,13a-hexahydroisoquinolino[2,1-b]isoquinolin-9-yl 3-fluorobenzenesulfonate | C32H30FNO5S | 559.64 | 560.1 |
| 155 | 3-Hydroxy-10-methoxy-13-methyl-5,6,7,8,13,13a-hexahydroisoquinolino[2,1-b]isoquinolin-9-yl 3-fluorobenzenesulfonate | C25H24FNO5S | 469.53 | 470.1 |
| 156 | 10-Methoxy-5,6,7,8,13,13a-hexahydro-2H-1,3-dioxolano[4,5-g]isoquinolino[3,2-a]isoquinolin-9-yl 5-((5S,1R,2R)-7-oxo-3-thia-6,8-diazabicyclo[3.3.0]oct-2-yl)pentanoate | C29H33N3O6S | 551.65 | 552.1 |
| 157 | 2,3,10-Trimethoxy-5,6,7,8,13,13a-hexahydroisoquinolino[2,1-b]isoquinolin-9-yl benzenesulfonate hydrochloride | $C_{26}H_{27}NO_6S$ | 518.01 | 482.1 |
| 158 | 2,3,10-Trimethoxy-5,6,7,8,13,13a-hexahydroisoquinolino[2,1-b]isoquinolin-9-yl benzenesulfonate sulfate | $C_{26}H_{27}NO_6S$ | 579.64 | 482.1 |
| 159 | 2,3,10-Trimethoxy-5,6,7,8,13,13a-hexahydroisoquinolino[2,1-b]isoquinolin-9-yl benzenesulfonate phosphate | C26H27NO6S | 579.56 | 482.1 |
| 160 | 2,3,10-Trimethoxy-5,6,7,8,13,13a-hexahydroisoquinolino[2,1-b]isoquinolin-9-yl benzenesulfonate lactate | C26H27NO6S | 571.64 | 482.1 |

TABLE 5-continued

| | | | | |
|---|---|---|---|---|
| 161 | 2,3,10-Trimethoxy-5,6,7,8,13,13a-hexahydroisoquinolino[2,1-b]isoquinolin-9-yl benzenesulfonate citrate | C26H27NO6S | 673.68 | 482.1 |

*unless a different ion is indicated
**molecular weight of free base

Example 10

Lipid Lowering Effects of (14R,13S)—CRDL Hydrochloride Salt in Wister Rats

Male Wister rats were used as an animal model to examine the in vivo effects of (14R,13S)—CRDL in plasma lipid levels.

In one experiment, 18 Wister male rats under a high fat and high cholesterol diet were divided into 2 groups. One group was given (14R,13S)—CRDL hydrochloride salt orally at a daily dose of 75 mg/kg by an orogastric tube for 4 weeks, and the control group received daily treatment of equal amount of vehicle (0.1 M sodium phosphate, pH 3.5). Serum lipid levels were measured weekly. CRDL treatment resulted in a strong time-dependent reduction of serum lipid levels.

Figure 7A:
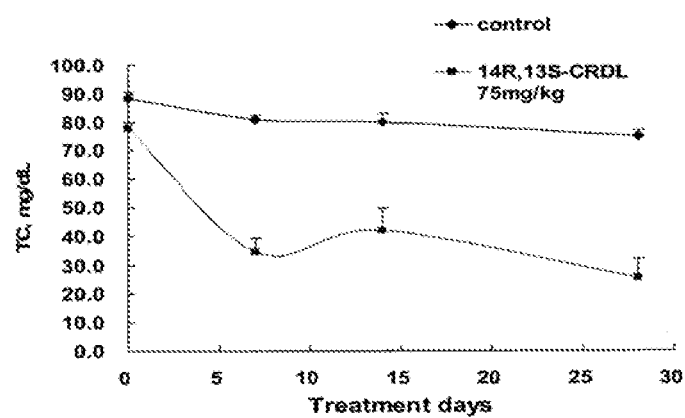
FIG. 7A shows a TC vs. time curve in Wister male rats treated with (14R, 13S)—CRDL HCl and demonstrates that CRDL treatment lowered TC to 33.8% compared to the control group and to 33.0% of the pretreatment level.

FIG. 7A shows that CRDL treatment lowered TC to 33.8% compared to the control group and to 33.0% of the pretreatment level.

Figure 7B:
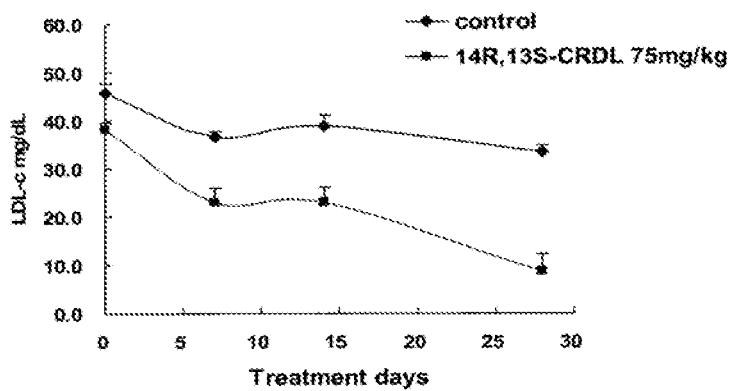
FIG. 7B shows a similar curve for LDL-c levels and shows that the LDL-c level was reduced by CRDL to 25.6% of control, and to 22.4% of day 0 by CRDL treatment.

FIG. 7B shows that the LDL-c level was reduced by CRDL to 25.6% of control, and to 22.4% of day 0 by CRDL treatment.

Figure 7C:
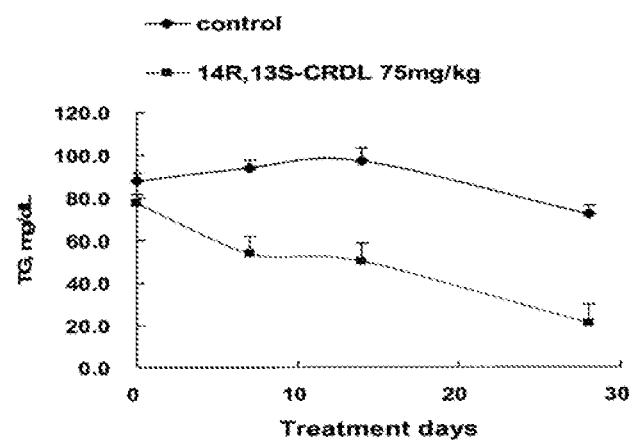
FIG. 7C shows a similar curve for TG levels which indicates that the TG level was decreased to 29% of the control and to 27% of the pretreatment level (day 0).

FIG. 7C shows that the TG level was decreased to 29% of the control and to 27% of the pretreatment level (day 0).

Figure 7D:
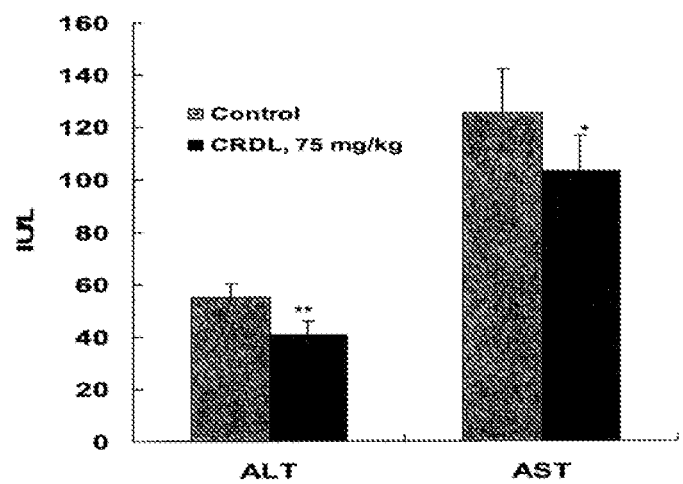
FIG. 7D is a bar graph showing the serum levels of AST and ALT in Wister male rats treated with (14R,13S)-CRDL HCl and that of the control group and indicates that liver function was not damaged by CRDL instead it was improved with statistical significance.

No any adverse effects were observed during the entire treatment. At the end of treatment, Rats were sacrificed and blood and sera were collected to measure several critical parameters for liver function and kidney function. FIG. 7D showed that the serum levels of AST and ALT were statistically lower in CRDL-treated group than control group, indicating that liver function was not damaged and was improved instead with statistical significance. Kidney function and blood glucose level were not changed by the treatment.

Example 11

Figure 8A:
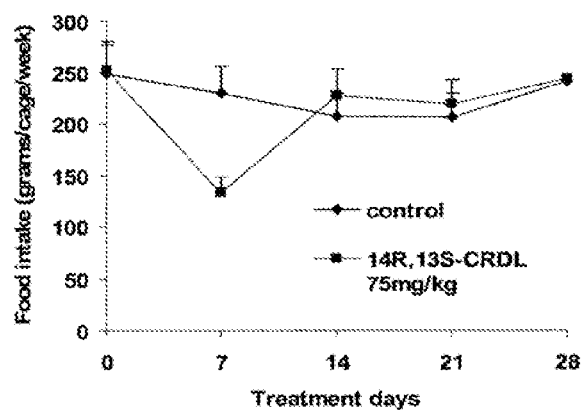
FIG. 8A shows the food intake vs. time curve for male Wister rats treated with CRDL and the control group. After an initial decrease in food consumption during the first week, it increase and leveled off at statistically similar level to the control group through the rest of treatment times.
Figure 8B:
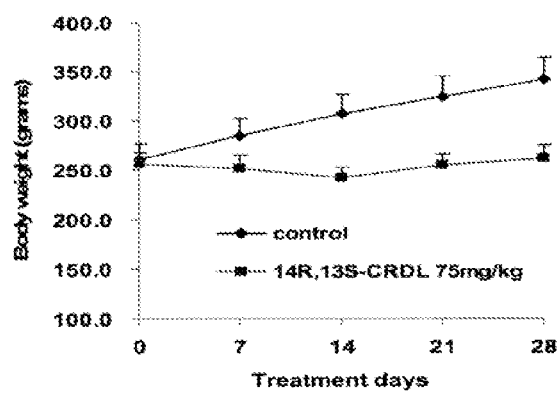
FIG. 8B shows the change in body weight vs. time cure for the CRDL-treated Wister rats and the control group fed with high fat and high cholesterol diet and shows that, while the control group gained over 30% of their body weight during the 4-weeks, the body weights of Wister rats in CRDL-treated group have maintained constant.
Figure 9:
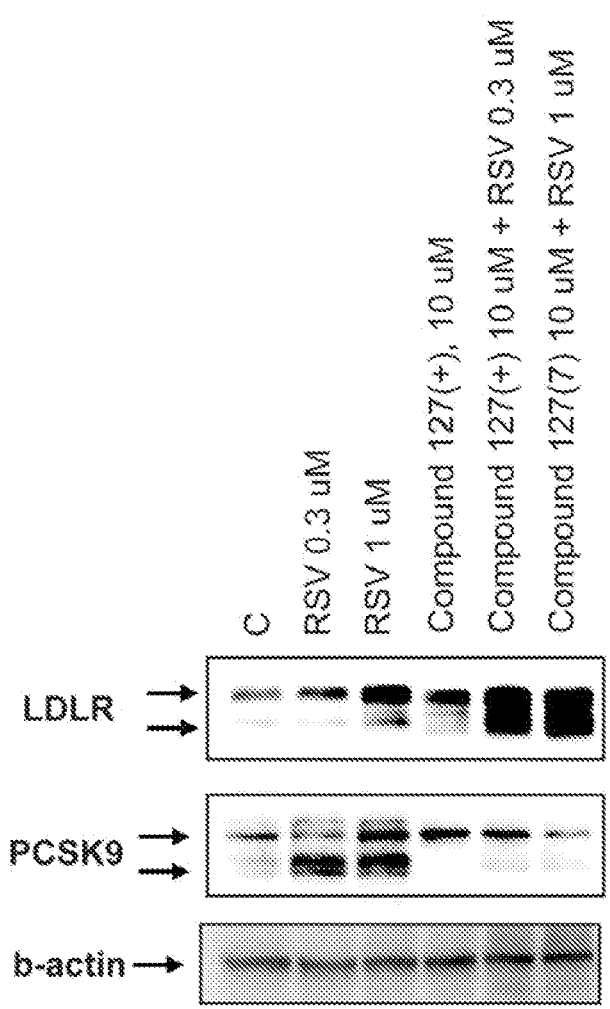
FIG. 9 shows a western blot analysis conducted to examine the protein levels of LDLR, PCSK9, and β-actin. To demonstrate the counteraction of compounds disclosed herein on statin-induced PCSK9 upregulation, HepG2 cells were treated with 0.3 μM or 1 μM of rosuvastatin (RSV) in the absence or presence of Compound 127(+) at 10 μM concentration for 2 days.

Body-Weight-Reducing Effect of (14R,13S)—CRDL Hydrochloride Salt in Wister Rats The food intake and body weight gains were measured every week during the 4-week treatment period. FIG. 8A shows the food intake during the treatment. In the first week, the amount of food consumed was decreased in CRDL-treated group. However, the food intake in CRDL-treated group was increased to the same amount as the control group in the second week and maintained at the level similar to the control group through the rest of treatment times. FIG. 8B shows the changes of body weight during the treatment period. Interestingly, while the control group gained 31% of their body weight from 260.5 g to 341.5 g during the 4-weeks fed high fat and high cholesterol diet, the body weights of Wister rats in CRDL-treated group have maintained constant under the same high fat and high cholesterol diet through the treatment duration. The ability of CRDL to activate AMPK signaling pathway to increase energy expenditure and to reduce fat accumulation likely contributes to this weight reducing effect.

Example 12

Lipid Lowering Effects of Compounds 128(+), 128(−) in Rabbits

In another experiment, the LDL-C and total cholesterol lowering effects of new compound 128(+) and 128(−) along with simvastatin (SMV) and atorvastatin (ATV) were examined in hyperlipidemic rabbits. Forty-two male Japanese rabbits were fed the cholesterol enriched rabbit diet for two weeks to induce hypercholesterolemia. Rabbits were then treated with Compound 128(+) and 128(−) at 30 mg/kg, and SMV and ATV at 3 mg/kg once a day by oral gavage. Serum samples were collected at day 0 (before the drug treatment) and day 7. After 7 days of treatment, the compound doses were increased to 60 mg/kg for Compound 128(+) and 128(−) and to 10 mg/kg for SMV and ATV and the treatment was continued for another 7 days. All tested animals were sacrificed at the end of a total of 14 days treatment and serum samples were analyzed for TC, LDL-C, TG, and HDL-C. In addition to lipid profiles, a number of biochemical parameters were also analyzed to aseesee the effects of drug treatments on liver function, muscle function, kidney function, and heart function. The results are summarized in FIG. 13 for reduction of LDL-C, Table 6 for changes in total cholesterol from pre dose to 14 days, and Table 7 showing the final results of all measured lipid and blood chemistry parameters. Altogether, these data clearly show the strong TC and LDL-C reduction of Compound 128(−) and 128(−) in the absence of any adverse effect, which is in contrast to the actions of statins which lipid lowering effects were associated with prominent toxicities to liver, muscle, and even kidney, and heart.

TABLE 6

Changes in serum total cholesterol levels of hyperlipidemic rabbits. Data are mean ± SD, n = 6

| Treatment days | Control | 128(+) | 128(−) | SMV | ATV |
|---|---|---|---|---|---|
| 0 | 28.3 ± 6.7 | 28.6 ± 6.7 | 28.5 ± 6.3 | 28.8 ± 7.4 | 28.9 ± 6.0 |
| 4 | 30.5 ± 7.3 | 31.9 ± 7.5 | 29.9 ± 8.0 | 24.8 ± 6.1 | 26.5 ± 5.2 |
| 7 | 32.8 ± 5.2 | 33.9 ± 7.2 | 29.0 ± 7.9 | 26.1 ± 4.4 | 31.5 ± 4.9 |
| 10 | 34.4 ± 5.0 | 33.8 ± 7.8 | 27.9 ± 5.2 | 25.4 ± 6.1 | 32.5 ± 4.5 |
| 14 | 36.1 ± 5.3 | 34.2 ± 7.4 | 29.7 ± 4.9 | 26.2 ± 5.5 | 33.9 ± 6.5 |

TABLE 7

| Compound Name | TC (mmol/L) | LDL-C (mmol/L) | TG (mmol/L) | HDL-C (mmol/L) | ALT (IU/L) | AST (IU/L) | ALP (IU/L) | GLU (mmol/L) | CREA (umol/L) | CK (U/L) | LDH (IU/L) | Body weight (kg) |
|---|---|---|---|---|---|---|---|---|---|---|---|---|
| Control, mean | 36.1 | 34.7 | 0.8 | 3.5 | 61.0 | 18.7 | 164.5 | 7.7 | 93.5 | 672.0 | 48.3 | 2.6 |
| Control, SD | 5.4 | 10.9 | 0.2 | 0.4 | 11.7 | 6.4 | 69.9 | 0.6 | 8.3 | 337.5 | 13.2 | 0.2 |
| 128(+), mean | 34.2 | 29.7 | 1.0 | 3.6 | 68.7 | 20.8 | 165.2 | 7.9 | 97.2 | 1172.3 | 47.7 | 2.6 |
| 128(+), SD | 7.4 | 9.0 | 0.4 | 0.2 | 23.8 | 9.0 | 67.3 | 0.3 | 16.9 | 1184.6 | 11.9 | 0.1 |
| 128 (−), mean | 29.7 | 24.4 | 0.9 | 3.5 | 50.2 | 20.8 | 155.5 | 7.9 | 105.2 | 997.5 | 50.3 | 2.7 |
| 128(−), SD | 5.0 | 4.8 | 0.5 | 0.5 | 13.7 | 5.6 | 43.8 | 0.6 | 7.4 | 441.0 | 11.9 | 0.2 |
| SMV, mean | 26.2 | 23.3 | 1.7 | 2.9 | 687.8 | 569.6 | 288.7 | 7.9 | 242.2 | 6492.8 | 530.3 | 2.3 |
| SMV, SD | 5.5 | 4.8 | 0.9 | 0.4 | 442.5 | 567.5 | 203.6 | 0.5 | 221.5 | 10381.8 | 887.2 | 0.2 |
| ATV, mean | 33.9 | 29.6 | 1.7 | 3.6 | 795.6 | 767.0 | 333.5 | 6.7 | 238.2 | 7270.0 | 675.0 | 2.3 |
| ATV, SD | 6.5 | 8.6 | 1.4 | 0.7 | 411.5 | 450.4 | 161.4 | 1.6 | 283.6 | 14845.1 | 892.3 | 0.3 |

In-Vitro Study Results

Example 13

Upregulation of LDLR mRNA Expression in Human Hepatoma Derived Cell Line HepG2 by 6 Active Compounds Derived from *Corydalis* Genus that are All d-(+) Enantiomers A: Compound Structures

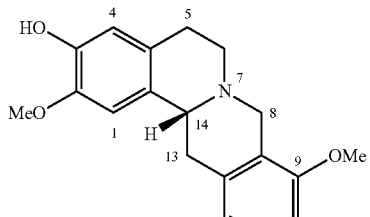

(14R,13S)-corydaline(CRDL)

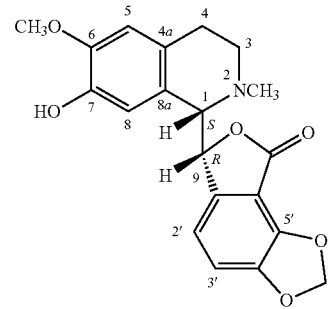

(+)-egenine (EGN)

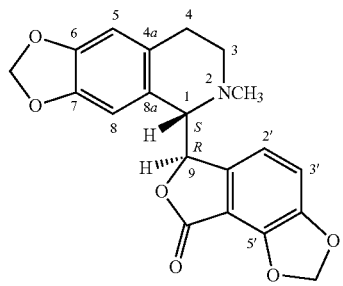

d-(+)-tetrahydropalmatine (THP)

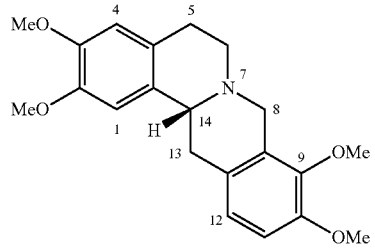

d-(+)-bicuculline (BCCL)

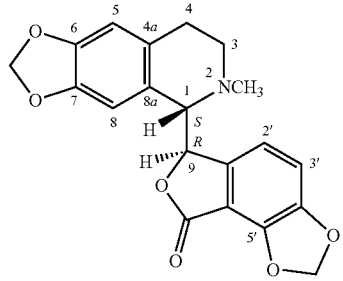

d-(+)-corlumidin (CLMD)

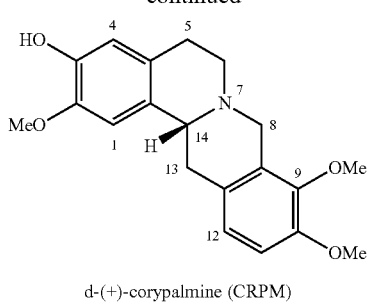

d-(+)-corypalmine (CRPM)

B: Biological Activity

HepG2 cells obtained from American Tissue Culture Collection (Manassas, Va., USA) were seeded in 6-well culture plates at a density of 0.8×10⁶ cells/well cultured in EMEM containing 0.5% FBS and were treated with each purified compound at indicated doses for 8 hours. Total RNA was isolated, and 2 µg per sample was reverse transcribed with random primers using M-MLV (Promega) at 37° C. for 1 hour. PCR was carried out at 94° C. for 30 sec, 60° C. for 30 sec, and 72° C. for 30 sec with initial activation of the enzyme at 94° C. for 1 minute. Thirty cycles were performed for LDLR and GAPDH. PCR was performed using primers HLDLR-up and HLDLR-lo for LDLR and primers HGAPDH-up and HGAPDH-lo for GAPDH. The PCR products were separated on a 1% agarose gel and the band intensity was quantitated. LDLR mRNA levels were corrected by measuring GAPDH mRNA levels.

Figure 3:
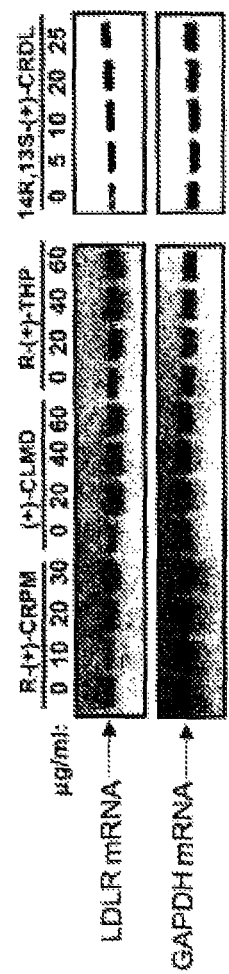
FIG. 3 shows the potent and dose-dependent effects of (+)-CLMD, 14R-(+)-CRPM, 14R,13S-(+)-CRDL, and 14R-(+)-THP on LDLR mRNA expression in HepG2 cells by a semi-quantitative RT-PCR analysis.

The potent and dose-dependent effects of (+)-CLMD, 14R-(+)-CRPM, 14R,13S-(+)-CRDL, and 14R-(+)-THP on LDLR mRNA expression in HepG2 cells by a semi-quantitative RT-PCR analysis are shown in FIG. 3.

Specific stereochemical requirements of +1-THP in the upregulation of LDLR mRNA expression were determined by a similar experiment. HepG2 cells were treated with the pure 14R-(+)-THP or the pure 14S-(−)-THP at the indicated concentrations for 24 hours. The levels of LDLR mRNA and GAPDH mRNA in untreated and the compound-treated HepG2 cells were assessed by semi-quantitative RT-PCR. The results are as shown in FIG. 4.

Example 14

Stimulation of LDLR Ligand Uptake Activity in HepG2 Cells by *Corydalis*-Derived Compounds and by Some New Compounds of Formula I, II, III, and IV HepG2 cells (2×10⁵ cells/well) in 24-well culture plates were treated with various compounds at indicated concentrations for 20 hours. The fluorescent 1.1′-dioctadecyl-3,3,3′,3′-tetramethylindocarbocyanin perchlorate (DiI-LDL) (Biomedical Technologies, Stoughton, Mass.) at a concentration of 2 µg/mL was added to cells at the end of treatment. After 4 hours, the medium was removed, cells were washed with cold PBS, and were examined immediately under a fluorescent microscope (Nikon) at 200× amplification. The fluorescent intensity in compound-treated cells was compared to that in untreated control cells. The compound activity was graded as follows: +, slightly increased fluorescent intensity over control; ++ modestly increased fluorescent intensity over control; +++, strongly increased fluorescent intensity over control. The results are summarized below in Table 8. In these experiments berberine chloride was used for comparison.

TABLE 8

| Compound No. | Activity on DiI-LDL uptake | A, compound dose ≤ 10 µM B, compound dose ≤ 40 µM |
|---|---|---|
| Berberine | + | B |
| d-(+)-THP | ++ | B |
| d-(+)-CRPM | ++ | A |
| d-(+)-CRDL | ++ | B |
| d-(+)-EGN | + | A |
| d-(+)-CLMD | + | B |
| 1 | + | A |
| 26 | ++ | A |
| 30 | + | A |
| 34 | ++ | A |
| 38 | ++ | A |
| 41 | ++ | A |
| 43 | ++ | A |
| 44 | ++ | A |
| 45 | ++ | A |
| 46 | ++ | A |
| 50 | +++ | A |
| 56 | +++ | A |
| 69 | +++ | A |

Example 15

Activities of some compounds of Formulas I, II, III, and IV on LDLR mRNA expression were determined. HepG2 cells were treated with new compounds individually at a dose less than or equal to 10 µM for 24 hours. Total RNA was harvested for quantitative real-time RT-PCR analysis using the method described in Example 16B. The fold activity was derived by dividing the amount of normalized LDLR mRNA in compound-treated cells over the amount of LDLR mRNA in untreated control cells. In these experiments, berberine chloride was included for comparison. Results are shown in Table 9.

TABLE 9

| Compound No. | Activity on LDLR mRNA expression (Fold of control) |
|---|---|
| BBR | 1.30 ± 0.11 |
| 1 | 1.56 ± 0.86 |
| 26 | 1.29 ± 0.10 |
| 30 | 1.47 ± 0.13 |
| 34 | 1.76 ± 0.17 |
| 37 | 2.47 ± 0.07 |
| 38 | 1.82 ± 0.10 |
| 41 | 1.60 ± 0.03 |
| 43 | 1.95 ± 0.18 |
| 44 | 2.20 ± 0.06 |
| 45 | 2.09 ± 0.11 |
| 46 | 1.80 ± 0.16 |
| 47 | 1.63 ± 0.09 |
| 48 | 1.45 ± 0.15 |
| 50 | 4.74 ± 0.96 |
| 51 | 3.79 ± 0.33 |
| 52 | 3.63 ± 0.17 |
| 53 | 3.96 ± 0.40 |
| 56 | 3.18 ± 0.63 |
| 57 | 2.62 ± 0.17 |
| 58 | 3.90 ± 0.01 |
| 59 | 3.73 ± 0.10 |
| 60 | 3.46 ± 0.75 |
| 61 | 1.33 ± 0.53 |
| 62 | 0.69 ± 0.02 |
| 63 | 2.94 ± 0.13 |
| 64 | 2.82 ± 0.45 |
| 65 | 2.58 ± 0.46 |
| 66 | 2.54 ± 0.06 |

TABLE 9-continued

| Compound No. | Activity on LDLR mRNA expression (Fold of control) |
| --- | --- |
| 69 | 2.21 ± 0.09 |
| 85 | 1.42 ± 0.30 |
| 86 | 2.48 ± 0.62 |
| 88 | 1.93 ± 0.24 |
| 89 | 1.92 ± 0.40 |
| 90 | 1.21 ± 0.07 |
| 91 | 3.77 ± 0.20 |
| 92 | 1.52 ± 0.07 |
| 93 | 1.42 ± 0.16 |
| 94 | 1.22 ± 0.18 |
| 95 | 1.43 ± 0.04 |
| 96 | 1.33 ± 0.05 |
| 100 | 1.44 ± 0.59 |
| 101 | 1.97 ± 0.00 |

Example 16

Figure 10:
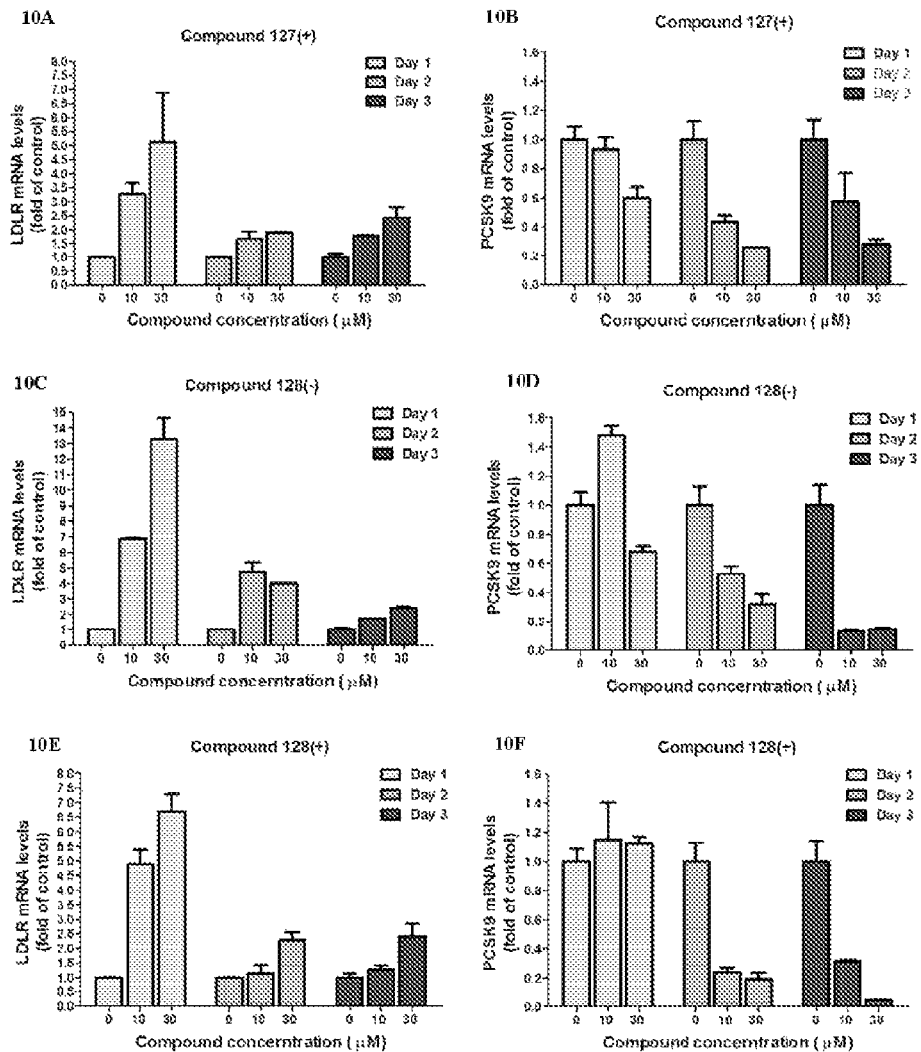
FIG. 10A-F show the time-dependent effects of compounds of Formula I, II, III, and IV on the upregulation of LDLR mRNA (10A, 10C, and 10E) and the inhibition of PCSK9 mRNA expression (10B, 10D, 10F), HepG2 cells were treated with new compounds individually at 20 μM dose for 1 day, 2 day, and 3 days. Total RNA was harvested for quantitative real-time RT-PCR analysis. The fold activity was derived by dividing the amount of normalized PCSK9 mRNA or LDLR mRNA in compound-treated cells over the amount of PCSK9 mRNA or LDLR mRNA in untreated control cells.

Dual Activations of ERK and AMPK Signaling Pathways by the Genus of *Corydalis* Derived Active Compounds HepG2 cells cultured in 60-mm dishes were treated with various compounds at a concentration of 15 µg/ml for 2 hours. Total cell lysate was isolated and 50 µg of protein was separated on SDS-PAGE and transferred to nitrocellulose membrane. Western blot was performed using anti-phosphorylated ERK and anti-phosphorylated AMPK antibodies to detect the activation of ERK and AMPK. The membranes were probed again with anti-ERK and anti-AMPK antibodies to demonstrate equal loadings of proteins. The results in FIG. 10 show that the levels of phosphorylated and activated ERK and AMPK were significantly increased in compound-treated cells as compared to untreated control cells.

Western blot analysis was performed to determine the activation of ERK in HepG2 cells by 14R,13S-(+)-CRDL and 14R-(+)-THP. HepG2 cells were treated with 20 µg/mL 14R,13S-(+)-CRDL and 14R-(+)-THP respectively for 0.5, 2, or 8 hours. Cells were then lysed. After protein quantitation using the BCA™ protein assay reagent (PIERCE), 50 µg protein from each sample was subjected to SDS-PAGE, followed by Western blotting using anti-phosphorylated ERK (Cell Signaling) and subsequently reprobed with antibody against β-actin. Results are as shown in FIG. 5.

Figure 6:
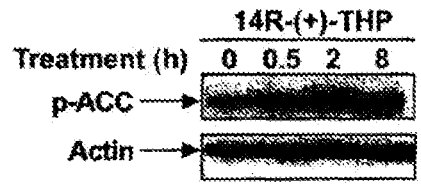
FIG. 6 shows western blot analysis of the induction of acetyl coenzyme A carboxylase (ACC) phosphorylation by 14R-(+)-THP.

FIG. 6 shows Western blot analysis of the induction of ACC phosphorylation by 14R-(+)-THP. HepG2 cells were treated with 20 µg/ml 14R-(+)-THP for 0.5, 2, or 8 hours. Cells were lysed, and 50 µg protein from each sample was subjected to SDS-PAGE, followed by Western blotting using anti-phosphorylated ACC (Cell Signaling) and subsequently reprobed with antibody against β-actin.

Example 17

Figure 11:
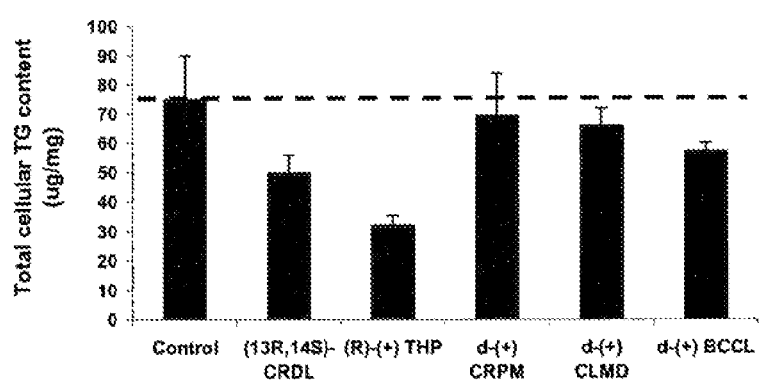
FIG. 11 compares total cellular TG content of cells exposed to compounds disclosed herein.

Reduction of Cellular Triglyceride Content by *Corydalis* Derived Active Compounds HepG2 cells seeded in 12-well plate were untreated or treated with various active compounds (20 µg/ml) for 24 hours. After treatment, cells were washed by Tris Buffer (75 NaCl, 50 µM Tris-HCl, pH 7.4) twice, and cellular lipids were extracted by 1 ml hexane:isopropanol (3:2) twice. The extractions were evaporated in a chemical hood overnight. Next day, the dried lipids were dissolved in 100 µl isopropanol containing 10% Triton-X100. Ten ttl per sample was used for TG measurements with the commercial available kit obtained from Stanbio. To normalize the TG content with cellular protein, after lipid extraction, the cells were lysed in 0.1N NaOH to determine protein concentrations using BCA Protein Assay Reagent (Pierce). The results (FIG. 11) show that the total cellular TG contents were reduced by the compound treatments compared to control. It has been demonstrated that AMPK activation stimulates energy expenditure and reduces TG synthesis. The activated AMPK in compound treated cells may account for the reduced TG content in cells that were treated with these compounds.

Example 18

Demonstration of Reduction of Intracellular Triglyceride in HepG2 Cells Treated with Compounds Disclosed Herein Berberine chloride was used for comparison. The amount of TG in untreated control cells was defined as 100% and the amounts of TG in compound-treated cells were divided to that value. Results are shown in Table 10.

TABLE 10

| Compound No. | Activity on reduction of cellular TG accumulation (% of control) | A, compound dose ≤ 10 µM B, compound dose ≤ 40 µM |
| --- | --- | --- |
| Control | 100 | |
| Berberine | 70.9 ± 5.4 | B |
| 69 | 60.4 ± 7.34 | A |
| 82 | 53.2 ± 21.3 | B |
| 83 | 63.0 ± 0.90 | B |
| 22 | 53.35 ± 12.68 | B |
| 91 | 71.17 ± 2.23 | B |

Example 19

Figure 12:
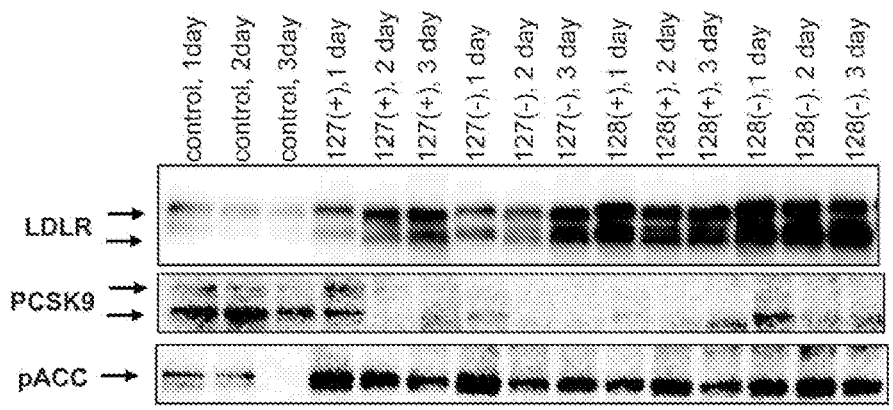
FIG. 12 compares the time-dependent effects of the enantiomers of positive rotation (+) with the enantiomers of negative rotation (−) of Compound 127 and 128 on LDLR protein upregulation, inhibition of PCSK9, and induction of the phosphorylation of ACC (pACC). HepG2 cells were treated with indicated compounds for 1-3 days and total cell lysates were isolated for western blotting using anti-LDLR, anti-PCSK9, and pACC antibodies.

Comparison of the Biological Effects of Steroisomers of Compounds Disclosed Herein To determine whether the compounds exhibit stereoisomaric difference in the biological activities of upregulation of LDLR protein expression, inhibition of PCSK9 protein expression, and induction of phosphorylation of ACC, HepG2 cells were treated with compound 127(+), 127(−), 128(+), and 128(−) at a concentration of 20 µM. Cells were harvested after 1, 2, and 3 days treatment and western blot analysis was conducted using antibodies directed to LDLR and PCSK9. Chicken anti-LDLR was purchased from Abcam, the mouse anti-PCSK9 was purchased from Cayman Chemicals, and anti-pACC was purchased from Cell Signaling. The results in FIG. 12 showed that while all these compounds effectively increased LDLR protein levels, and strongly inhibited the expression of PCSK9, and induced ACC phosphorylation, the activities of enantiomers with a negative rotation property appeared to be stronger than that of the enantiomers with a positive rotation. This demonstrated stereoisomeric preference differs from the natural compounds disclosed herein that have a stereoisomeric preference of positive optical rotation property.

247

Example 20

Figure 13:
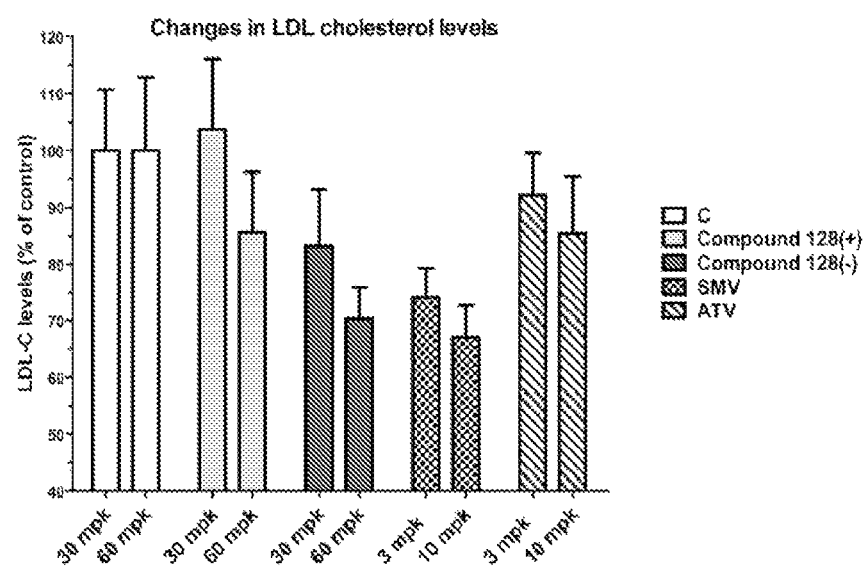
FIG. 13 shows LDL-c reducing effects of new compound invented herein in hypercholesterolemic rabbits. Forty-two male Japanese rabbits were fed the cholesterol enriched rabbit diet for two weeks to induce hypercholesterolemia. Rabbits were then treated with Compound 128(+) and 128(−) at 30 mg/kg, and simvastatin (SMV) and atorvastatin (ATV) at 3 mg/kg once a day by oral gavage. Serum samples were collected at day 0 (before the drug treatment) and day 7. After 7 days of treatment, the compound doses were increased to 60 mg/kg for Compound 128(+) and 128(−) and to 10 mg/kg for SMV and ATV and the treatment was continued for another 7 days. All tested animals were sacrificed at the end of a total of 14 days treatment and serum samples were analyzed for TC, LDL-C, TG, and HDL-C. The data shown are % changes of LDL-c in compound-treated groups as compared to vehicle group.
Figure 14:
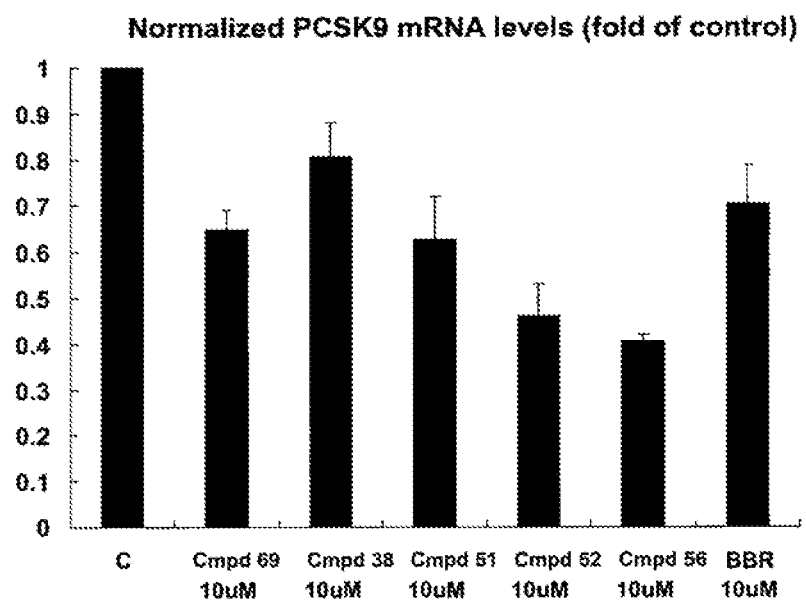
FIG. 14 shows that compounds disclosed herein strongly inhibit the mRNA expression of PCSK9.

Examination of the Combined Effects of Statins and New Compound 127(+) on LDLR and PCSK9 Protein Expression To determine whether the stimulatory effects of statins on LDLR protein expression could be enhanced by some new compounds invented herein, HepG2 cells were untreated or treated with a low dose of rosuvastatin (RSV) at 0.3 and 1 uM concentration in the absence or the presence of Compound 127(+), or treated with low concentrations of Compound 127(+) alone for 2 days. Western blot analysis was conducted to examine LDLR and PCSK9 protein levels. Compound 127(+) is the single enantiomer of compound 127 with a positive optical rotation. Results are shown in FIG. 13. These data demonstrate that activities of statins on upregulation of LDLR expression were not inhibited by Compound 127(+). Instead, addition of Compound 127(+) to statin-treated cells further improved the stimulatory effects of statins on LDLR protein expression. Furthermore, the inducing effects of RSV on PCSK9 protein levels were antagonized by compound 127(+). These preliminary results suggested that *corydalis*-derived active compounds of natural origins or synthetic origins have potentials to be used in combinational therapies with HMG CoA reductase inhibitors to treat hyperlipidemic patients.

Example 21

Effect of Compounds of Present Technology on LDLR and PCSK9 mRNA Expression

The time-dependent effects of compounds of Formula I, II, III, and IV on the upregulation of LDLR mRNA and the inhibition of PCSK9 mRNA expression were examined (Horton J D, Cohen J C, Hobbs H I T. "Molecular biology of PCSK9: its role in LDL metabolism" TRENDS in Biochemical Sciences 2007; 32:71-77). HepG2 cells were treated with new compounds individually at 20 uM dose for 1 day, 2 day, and 3 days. Total RNA was isolated and 2 µg was used to generate cDNA in a reaction containing random primers and M-MLV at 37° C. for 1 hour in a volume of 25 µl. Real-time PCR was performed on the cDNA using MCEP REALPLEX 2 SYSTEM (Eppendorf) and Universal MasterMix (Applied Biosystems). Human LDLR, PCSK9, and GAPDH Pre-Developed TaqMan Assay Reagents (Applied Biosystems) were used to assess the levels of mRNA expressions in HepG2. The levels of LDLR mRNA or PCSK9 mRNA were normalized to that of GAPDH. Each RNA samples was assayed in triplicate. The abundance of LDLR mRNA or PCSK9 mRNA in untreated cells was defined as 1, and the amounts of LDLR mRNA or PCSK9 from compound-treated cells were plotted relative to that value (FIG. 10). The data shown are mean±s.d. These results showed that these new compounds strongly inhibit the mRNA expression of PCSK9 while upregulating LDLR mRNA, thereby providing another means to increase LDLR expression by reducing PCSK9-mediated degradation of LDLR protein.

Example 22

Figure 15A:
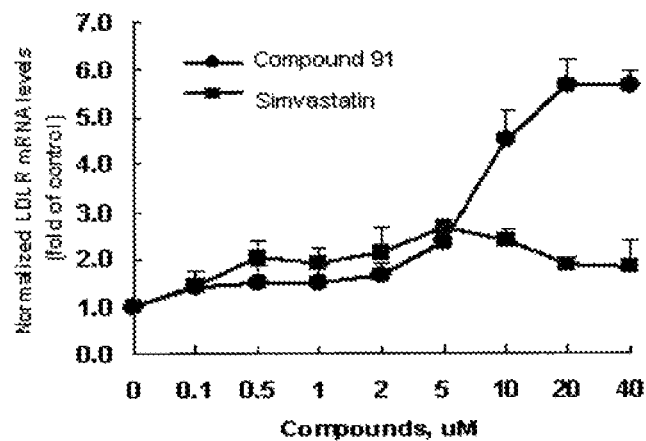
FIG. 15A shows a LDLR mRNA level vs. concentration curve for compound 91 and simvastatin
Figure 15B:
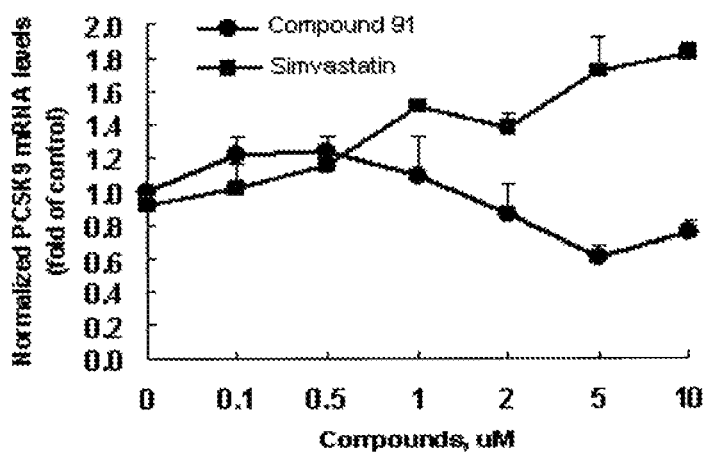
FIG. 15B shows a PCSK9 mRNA levels vs. concentration curve for curve compound 91.

Comparisons of Simvastatin and New Compound 91 on LDLR and PCSK9 mRNA Expressions HepG2 cells were treated with simvastatin or compound 91 at the indicated concentrations for 24 hours. Total RNA was harvested for quantitative real-time RT-PCR analysis using method described in Examples 16B. The fold activity was derived by dividing the amount of normalized LDLR or PCSK9 mRNA in compound-treated cells over the amount of LDLR or PCSK9 mRNA in untreated control cells. These results as shown in FIG. 15A and FIG. 15B demonstrated that the new compound 91 dose-dependently increases LDLR mRNA expression but inhibits the PCSK9 mRNA expression, whereas simvastatin increases both LDLR and PCSK9 mRNA expression.

Example 23

The effects of 23 compounds on the mRNA expressions of LDLR and PCSK9 were examined using quantitative real-time RT-PCR assays. HepG2 cells were treated with various compounds at 10 and 40 uM concentrations for 24 hours. Total RNA was isolated and 2 ng was used to generate cDNA in a reaction containing random primers and M-MLV at 37° C. for 1 h in a volume of 25 µl. Real-time PCR was performed on the cDNA using MCEP REALPLEX 2 SYSTEM (Eppendorf) and Universal MasterMix (Applied Biosystems). Human LDLR, PCSK9, and GAPDH Pre-Developed TaqMan Assay Reagents (Applied Biosystems) were used to assess the levels of mRNA expressions in HepG2. The levels of LDLR and PCSK9 mRNA were normalized to that of GAPDH. Each RNA samples was assayed in duplicate. The fold activity was calculated by dividing mRNA abundance in compound treated cells with that of control. The data (mean±s.d.) are summarized in Table 11 columns 2-5. These results showed that these synthetic compounds strongly increase LDLR mRNA expression and also exhibit inhibitory activity on PCSK9 mRNA expression in dose-dependent manners.

The combined beneficial effects of these novel compounds on elevation of LDLR mRNA levels likely through the mechanism of mRNA stabilization and their inhibitory activity towards PCSK9, the secreted protease that degrades LDLR protein, result in strong increases in LDL ligand uptake activity through increased receptor surface abundance. The ligand uptake activity was demonstrated measuring the intracellular accumulation of fluorescent labeled LDL. Briefly, HepG2 cells ($2\times10^5$ cells/well) in 24-well culture plates were treated with various compounds at 10 and 40 uM concentrations for 20 hours. The fluorescent 1.1'-dioctadecyl-3,3,3',3'-tetramethylindocarbocyanin perchlorate (DiI-LDL) (Biomedical Technologies, Stoughton, Mass.) at a concentration of 2 µg/ml was added to cells at the end of treatment. After 4 hours, the medium was removed; cells were washed with cold PBS, and were examined immediately under a fluorescent microscope (Nikon) at 200× amplification. The fluorescent intensity in compound-treated cells was compared to that in untreated control cells. The compound activity was graded as follows: +, slightly increased fluorescent intensity over control; ++ modestly increased fluorescent intensity over control; +++, strongly increased fluorescent intensity over control. The results are summarized below in Table 11.

Figure 16:
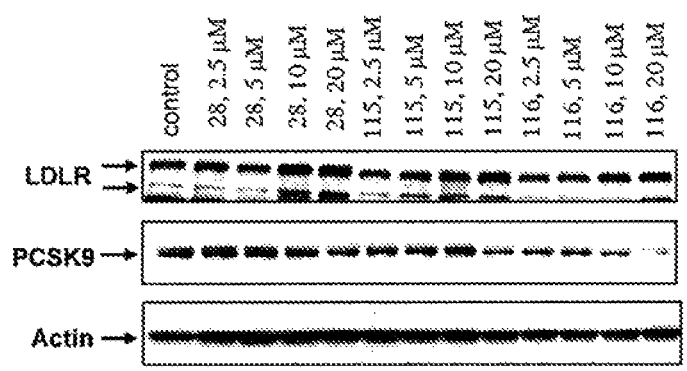
FIG. 16 is a Western blot demonstrating enhanced LDLR expression and reduced PCSK9 expression. Actin is a positive control showing equal protein loading levels.

To further demonstrate the stimulating effects of compounds on LDLR protein expression and their inhibitory activities on PCSK9 expression western blot analyses were performed using antibodies directed to LDLR and PCSK9. Chicken anti-LDLR was purchased from Abcam and the mouse anti-PCSK9 was purchased from Cayman Chemicals. HepG2 cells cultured in 60-mm dishes were incubated overnight in medium containing 0.5% fetal bovine serum prior to the addition of compounds at 20 uM concentration for 1-3 days. Total cell lysate was isolated and 50 µg of protein was separated on SDS-PAGE and transferred to nitrocellulose membrane for immunoblotting with anti-LDLR, anti-PCSK9, and anti-p-ACC. The results are shown in FIG. 16. These results corroborate the data obtained from mRNA analysis and ligand uptake assays, and clearly demonstrate the bioactivities of this series of compounds in enhancing LDLR protein expression and reducing PCSK9 protease levels.

TABLE 11

| Compound No. | Activity on LDLR mRNA at 10 uM (fold of control) | Activity on LDLR mRNA at 40 uM (fold of control) | Activity on PCSK9 mRNA reduction at 10 uM (fold of control) | Activity on PCSK9 mRNA reduction at 40 uM (fold of control) | Activity in LDL uptake at 10 and 40 uM (relative to control) |
|---|---|---|---|---|---|
| 115 | 0.51 ± 0.11 | 2.65 ± 0.06 | n.d. | n.d. | −/+++ |
| 116 | 1.41 ± 0.04 | 7.19 ± 1.29 | n.d. | n.d. | +++/+++ |
| 121 | 3.56 ± 0.03 | 3.43 ± 0.81 | n.d. | n.d. | +++/+ |
| 127 | 1.80 ± 0.13 | 2.38 ± 0.38 | 0.197 ± 0.014 | 0.192 ± 0.016 | +++/+++ |
| 128 | 7.52 ± 0.26 | 13.36 ± 0.46 | 0.96 ± 0.00 | 0.86 ± 0.029 | +++/+++ |
| 129 | 2.49 ± 0.18 | 1.99 ± 0.13 | 1.57 ± 0.07 | 1.68 ± 0.41 | +/++ |
| 130 | 4.29 ± 0.65 | 9.00 ± 1.49 | 2.11 ± 0.11 | 0.84 ± 0.12 | ++/+ |
| 131 | 0.67 ± 0.05 | 2.25 ± 0.13 | 0.87 ± 0.04 | 0.72 ± 0.10 | +/+ |
| 132 | 2.33 ± 0.04 | 6.62 ± 0.90 | 1.85 ± 0.12 | 0.73 ± 0.15 | ++/+ |
| 133 | 4.92 ± 0.00 | 6.61 ± 0.16 | 1.04 ± 0.08 | 0.49 ± 0.01 | ++/+ |
| 134 | 1.41 ± 0.07 | 6.23 ± 0.64 | 1.25 ± 0.03 | 0.86 ± 0.02 | ±/+ |
| 135 | 1.72 ± 0.13 | 1.86 ± 0.00 | 0.97 ± 0.04 | 1.10 ± 0.14 | ±/+ |
| 136 | 0.91 ± 0.05 | 1.92 ± 0.32 | 0.48 ± 0.03 | 0.62 ± 0.02 | +/++ |
| 137 | 1.61 ± 0.19 | 2.66 ± 0.04 | 0.45 ± 0.06 | 0.34 ± 0.00 | +/+++ |
| 138 | 1.60 ± 0.29 | 2.45 ± 0.20 | 0.63 ± 0.14 | 0.35 ± 0.02 | +/+++ |
| 139 | 11.5 ± 1.29 | 3.02 ± 0.34 | 0.46 ± 0.04 | 0.27 ± 0.02 | ++/++ |
| 140 | 6.65 ± 0.68 | 8.60 ± 2.00 | 0.43 ± 0.08 | 0.51 ± 0.08 | ++/++ |
| 142 | 2.64 ± 0.01 | 12.98 ± 1.96 | 0.62 ± 0.07 | 0.52 ± 0.02 | +/++ |
| 143 | 1.87 ± 0.03 | 14.97 ± 1.68 | 1.09 ± 0.09 | 0.48 ± 0.06 | −/++ |
| 144 | 1.02 ± 0.09 | 2.69 ± 0.31 | 0.99 ± 0.09 | 1.84 ± 0.15 | −/− |
| 149 | n.d. | n.d. | n.d. | n.d. | +/+ |
| 150 | n.d. | n.d. | n.d. | n.d. | +/++ |
| 151 | n.d. | n.d. | n.d. | n.d. | −/+ |

The disclosures of each and every patent, patent application and publication (for example, journals, articles and/or textbooks) cited herein are hereby incorporated herein by reference in their entirety, except to the extent that they contradict definitions herein. Also, as used herein and in the appended claims, singular articles such as "a", "an" and "one" are intended to refer to singular or plural. While the present technology has been described herein in conjunction with a preferred aspect, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect described above can also have included or incorporated therewith such variations or aspects as disclosed in regard to any or all of the other aspects. The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

What is claimed is:
1. A compound of Formula V,

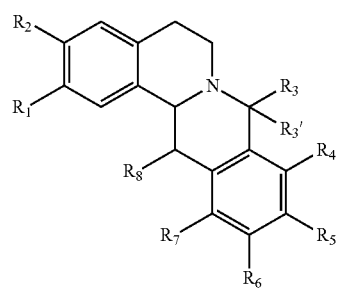

stereoisomers thereof, tautomers thereof, solvates thereof, and pharmaceutically acceptable salts thereof;
wherein
$R_1$ and $R_2$ are independently —H, —$(CH_2)_{0-6}COOR'$, —C(O)R", —OR', —$NR_{10}R_{11}$, —$C(O)NR_{10}R_{11}$, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group; or $R_1$ and $R_2$ together are a 1,2-dioxyethylene group; provided that $R_1$ and $R_2$ are not both —OR';

$R_3$ and $R_8$ are independently —H, —OH, —Cl, —Br, —F, —I, —CN, —NH$_2$, —C(O)NH$_2$, —COOH, or a substituted or unsubstituted alkyl, alkenyl, alkoxy or aralkyl group;

$R_3$' is —H, or $R_3$ and $R_3$' together are an oxo group;

$R_4$ is —OSO$_2$R'';

$R_5$ and $R_6$ are independently —H, halogen, —OH, or a substituted or unsubstituted alkoxy group; or $R_4$ and $R_5$ together are a methylenedioxy group, or $R_5$ and $R_6$ together are a methylenedioxy group;

$R_7$ is —H, halogen, —OH, or a substituted or unsubstituted alkyl or alkoxy group;

$R_{10}$ and $R_{11}$ are independently H, —C(O)OR'', or a substituted or unsubstituted alkyl group;

each R' is independently a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group; and each R'' is independently a substituted or unsubstituted alkyl, alkenyl, cycloalkyl, cycloalkylalkyl, aryl, aralkyl, heteroaryl, heteroarylalkyl, heterocyclyl, or heterocyclylalkyl group.

2. The compound of claim 1, wherein $R_1$ and $R_2$ are independently —H, —(CH$_2$)$_{0-6}$COOR', —NR$_{10}$R$_{11}$, —C(O)NR$_{10}$R$_{11}$, or a substituted or unsubstituted alkyl group; or $R_1$ and $R_2$ together are a 1,2-dioxyethylene group.

3. The compound of claim 1, wherein one of $R_1$ and $R_2$ is OR' and the other is —H, —(CH$_2$)$_{0-6}$COOR', —NR$_{10}$R$_{11}$, —C(O)NR$_{10}$R$_{11}$, or a substituted or unsubstituted alkyl group; or $R_1$ and $R_2$ together are a 1,2-dioxyethylene group.

4. The compound of claim 1, wherein $R_{10}$ and $R_{11}$ are independently H, or a C$_{1-6}$ alkyl group optionally substituted with a hydroxy group.

5. The compound of claim 1, wherein $R_1$ and $R_2$ together are a 1,2-dioxyethylene group.

6. The compound of claim 1, wherein $R_3$ and $R_3$' are each —H, or $R_3$ and $R_3$' together are an oxo group.

7. The compound of claim 1, wherein the 14-position in Formula V is the R-(+) stereochemical configuration.

8. The compound of claim 1, wherein $R_5$ is OH or unsubstituted alkoxy and $R_6$ is H.

9. The compound of claim 1, wherein $R_6$ is H, and $R_7$ is H.

10. The compound of claim 1, wherein $R_8$ is —H, —OH, —COOH, or an unsubstituted alkyl or —(CH$_2$)$_{1-6}$-phenyl group.

11. The compound of claim 1, wherein
$R_1$ and $R_2$ are independently —H, —(CH$_2$)$_{0-6}$COOR', —NR$_{10}$R$_{11}$, —C(O)NR$_{10}$R$_{11}$, or a substituted or unsubstituted alkyl group; or $R_1$ and $R_2$ together are a 1,2-dioxyethylene group;
$R_3$ and $R_3$' are each —H, or $R_3$ and $R_3$' together are an oxo group;
$R_5$ and $R_6$ are independently —H, —OH, or an unsubstituted C$_{1-6}$ alkoxy group; or $R_4$ and $R_5$ together are a methylenedioxy group, or $R_5$ and $R_6$ together are a methylenedioxy group; and
$R_8$ is —H, —OH, —COOH, or an unsubstituted alkyl or —(CH$_2$)$_{1-6}$-phenyl group.

12. The compound of claim 1, wherein
$R_1$ and $R_2$ are independently —H, —CH$_3$, —CH$_2$OH, —OH, —OCH$_3$, —OCH$_2$CH$_3$, —OCH$_2$CH$_2$OH, —COOH, —C(O)N(CH$_3$)$_2$, —C(O)NH(CH$_2$CH$_2$OH), —C(O)OCH$_3$, —NHCH$_3$, —N(CH$_3$)$_2$, —NC(O)OCH$_2$CH$_3$, benzyloxy, or $R_1$ and $R_2$ together are a 1,2-dioxyethylene group;
$R_3$ and $R_3$' are each —H, or $R_3$ and $R_3$' together are an oxo group;
$R_5$ and $R_6$ are independently —H, —OH, or —OCH$_3$; and
$R_8$ is —H, methyl, ethyl, —COOH, or benzyl.

13. The compound of claim 12, wherein $R_4$ is —O—SO$_2$-phenyl, wherein the phenyl group is optionally substituted with one or two substituents selected from the group consisting of methyl, methoxy, fluoro, chloro, trifluoromethyl, and nitro.

14. The compound of claim 1, wherein,
$R_1$ is selected from —(CH$_2$)$_{0-6}$COOR', —C(O)R'', —OR', —NR$_{10}$R$_{11}$, —C(O)NR$_{10}$R$_{11}$, or a substituted or unsubstituted alkyl, group;
$R_2$ is selected from —H, —(CH$_2$)$_{0-6}$COOR', —C(O)R'', —O(CH$_2$)$_{1-4}$—CO$_2$R', —NR$_{10}$R$_{11}$, —C(O)NR$_{10}$R$_{11}$, or a substituted or unsubstituted alkyl group; or $R_1$ and $R_2$ together are a 1,2-dioxyethylene group;
$R_8$ is —H, or an unsubstituted C$_{1-4}$ alkyl group;
$R_3$ and $R_3$' are both —H;
$R_5$ is —H, halogen, —OH, or a substituted or unsubstituted alkoxy group; or $R_4$ and $R_5$ together are a methylenedioxy group, or $R_5$ and $R_6$ together are a methylenedioxy group;
$R_6$ and $R_7$ are independently selected from —H or halogen;
$R_{10}$ and $R_{11}$ are independently H, —C(O)OR'', or a substituted or unsubstituted alkyl group;
each R' is independently a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group; and
each R'' is independently a substituted or unsubstituted alkyl, alkenyl, cycloalkyl, cycloalkylalkyl, aryl, aralkyl, heteroaryl, heteroarylalkyl, heterocyclyl, or heterocyclylalkyl group.

15. The compound of claim 14, wherein R'' is a substituted or unsubstituted aryl group.

16. The compound of claim 15, wherein R'' is phenyl, optionally substituted with one or two halogen.

17. The compound of claim 14, wherein $R_4$ is –OSO$_2$-phenyl wherein the phenyl is optionally substituted with a fluorine.

18. A composition comprising the compound of claim 1 and a pharmaceutically acceptable carrier.

19. A pharmaceutical composition for treating a condition selected from the group consisting of hyperlipidemia, hypercholesterolemia, hypertriglyceridemia, hepatic steatosis, and metabolic syndrome, the composition comprising a lipid-lowering effective amount of the compound of claim 1.

20. A method of reducing plasma and/or hepatic lipid levels in a subject in need thereof, which comprises administering to the subject a lipid-lowering effective amount of the compound of claim 1.

21. A method for treating a disease or condition selected from the group consisting of hyperlipidemia, hypercholesterolemia, hypertriglyceridemia, hepatic steatosis and metabolic syndrome, comprising administering to a subject in need thereof a therapeutically effective amount of the compound of claim 1.

22. A method of increasing LDLR expression, comprising administering to a subject in need thereof a therapeutically effective amount of the compound of claim 1, whereby LDLR expression in said subject is increased.

23. A method of decreasing plasma LDL-cholesterol and/or plasma triglyceride, comprising administering to a subject in need thereof a therapeutically effective amount of the compound of claim 1, whereby plasma LDL-cholesterol in said subject is decreased.

24. The compound of claim 1, wherein the 14-position in Formula V is the R stereochemical configuration.

25. A compound that is
3,10-dimethoxy-5,6,7,8,13,13a-hexahydroisoquinolino [2,1-b]isoquinolin-9-yl 3 fluorobenzenesulfonate; or
11-methoxy-6,7,8,9,14,14a-hexahydro-2H,3H-1,4-dioxano[5,6-g]isoquinolino[3,2-a]isoquinolin-10-yl 3-fluorobenzenesulfonate.

26. The compound of claim 25, wherein the 14-position in Formula V is the R-(+) stereochemical configuration.

27. A composition comprising the compound of claim 25 and a pharmaceutically acceptable carrier.

28. A pharmaceutical composition for treating a condition selected from the group consisting of hyperlipidemia, hypercholesterolemia, hypertriglyceridemia, hepatic steatosis, and metabolic syndrome, the composition comprising a lipid-lowering effective amount of the compound of claim 25.

29. A method of reducing plasma and/or hepatic lipid levels in a subject in need thereof, which comprises administering to the subject a lipid-lowering effective amount of the compound of claim 25.

30. A method for treating a disease or condition selected from the group consisting of hyperlipidemia, hypercholesterolemia, hypertriglyceridemia, hepatic steatosis and metabolic syndrome, comprising administering to a subject in need thereof a therapeutically effective amount of the compound of claim 25.

31. A method of increasing LDLR expression, comprising administering to a subject in need thereof a therapeutically effective amount of the compound of claim 25, whereby LDLR expression in said subject is increased.

32. A method of decreasing plasma LDL-cholesterol and/or plasma triglyceride, comprising administering to a subject in need thereof a therapeutically effective amount of the compound of claim 25, whereby plasma LDL-cholesterol in said subject is decreased.

33. A compound that is
2,3,10-trimethoxy-5,6,7,8,13,13a-hexahydroisoquinolino [2,1-b]isoquinolin-9-yl 3-fluorobenzenesulfonate.

34. The compound of claim 33, wherein the position corresponding to the 14-position in Formula V is the R-(+) stereochemical configuration.

35. A composition comprising the compound of claim 33 and a pharmaceutically acceptable carrier.

36. A pharmaceutical composition for treating a condition selected from the group consisting of hyperlipidemia, hypercholesterolemia, hypertriglyceridemia, hepatic steatosis, and metabolic syndrome, the composition comprising a lipid-lowering effective amount of the compound of claim 33.

37. A method of reducing plasma and/or hepatic lipid levels in a subject in need thereof, which comprises administering to the subject a lipid-lowering effective amount of the compound of claim 33.

38. A method for treating a disease or condition selected from the group consisting of hyperlipidemia, hypercholesterolemia, hypertriglyceridemia, hepatic steatosis and metabolic syndrome, comprising administering to a subject in need thereof a therapeutically effective amount of the compound of claim 33.

39. A method of increasing LDLR expression, comprising administering to a subject in need thereof a therapeutically effective amount of the compound of claim 33, whereby LDLR expression in said subject is increased.

40. A method of decreasing plasma LDL-cholesterol and/or plasma triglyceride, comprising administering to a subject in need thereof a therapeutically effective amount of the compound of claim 33, whereby plasma LDL-cholesterol in said subject is decreased.

* * * * *